US011384401B2

(12) United States Patent
Ahlquist et al.

(10) Patent No.: US 11,384,401 B2
(45) Date of Patent: *Jul. 12, 2022

(54) DETECTING GASTROINTESTINAL NEOPLASMS

(71) Applicant: Mayo Foundation for Medical Education and Research, Rochester, MN (US)

(72) Inventors: David A. Ahlquist, Rochester, MN (US); William R. Taylor, Lake City, MN (US); John B. Kisiel, Rochester, MN (US); Douglas W. Mahoney, Elgin, MN (US); Tracy C. Yab, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 23 days.

This patent is subject to a terminal disclaimer.

(21) Appl. No.: 16/908,056

(22) Filed: Jun. 22, 2020

(65) Prior Publication Data

US 2020/0318202 A1 Oct. 8, 2020

Related U.S. Application Data

(63) Continuation of application No. 16/030,313, filed on Jul. 9, 2018, now Pat. No. 10,704,107, which is a continuation of application No. 15/054,860, filed on Feb. 26, 2016, now Pat. No. 10,030,272.

(60) Provisional application No. 62/126,061, filed on Feb. 27, 2015.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/154* (2013.01)

(58) Field of Classification Search
CPC ............ C12Q 1/6886; C12Q 2600/112; C12Q 2600/154
See application file for complete search history.

(56) References Cited

U.S. PATENT DOCUMENTS

| | | |
|---|---|---|
| 5,352,775 A | 10/1994 | Albertsen |
| 5,362,623 A | 11/1994 | Vogelstein |
| 5,527,676 A | 6/1996 | Vogelstein |
| 5,541,308 A | 7/1996 | Hogan et al. |
| 5,648,212 A | 7/1997 | Albertsen |
| 5,670,325 A | 9/1997 | Lapidus et al. |
| 5,691,454 A | 11/1997 | Albertsen |
| 5,741,650 A | 4/1998 | Lapidus et al. |
| 5,783,666 A | 7/1998 | Albertsen |
| 5,786,146 A | 7/1998 | Herman |
| 5,891,651 A | 4/1999 | Roche |
| 5,928,870 A | 7/1999 | Lapidus et al. |
| 5,952,178 A | 9/1999 | Lapidus et al. |
| 5,955,263 A | 9/1999 | Vogelstein |
| 6,020,137 A | 2/2000 | Lapidus et al. |
| RE36,713 E | 5/2000 | Vogelstein |
| 6,090,566 A | 7/2000 | Vogelstein |
| 6,114,124 A | 9/2000 | Albertsen |
| 6,235,470 B1 | 5/2001 | Sidransky |
| 6,245,515 B1 | 6/2001 | Vogelstein |
| 6,413,727 B1 | 7/2002 | Albertsen |
| 6,630,314 B2 | 10/2003 | Nair et al. |
| 6,677,312 B1 | 1/2004 | Vogelstein |
| 6,800,617 B1 | 10/2004 | Vogelstein |
| RE38,916 E | 12/2005 | Vogelstein |
| 7,037,650 B2 | 5/2006 | Gonzalgo et al. |
| 7,087,583 B2 | 8/2006 | Vogelstein |
| 7,267,955 B2 | 9/2007 | Vogelstein |
| 7,368,233 B2 | 5/2008 | Shuber et al. |
| 7,432,050 B2 | 10/2008 | Markowitz |
| 7,485,402 B2 | 2/2009 | Arai |
| 7,485,418 B2 | 2/2009 | Goggins |
| 7,485,420 B2 | 2/2009 | Markowitz |
| 8,808,990 B2 | 8/2014 | Lidgard et al. |
| 8,969,046 B2 | 3/2015 | Van Engeland et al. |
| 8,980,107 B2 | 3/2015 | Domanico et al. |
| 8,993,341 B2 | 3/2015 | Bruinsma et al. |
| 8,999,176 B2 | 4/2015 | Domanico et al. |
| 9,000,146 B2 | 4/2015 | Bruinsma et al. |
| 9,506,116 B2 | 11/2016 | Ahlquist et al. |
| 2003/0224040 A1 | 12/2003 | Baylin et al. |
| 2004/0234960 A1 | 11/2004 | Hogan |
| 2006/0253259 A1 | 11/2006 | Fernandez |
| 2007/0054295 A1 | 3/2007 | Spivack |
| 2008/0081333 A1 | 4/2008 | Mori et al. |
| 2008/0213870 A1 | 9/2008 | Cao et al. |
| 2009/0208505 A1 | 8/2009 | Samuels |
| 2010/0167940 A1 | 7/2010 | Feinberg |
| 2010/0317000 A1 | 12/2010 | Zhu |
| 2011/0136687 A1 | 6/2011 | Olek et al. |
| 2011/0318738 A1 | 12/2011 | Jones et al. |
| 2012/0034605 A1 | 2/2012 | Hinoda et al. |
| 2012/0122088 A1 | 5/2012 | Zou |

(Continued)

FOREIGN PATENT DOCUMENTS

| | | |
|---|---|---|
| EP | 2391729 | 12/2011 |
| WO | WO 00/26401 | 5/2000 |

(Continued)

OTHER PUBLICATIONS

Abbaszadegan, "Stool-based DNA testing, a new noninvasive method for colorectal cancer screening, the first report from Iran," World Journal of gastroenterology: WJG, vol. 13, p. 1528-1533, 2007.

(Continued)

*Primary Examiner* — Joseph G. Dauner
(74) *Attorney, Agent, or Firm* — Casimir Jones, SC; Robert A. Goetz

(57) ABSTRACT

Provided herein is technology for gastrointestinal neoplasia screening and particularly, but not exclusively, to methods, compositions, and related uses for detecting the presence of gastrointestinal neoplasm, and classifying the site location of such a gastrointestinal neoplasm (e.g., a colorectal region, a pancreaticobiliary region, a gastroesophageal region).

9 Claims, 102 Drawing Sheets

Specification includes a Sequence Listing.

(56) References Cited

U.S. PATENT DOCUMENTS

| | | |
|---|---|---|
| 2012/0122106 A1 | 5/2012 | Zou |
| 2012/0164110 A1 | 6/2012 | Feinberg et al. |
| 2012/0164238 A1 | 6/2012 | Joost |
| 2013/0012410 A1 | 1/2013 | Zou et al. |
| 2013/0022974 A1 | 1/2013 | Chinnaiyan |
| 2013/0065228 A1 | 3/2013 | Hinoue et al. |
| 2013/0288247 A1 | 10/2013 | Mori et al. |
| 2014/0057262 A1 | 2/2014 | Ahlquist et al. |
| 2014/0137274 A1 | 5/2014 | Ishikawa |
| 2014/0193813 A1 | 7/2014 | Bruinsma et al. |
| 2014/0194607 A1 | 7/2014 | Bruinsma et al. |
| 2014/0194608 A1 | 7/2014 | Bruinsma et al. |
| 2014/0274748 A1 | 9/2014 | Ahlquist et al. |
| 2015/0126374 A1 | 5/2015 | Califano |
| 2015/0240318 A1 | 8/2015 | Van Engeland et al. |
| 2016/0194723 A1 | 7/2016 | Louwagie |

FOREIGN PATENT DOCUMENTS

| | | |
|---|---|---|
| WO | WO 2007/116417 | 10/2007 |
| WO | WO 2008/084219 | 7/2008 |
| WO | WO 2010/086389 | 8/2010 |
| WO | WO 2010/089538 | 8/2010 |
| WO | WO 2011/119934 | 9/2011 |
| WO | WO 2012/175562 | 12/2012 |
| WO | WO 2015/153283 | 10/2015 |

OTHER PUBLICATIONS

Ahlquist D et al. (2010) "Next Generation Stool DNA Testing for Detection of Colorectal Neoplasia—Early Marker Evaluation", presented at *Colorectal Cancer: Biology to Therapy*, American Association for Cancer Research, 1 page.

Ahlquist D.A. et al., "Novel use of hypermethylated DNA markers in stool for detection of colorectal cancer: a feasibility study." Gastroenterology, 2002;122(Suppl):A40.

Ahlquist D.A., et al., "Colorectal cancer screening by detection of altered human DNA in stool: feasibility of a multitarget assay panel." Gastroenterology, 2000, 119(5):1219-27.

Ahlquist et al., "Next-generation stool DNA test accurately detects colorectal cancer and large adenomas." Gastroenterology (2012), 142, pp. 248-256.

Ahlquist et al., 1984, "HemoQuant, a new quantitative assay for fecal hemoglobin. Comparison with Hemoccult." Ann Intern Med, 101: 297-302.

Ahlquist et al., 1985, "Fecal blood levels in health and disease. A study using HemoQuant." N Engl J Med, 312: 1422-8.

Ahlquist et al., 1989, "Patterns of occult bleeding in asymptomatic colorectal cancer." Cancer, 63: 1826-30.

Ahlquist et al., 1993, "Accuracy of fecal occult blood screening for colorectal neoplasia. A prospective study using Hemoccult and HemoQuant tests." JAMA, 269: 1262-7.

Ahlquist et al., 2000, "Colorectal cancer screening by detection of altered human DNA in stool: feasibility of a multitarget assay panel." Gastroenterology, 119: 1219-27.

Ahlquist et al., 2008, "Stool DNA and occult blood testing for screen detection of colorectal neoplasia." Ann Intern Med, 149: 441-501.

Allison et al., 2007, "Screening for colorectal neoplasms with new fecal occult blood tests: update on performance characteristics." J Natl Cancer Inst, 99: 1462-70.

Anderson et al. Am. J. of Gastroenterology, Abstracts S1033, Oct. 2015.

Asai et al. "IKZF1 deletion is associated with a poor outcome in pediatric B-cell precursor acute lymphoblastic leukemia in Japan." Cancer Med. 2013; 2:412-9.

Aust De, "Mutations of the BRAF gene in ulcerative colitis-related colorectal carcinoma." Int. J. Cancer (2005), 115, pp. 673-677.

Azuara et al. "Novel Methylation Panel for the Early Detection of Colorectal Tumors in Stool DNA." Clinical Colorectal Cancer, vol. 9, No. 3, pp. 168-176, Jul. 2010.

Baxter, Eva "Investigating the association between BRAFv600E and methylation in sporadic colon cancer" PhD the University of Edinburgh, 2011.

Belinsky S.A., et al., "Promoter Hypermethylation of Multiple Genes in Sputum Precedes Lung Cancer Incidence in a High-Risk Cohort." Cancer Res, 2006;66:3338-44.

Bell et al., "c-Ki-ras gene mutations in dysplasia and carcinomas complicating ulcerative colitis." Br J Cancer (1991), 64, pp. 174-178.

Biankin et al. (2003) "Molecular pathogenesis of precursor lesions of pancreatic ductal adenocarcinoma" Pathology 35:14-24.

Brune, et al. (2008). "Genetic and epigenetic alterations of familial pancreatic cancers." Cancer Epidemiol Biomarkers Prev. 17 (12): 3536-3542.

Buck et al. "Design Strategies and Performance of Custom DNA Sequencing Primers" Biotechniques, 1999, 27(3): 528-536.

Cairns et al., "Guidelines for colorectal cancer screening and surveillance in moderate and high risk groups." Gut (2010); 59, pp. 666-689.

Cameron et al. (1995) "Adenocarcinoma of the esophagogastric junction and Barrett's esophagus" Gastroenterology 109: 1541-1546.

Cameron et al. Blood, vol. 94, No. 7, pp. 2445-2451, Oct. 1999.

Camoes et al. "Potential downstream target genes of aberrant ETS transcription factors are differentially affected in Ewing's sarcoma and prostate carcinoma." PLoS ONE. 2012;7:e49819.

Campbell et al. "Aberrant expression of the neuronal transcription factor FOXP2 in neoplastic plasma cells." British journal of haematology. 2010; 149:221-30.

Chen "Expression and promoter methylation analysis of ATP-binding cassette genes in pancreatic cancer" Oncology Reports, 2012, 27:265-269.

Chen W.D., et al., "Detection in Fecal DNA of Colon Cancer-Specific Methylation of the Nonexpressed Vimentin Gene." J Natl Cancer Inst 2005;97:1124 32.

De Kok, 2003, "Quantification and integrity analysis of DNA in the stool of colorectal cancer patients may represent a complex alternative to fecal occult blood testing." Clin Chem, 49: 2112-3.

Eads, et al. (1999). "CpG island hypermethylation in human colorectal tumors is not associated with DNA methyltransferase overexpression." Cancer Res. 59: 2302-2306.

Ebert M.P., et al., "Aristaless-like homeobox-4 gene methylation is a potential marker for colorectal adenocarcinomas." Gastroenterology 2006;131:1418-30.

Edge, S.; Fritz, A.G.; Greene, F.L.; Trotti, A. (Eds.), AJCC Cancer Staging Manual. 7th ed: Springer, New York; 2010; Book—only table of contents provided.

Esteller et al. "Inactivation of Glutathione S-Transferase P1 Gene by Promoter Hypermethylation in Human Neoplasia" Cancer Resarch, vol. 58, pp. 4515-4518, Oct. 1998.

Feng "Conservation and divergence of methylation patterning in plants and animals" PNAS 2010 vol. 107, No. 19, pp. 8689-8694.

Garrity-Park et al. "Methylation status of genes in non-neoplastic mucosa from patients with ulcerative colitis-associated colorectal cancer." Am J Gastroenterol (2010), 105, pp. 1610-1619.

Glockner, et al. (2009). "Methylation of TFPI2 in stool DNA: a potential novel biomarker for the detection of colorectal cancer." Cancer Res. 69: 4691-4699.

Goggins, M. "Molecular markers of early pancreatic cancer." J Clin Oncol 2005; 23: 4524.

Gonzalgo, et al. (1997) "Identification and characterization of differentially methylated regions of genomic DNA by methylation-sensitive arbitrarily primed PCR." Cancer Res. 57: 594-599.

Gonzalgo, et al. (1997). "Rapid quantitation of methylation differences at specific sites using methylation-sensitive single nucleotide primer extension (Ms-SNuPE)." Nucleic Acids Res. 25 (12): 2529-2531.

Grady W.M., et al., "Detection of Aberrantly Methylated hMLH1 Promoter DNA in the Serum of Patients with Microsatellite Unstable Colon Cancer 1." Cancer Res, 2001;61:900-2.

(56) References Cited

OTHER PUBLICATIONS

Grutzmann et al., "Sensitive Detection of Colorectal Cancer in Peripheral Blood by Septin 9 DNA Methylation Assay." PLoS ONE (2008), 3:e3759.
Grutzmann, et al. (2008), "Sensitive detection of colorectal cancer in peripheral blood by septin—DNA methylation assay," PLoS ONE 3(11): e3759 which is 8 pages long.
Gu et al. "Genome-scale DNA methylation mapping of clinical samples at single-nucleotide resolution." Nat Methods. 2010; 7:133-6.
Gu, et al. (2011). "Preparation of reduced representation bisulfite sequencing libraries for genome-scale DNA methylation profiling." Nature Protocols. 6 (4): 468-481.
Gurung et al. "Menin epigenetically represses Hedgehog signaling in MEN1 tumor syndrome." Cancer research. 2013;73:2650-8.
Guzinska-Ustymowicz et al., (2009), "Correlation between proliferation makers: PCNA, Ki-67, MCM-2 and antiapoptopic protein Bcl2 in colorectal cancer," Anticancer Research. 29:3049-3052.
Hardcastle et al., 1996, "Randomised controlled trial of faecal-occult-blood screening for colorectal cancer." Lancet, 348: 1472-7.
Harewood et al., 2000, "Fecal occult blood testing for iron deficiency: a reappraisal." Dig Dis, 18(2): 75-82.
Heresbach et al., 2006, "Review in depth and meta-analysis of controlled trials on colorectal cancer screening by faecal occult blood test." Eur J Gastroenterol Hepatol, 18: 427-33.
Herman, et al. (1996). "Methylation-specific PCR: A novel PCR assay for methylation status of CpG islands." Proc. Natl. Acad. Sci. USA. 93: 9821-9826.
Hibi et al. (2010) "Methylation of the TFPI2 gene is frequently detected in advanced gastric carcinoma" *Anticancer Res* 30: 4131-3.
Hibi, et al. (2010). "Methylation of TFPI2 gene is frequently detected in advanced well-differentiated colorectal cancer." Anticancer Res. 30: 1205-1207.
Hirota et al., "pS2 expression as a possible diagnostic marker of colorectal carcinoma in ulcerative colitis." Oncol Rep (2000), 7, pp. 233-239.
Hoang et al., 1997, "BAT-26, an indicator of the replication error phenotype in colorectal cancers and cell lines." Cancer Res, 57: 300-3.
Holzmann et al., "Comparative analysis of histology, DNA content, p53 and Ki-ras mutations in colectomy specimens with long-standing ulcerative colitis." Int J Cancer (1998) 76, pp. 1-6.
Hong, et al. (2008). "Multiple genes are hypermethylated in intraductal papillary mucinous neoplasms of the pancreas." Mod Pathol. 21 912): 1499-1507.
Hoque M.O., et al., "Quantitative methylation-specific polymerase chain reaction gene patterns in urine sediment distinguish prostate cancer patients from control subjects." J Clin Oncol, 2005;23:6569-75.
Howe, et al., "Annual report to the nation on the status of cancer, 1975-2003, featuring cancer among U.S. Hispanic/Latino populations." Cancer (2006) 107, pp. 1711-1742.
Imperiale et al. "Multitarget Stool DNA Testing for Colorectal-Cancer Screening" New England Journal of Medicine, vol. 370, No. 14, Apr. 3, 2014, pp. 1287-1297.
Imperiale et al., "Fecal DNA versus fecal occult blood for colorectal-cancer screening in an average-risk population." N Engl J Med (2004), 351, pp. 2704-2714.
Imperiale et al., 2004, "Fecal DNA versus fecal occult blood for colorectal-cancer screening in an average-risk population." N Engl J Med, 351: 2704-14.
International Search Report and Written Opinion dated Dec. 28, 2011 from International Patent Application No. PCT/US2011/029959, international filing date Mar. 25, 2011.
International Search Report and Written Opinion, Int'l Patent Application No. PCT/US2015/022749, dated Aug. 19, 2015, 12 pages.
International Search Report and Written Opinion, Int'l Patent Application No. PCT/US2015/022751, dated Aug. 26, 2015, 25 pages.
International Search Report dated Jun. 10, 2013 from related International Patent Application No. PCT/US2013/027227.

Itzkowitz et al. "Diagnosis and management of dysplasia in patients with inflammatory bowel diseases." Gastroenterology (2004) 126, pp. 1634-1648.
Itzkowitz S.H., et al., "Improved fecal DNA test for colorectal cancer screening." Clin Gastroenterol Hepatol 2007;5:111-7.
Jacobs et al. "Dysregulated methylation at imprinted genes in prostate tumor tissue detected by methylation microarray." BMC Urol. 2013;13:37.
Jess et al., "Risk of intestinal cancer in inflammatory bowel disease: a population-based study from olmsted county, Minnesota." Gastroenterology (2006) 130, pp. 1039-1046.
Jiang et al. Gastroenterology Apr. 2008 vol. 134, No. 4., suppl 1, pp. A484.
Jiao et al. "Somatic mutations in the Notch, NF-KB, PIK3CA, and Hedgehog pathways in human breast cancers." Genes, chromosomes & cancer. 2012; 51:480-9.
Kaiser. (2008). "Cancer genetics. A detailed genetic portrait of the deadliest human cancers." Science. 321: 1280-1281.
Kann L., et al., "Improved marker combination for detection of de novo genetic variation and aberrant DNA in colorectal neoplasia." Clin Chem 2006;52:2299-302.
Kariya et al., 1987, "Revision of consensus sequence of human Alu repeats—a review." Gene, 53: 1-10.
Kawai, et al. (1994). "Comparison of DNA methylation patterns among mouse cell lines by restriction landmark genomic screening." Mol. Cell Biol. 14 (11): 7421-7427.
Kim, H., et al., "Noninvasive molecular biomarkers for the detection of colorectal cancer," BMB Reports, 2008, vol. 41, No. 10, pp. 685-692.
Kisiel et al. "New DNA Methylation Markers for Pancreatic Cancer: Discovery, Tissue Validation, and Pilot Testing in Pancreatic Juice" Clinical Cancer Research, vol. 21, No. 19, May 28, 2015, pp. 4473-4481.
Kisiel et al. "Stool DNA testing for the detection of pancreatic cancer: assessment of methylation marker candidates." Cancer. 2012; 118:2623-31.
Kisiel et al. (AGA Abstracts, VS-68, vol. 138, No. 5, May 2010).
Kisiel, et al. (2011). "Stool DNA screening for colorectal cancer: opportunities to improve value with next generation tests." J Clin Gastroenterol. 45 (4): 301-8.
Kober et al. "Methyl-CpG binding column-based identification of nine genes hypermethylated in colorectal cancer." Molecular carcinogenesis. 2011; 50:846-56.
Kraus, et al., "Inflammation and colorectal cancer," Current Opinion in Pharmacology, vol. 9, No. 4, pp. 405-410 (2009).
Kronborg et al., 1996, "Randomised study of screening for colorectal cancer with faecal-occult-blood test." Lancet, 348: 1467-71.
Kronborg et al., 2004, "Randomized study of biennial screening with a faecal occult blood test: results after nine screening rounds." Scand J Gastroenterol, 39: 846-51.
Kuppuswamy et al. "Single nucleotide primer extension to detect genetic diseases: Experimental application to hemophilia B (factor IX) and cystic fibrosis genes" (1991) Proc. Natl. Acad. Sci. USA 88: 1143-1147.
Laird. (2010). "Principles and challenges of genome-wide DNA methylation analysis." Nat Rev Genet. 11: 191-203.
Lashner BA, "Evaluation of the Usefulness of Testing for p53 Mutations in Colorectal Cancer Surveillance for Ulcerative Colitis" Am J Gastroenterol (1999), 94, pp. 456-462.
Lee et al. "Pituitary homeobox 2 (PITX2) protects renal cancer cell lines against doxorubicin toxicity by transcriptional activation of the multidrug transporter ABCB1." International journal of cancer Journal international du cancer. 2013; 133:556-67.
Leung W.K., et al., "Detection of epigenetic changes in fecal DNA as a molecular screening test for colorectal cancer: A feasibility study." Clin Chem 2004; 50(11):2179-82.
Levin B, "Screening and Surveillance for Early Detection of Colorectal Cancer . . . " Gastroenterology (2008); 134, pp. 1570-1595.
Levin et al., 2008, "Screening and surveillance for the early detection of colorectal cancer and adenomatous polyps, 2008: a joint guideline from the American Cancer Society, the US Multi-Society Task Force on Colorectal Cancer, and the American College of Radiology." CA Cancer J Clin, 58: 130-60.

(56) References Cited

OTHER PUBLICATIONS

Li et al. "Association between Galphai2 and ELMO1/Dock180 connects chemokine signalling with Rac activation and metastasis." Nat Commun. 2013; 4:1706.

Lim, et al. (2010). "Cervical dysplasia: assessing methylation status (Methylight) of CCNA1, DAPK1, HS3ST2, PAX1 and TFPI2 (to improve diagnostic accuracy." Gynecol Oncol. 119: 225-231.

Lin, et al., Identification of disease-associated DNA methylation in intestinal tissues from patients with inflammatory bowel disease, Clinical Genetics, vol. 80, No. 1, pp. 59-67 (2011).

Liu et al. "Medulloblastoma expresses CD1d and can be targeted for immunotherapy with NKT cells." Clin Immunol. 2013;149:55-64.

Ma, et al. (2011). "MicroRNA-616 induces androgen-independent growth of prostate cancer cells by suppressing expression of tissue factor pathway inhibitor TFPI-2." Cancer Res. 71: 583-592.

Maeda, et al., "DNA hypermethylation in colorectal neoplasms and inflammatory bowel disease: a mini review," Inflammapharmacology, vol. 14, No. 5-6, pp. 204-206 (2006).

Mandel et al., 1993, "Reducing mortality from colorectal cancer by screening for fecal occult blood. Minnesota Colon Cancer Control Study." N Engl J Med, 328: 1365-71.

Matsubayashi, et al. (2006). "DNA methylation alterations in the pancreatic juice of patients with suspected pancreatic disease." Cancer Res. 66: 1208-1217.

Meissner et al. (2008). "Genome-scale DNA methylation maps of pluripotent and differentiated cells." Nature. 454: 766-70.

Meissner, 2006, "Patterns of colorectal cancer screening uptake among men and women in the United States." Cancer Epidemiol Biomarkers Prev, 15: 389-94.

Melle, et al. (2005), "Discovery and identification of a-defensins as low abundant, tumor-derived serum markers in colorectal cancer," 129(1): 66-73 abstract only.

Melotte et al., "N-Myc Downstream-Regulated Gene 4 (NDRG4): A Candidate Tumor Suppressor Gene and Potential Biomarker for Colorectal Cancer" (JNCL, vol. 101, No. 13, pp. 916-927, Jul. 2009).

Meuwis, "Contribution of proteomics to colorectal cancer diagnosis," Acta Endoscopica, vol. 37, p. 295-303, including translation, 2007.

Muller et al., 2004, "Methylation changes in faecal DNA: a marker for colorectal cancer screening?" Lancet, 363: 1283-5.

Naumov "Genome-scale analysis of DNA methylation in colorectal cancer using Infinium HumanMethylation450 BeadChips" Epigenetics, 2013, vol. 8, issue 9, pp. 921-934.

Nosho, et al. (2008): "PIK3CA mutation in colorectal cancer: Relationship with genetic and epigenetic alterations," Neoplasia. 10(6) 034-541, abstract only.

Obusez et al. "Adenocarcinoma in the ileal pouch: early detection and potential role of fecal DNA methylated markers in surveillance" (Int. J. Colorectal Dis. vol. 26, pp. 951-953, 2011).

Obusez et al. "Fecal methylated markers for the detection of adenocarcinoma in ileal pouches of patients with underlying ulcerative colitis" (Inflammatory Bowel Diseases: vol. 14, Issue pS42, Dec. 2008, p. 0106).

Odze RD, "Genetic Alterations in Chronic Ulcerative Colitis-Associated Adenoma-Like DALMs Are Similar to Non-Colitic Sporadic Adenomas" Am J Surg Pathol (2000), 24, pp. 1209-1216.

Olaru, et al., "Unique patterns of CpG island methylation in inflammatory bowel disease-associated colorectal cancers," Inflammatory Bowel Diseases, vol. 18, No. 4, pp. 641-648 (Epub Aug. 9, 2011).

Olson et al., 2005, "DNA stabilization is critical for maximizing performance of fecal DNA-based colorectal cancer tests." Diagn Mol Pathol, 14: 183-91.

Omura, et al. (2008). "Genome-wide profiling of methylated promoters in pancreatic adenocarcinoma." Cancer Biol Ther. 7 (7): 1146-1156.

Omura, et al. (2009). "Epigenetics and epigenetic alterations in pancreatic cancer." Int. J. Clin Exp Pathol. 2: 310-326.

Osborn et al., 2005, "Stool screening for colorectal cancer: molecular approaches." Gastroenterology, 128: 192-206.

Osborn NK, and Ahlquist DA, "Stool screening for colorectal cancer: molecular approaches." Gastroenterology 2005;128:192-206.

Osborn, et al., "Aberrant methylation of the eyes absent 4 gene in ulcerative colitis-associated dysplasia," Clinical Gastroenterology and Hepatology, vol. 4, No. 2, pp. 212-218 (2006).

Oster, B. et al., "Identification and validation of highly frequent CpG island hypermethylation in colorectal adenomas and carcinomas." Int J Cancer. 2011;129(12):2855-66.

Pao et al. "The endothelin receptor B (EDNRB) promoter displays heterogeneous, site specific methylation patterns in normal and tumor cells" Human Molecular Genetics, vol. 10, No. 9, pp. 903-910.

Park, et al. (2002), "Expressiono f melanoma antigen-encoding genes (MAGE) by common primers for MAGE-A1 to -A6 in colorectal carcinomas among Koreans," J. Korean Med. Sci 17: 497-501.

Person et al. "Chronic cadmium exposure in vitro induces cancer cell characteristics in human lung cells." Toxicol Appl Pharmacol. 2013; 273(2):281-8.

Petko Z., et al., "Aberrantly Methylated CDKN2A, MGMT, and MLH1 in Colon Polyps and in Fecal DNA from Patients with Colorectal Polyps." Clin Cancer Res 2005; 11:1203-9.

Raimondo et al. "Methylated DNA Markers in Pancreatic Juice Discriminate Pancreatic Cancer From Chronic Pancreatitis and Normal Controls" Gastroenterology 2013; 144:S-90.

Rex et al. "American College of Gastroenterology guidelines for colorectal cancer screening 2008." Am J Gastroenterol (2009); 104, pp. 739-750.

Ruppenthal et al. "TWIST1 Promoter Methylation in Primary Colorectal Carcinoma" Pathol. Oncol. Res., 2011, 17:867-872.

Sadri and Hornsby "Rapid Analysis of DNA Methylation Using New Restriction Enzyme Sites Created by Bisulfite Modification." (1996) Nucl. Acids Res. 24: 5058-5059.

Saitoh et al. (1995), "Intestinal protein loss and bleeding assessed by fecal hemoglobin, transferrin, albumin, and alpha-1-antitrypsin levels in patients with colorectal diseases," Digestion. 56(1): 67-75, abstract only.

Sambrook et al., 1989, Fritsch, E.F., Maniatis, T. (ed.), Molecular Cloning, Cold Spring Harbor Lab. Press, Cold Spring Harbor, N.Y., 30 pages.

Samowitz et al., 1999, "BAT-26 and BAT-40 instability in colorectal adenomas and carcinomas and germline polymorphisms." Am J Path, 154: 1637-41.

Sato et al., "Aberrant methylation of the HPP1 gene in ulcerative colitis-associated colorectal carcinoma." Cancer Res (2002), 62, pp. 6820-6822.

Sato, et al. (2003). "Discovery of novel targets of aberrant methylation in pancreatic carcinoma using high-throughput microarrays." Cancer Res. 63: 3735-3742.

Schulmann, et al., Molecular phenotype of inflammatory bowel disease-associated neoplasms with microsatellite instability, Gastroenterology, vol. 129, No. 1, pp. 74-85 (2005).

Schwartz et al., 1983, "The "HemoQuant" test: a specific and quantitative determination of heme (hemoglobin) in feces and other materials." Clin Chem, 29: 2061-7.

Schwartz et al., 1985, "Quantitative fecal recovery of ingested hemoglobinheme in blood: comparisons by HemoQuant assay with ingested meat and fish." Gastroenterology, 89: 19-26.

Sen-Yo et al. "TWIST1 hypermethylation is observed in pancreatic cancer" Biomedical Reports; 1:33-33, 2013.

Seshagiri et al. "Recurrent R-spondin fusions in colon cancer." Nature. 2012; 488:660-4.

Shin et al. "Bile-based detection of extrahepatic cholangiocarcinoma with quantitative DNA methylation markers and its high sensitivity." The Journal of molecular diagnostics : JMD. 2012;14:256-63.

Singer-Sam et al. "A quantitative Hpall-PCR assay to measure methylation of DNA from a small number of cells" (1990) Nucl. Acids Res. 18(3): 687.

Singer-Sam et al. "A sensitive, quantitative assay for measurement of allele-specific transcripts differing by a single nucleotide." (1992) PCR Methods Appl. 1: 160-163.

(56) References Cited

OTHER PUBLICATIONS

Singh et al., 2006, "Risk of developing colorectal cancer following a negative colonoscopy examination: evidence for a 10-year interval between colonoscopies." JAMA, 295: 2366-73.
Stumm et al. "Strong expression of the neuronal transcription factor FOXP2 is linked to an increased risk of early PSA recurrence in ERG fusion-negative cancers." Journal of clinical pathology. 2013;66:563-8.
Summons to attend oral proceedings, European patent application No. 11760295.3, mailed Mar. 4, 2016.
Surdez et al. "Targeting the EWSR1-FLI1 oncogene-induced protein kinase PKC-beta abolishes ewing sarcoma growth." Cancer research. 2012;72:4494-503.
Szabo and Mann "Allele-specific expression and total expression levels of imprinted genes during early mouse development: implications for imprinting mechanisms." (1995) Genes Dev. 9(24): 3097-3108.
Tan et al. "Variable promoter region CpG island methylation of the putative tumor suppressor gene Connexin 26 in breast cancer" Carcinogenesis. 2002 23(2): 231-236.
Tang, et al. (2010). "Prognostic significance of tissue factor pathway inhibitor 2 in pancreatic carcinoma and its effect on tumor invasion and metastatis." Med Oncol. 27: 867-875.
Taylor et al. "Expression of p53 in colorectal cancer and dysplasia complicating ulcerative colitis." Br J Surg (1993), 80, pp. 442-444.
Tibble, et al. (2001), "Faecal capprotectin and faecal occult blood tests in the diagnosis of colorectal carcinoma and adenoma.," Gut. 49:402-408.
Tonack, et al. (2009). "Pancreatic cancer: proteomic approaches to a challenging disease." Pancreatology. 9: 567-576.
Toyota, et al. (1999). "Identification of differentially methylated sequences in colorectal cancer by methylated CpG island amplification." Cancer Res. 59: 2307-2312.
Tsunoda, et al. (2009). "Methylation of CLDN6, FBN2, RBP1, RBP4, TFPI2 and TMEFF2 in esophageal squamous cell carcinoma." Oncol Rep. 21: 1067-1073.
Uchida, et al. (1994), "Immunochemical detection of human lactoferrin in feces as a new marker for inflammatorygastrointestinal disorders and colon cancer," Clinical Biochemistry. 27(4)L 259-264, abstract only.
Vincent et al. "Genome-wide analysis of promoter methylation associated with gene expression profile in pancreatic adenocarcinoma." Clinical cancer research : an official journal of the American Association for Cancer Research. 2011; 17:4341-54.
Wang, "Gene expression profiles and molecular markers to predict recurrence of duke's B Colon Cancer," vol. 22, p. 1564-1571, 2004.
Watanabe, T., "RUNX3 copy number predicts the development of UC-associated colorectal cancer" International Journal of Oncology (2011), 38, pp. 201-207.

Wen, et al. (2006), "Frequence epigenetic silencing of the borne morphogenic protein 2 gene through methylation in gastic carcinomas," Onogene. 25:2666-2673.
Wheeler et al. "Hypermethylation of the promoter region of the E-cadherin gene (CDH1) in sporadic and ulcerative colitis associated colorectal cancer." Gut (2001), 48, pp. 367-371.
Winawer et al., 1993, "Screening for colorectal cancer with fecal occult blood testing and sigmoidoscopy." J Natl Cancer Inst, 85: 1311-8.
Wittekind et al. (1986), "Localization of CEA, HCG, lysozyme, alpha-1-antitrypsin, and alpha-1-antichymotrypsin in gastric cancer and prognosis," Virchows Arch 409:715-724.
Wu, "Aberrant Gene Methylation in the Neoplastic Progression of Barrett's Esophagus: Identification of Candidate Diagnostic Markers" Gastroenterology (2011) 14: S-222.
Xiong, et al. (1997). Nucleic Acids Res. 25 (12): 2532-2534.
Yachida, et al. (2010). "Distant metastasis occurs late during the genetic evolution of pancreatic cancer." Nature. 467: 1114-1117.
Yamaguchi, et al. (2005). "Pancreatic juice cytology in intraductal papillary mucinous neoplasm of the pancreas." Pancreatology. 5: 416-421.
Yang N. et al. "Methylation markers for CCNA1 and C13ORF18 are strongly associated with high-grade cervical intraepithelial neoplasia and cervical cancer in cervical scrapings." Cancer epidemiology, biomarkers & prevention : a publication of the American Association for Cancer Research, cosponsored by the American Society of Preventive Oncology. 2009;18:3000-7.
Young, "Fecal Immunochemical Tests (FIT) vs. Office-based guaiac fecal occult blood test (FOBT)," Practical Gastroenterology, Colorectal Cancer, series 3, p. 46-56, 2004.
Zhao et al. "Genome-wide identification of Epstein-Barr virus-driven promoter methylation profiles of human genes in gastric cancer cells." Cancer. 2013;119:304-12.
Zijlstra et al., 2002, "A quantitative analysis of rate-limiting steps in the metastatic cascade using human-specific real-time polymerase chain reaction." Cancer Res, 62: 7083-92.
Zou H., et al., "A Sensitive Method to Quantify Human Long DNA in Stool: Relevance to Colorectal Cancer Screening." Cancer Epidemiol Biomarkers Prev 2006;15:1115-9.
Zou H.Z., et al., "Detection of aberrant p16 methylation in the serum of colorectal cancer patients." Clin Cancer Res 2002;8(1):188-91.
Zou, et al. (2007), "Highly methylated genes in colorectal neoplasia: Implications for screening," Cancer Epidemilogy Biomarkers Prev. 16(12): 2686-2696.
Zou, et al. (2009). "T2036 Pan-Detection of Gastrointestinal Neoplasms by Stool DNA Testing Establishment of Feasibility." *Gastroenterology*. 136: A-625.
Zou, et al., "High Detection Rates of Colorectal Neoplasia by Stool DNA Testing with a Novel Digital Melt Curve Assay," Gastroenterology, vol. 136, No. 2, Feb. 1, 2009, pp. 459-470.
Zou, et al., "T2034 Stool DNA and Occult Blood for Detection of Colorectal Cancer: Complementary Markers," Gastroenterology, vol. 136, No. 5, May 1, 2009, p. A-625.

FIG. 1AAA
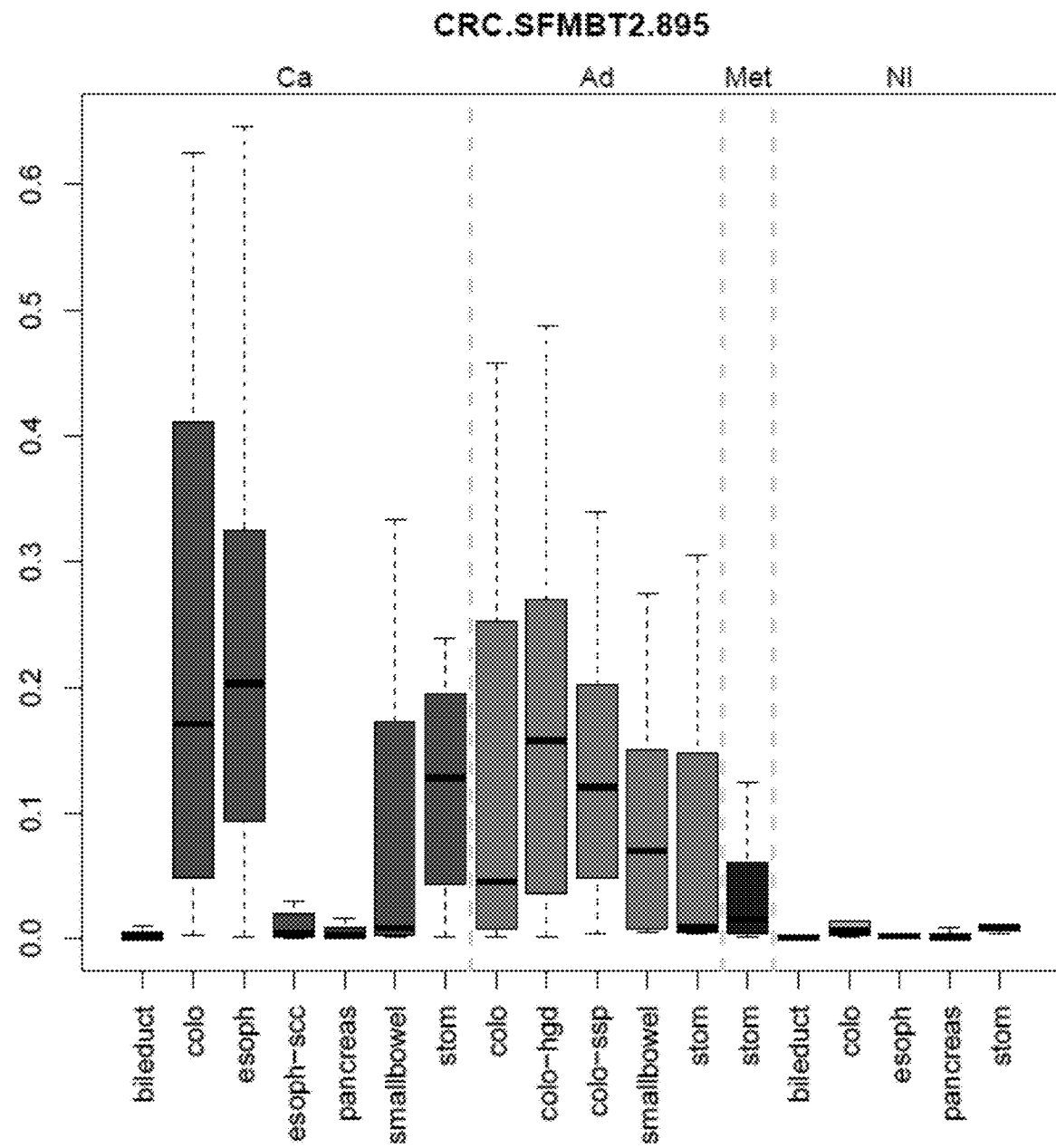

FIG. 1BBB
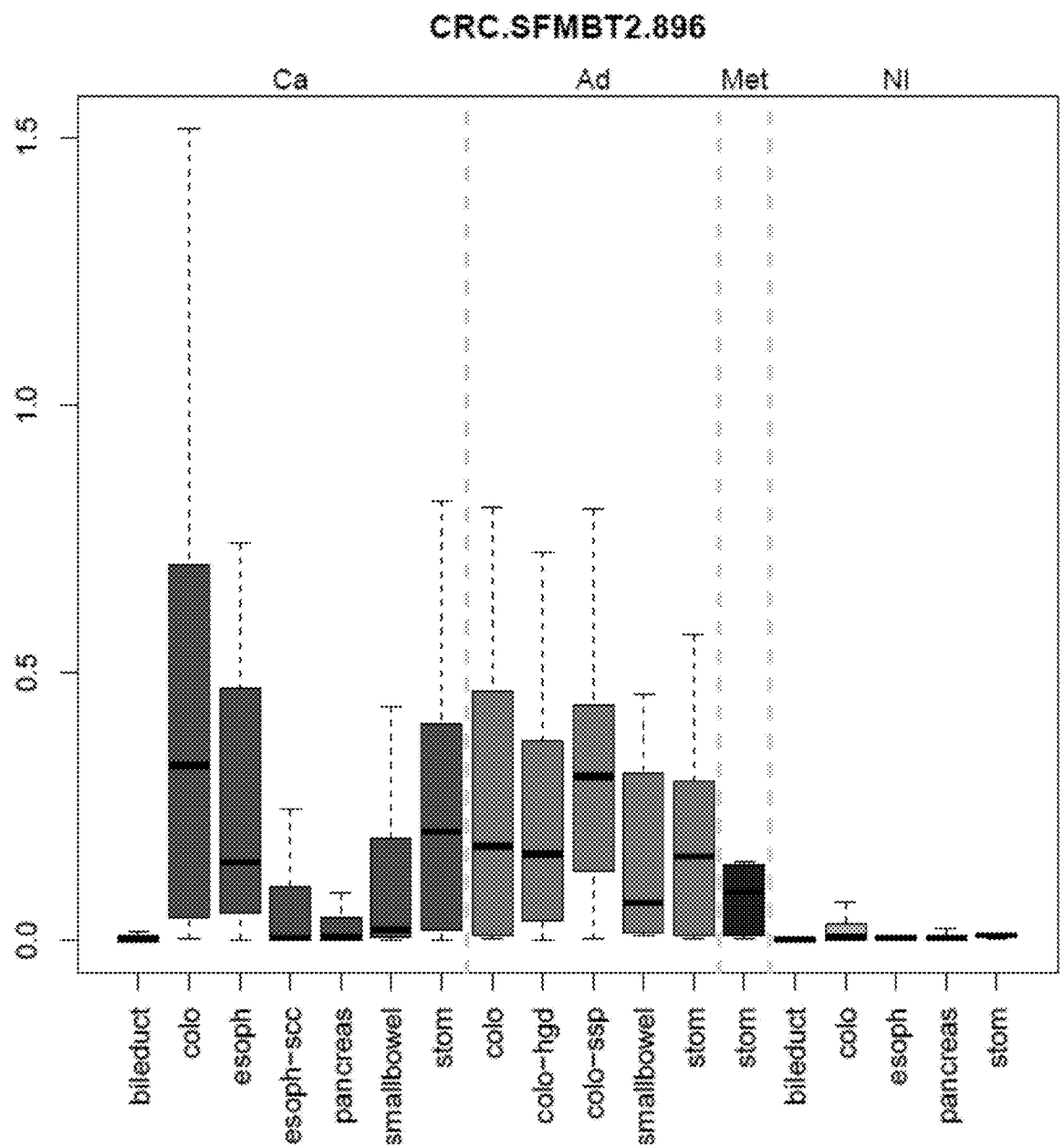

FIG. 1CCC
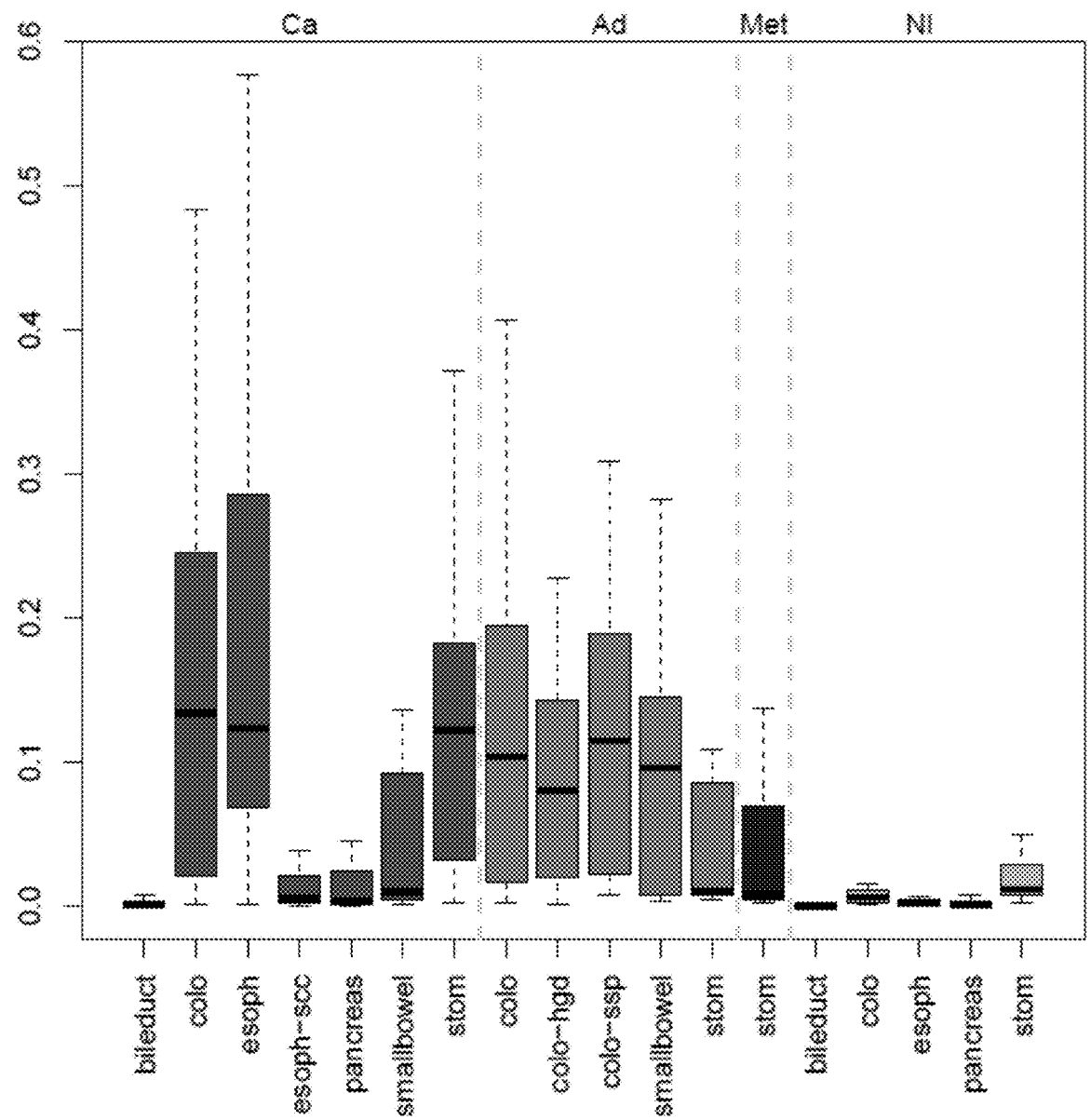

FIG. 1DDD
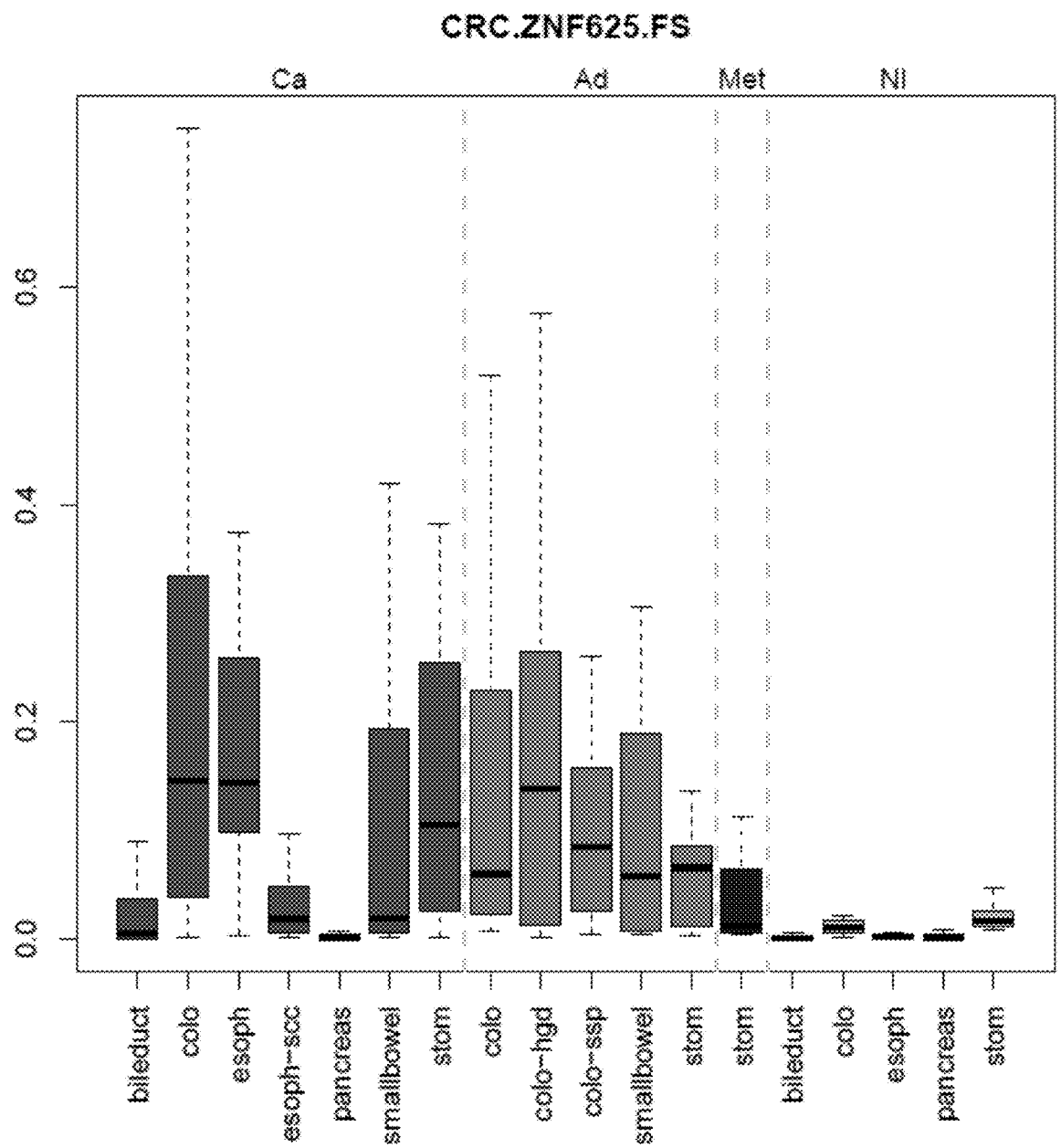

FIG. 1EEE
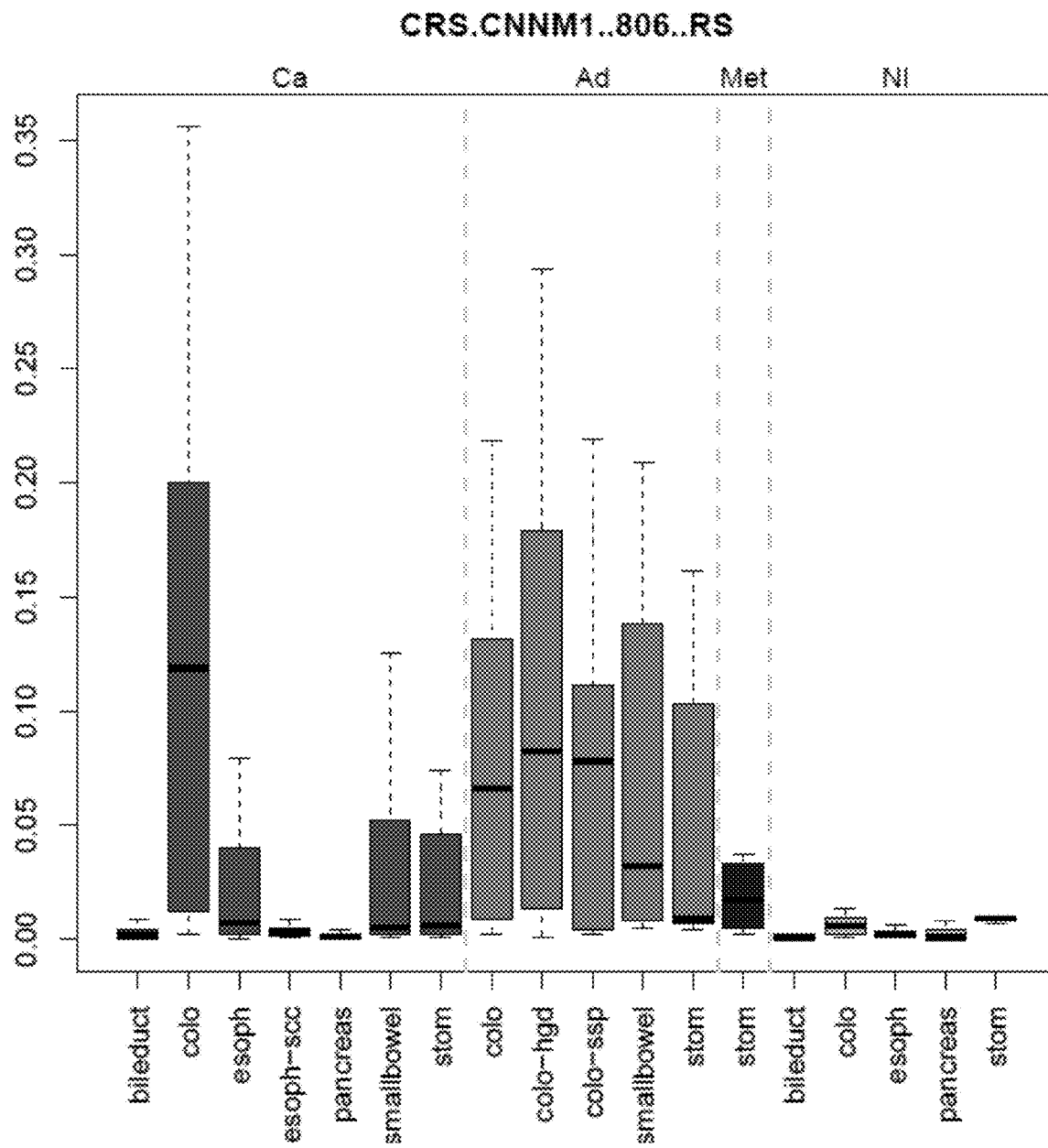

FIG. 1FFF
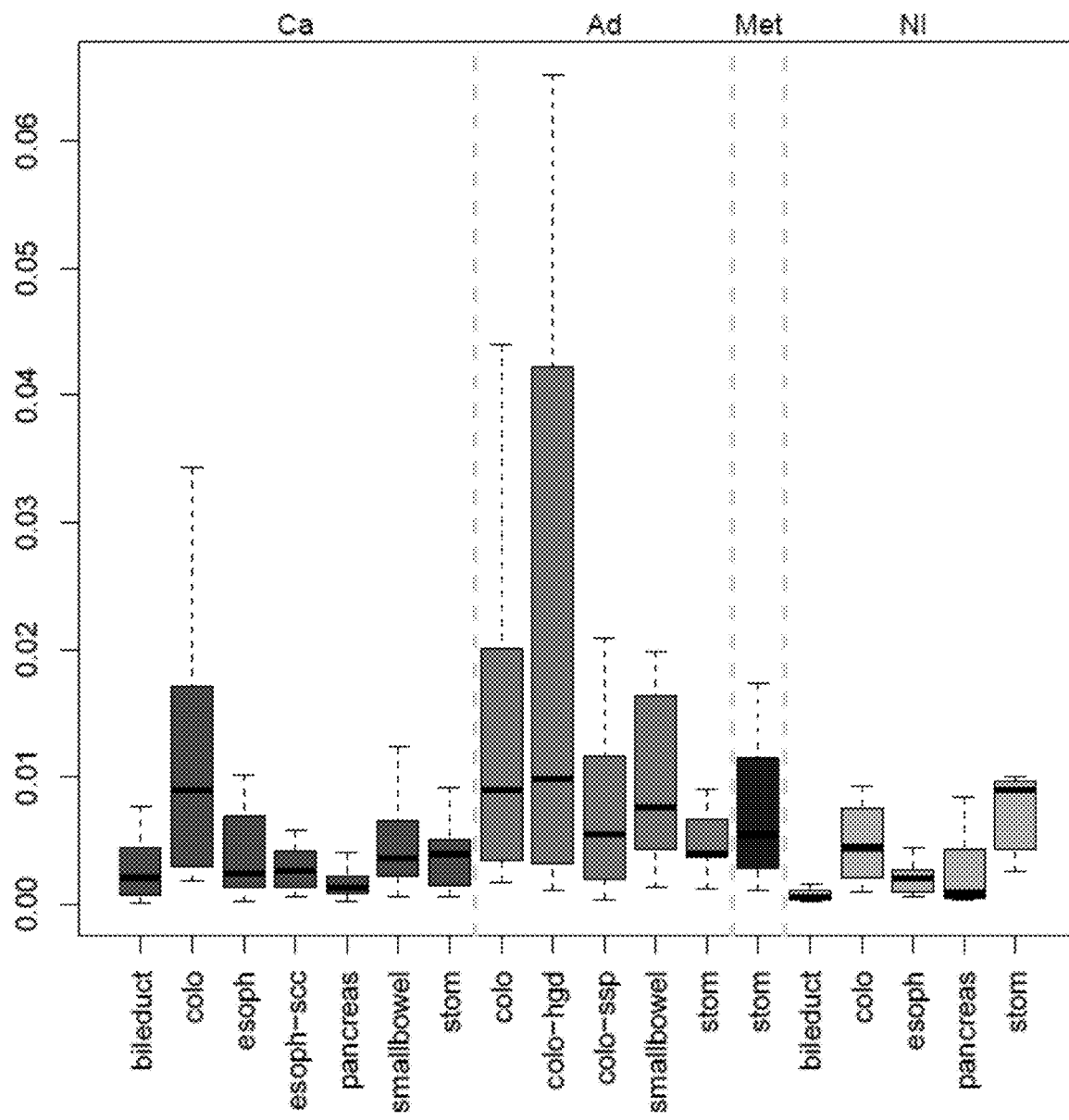

FIG. 1GGG
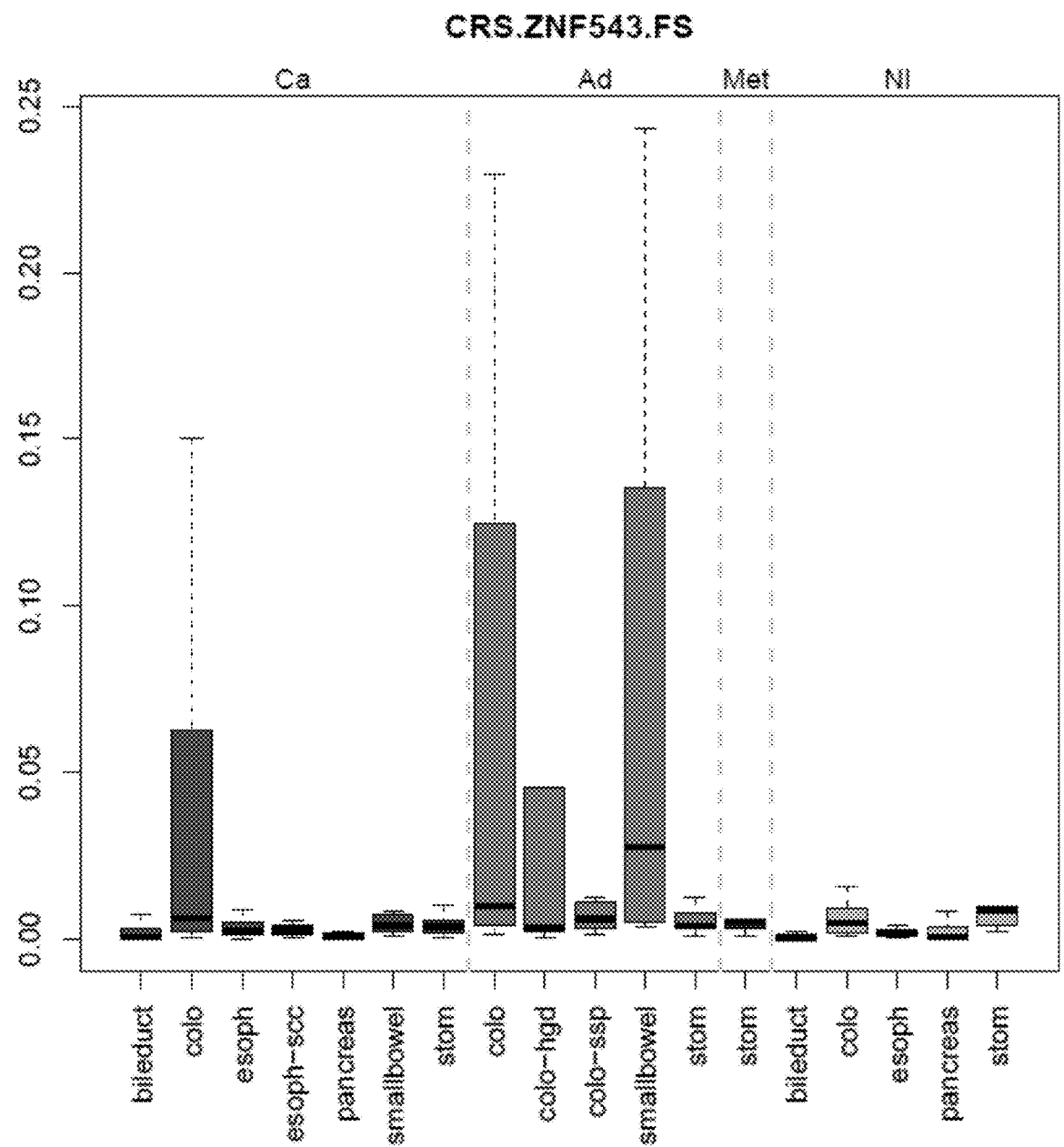

FIG. 1HHH
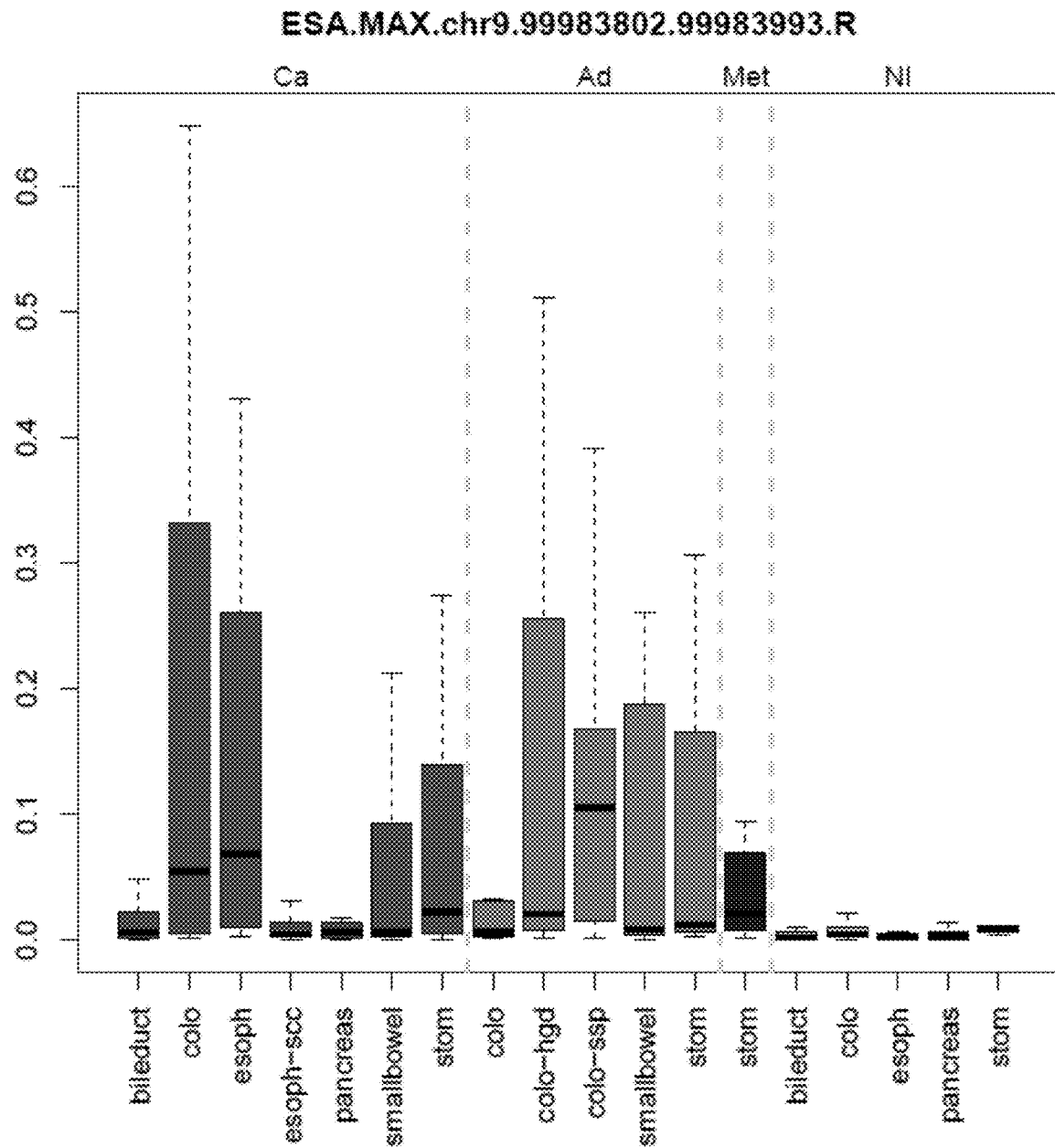

FIG. 1III
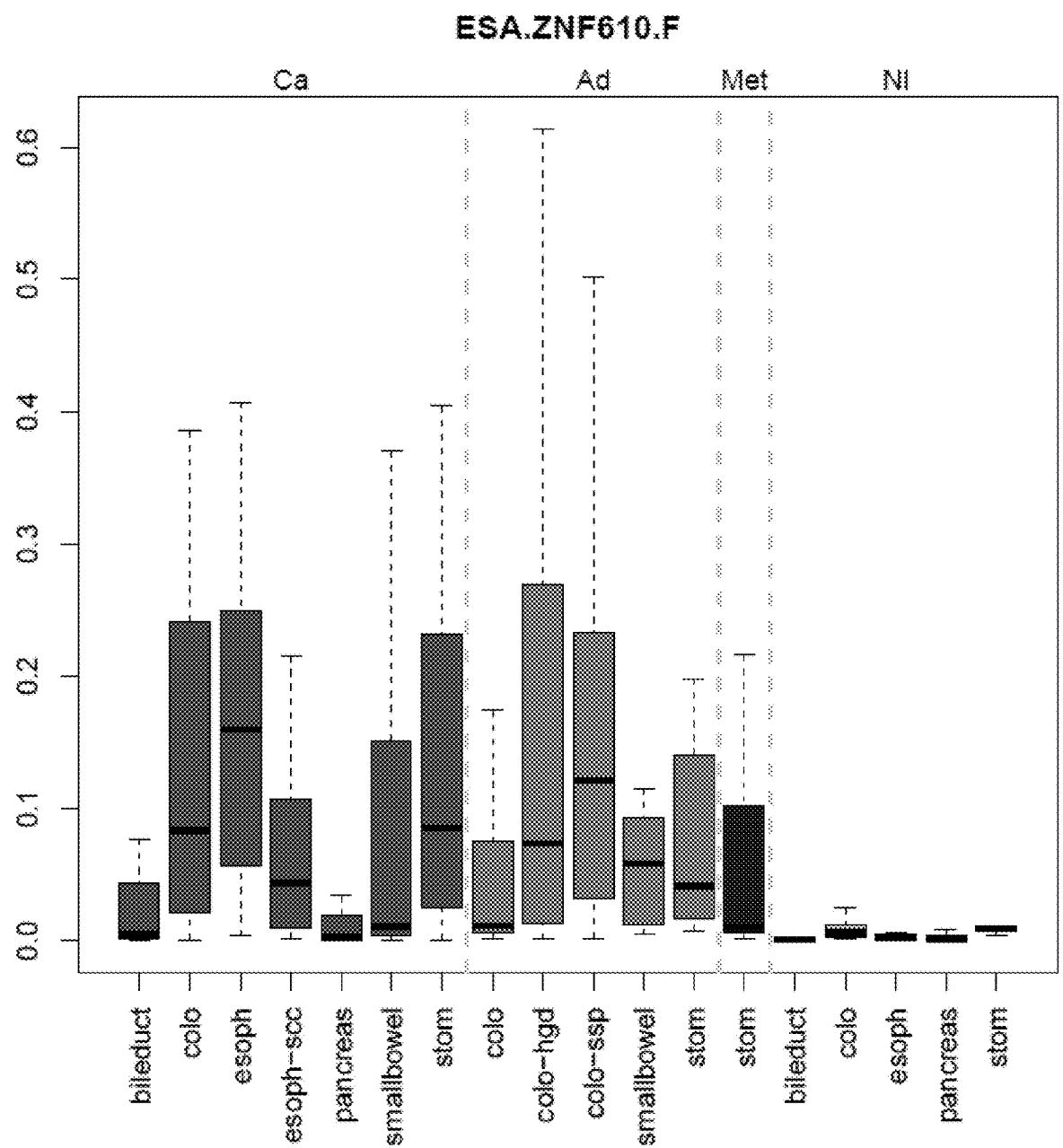

FIG. 1JJJ
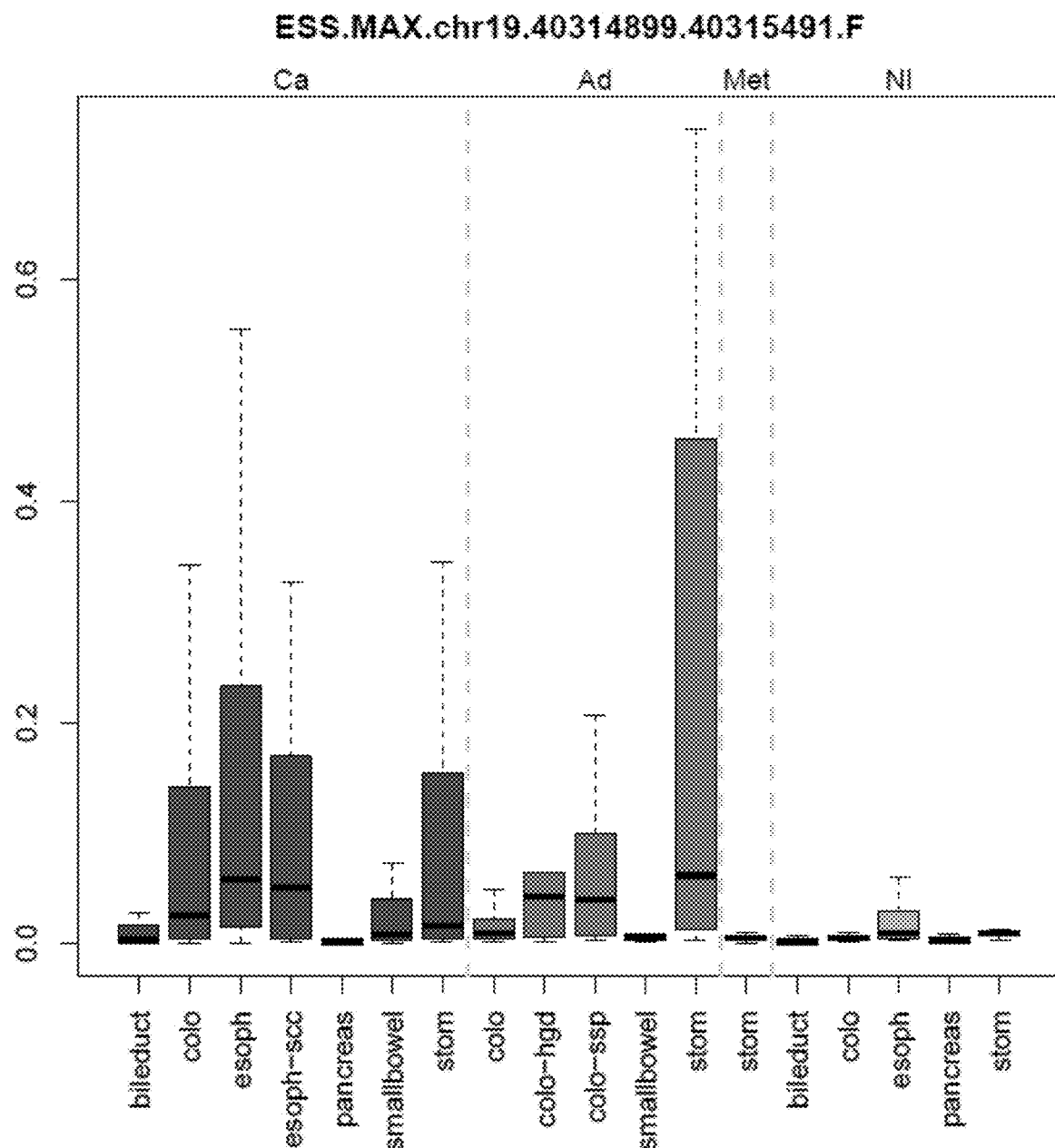

FIG. 1KKK
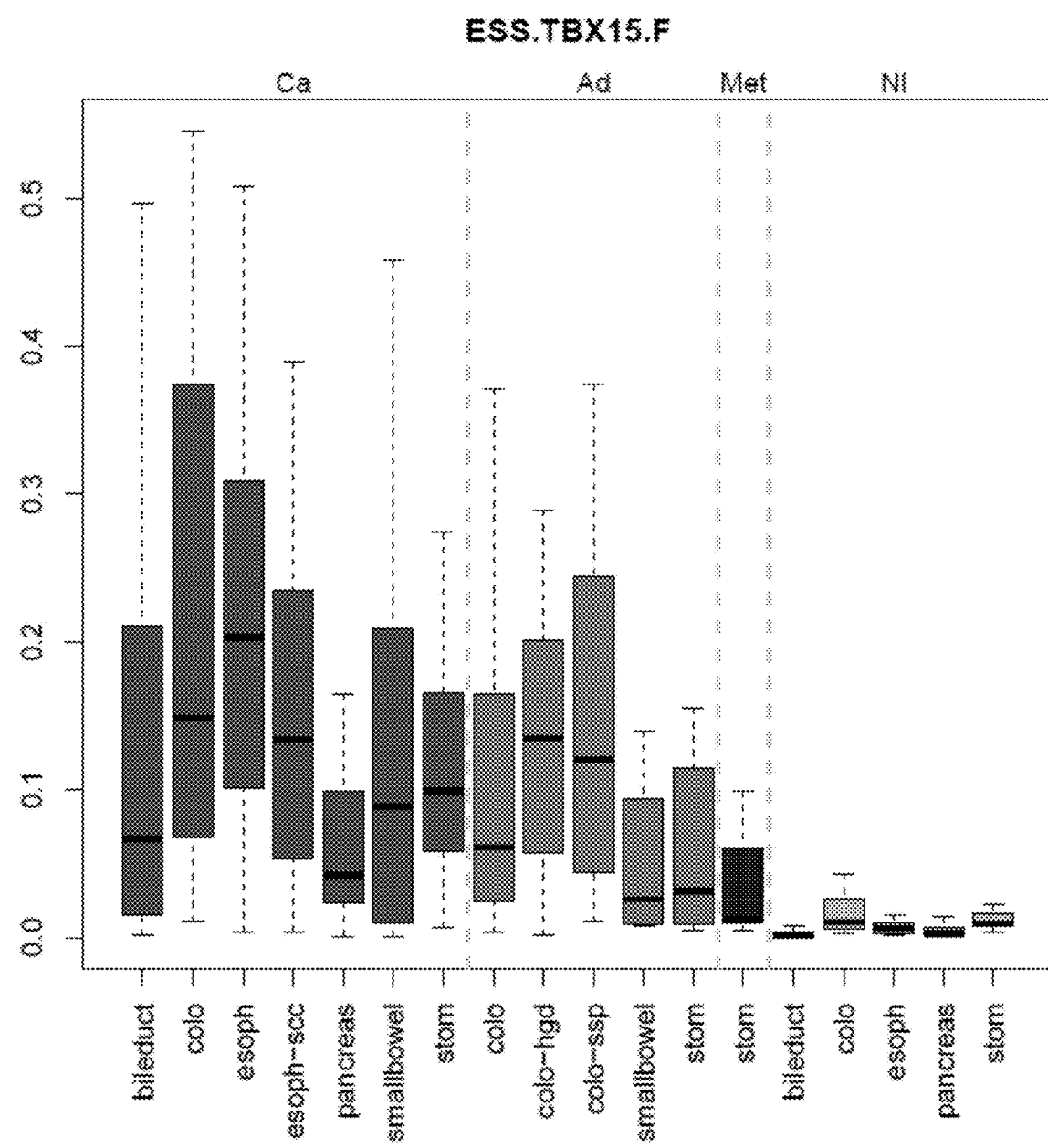

FIG. 1LLL
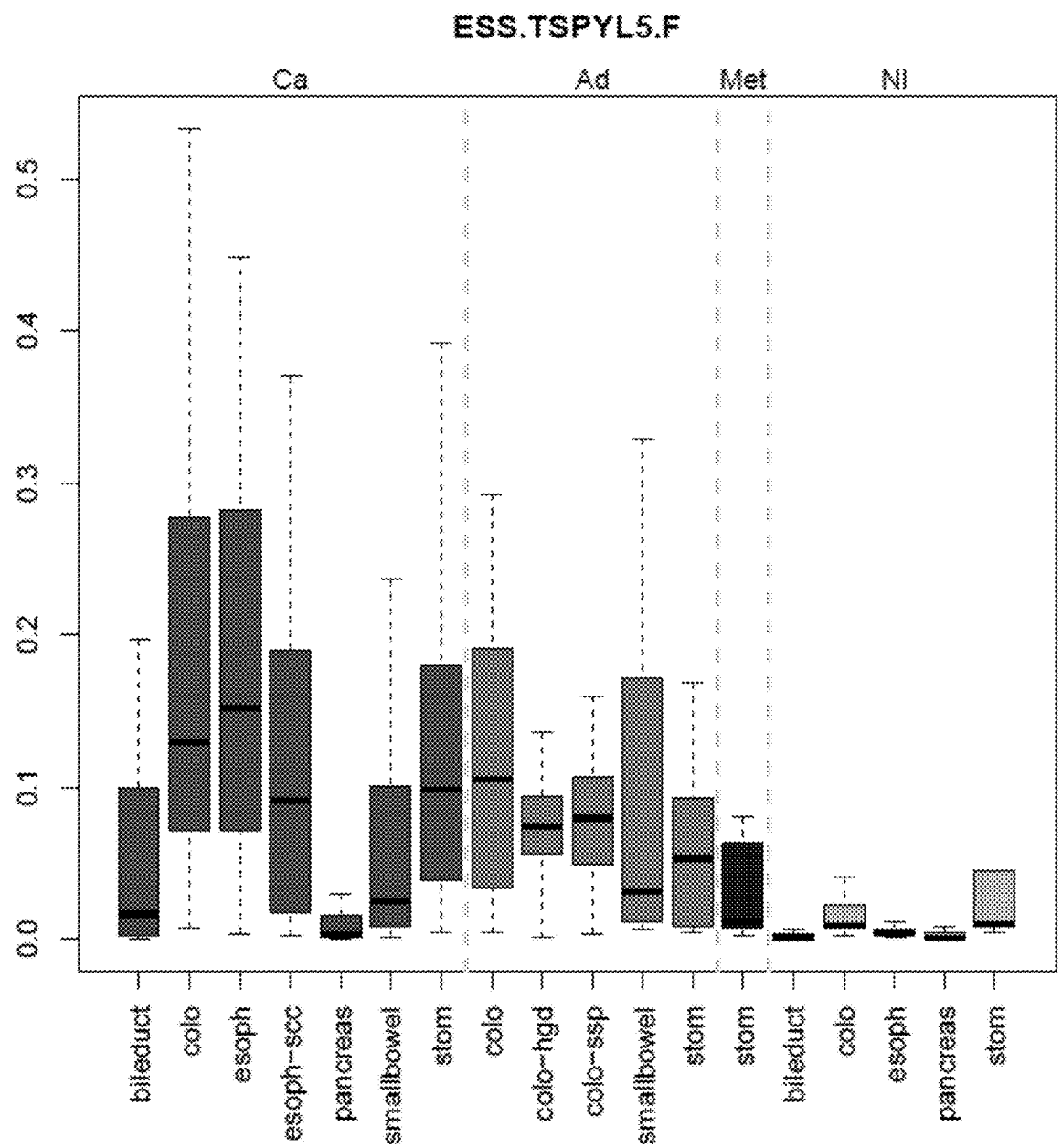

FIG. 1MMM
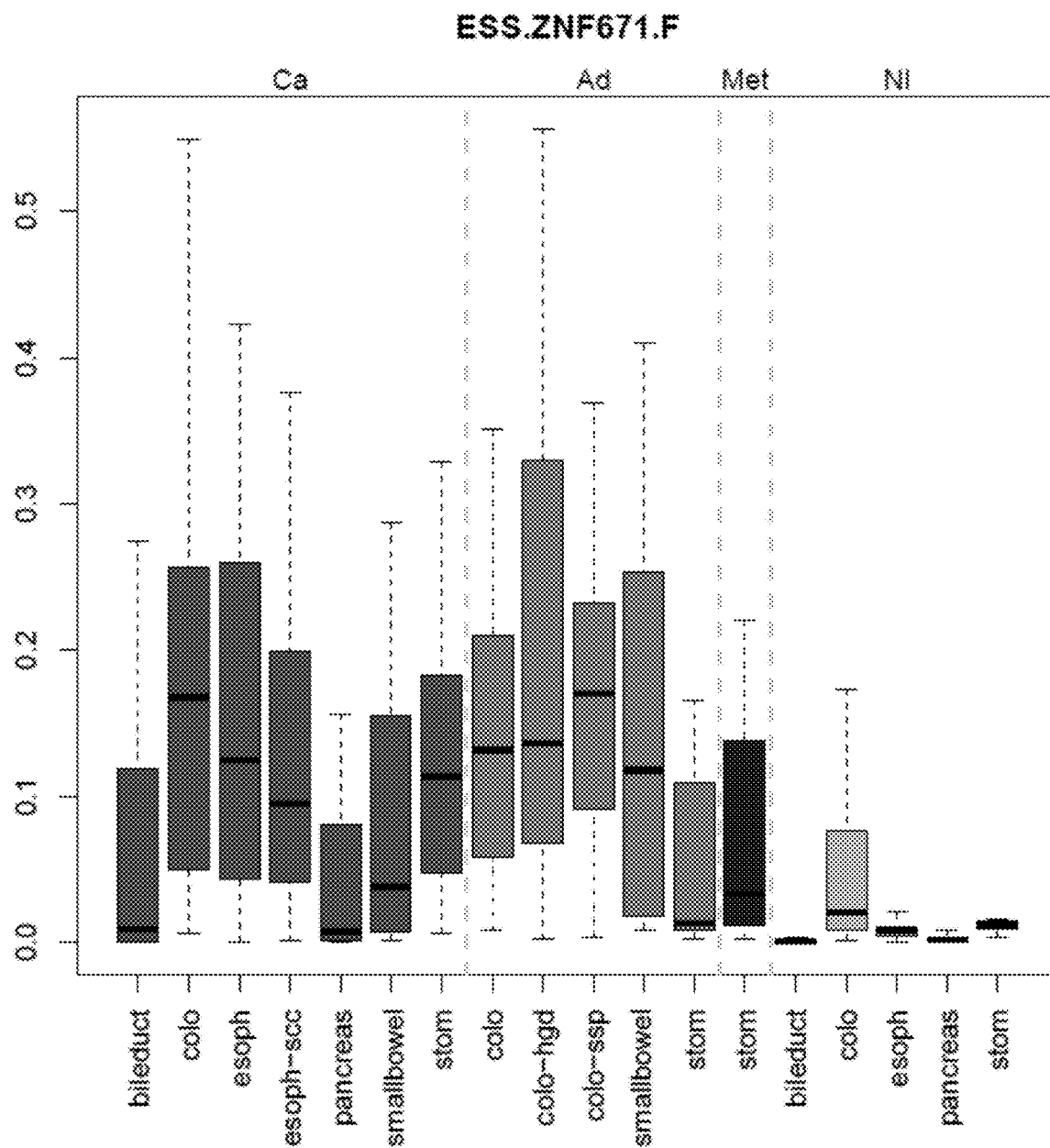

FIG. 1NNN
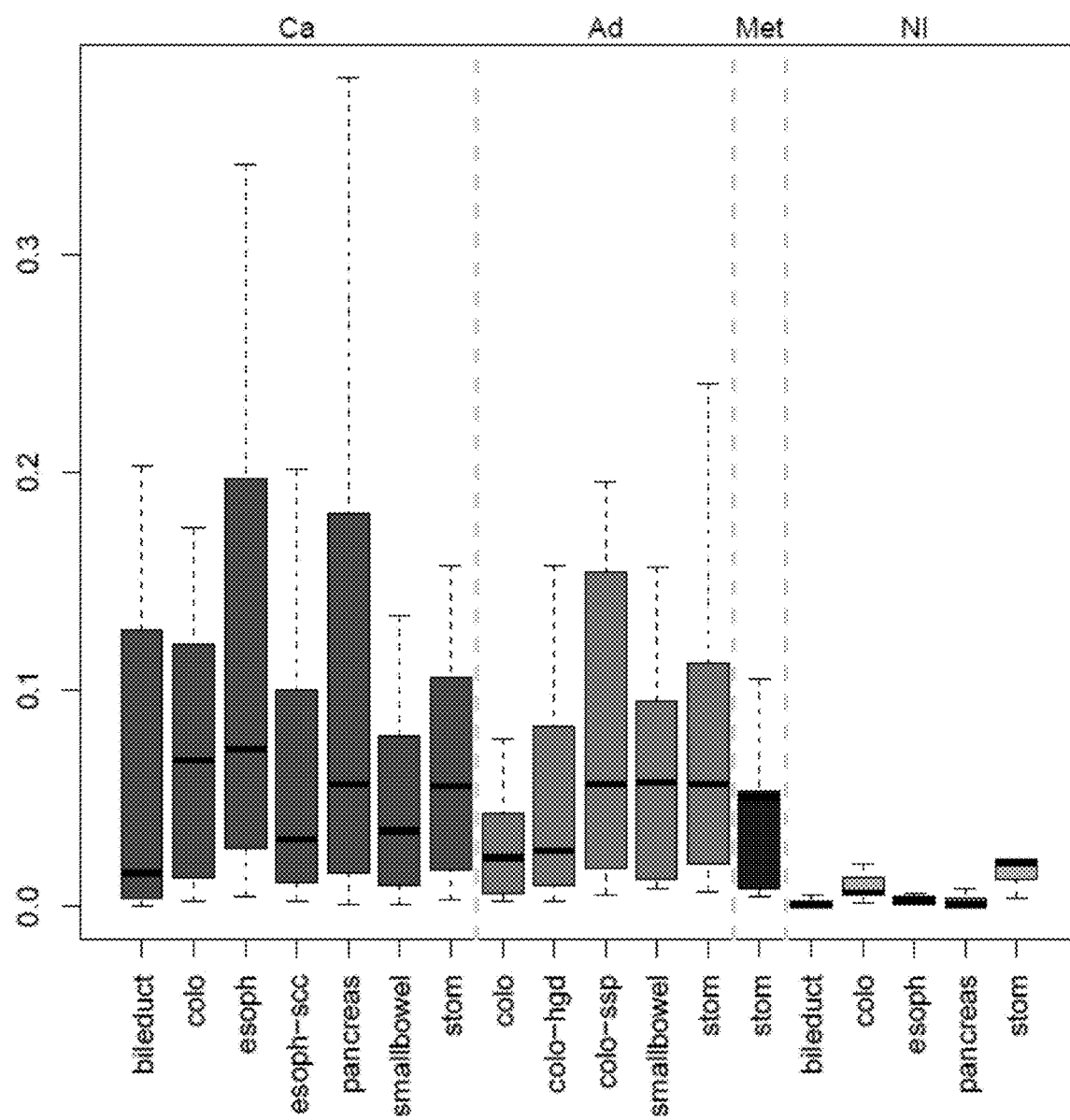

FIG. 1000
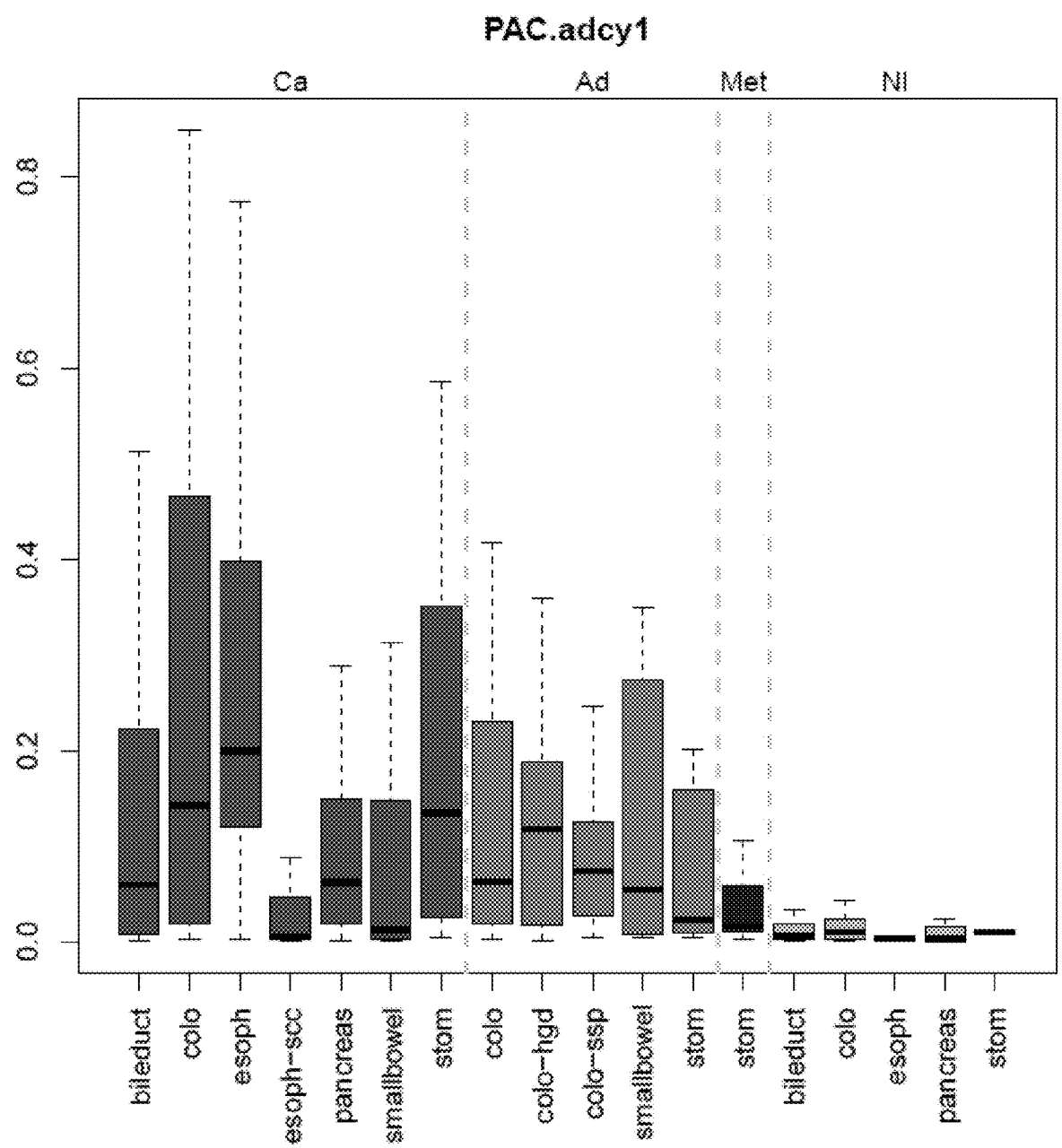

FIG. 1PPP
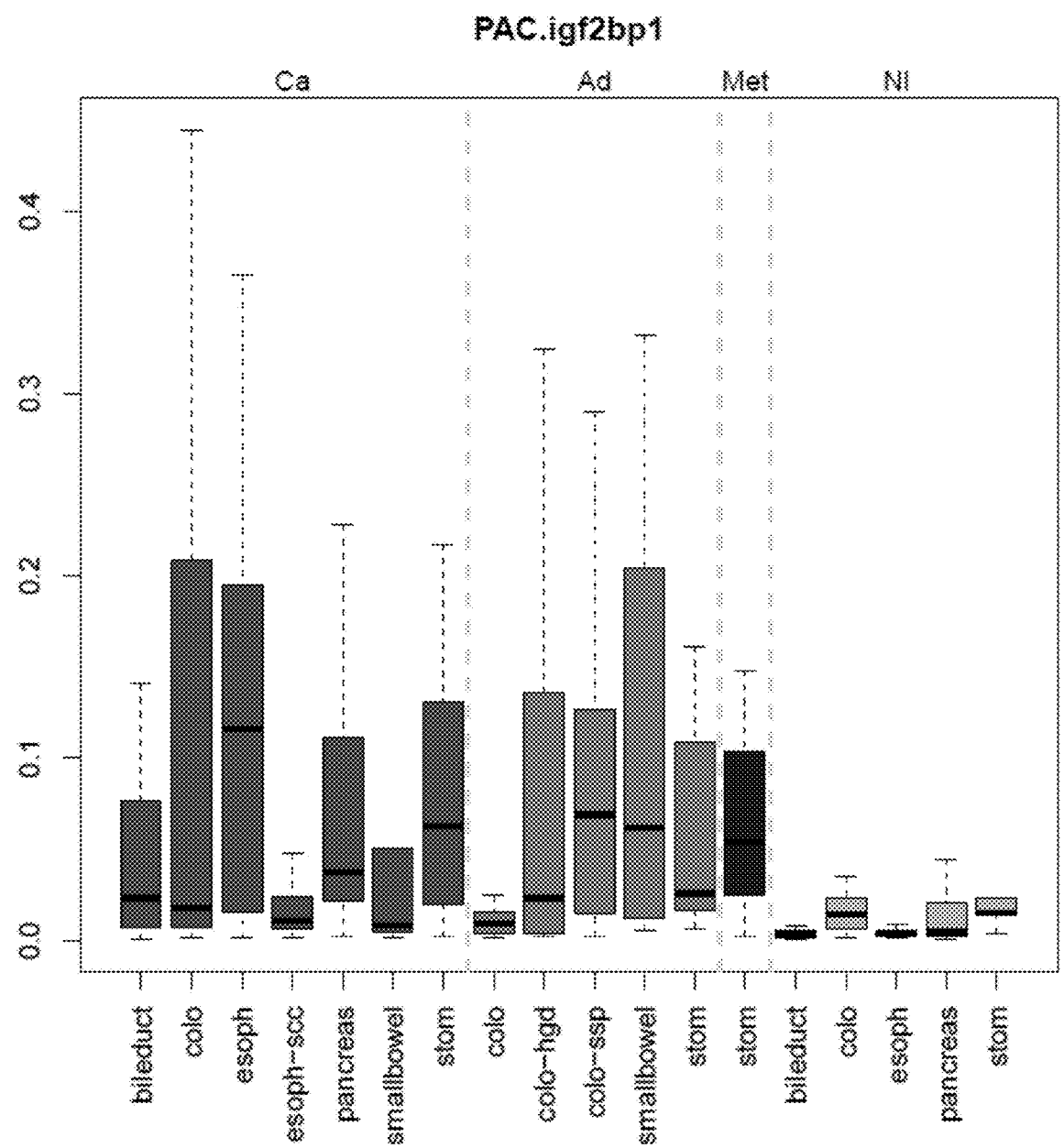

FIG. 1QQQ
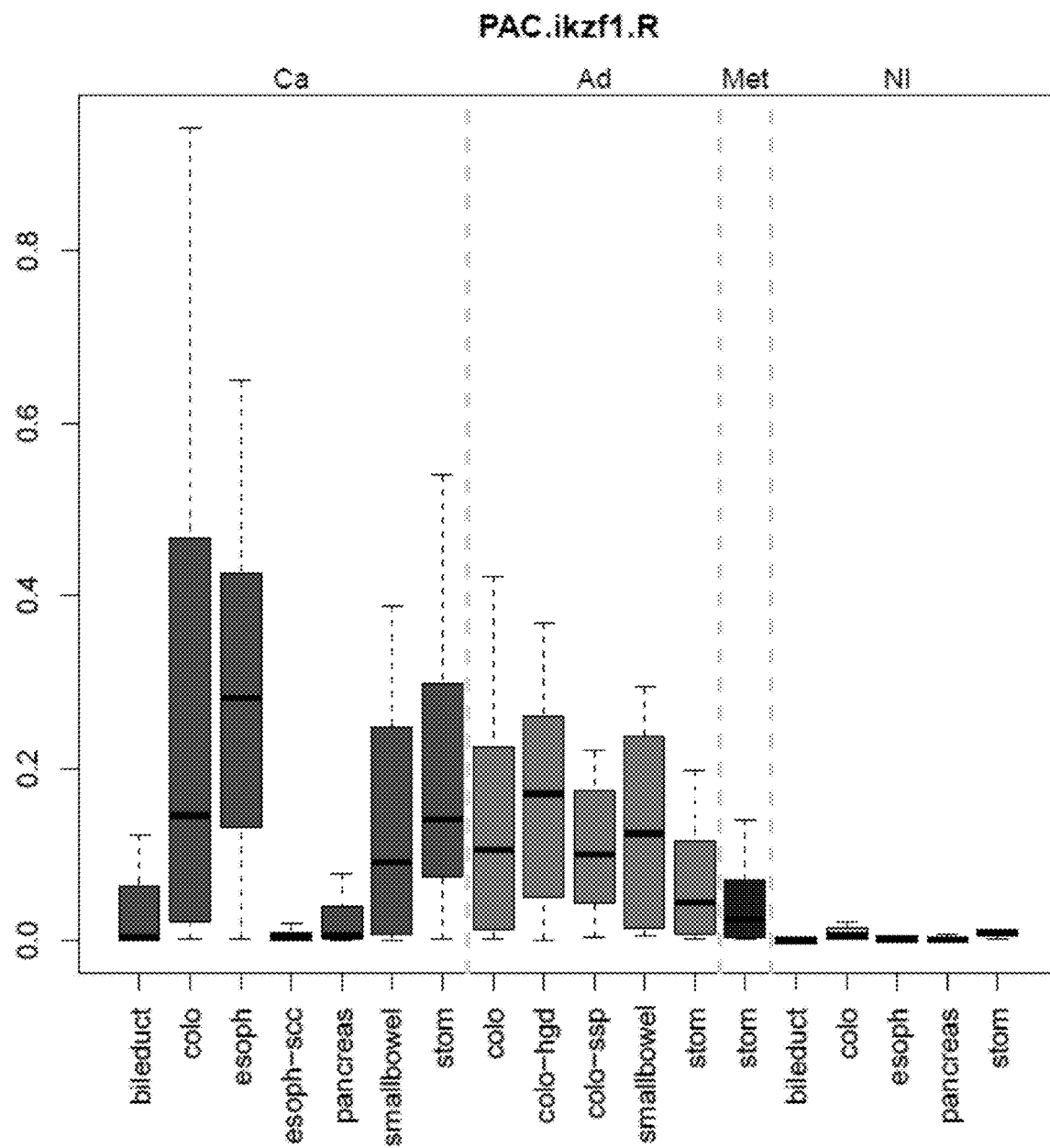

FIG. 1RRR
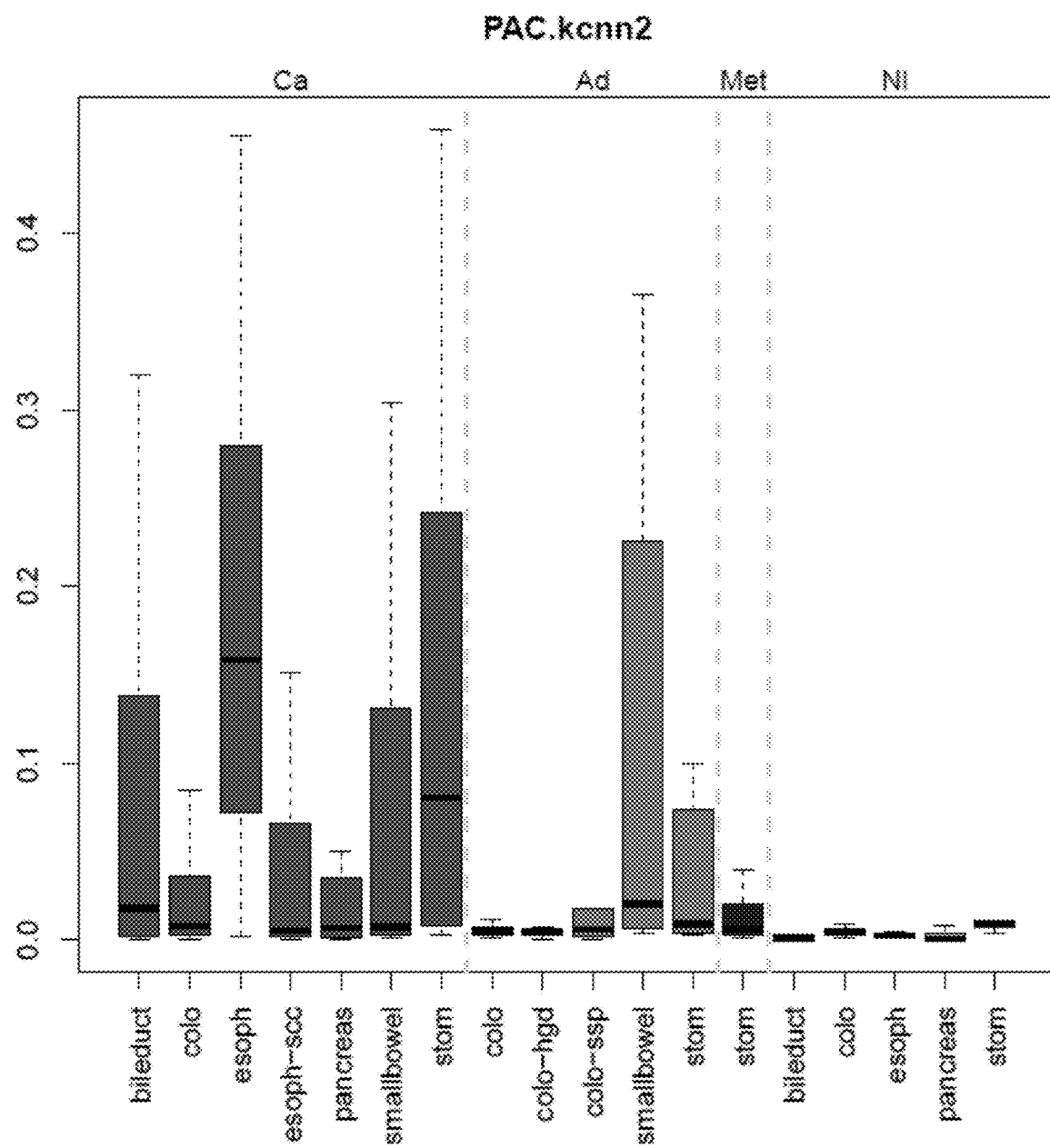

FIG. 1SSS
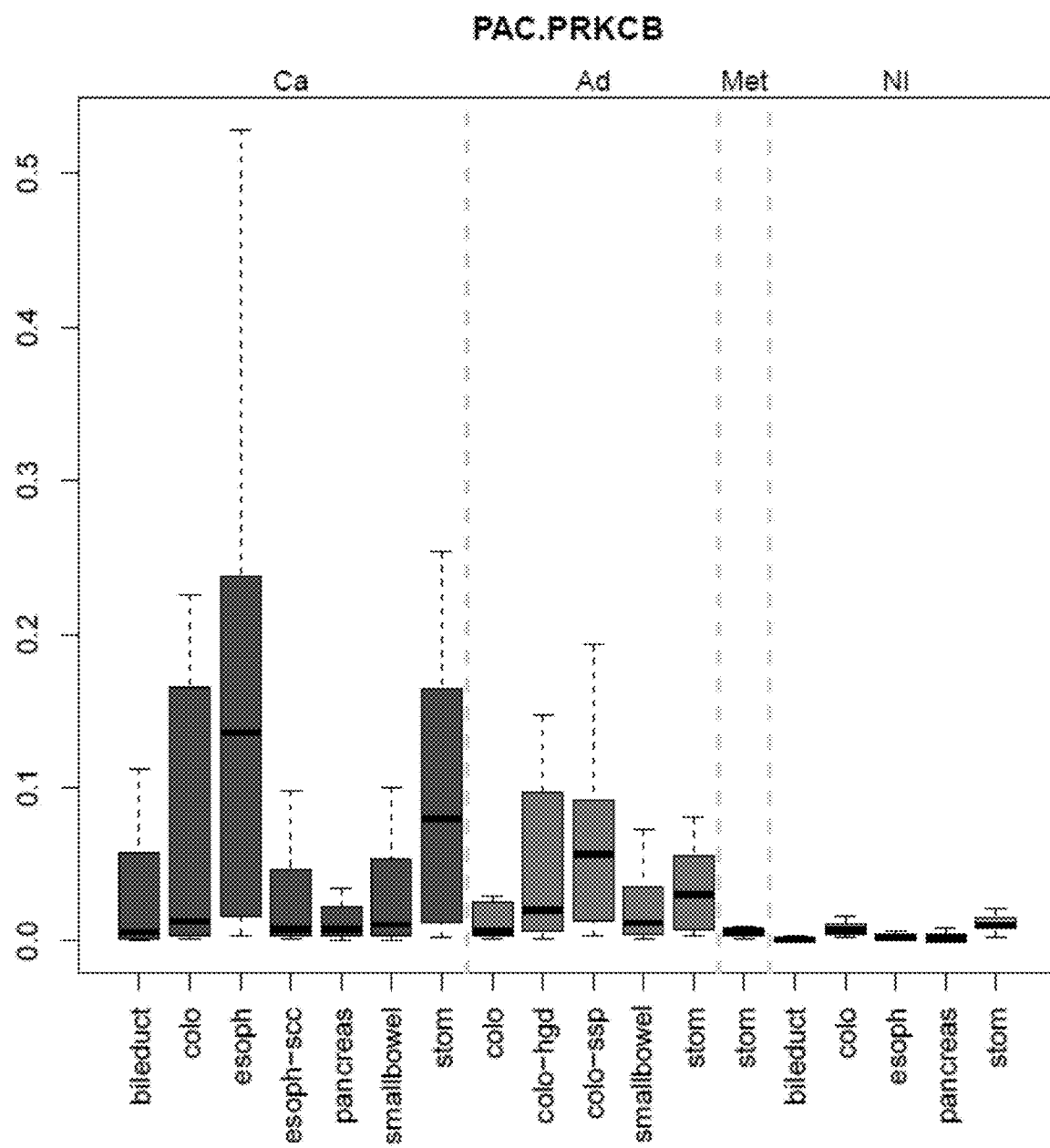

FIG. 1TTT
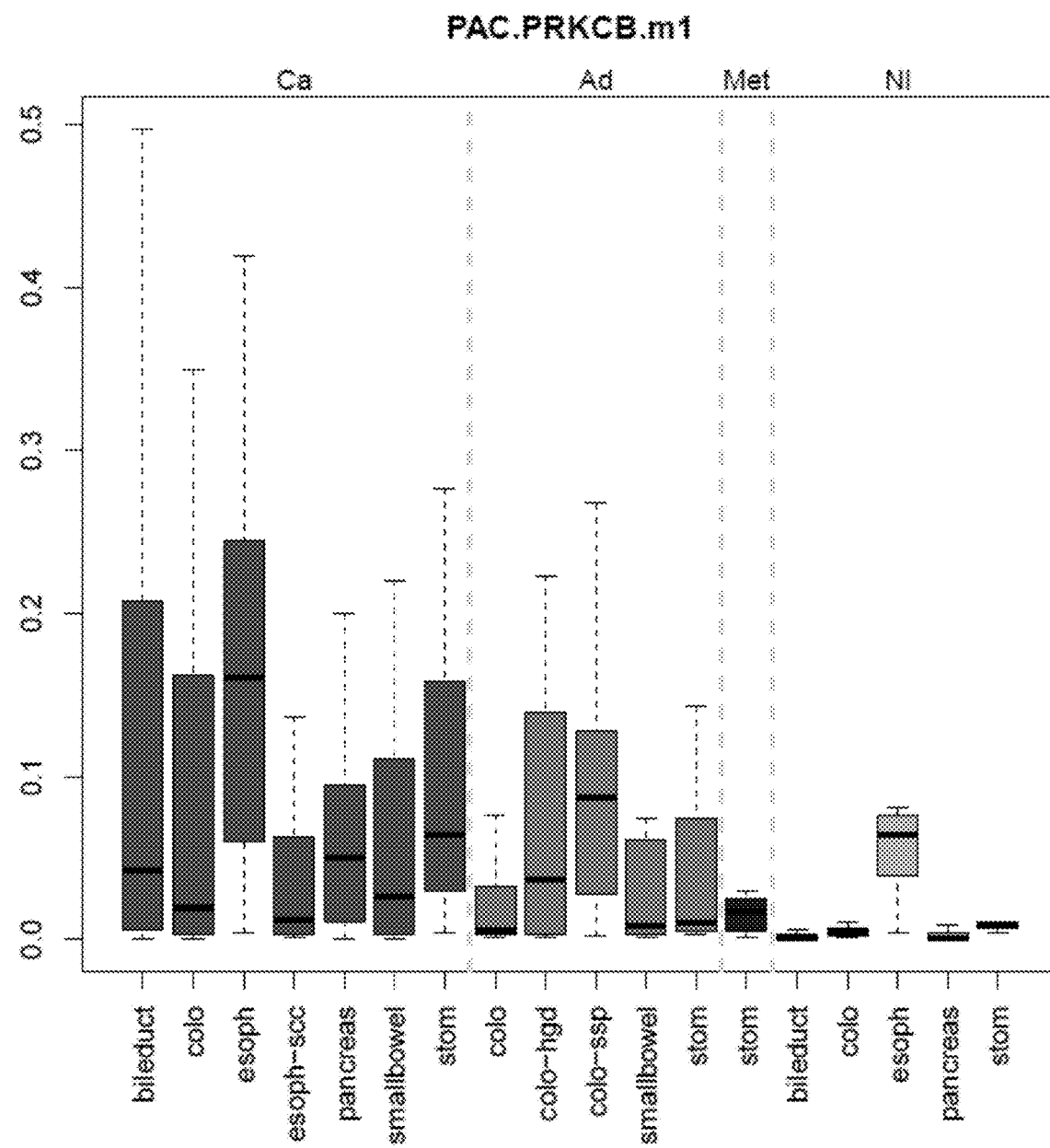

FIG. 1UUU
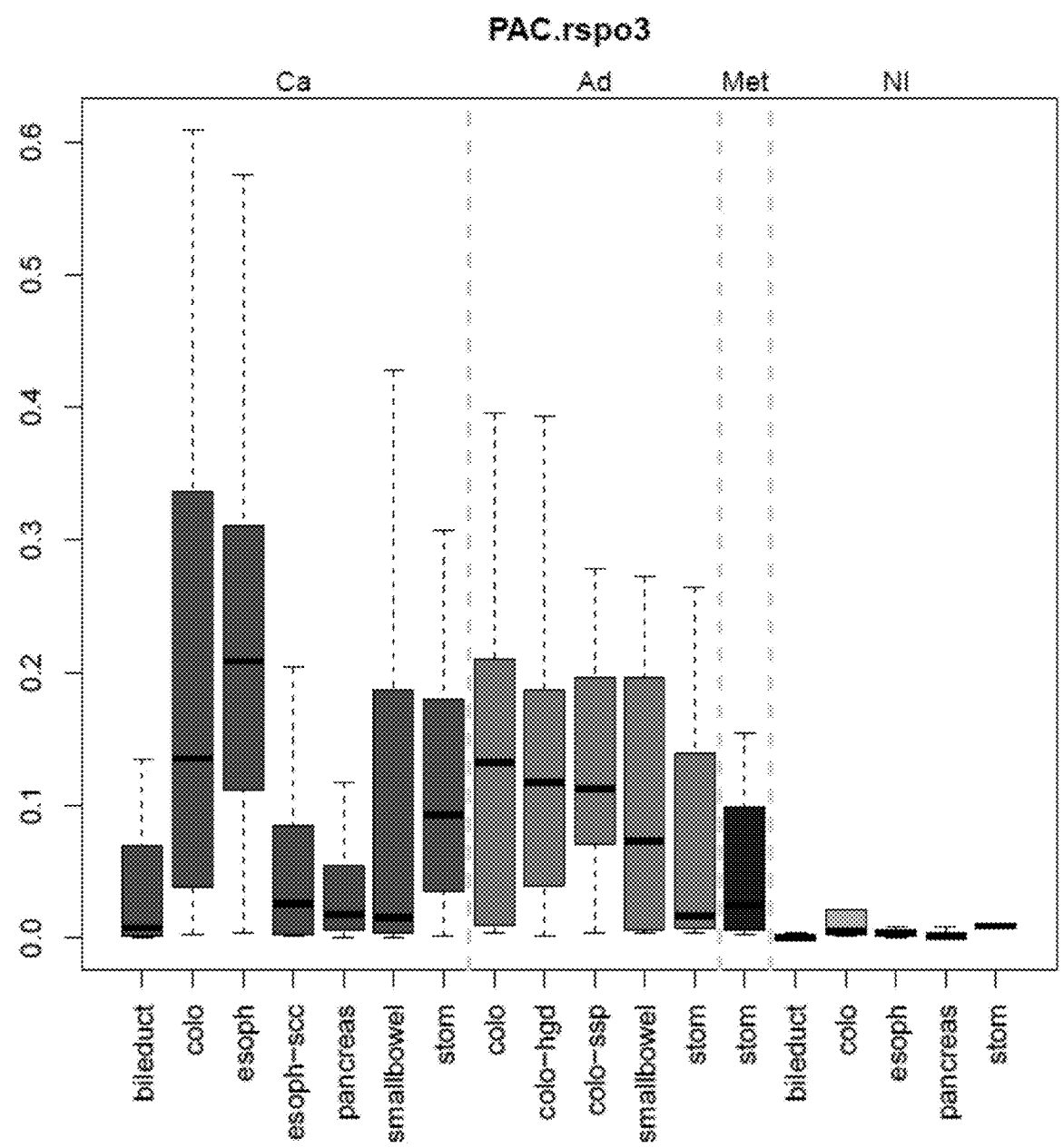

FIG. 1VVV
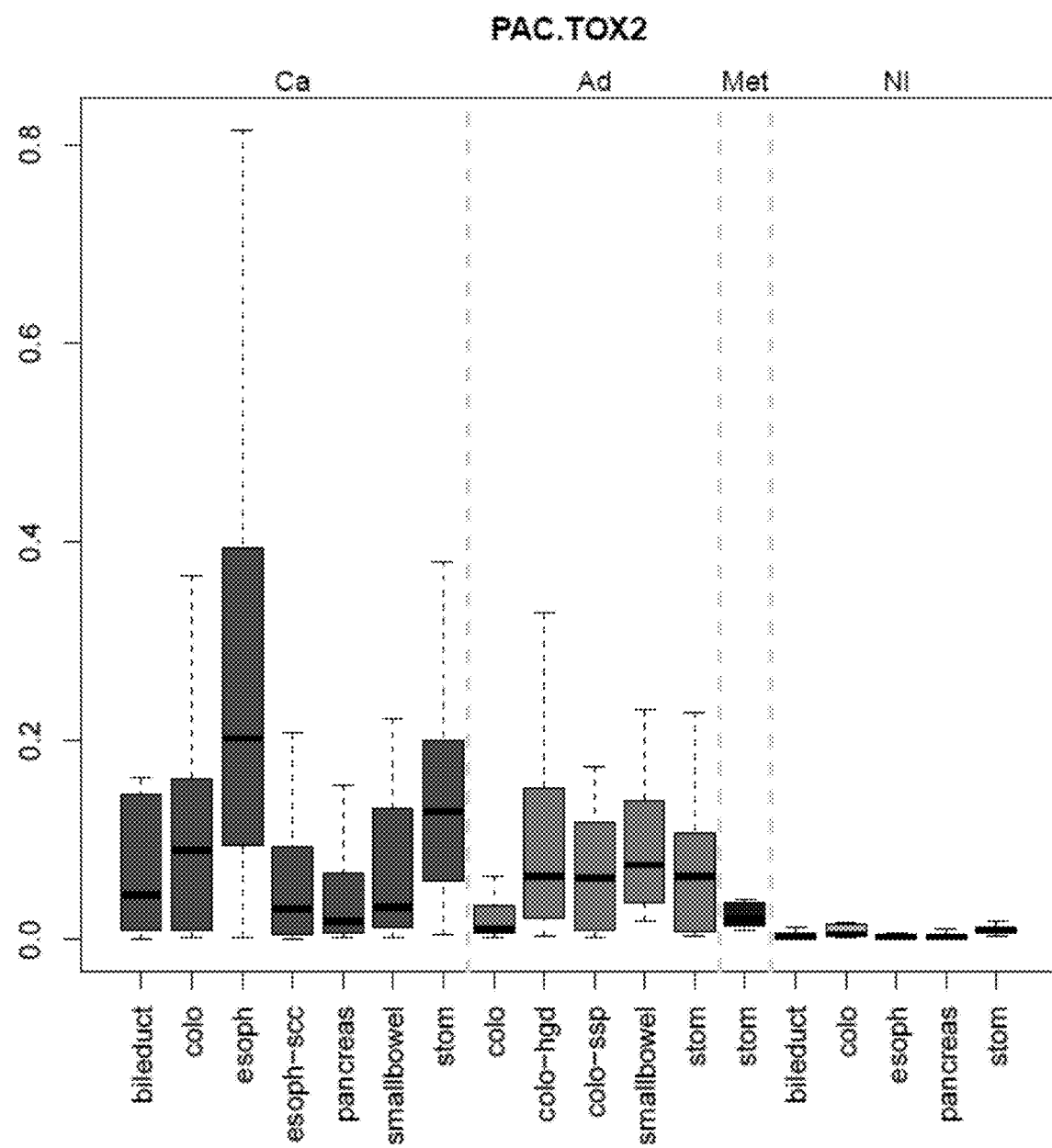

FIG. 1WWW
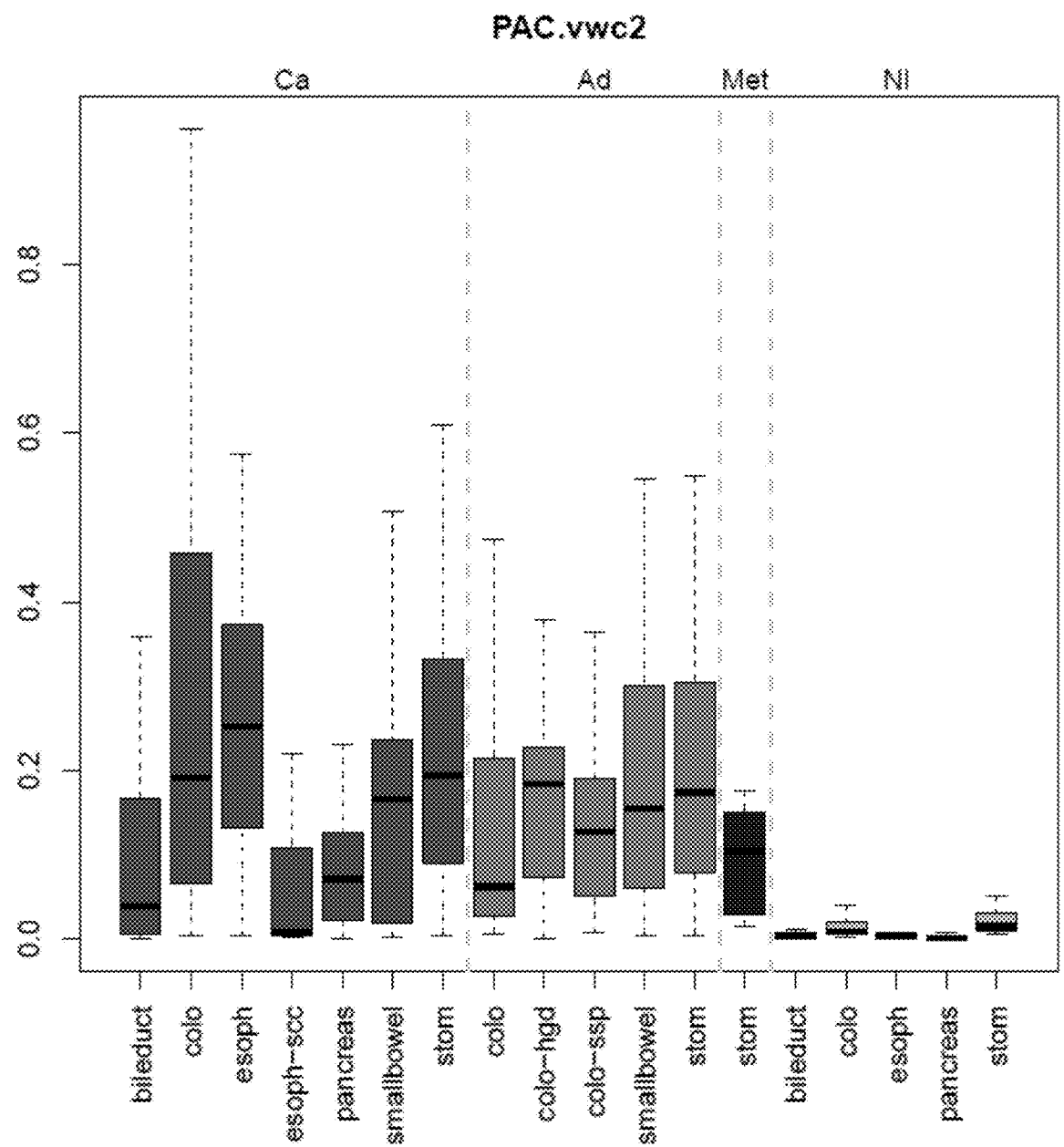

FIG. 1XXX
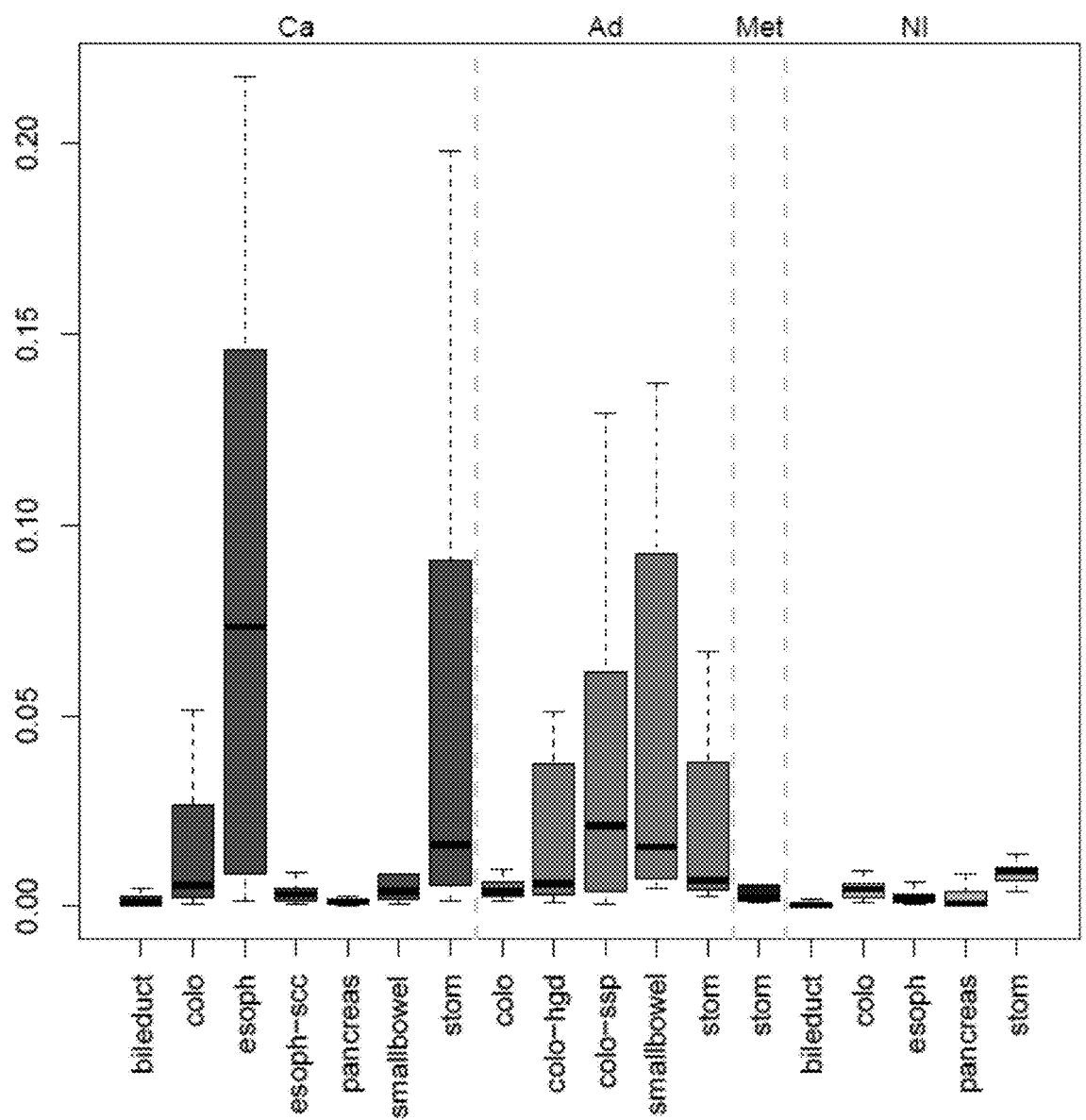

FIG. 1YYY
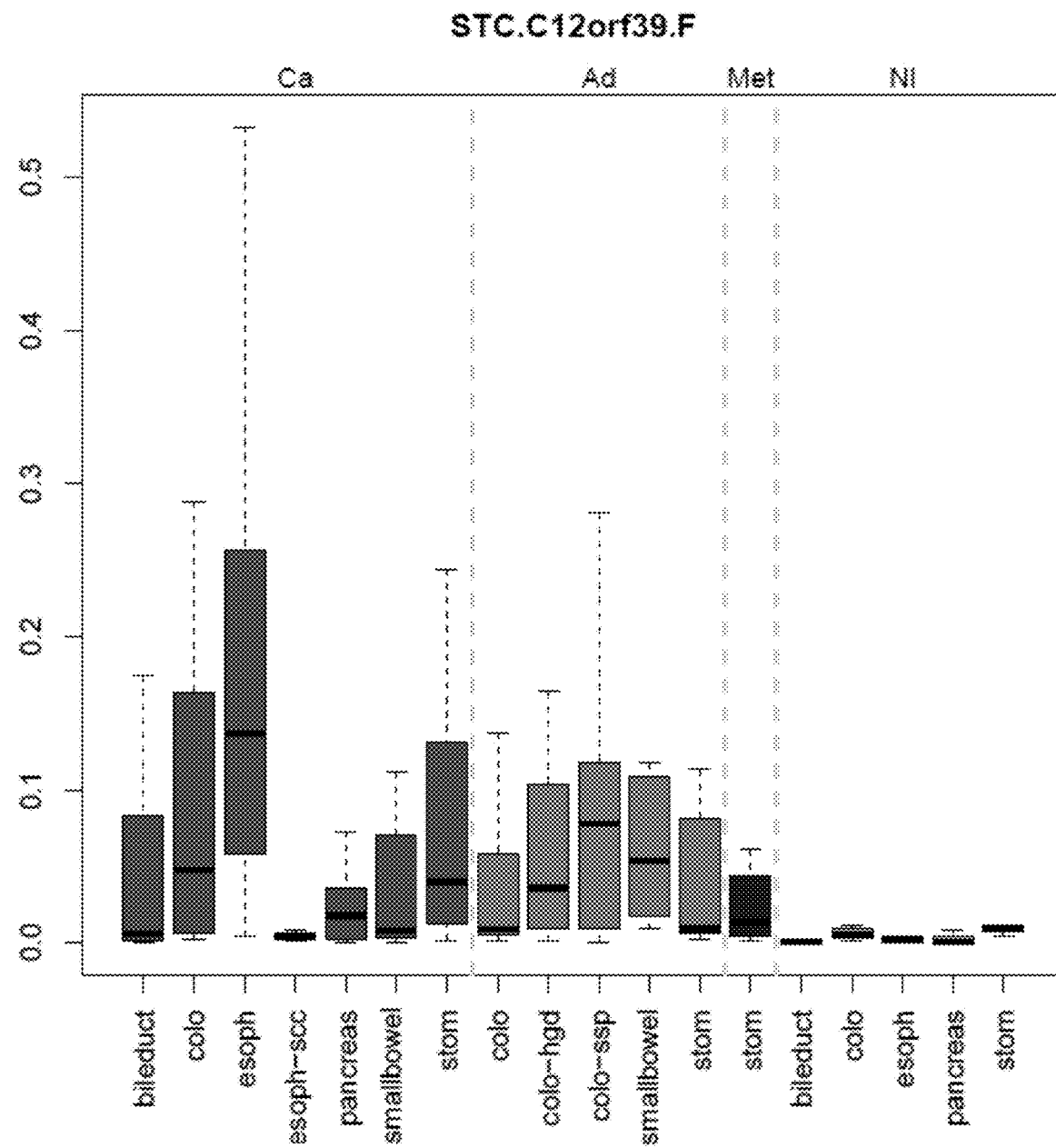

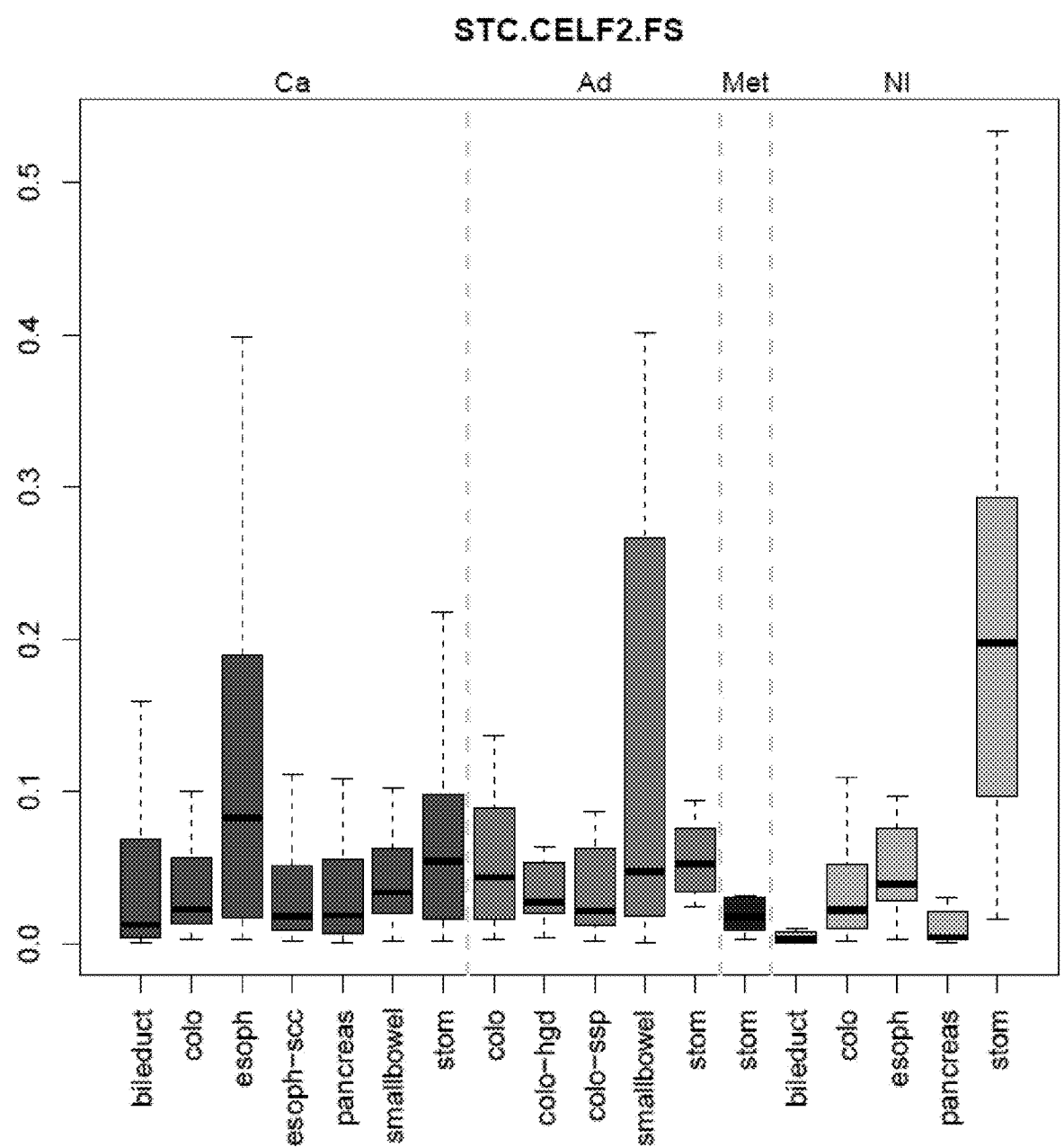
FIG. 1ZZZ

FIG. 1AAAA
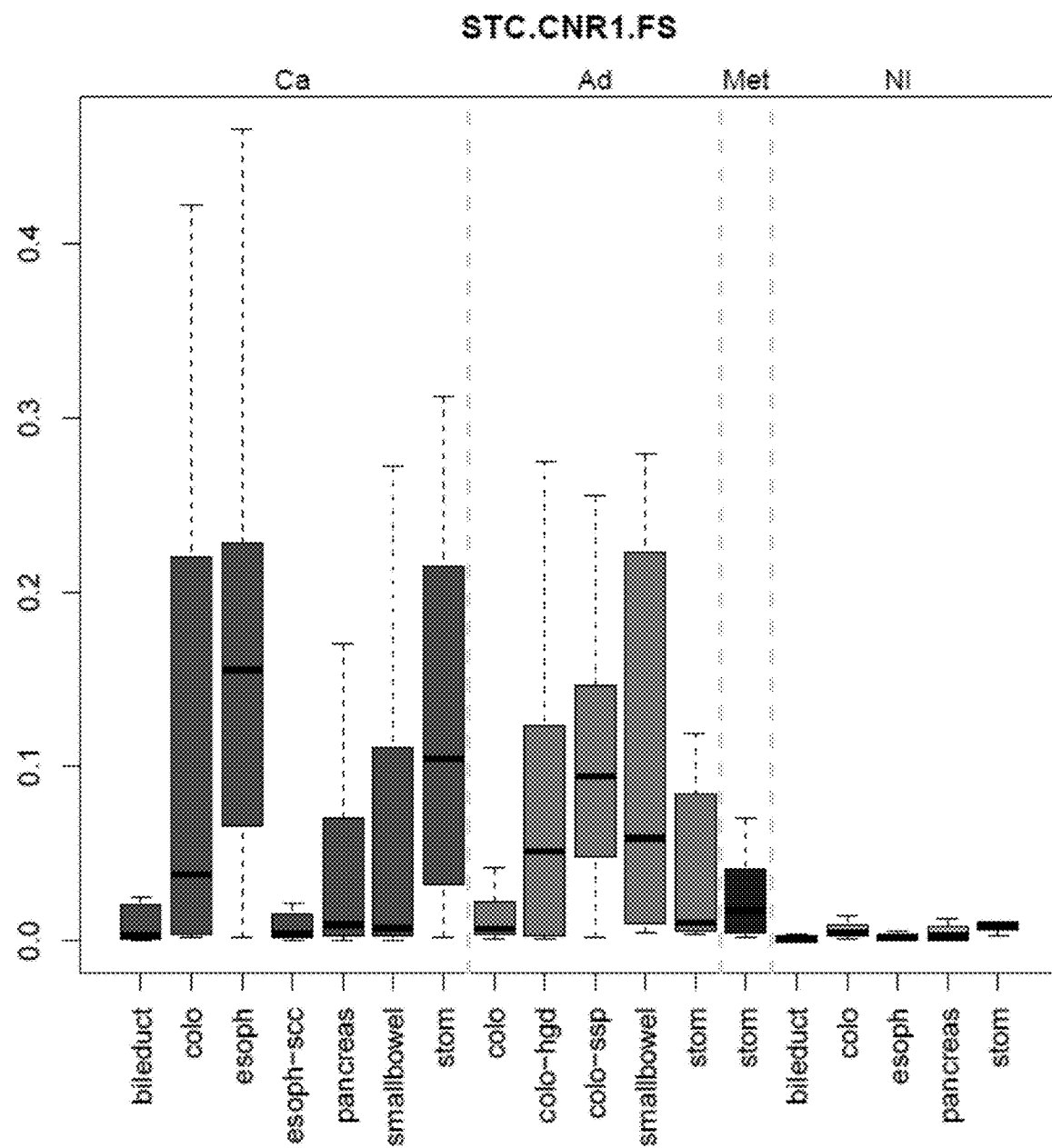

FIG. 1BBBB
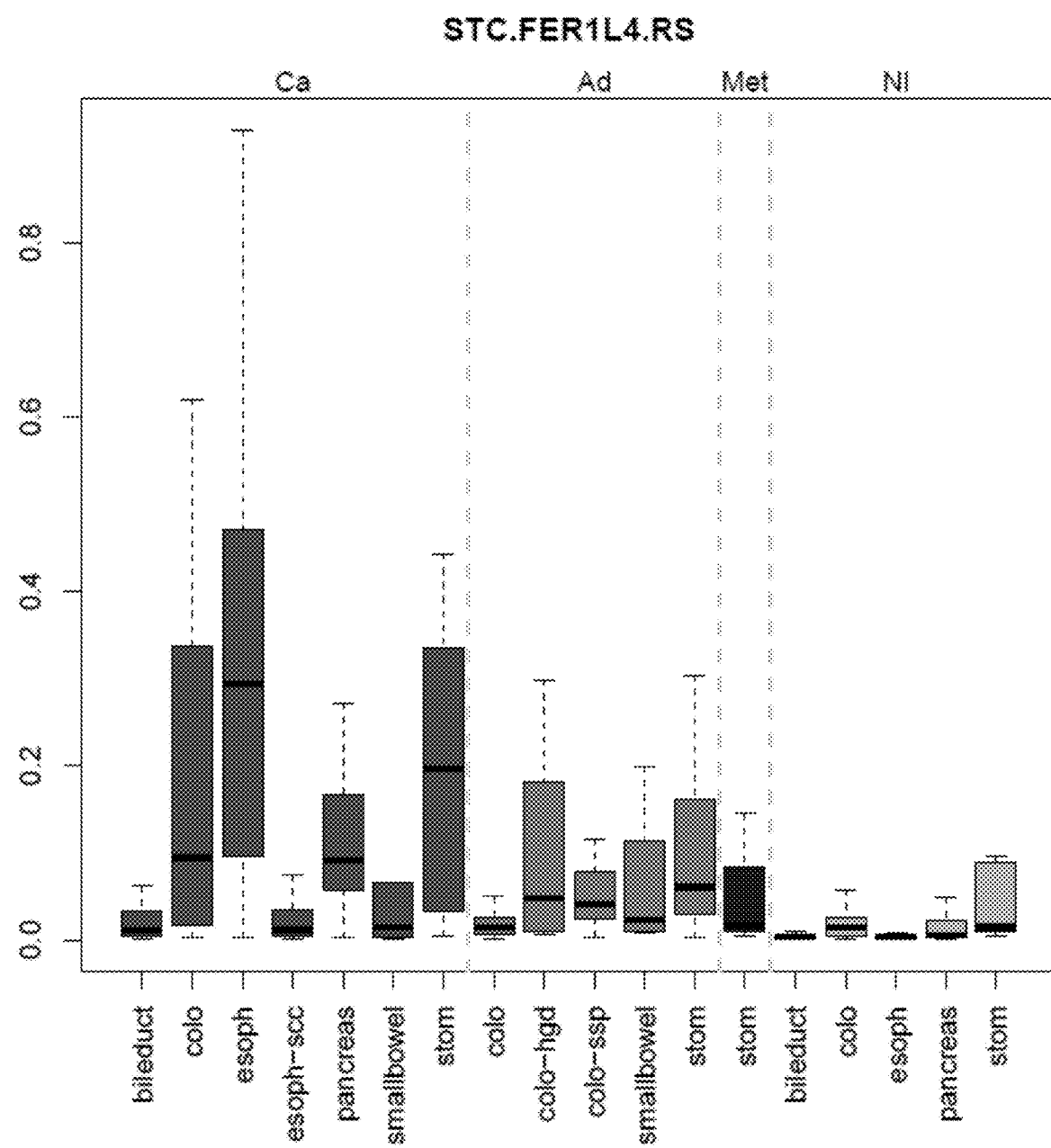

FIG. 1CCCC
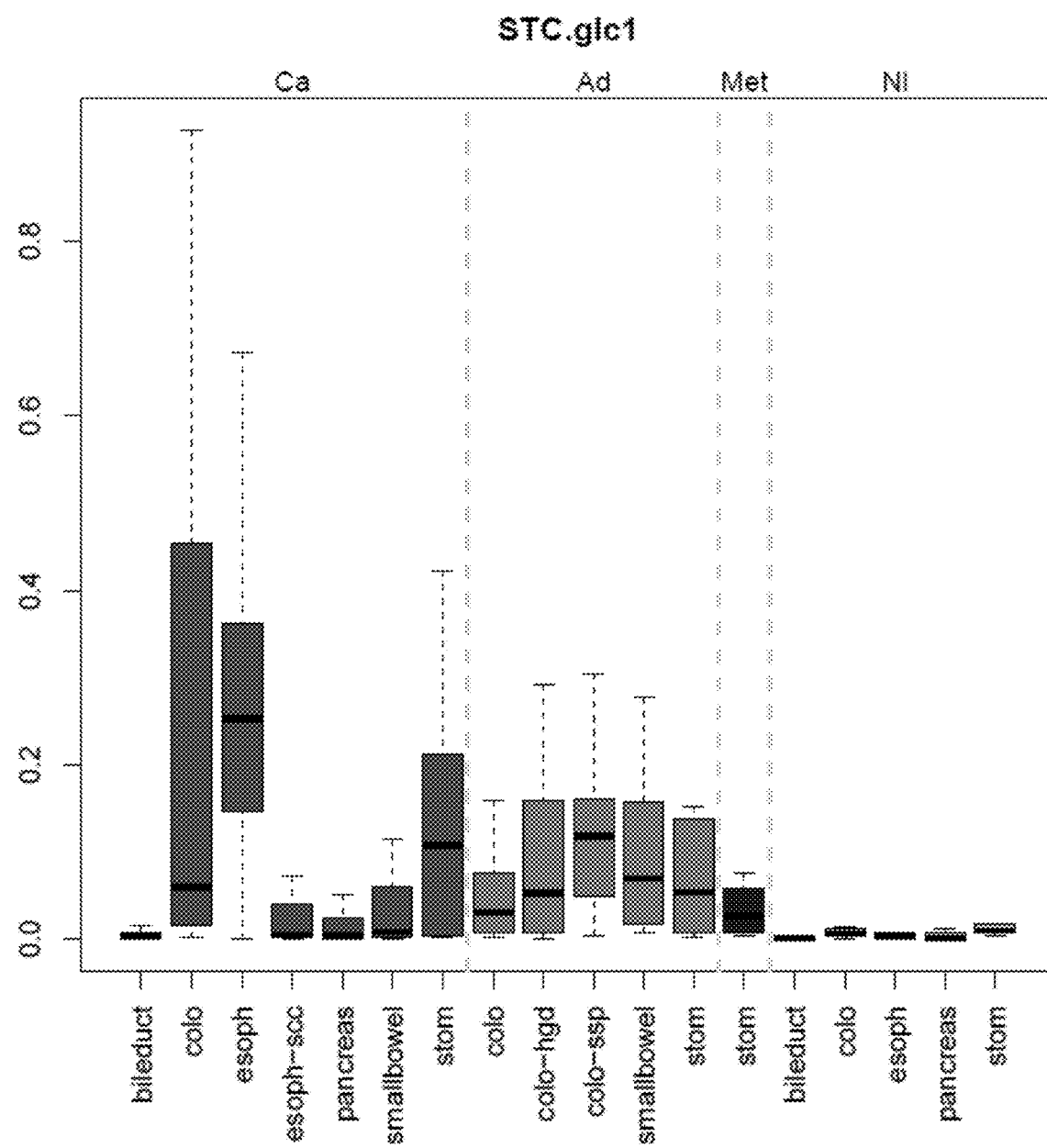

FIG. 1DDDD
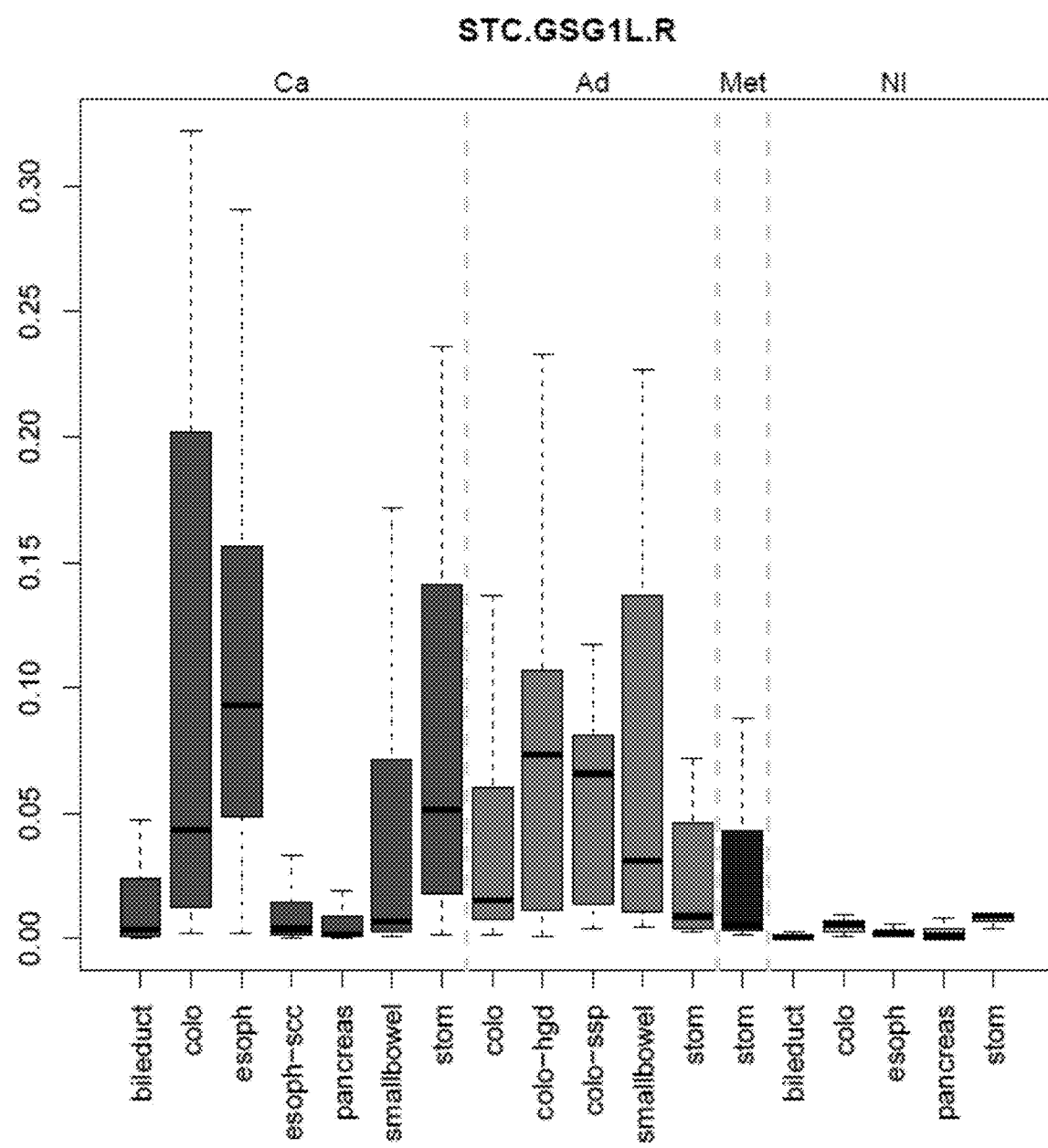

FIG. 1EEEE
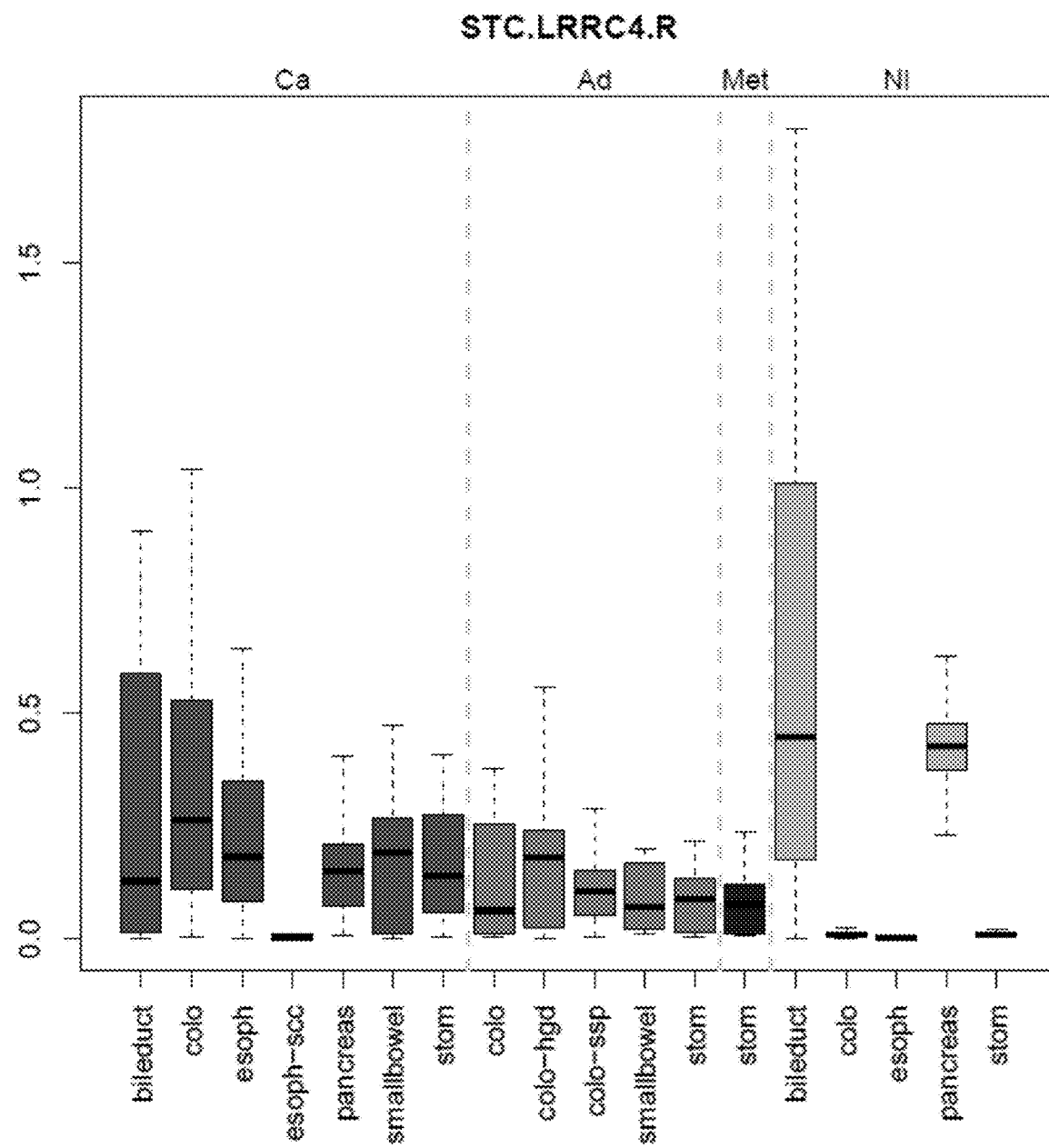

FIG. 1FFFF
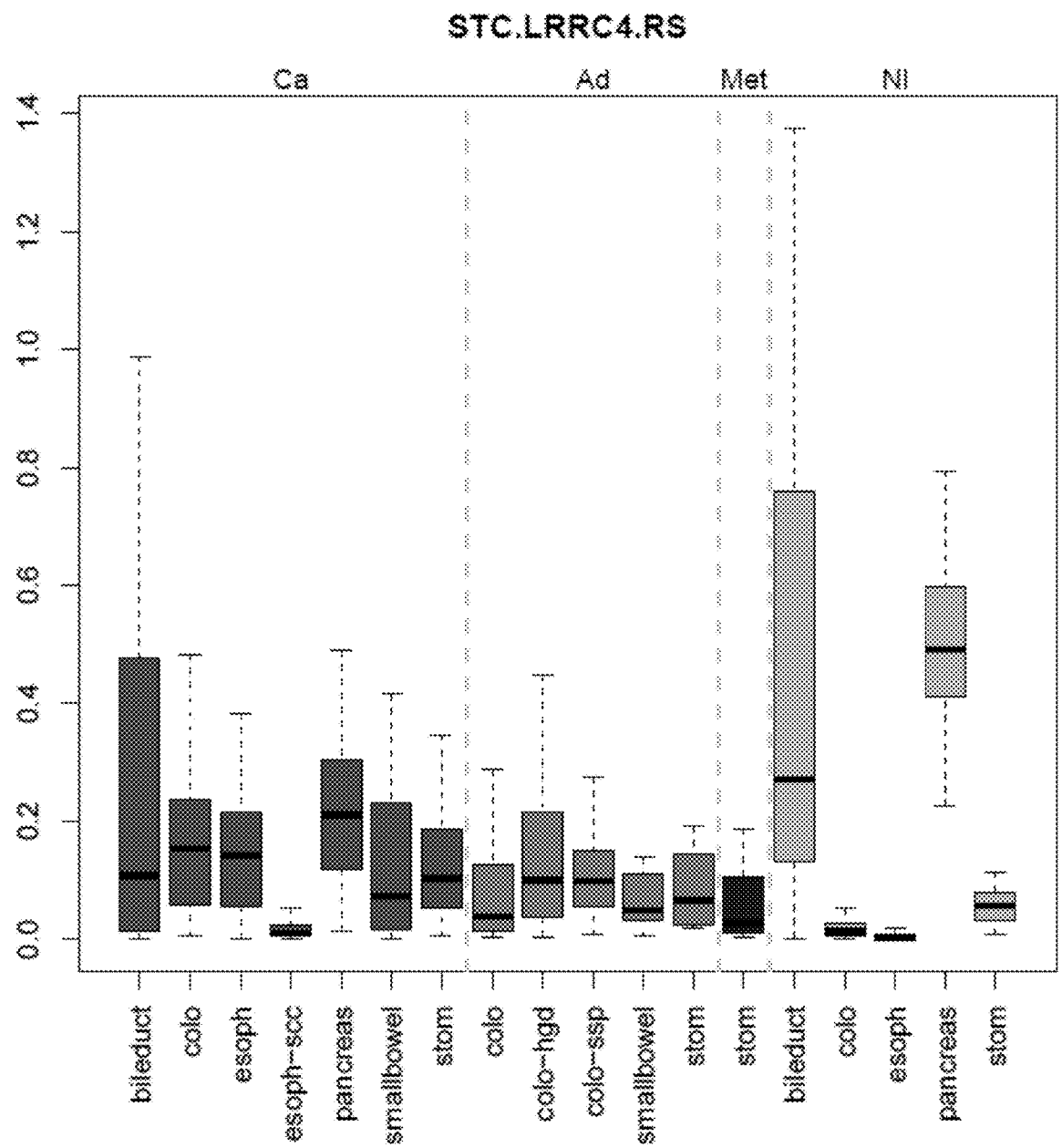

FIG. 1GGGG
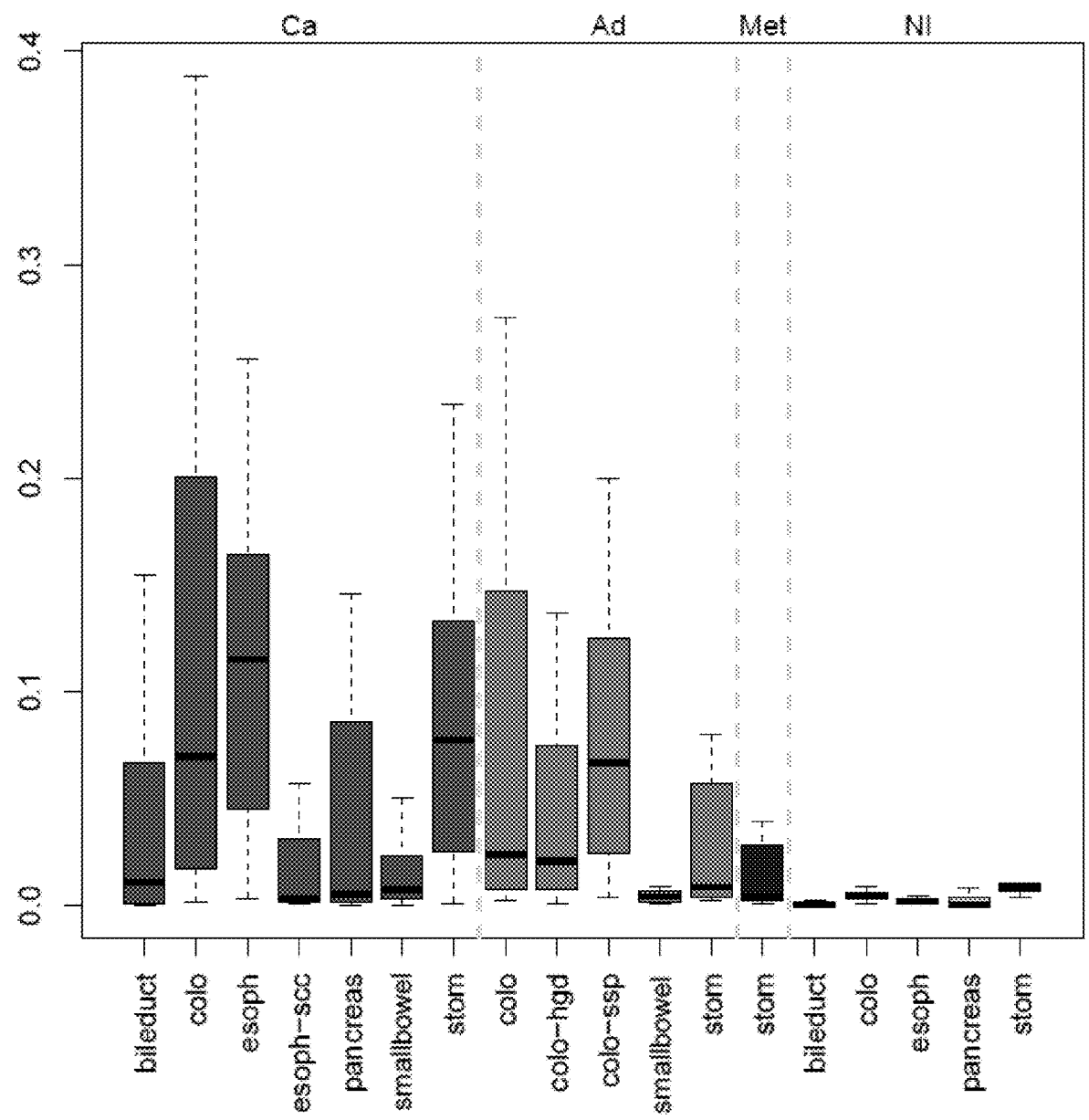

FIG. 1HHHH
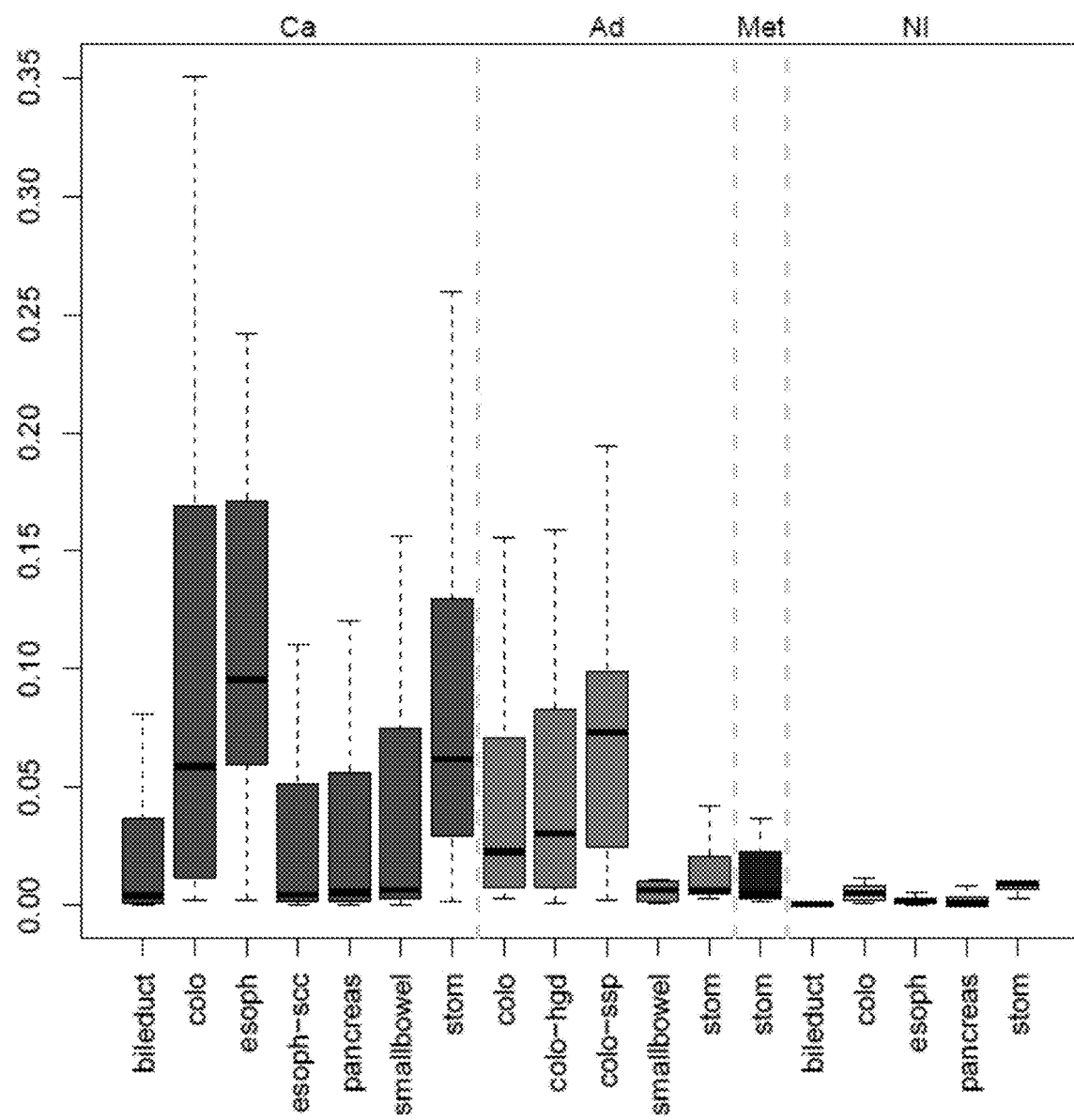

FIG. 1IIII
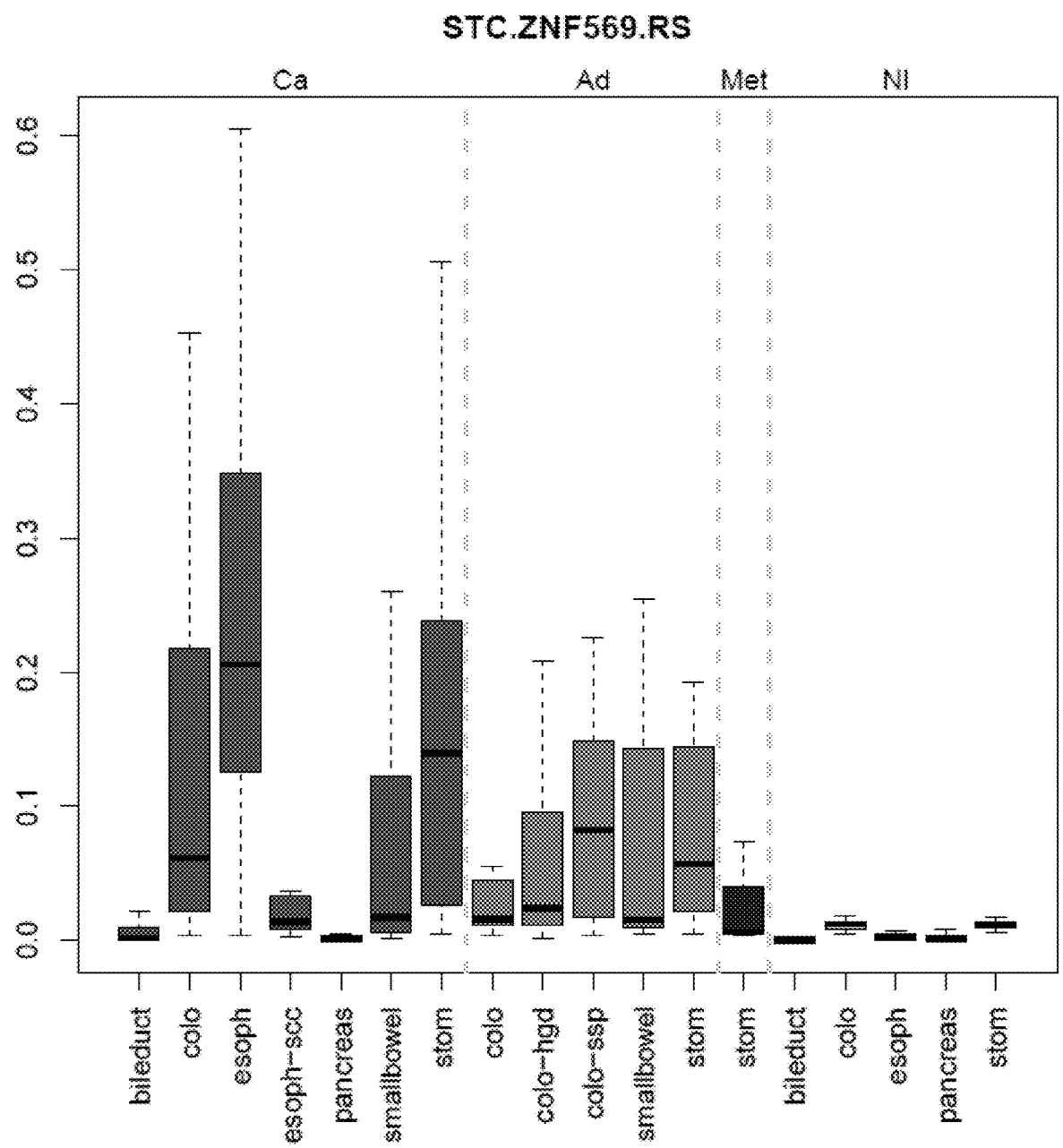

FIG. 1JJJJ
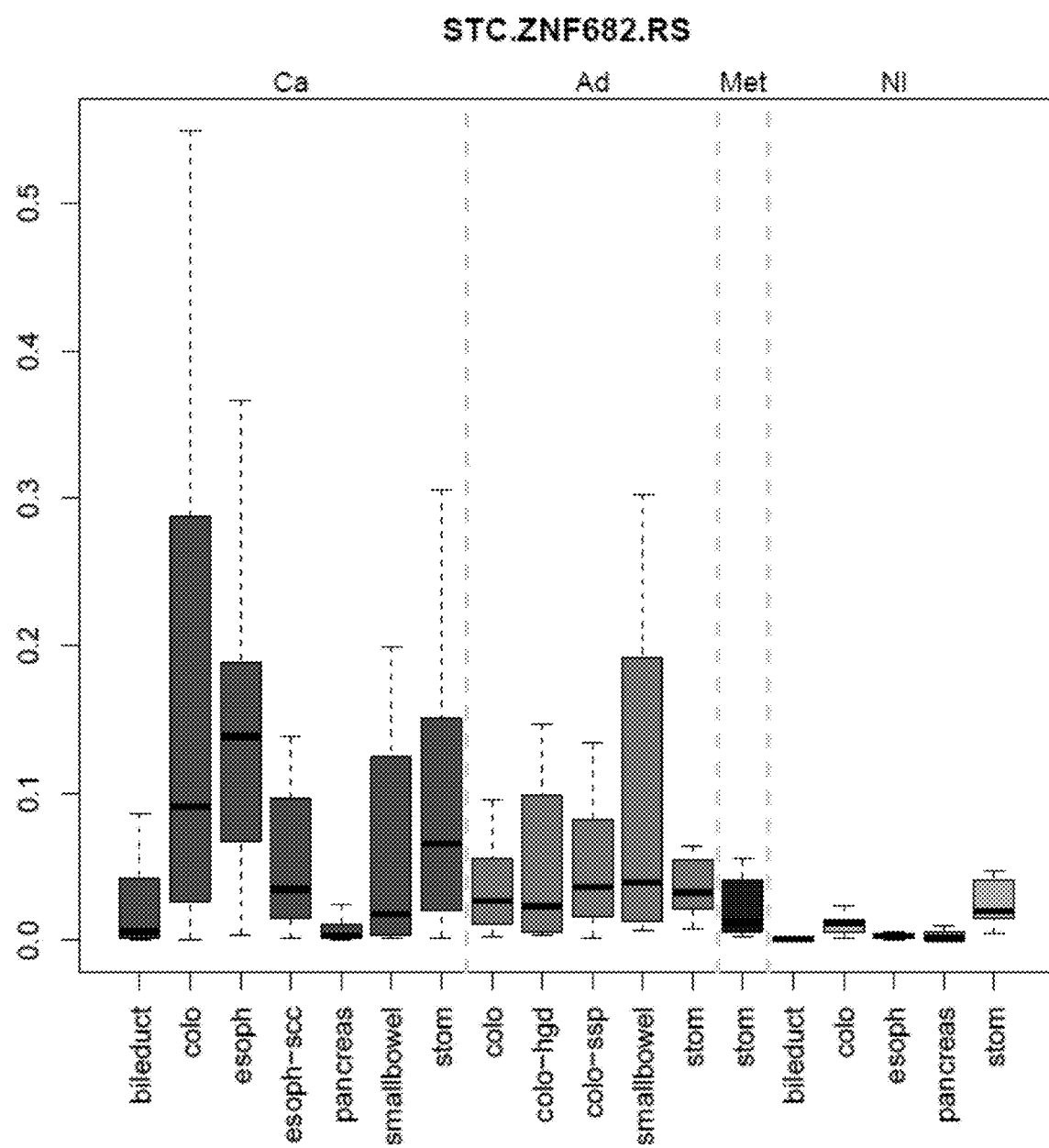

FIG. 1KKKK
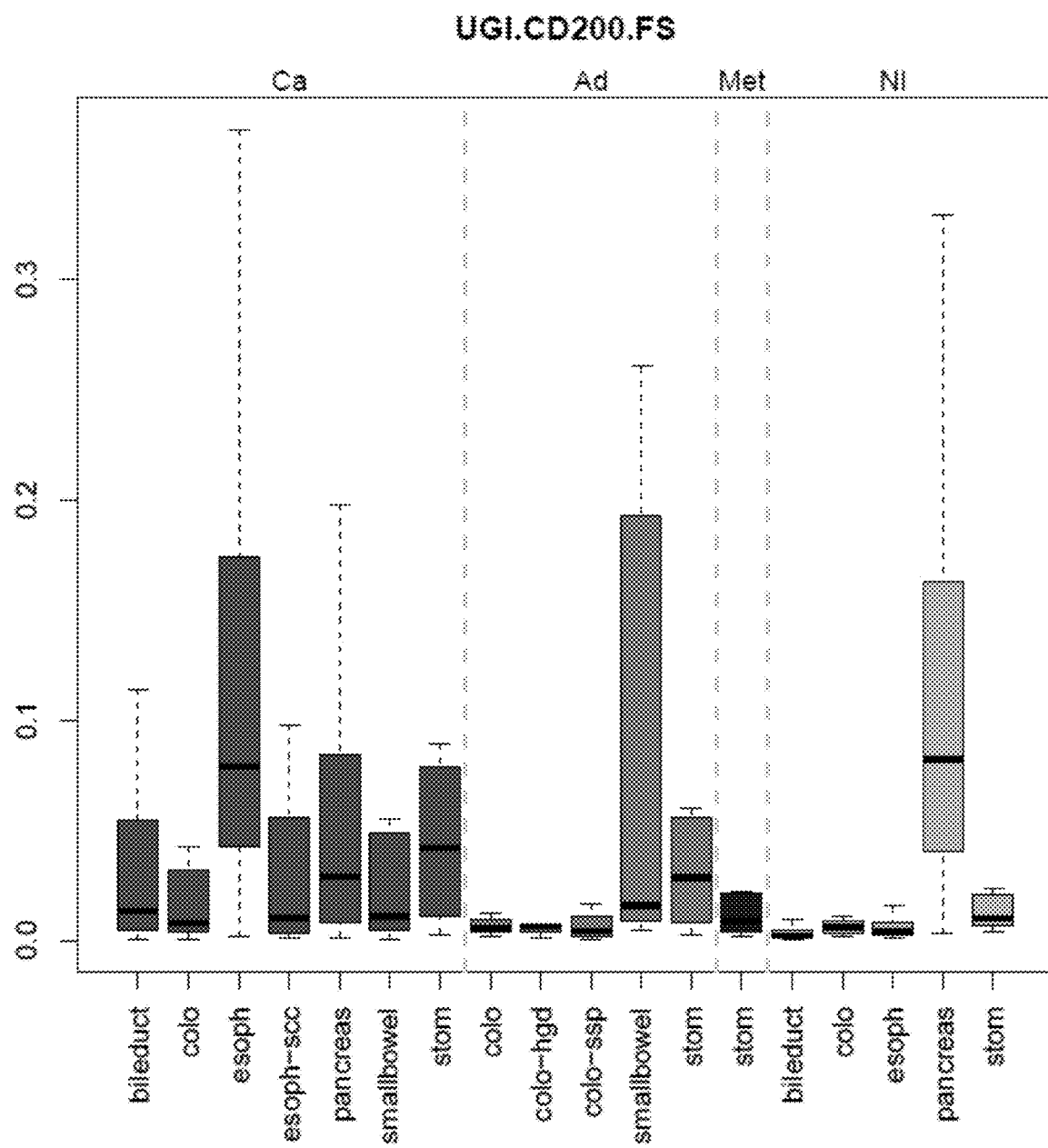

FIG. 1LLLL
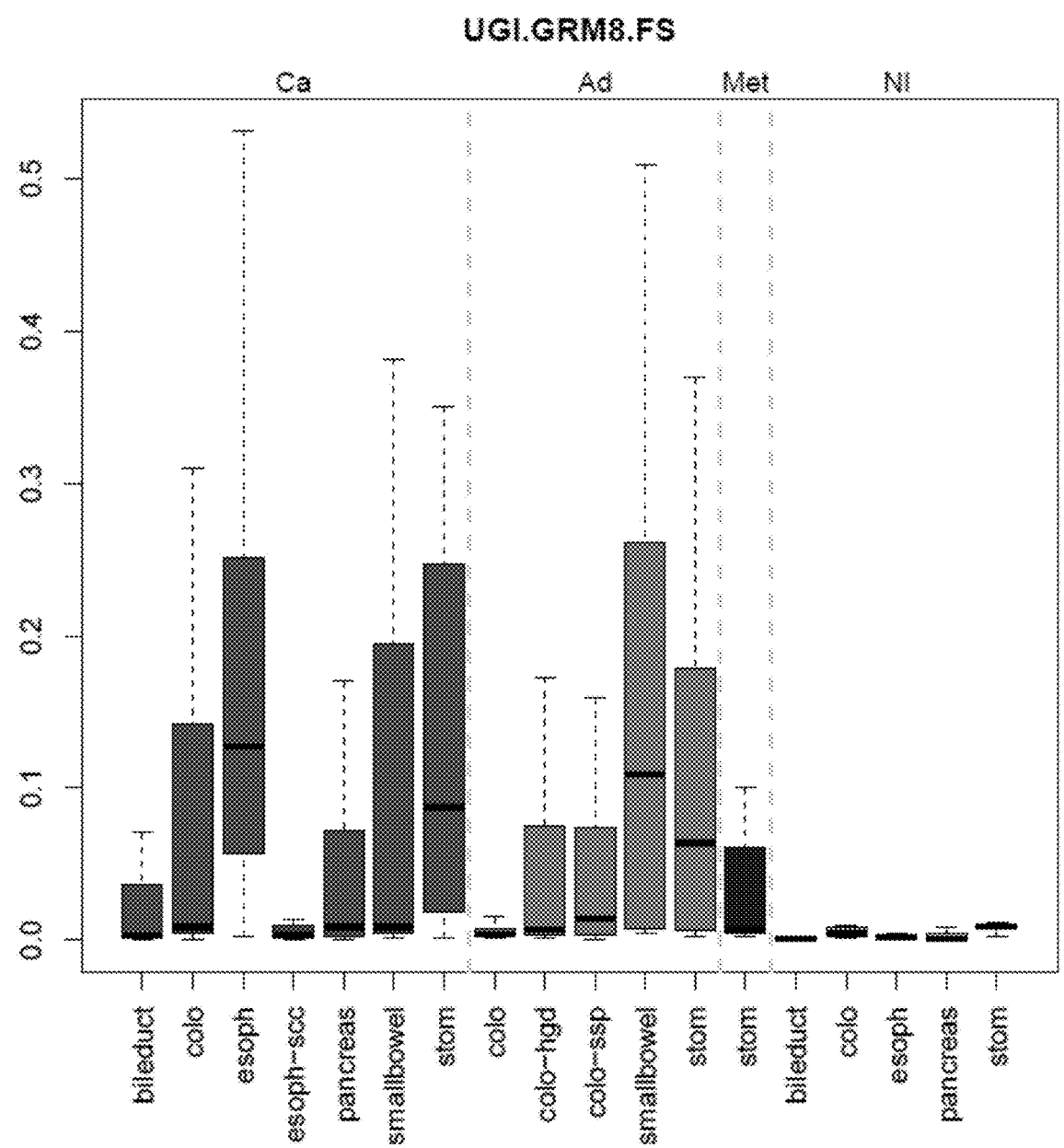

FIG. 1MMMM
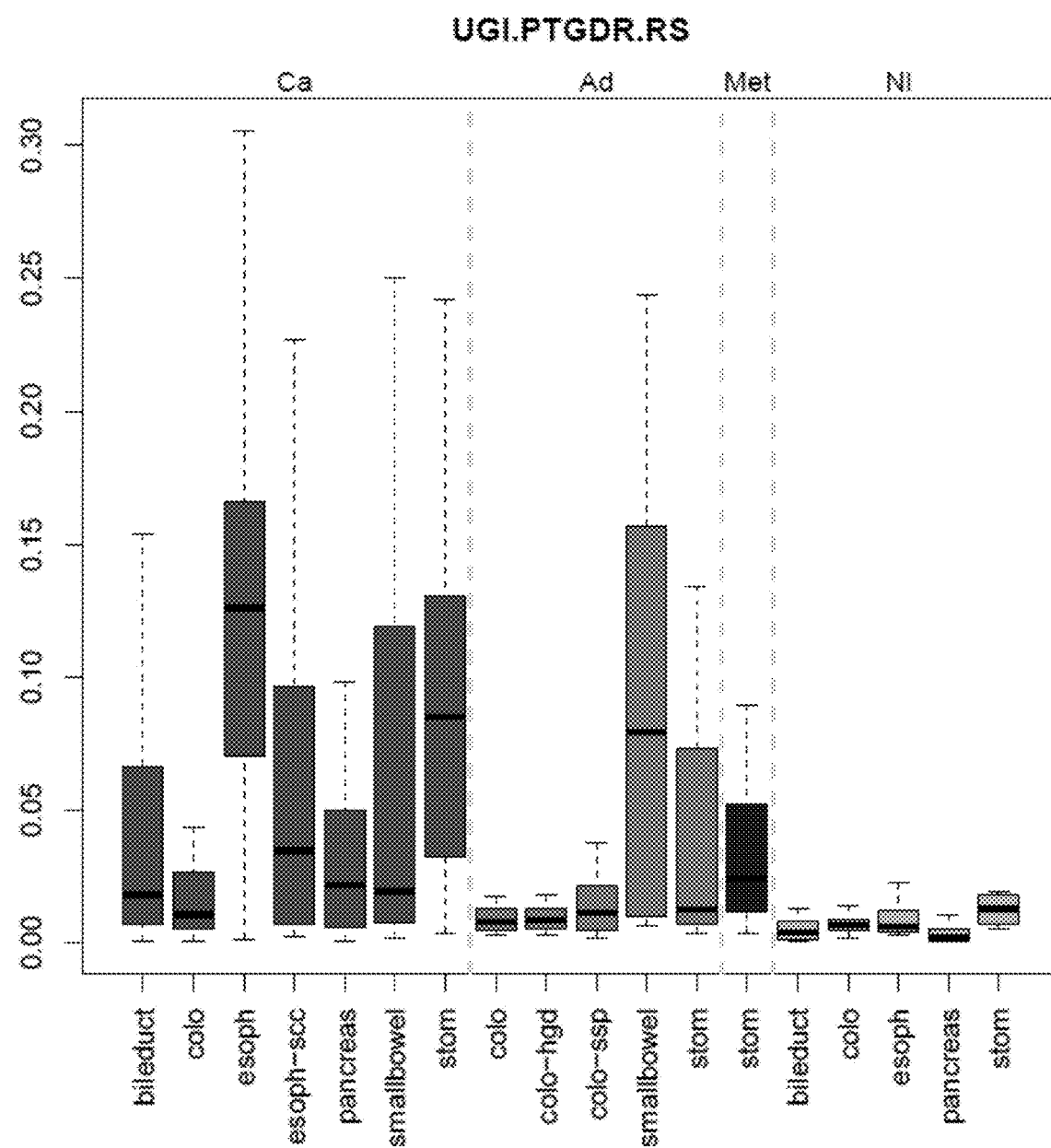

FIG. 1NNNN
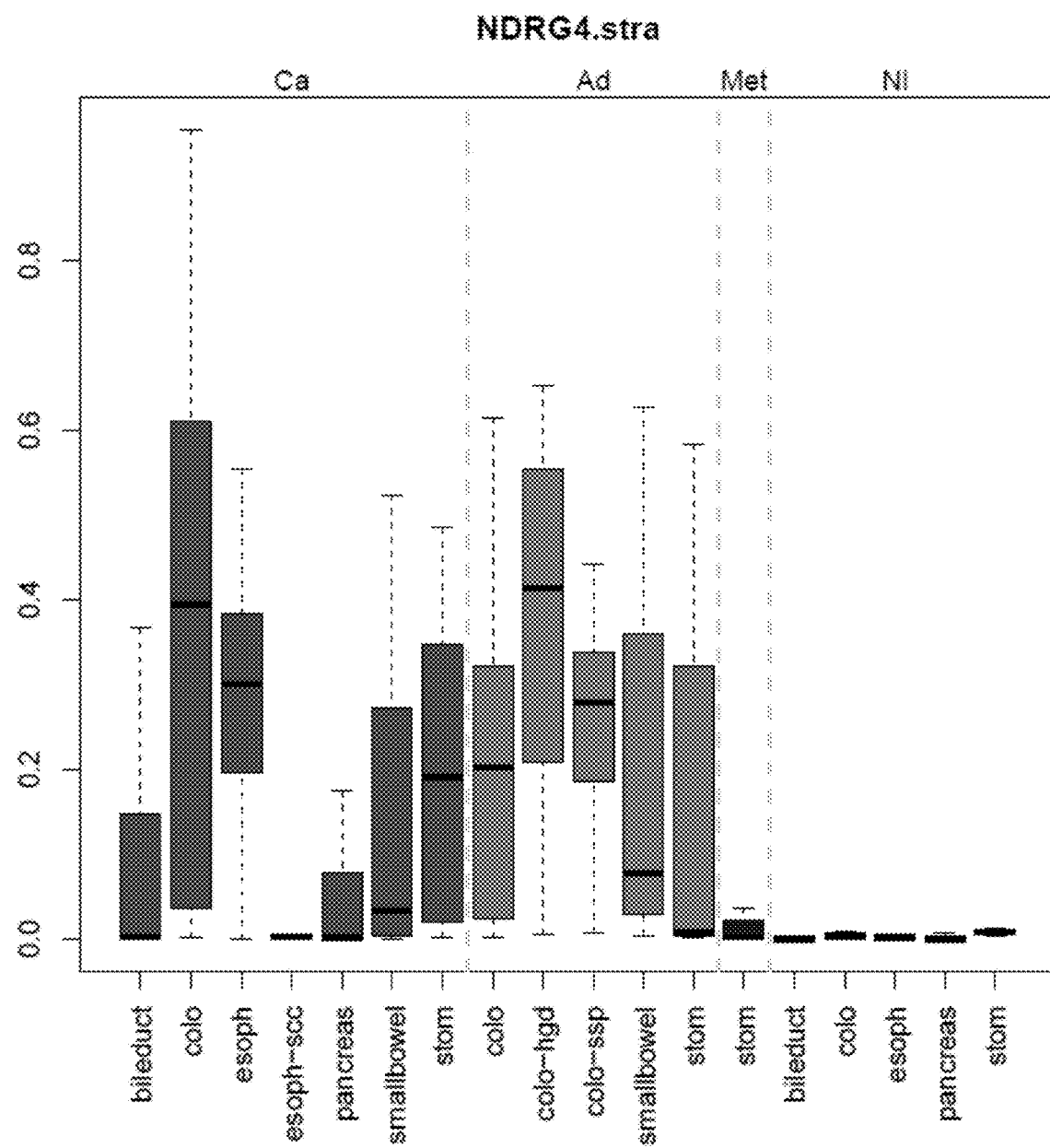

FIG. 10000
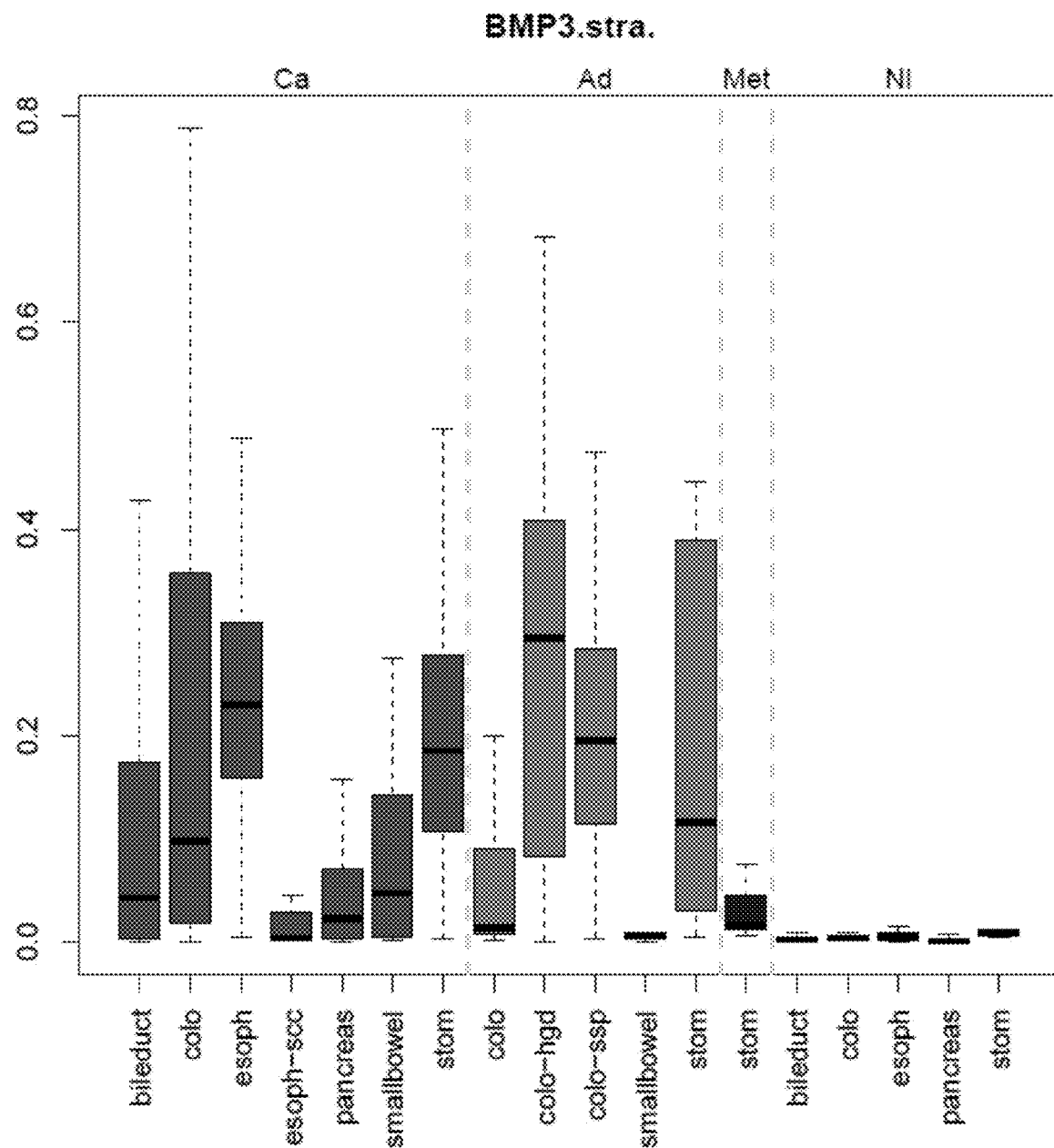

FIG. 2A

| Pancreas | Median PanC % Methylation | Median Nlm pancreas Methylation | Fold Change | AUC | Boot Strap Accuracy | ICC | Chr | Genomic Region Feb 2009 (GRCh37/hg19) assembly |
|---|---|---|---|---|---|---|---|---|
| PRKCB (pan) | 11.47727 | 0.011957 | 959.917 | 0.883 | 0.810 | 0.943 | 16 | 23846964-23848169 |
| NDRG4 | 32.62115 | 0.108826 | 301.223 | 0.934 | 0.848 | 0.961 | | |
| CD1D | 19.95748 | 0.092857 | 215.380 | 0.935 | 0.926 | 0.967 | 1 | 158150797-158151226 |
| RSPO3 | 12.56668 | 0.132478 | 94.858 | 0.899 | 0.839 | 0.959 | 6 | 127440492-127441039 |
| CLEC11A | 46.56978 | 0.717877 | 64.868 | 0.975 | 0.942 | 0.971 | 19 | 51226217-51228732 |
| BMP3 | 9.782619 | 0.172034 | 56.864 | 0.884 | 0.914 | 0.934 | | |
| ELMO1 (pan) | 45.41711 | 0.953 | 47.673 | 0.906 | 0.849 | 0.974 | 7 | 37487539-37480498 |
| ADCY11 | 82.22146 | 1.779 | 46.230 | 0.919 | 0.873 | 0.977 | 3 | 45013677-45014572 |
| IGF2BP1 | 18.95730 | 0.568 | 33.851 | 0.860 | 0.774 | 0.965 | 17 | 47073394-47073451 |
| AK055957 (chr12.133) | 43.41231 | 1.279 | 33.844 | 0.977 | 0.833 | 0.977 | 12 | 133484878-133485739 |
| TOX2 | 30.07744 | 1.184 | 25.396 | 0.823 | 0.825 | 0.944 | 20 | 42584780-42544835 |
| C13orf18 | 31.54265 | 1.371 | 23.003 | 0.848 | 0.858 | 0.968 | 13 | 46960767-46961669 |
| KCNK12 | 18.44448 | 0.859 | 21.486 | 0.916 | 0.865 | 0.968 | 2 | 47797280-47797371 |
| VWC2 | 55.31031 | 3.061 | 18.072 | 0.900 | 0.822 | 0.972 | 7 | 49813126-49814168 |
| KCNN2 | 6.28232 | 0.461 | 13.930 | 0.891 | 0.828 | 0.933 | 5 | 113619671-113697058 |
| ABCB1 (#2) | 12.52988 | 1.017 | 12.335 | 0.881 | 0.842 | 0.967 | 7 | 87229775-97229856 |
| PRKCB MF1 | | | | | | | 16 | 23846964-23848169 |
| IKZF1.R | | | | | | | 7 | 50343848-50343927 |

18 markers

| Pancreas | SEQ ID NO: | Forward MSP Primer (5'-3') | SEQ ID NO: | Reverse MSP Primer (5'-3') |
|---|---|---|---|---|
| PRKCB (pan) | 17 | AGG TTC GGG TTC GAC GAT TTC | 18 | AAC TCT ACA ACG DCG AAA CCG |
| NDRG44 | | | | |
| CD1D | 19 | GCG CGT AGC GGC GTT TC | 20 | CCC ATA TCG CCC GAC GTA A |
| RSPO3 | 21 | CGT TTA TTT AGC GTA ATC GTT TCG C | 22 | GAA TAA CGA AGG TTC GAC GAC CGA |
| CLEC11A | 23 | AGT TTG GCG TAG TCG GTA GAT C | 24 | GCG CGC AAA TAC CGA ATA AAC G |
| BMP3 | | | | |
| ELMO1 (pan) | 25 | TTT CGG GTT TTG CGT TTT ATT CGC | 26 | GAA AAA AAA AAA CGC TAA AAA TAC GAC G |
| ADCY11 | 27 | GGT TCG GTT GTC GTA GCG C | 28 | CCG ACC GTA ATC CTC GAC GA |
| IGF2BP1 | 29 | CGA GTA GTT TTT TTT TT ATC GTT TAG AC | 30 | CAA AAA ACG ACA CGT AAA CGA TCG |
| AK055957 (chr12.133) | 31 | TCG GCG TAT TTT TTT TCG TAG ACG C | 32 | CGC AAT CTT AAA CGT ACG CTT CGA |
| TOX2 | 33 | AGT TCG CGT TTT TTT CGG TCG TC | 34 | AAC CGA CGC ACC GAC TAA CGA |
| C13orf18 | 35 | TTT AGG GAA GTA AAG CGT CGT TTT C | 36 | AAC GAC GTC TCG ATA CCT ACG A |
| KCNK12 | 37 | GCG TCG TTA GTA CGA AGC | 38 | GCA CCT CAC CCT AAC CCG G |
| VWC2 | 39 | TTG GAG AGT TTT CG AAT TTT TTC GC | 40 | GAA AAC CAC CGG AAC CGC G |
| KCNN2 | 41 | TCG AGG CGG TTA ATT TTA TTC GC | 42 | GCT CTA ACC CAA ATA CGC TAC GA |
| ABCB1 (#2) | 43 | GAT TT GTT CGT CGT TAG TGC | 44 | TCT CTA AAC CCG CGA ACG A |
| PRKCB MF1 | 45 | AGT TGT TTT ATA TAT CGG CGT TCG G | 46 | GAC TAT ACA CGC TTA AGC GCG 4A |
| IKZF1.R | 47 | TAG AAG GGC GTA GAG CGG GAT ACG G | 48 | GAC GAA ACG AAA ACG AAA CGA CGC A |

| Stomach | Stomach % Methylation | stomach % Methylation | Fold Change | AUC | Boot Strap Accuracy | ICC | Chr | Genomic Region Feb 2009 (GRCh37/hg19) assembly |
|---|---|---|---|---|---|---|---|---|
| ADAM19.FS | 5.074627 | 0.000 | >1000 | 0.976 | 0.981 | 0.978 | 5 | 157092984-157086755 |
| CNR1.FS | 7.058074 | 0.000 | >1000 | 0.922 | 0.865 | 0.973 | 6 | 88875414-88875452 |
| GSG1L.R | 12.055738 | 0.000 | >1000 | 0.982 | 0.948 | 0.968 | 16 | 28674472-28674291 |
| LRRC4.R | 15.645418 | 0.000 | >1000 | 0.989 | 0.944 | 0.973 | 7 | 127971983-127972310 |
| NDRG4 | 10.424066 | 0.000 | >1000 | 0.891 | 0.916 | 0.978 | | |
| MAX.chr11.123301866-123301255.R | 7.750375 | 0.000 | 882.368 | 0.973 | 0.975 | 0.975 | 11 | 123301065-123301255 |
| FER1L4.R | 18.713853 | 0.028 | 577.516 | 0.972 | 0.948 | 0.984 | 20 | 34184488-34183566 |
| MAX.chr11.123301366-123301596.F | 13.624686 | 0.040 | 347.430 | 0.998 | 0.974 | 0.978 | 11 | 123301366-123301596 |
| BMP2 | 7.008323 | 0.021 | 333.815 | 0.946 | 0.822 | 0.976 | | |
| ZNF682RS | 10.334482 | 0.078 | 207.706 | 0.954 | 0.885 | 0.975 | 19 | 20149796-20149923 |
| AK055957 (chr12.133) | 15.435335 | 0.088 | 175.878 | 0.990 | 0.983 | 0.982 | 12 | 133434478-133436738 |
| CD1D | 12.449230 | 0.074 | 167.163 | 0.896 | 0.976 | 0.987 | 1 | 158150797-158161205 |
| DOCK10.FS | 9.443943 | 0.059 | 162.577 | 0.904 | 0.903 | 0.975 | 2 | 225597225-225597322 |
| ZNF569RS | 13.650099 | 0.124 | 109.991 | 0.937 | 0.921 | 0.973 | 19 | 37957763-37958046 |
| LRRC4.RS | 13.450491 | 0.177 | 76.160 | 0.891 | 0.919 | 0.976 | 7 | 127971983-127972310 |
| C12orf39.F | 7.611940 | 0.104 | 72.486 | 0.911 | 0.903 | 0.993 | 12 | 21580525-21580828 |
| GLC1 | 8.965438 | 0.147 | 67.680 | 0.904 | 0.817 | 0.992 | 17 | 42807289-42807997 |
| CELF2FS | 5.474171 | 0.085 | 64.511 | 0.873 | 0.878 | 0.971 | 10 | 11059947-11060085 |
| ZNF71 | 8.947576 | 0.162 | 55.075 | 0.985 | 0.978 | 0.992 | 19 | 57195756-57196947 |
| CLEC11 | 13.251966 | 0.293 | 45.261 | 1.000 | 0.995 | 0.959 | 19 | 51225217-51226733 |
| ST8SIA1 (stomach) | 10.647147 | 0.249 | 42.806 | 0.967 | 0.819 | 0.982 | 12 | 22287509-22487846 |
| C13orf18 | 9.351185 | 0.224 | 39.916 | 0.947 | 0.939 | 0.976 | 13 | 46560797-46561659 |

22 (8) markers

| Stomach | SEQ ID NO | Forward MSP Primer (5'-3') | SEQ ID NO | Reverse MSP Primer (5'-3') |
|---|---|---|---|---|
| ADAM19.FS | 89 | TTT TAG CGT TCG GCG TAT TTA TAT AC | 90 | ACG AAC CGA AAA ATT CCA AAC G |
| CNR1.FS | 91 | CGA TTT CGG CGT TAT TAA TTA TAC GTT TTC | 92 | ACG CCC GCG AAA GAT ATT AAC G |
| GSG1L.R | 93 | GCG GGC GCG TTA ATT GTT GTT TC | 94 | ACG ATA CGG TTA ACG STA ACG TT |
| LRRC4.R | 95 | GTT ATT TTC GCG ACG TAG GCG ACG | 96 | CGT AAT AGG ATA CTC TTA TAT AAC GGC GCT |
| NDRG4 | | | | |
| MAX.chr11.123301866-123301255.R | 97 | GTT GCG TTT TTT CGT TTG TTG GC | 98 | AAC CCC TAA CGA CCG AAT CGC GCT |
| FER1L4.R | 99 | TAG AGT TTT TTT CGT CGT TGA CGC | 100 | AAT ACG GCG TCG ACG AAA AAC G |
| MAX.chr11.123301366-123301596.F | 101 | CAG AGC CGA ATT AGG TCG TTG GC | 102 | CGA CAT AAA AAC CGT CGC TAC G |
| BMP2 | | | | |
| ZNF682RS | 103 | AGA GTT TAT GTT GGC AAG AGT CGC | 104 | CCC GCC AAT CGA AAC CGA AAA CG |
| AK055957 (chr12.133) | 105 | TCG CCG TAT TTT TCG TAG TAC GTT TTC | 106 | CCC AAT CCT AAA CGT ACG CTT CGA |
| CD1D | 107 | CGG GGC CGC GTT ATC GTT TC | 108 | CCG CATA CCG TTA ACG CTA ACG G |
| DOCK10.FS | 109 | TCG CGT TAA TTC GCG TTT CGC GGT C | 110 | GCG CCG TCG AAA TAC GGC G |
| ZNF569RS | 111 | TGT GGA ATC GCG GTT TGT GTT CGC | 112 | CGC AGG CGA CGA AAA AAA TCC GAC G |
| LRRC4.RS | 113 | CGT TGT TTA AGC GTA TAA CGT TCG GC | 114 | ATA ATC GCT AAT TAG TAA CGA CG |
| C12orf39.F | 115 | TAG TGA TTA CGG CGT TTG TAA GCG T | 116 | CTT TCT TTC CGC ACG AAC GCG AA |
| GLC1 | 117 | TCG ACG CGA GCG TTA ATT TTC | 118 | CGA ACT ATC CGA AAA ACG ACG AA |
| CELF2FS | 119 | GTA TTT GTT TTT CGT CGT TCG CGG TC | 120 | ACA ACG ACG CGC CAC AAT ACG |
| ZNF71 | 121 | CGT AGT TCG GCG TAG TTC GC | 122 | CCC CCG ATT KCG CCG ATT ACG |
| CLEC11 | 123 | AGT TTC CGG TAG TCG GTA CGT ATC C | 124 | CCG CGG AAT AKG CGG ACT ACG |
| ST8SIA1 (stomach) | 125 | TCC AGA CGC GTT TTT TGC GTC | 126 | AAC GAT CGC GAA ACG CGT A |
| C13orf18 | 127 | TTT AGG GAA GTA AGG CGT TTT C | 128 | AAG GAC GTC TCG ATA CGT ACG A |

FIG. 2D

| Bile Duct | Median BDC % Methylation | Median Nlm bile duct % Methylation | Fold Change | AUC | Boot Strap Accuracy | ICC | Chr | Genomic Region Feb 2009 (GRCh37/hg19) assembly |
|---|---|---|---|---|---|---|---|---|
| ST8SIA1.R (bd) | 5.945 | 0.000 | >1000 | 0.853 | 0.842 | 0.973 | 12 | 22488861-22487019 |
| LOC645323.R | 2.535 | 0.008 | 329.064 | 0.879 | 0.869 | 0.971 | 5 | 87970706-87970894 |
| PCBP3 | | | 37.750 | | | | 21 | 47063793-47064177 |
| PRKCB.R (BD) | 2.052 | 0.058 | 35.273 | 0.903 | 0.836 | 0.957 | 16 | 23847825-23848025 |
| CYP26C1.F | 8.454 | 0.241 | 35.143 | 0.922 | 0.858 | 0.979 | 10 | 94822416-94822607 |
| KLHDC7B.R | 6.158 | 0.178 | 34.615 | 0.899 | 0.874 | 0.937 | 22 | 50987205-50987270 |
| EMX1.F | 8.389 | 0.287 | 29.240 | 0.944 | 0.921 | 0.978 | 2 | 73147710-73147772 |
| SP9.F | 9.091 | 0.399 | 22.784 | 0.874 | 0.886 | 0.985 | 2 | 175202025-175202158 |
| HOXA1.F | 8.805 | 0.493 | 17.876 | 0.948 | 0.934 | 0.984 | 7 | 27135145-27135425 |
| MAX.chr7.25896389.25896501.R | 18.317 | 1.649 | 11.110 | 0.910 | 0.870 | 0.984 | 7 | 25896389-25896501 |
| 10 markers | | | | | | | | |

| Bile Duct | SEQ ID NO: | Forward MSP Primer (5'-3') | SEQ ID NO: | Reverse MSP Primer (5'-3') |
|---|---|---|---|---|
| ST8SIA1.R (bd) | 129 | CGG TTG TTT AAC GAG AAA GAG ATC GT | 130 | GAT GTA ATT CCT CCT CCA CGC CGT A |
| LOC645323.R | 131 | GGT AGT GTT TTT TCG AGA CGC GGT C | 132 | GAT ACG CGA ACA CGC ACA CG |
| PCBP3 | 133 | GGT CGC GTC GTT TTC GAT C | 134 | GCC GGA AAC GCC GAC GA |
| PRKCB.R (BD) | 135 | GTC GTT TTT GGG CGT TTT AGA GGC | 136 | TAA TCC CGA ACG AAC CGC CG |
| CYP26C1.F | 137 | GGT TTG GTT ATT TCG GAA TCG T | 138 | TAT AAA AAC GCG CGT AAT CAA CGC T |
| KLHDC7B.R | 139 | TAG TAC GTT TAG GTA ATT GTT TAG GTT TAG TCG T | 140 | CGA AAA CCC AAC TCC CGA A |
| EMX1.F | 141 | CGG GTT TTA GCG ATG TTT ATT TTA GTT TCG T | 142 | CCT TTT CGT TCG TAT AAA ATT TCG TT |
| SP9.F | 143 | CGG GGG TAA AAA GGG TAG CGA TAG TGA TAC | 144 | CGA AAA ATT CGA AAC GAA ACG TC |
| HOXA1.F | 145 | TGG TTT ATC GGT TTT TTA AGT TCG G | 146 | GAA TTC CTC CCA ACC AAC CCT CTA CG |
| MAX.chr7.25896389.25896501.R | 147 | GTT TTT CGT TGA GTT AGA AGC GTT | 148 | ACC TCA ATA TAA ATA AAA ACG CAA |

FIG. 2E

| CRC | Fold Change AUC | Chr | Genomic Region Feb 2009 (GRCh37/hg19) assembly |
|---|---|---|---|
| CHST2_7880 | >1000 | 0.947 | 3 | 142839645-142839923 |
| DTX1 | >1000 | 0.974 | 12 | 113494586-113494957 |
| FLI1 | >1000 | 0.986 | 11 | 128561956-128564209 |
| KCNK12 | >1000 | 0.963 | 2 | 47797187-47797452 |
| PDGFD | >1000 | 0.944 | 11 | 104034769-104034920 |
| PKIA | >1000 | 0.945 | 8 | 79428486-79428884 |
| PPP2R5C | >1000 | 0.949 | 14 | 102247525-102247929 |
| SFMBT2_895 | >1000 | 0.931 | 10 | 7452089-7452452 |
| SFMBT2_897 | >1000 | 0.952 | 10 | 7453685-7453956 |
| VAV3_879 | >1000 | 0.882 | 1 | 108507609-108507674 |
| SLC8A3 | 590.000 | 0.883 | 14 | 70655516-70655712 |
| CHST2_7889 | 190.000 | 0.931 | 3 | 142838022-142838494 |
| VAV3_878 | 135.000 | 0.954 | 1 | 108507074-108507498 |
| SFMBT2_896 | 80.000 | 0.971 | 10 | 7452745-7452779 |
| ELOVL2 | 70.000 | 0.935 | 6 | 11044395-11044824 |
| OPLAH | 67.000 | 0.901 | 8 | 145109340-145109439 |
| MATK | 64.000 | 0.972 | 19 | 3786826-3786971 |
| QKI | 50.000 | 0.921 | 6 | 163834534-163834925 |

18 markers

| CRC | SEQ ID NO. | Forward MSP Primer (5'-3') | SEQ ID NO. | Reverse MSP Primer (5'-3') |
|---|---|---|---|---|
| CHST2_7880 | 149 | GGA ACG AGT GAT AGT CGG ATA GTT CGT C | 150 | CGC CGG AAA ACG ACC CCG |
| DTX1 | 151 | GAG TCG CGG TTT CGT TTT C | 152 | GAC GCG ACG ACC GAA AAC |
| FLI1 | 153 | CGG AGT GAG GGT AGG GCG TTC | 154 | CTC GCA ACC CCT TCG AAT TAA CCC G |
| KCNK12 | 155 | CGT ATC GTC GCG TTT TAG CGC | 156 | TCG AAA ACC CCG ACG AAA TAC CGA AAA CC |
| PDGFD | 157 | GCG AAT AAA TAA ACG TTA ATT TGT TGT TTG TTT C | 158 | CCG AAC GCG TAT AAA TAC CGC ATC AAC TCG |
| PKIA | 159 | CGG GGA TGA TTT TAT GTA GTC GGA GTT TCG C | 160 | CCC GCC GAA TAC TCG ATC AAC TCG |
| PPP2R5C | 161 | TCG ATT TAT TTT TTA TTT CGT TTA TAG ATT CGG | 162 | GGA AAA AGT AAA ATA CTA CAA AAT AAC CCG ACG |
| SFMBT2_895 | 163 | GCG ACG TAC TCG TCG TCG T | 164 | TAA ACG CGA AAA CGG CGG |
| SFMBT2_897 | 165 | GTC GTC GTT CGA GAG GGT A | 166 | CGA ACA AAA ACG AAC GAA CGA A |
| VAV3_879 | 167 | GGA TCG AGG AGT AGGA AGT TGC | 168 | CGGAACG AAAACCT AAC GCG TAC ACG |
| SLC8A3 | 169 | AGT TTT GCG CGT TTT TTT TGC | 170 | GCC GAA TCT CCG GCG AAA TCT AAA ACT |
| CHST2_7889 | 171 | CGA GTT CCG TAG TTG TAC GTA GA | 172 | AAA ATA TTA CCC AGC AAC CAC CGA A |
| VAV3_878 | 173 | GCG TAA GGT CGA ATA TTT GAG TCG A | 174 | CCT AAC CAA CCC ACT CAA CC |
| SFMBT2_896 | 175 | GCG TTT ATG TTC GTC GGA GA | 176 | CGA CTA CCG TAA ACA ACG CAT CGC |
| ELOVL2 | 177 | CGG TTT TAT TTA TTGA ATC GTA GCGG | 178 | ACA AAA CAC ATC CTA TTA ACG CGA A |
| OPLAH | 179 | TGC GTA GGT GAT AGG GAG GGG TTA C | 180 | CGC CCC CAA AAT GCG AAA ACG AA |
| MATK | 181 | TGT ATA TTT CGA GGC GGT TTC GG | 182 | |
| QKI | 183 | GAG GCG GAC GTC GCG GTA C | 184 | CGC CAC GAC GCA AAT GCG AAT TAC G |

FIG. 2F

| Upper GI | Median LGI % Methylation | Median UGI % Methylation | Median Nlm % Methylation | Fold Change LGI | Fold Change UGI | AnyCa AUC | Chr | Genomic Region Feb 2009 (GRCh37/hg19) assembly |
|---|---|---|---|---|---|---|---|---|
| GMR8 FS | 0.004 | 1.823 | 0.007 | 0.517 | 246.143 | 0.701 | 7 | 126891703-126892479 |
| C13orf18 | 0.000 | 1.534 | 0.010 | 0.021 | 151.110 | 0.569 | 13 | 46960767-46961669 |
| CLEC11A | 0.074 | 7.260 | 0.087 | 0.852 | 83.106 | 0.772 | 19 | 51228217-51228732 |
| KCNN2 | 0.016 | 1.184 | 0.020 | 0.820 | 59.417 | 0.727 | 5 | 113696971-113697058 |
| CD200 FS | 0.062 | 1.343 | 0.043 | 1.435 | 30.952 | 0.782 | 3 | 112052189-112052342 |
| PTGDR RS | 0.323 | 3.776 | 0.489 | 0.660 | 7.720 | 0.647 | 14 | 52735290-52735389 |

6 (3) markers

| Upper GI | SEQ ID NO: | Forward MSP Primer (5'-3') | SEQ ID NO: | Reverse MSP Primer (5'-3') |
|---|---|---|---|---|
| GMR8 FS | 185 | CGA AAG TTA TAA AAG AGG GGT ACG G | 186 | GTT CTC CGA ATT AAC ACG ACG AA |
| C13orf18 | 187 | TTT AGG GAA GTA AAG CGT CGT TTT C | 188 | AAC GAC GTC TCG ATA CCT ACG A |
| CLEC11A | 189 | AGT TTG GCG TAG TCG GTA GAT C | 190 | GCG CGC AAA TAC CGA ATA AAC G |
| KCNN2 | 191 | TCG AGG CGG TTA ATT TTA TTC GC | 192 | GCT CTA ACC CAA ATA CGC TAC GA |
| CD200 FS | 193 | TTA GAT TAG CGG TGT TGA TGG TAG CGT | 194 | CCA CCC TTT AAA AAA CAA AAT CCG TT |
| PTGDR RS | 195 | GGG TAG AGA ATA TAT AGT GAA GAG TAC GG | 196 | ACT AAA TCA CCT CCT ACT ACT AAC GCT |

FIG. 2G

| CRC (lower GI) Specific | Median LGI % Methylation | Median UGI % Methylation | Median Nlm % Methylation | Fold Change LGI | Fold Change UGI | AnyCa AUC | Chr | Genomic Region Feb 2009 (GRCh37/hg19) assembly |
|---|---|---|---|---|---|---|---|---|
| FAM72A-RS | 16.434 | 0.000 | | >1000 | 0.000 | 0.725 | 1 | 206137392-206137490 |
| ZNF304-RS | 54.156 | 0.001 | 0.015 | >1000 | 0.080 | 0.793 | 19 | 57862480-57862925 |
| CHST15 (1023)-FS | 30.649 | 0.000 | 0.000 | >1000 | 0.638 | 0.743 | 10 | 125852905-125853007 |
| TMEM163-FS | 24.649 | 0.025 | 0.003 | >1000 | 8.284 | 0.907 | 2 | 135476049-135476380 |
| ZNF543-FS | 8.899 | 0.004 | 0.005 | >1000 | 0.706 | 0.892 | 19 | 57832086-57832193 |
| DAB2IP (691)-FS | 46.446 | 0.091 | 0.071 | 651.859 | 1.276 | 0.801 | 9 | 124461305-124461420 |
| CNNM1 (806)-RS | 64.893 | 2.239 | 0.207 | 313.006 | 10.798 | 0.875 | 10 | 101088034-101089133 |
| FAM72D-RS | 16.448 | 0.000 | 0.091 | 181.053 | 0.000 | 0.639 | 1 | 143913353-143913603 |
| TRIB2-FS | 18.171 | 0.014 | 0.102 | 159.061 | 0.133 | 0.583 | 2 | 12858176-12858230 |
| 9 markers | | | | | | | | |
| Total = 94 + universal control = 95 | | | | | | | | |

| CRC (lower GI) Specific | SEQ ID NO: | Forward MSP Primer (5'-3') | SEQ ID NO: | Reverse MSP Primer (5'-3') |
|---|---|---|---|---|
| FAM72A-RS | 197 | ATT TTT TAG GAT TGC GAG TTT TTC | 198 | AAA CGA CTA AAT ACC GAC TAC G |
| ZNF304-RS | 199 | GGT AAG AGT TTA GTT TCG GTA GAT ATT TTC GC | 200 | AAT CCA TAA CCC CTA TCG TAA AAC GAA ACG |
| CHST15 (1023)-FS | 201 | TAT CCT GAA AGT ATT GGT TTG TTC GTC | 202 | AAC CCA ATA ATC GAA ATC GAA ACG |
| TMEM163-FS | 203 | GTC GGG TCG GGT AGT TCG C | 204 | AAC GAA AAC GAC CAA TTC AAC GAC C |
| ZNF543-FS | 205 | TTG GGG AAA TTG AGG TTT CGA GTG C | 206 | GAC CCC CAA CCC TTC TCT ATC CTA AAC GAA |
| DAB2IP (691)-FS | 207 | GGC GCG GTT CGG TTC | 208 | CCC CCT AAA CCG CTA TTA CCT TAA CG |
| CNNM1 (806)-RS | 209 | ACG TGA TAT TGT AGG AAG TCG AGC G | 210 | CGT ACG ACT AAA TTC CCA AAC T CCG A |
| FAM72D-RS | 211 | AGT TGA GGT ACG GTT AAT TGG GTC G | 212 | GAT CTC TAC TCT TTA TTA ATT AAA ATT CCC CGC |
| TRIB2-FS | 213 | TAT AGA GTA ATT AAA AGT GCG GCG A | 214 | TTA TTA CCC CAA AAT AAT CGA CGA T |

DETECTING GASTROINTESTINAL NEOPLASMS

CROSS-REFERENCE TO RELATED APPLICATIONS

This application is a continuation of U.S. patent application Ser. No. 16/030,313 filed Jul. 9, 2018, now allowed as U.S. Pat. No. 10,704,107, which is a continuation of U.S. patent application Ser. No. 15/054,860, filed Feb. 26, 2016, now allowed as U.S. Pat. No. 10,030,272, which claims priority to U.S. Provisional Patent Application No. 62/126,061, filed Feb. 27, 2015, the contents of which are incorporated by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 39,000 Byte ASCII (Text) file named "34363-US-4-CON_ST25" created on Jun. 22, 2020.

FIELD OF INVENTION

Provided herein is technology for gastrointestinal neoplasia screening and particularly, but not exclusively, to methods, compositions, and related uses for detecting the presence of gastrointestinal neoplasm, and classifying the site location of such a gastrointestinal neoplasm (e.g., a colorectal region, a pancreaticobiliary region, a gastroesophageal region).

BACKGROUND

When upper gastrointestinal cancers (UGC) are combined with colorectal cancer (CRC), mortality from GI cancers is greater than for any other organ system. In 2012, it was estimated that 120,000 men and women were diagnosed with UGC, which caused nearly 90,000 deaths (compared to <50,000 by CRC in the same time period) (see, e.g., Siegel R, et al., 2012. CA Cancer J Clin 2012; 62:10-29). Patients who present with symptoms typically have advanced stage disease; and only a minority, usually early stage patients, is cured (see, e.g., Cleary S P, et al., J Am Coll Surg 2004; 198:722-31; Talsma K, et al., Ann Surg Oncol 2012; 19:2142-8). Remarkably, although the aggregate death toll from UGC exceeds that of CRC, general population screening for UGC does not exist in this country. Tools considered to screen asymptomatic individuals for UGC have been dismissed as too invasive, insensitive, or cost-prohibitive for application at the population-wide level (see, e.g., Gudlaugsdottir S, et al., Eur J Gastroenterol Hepatol 2001; 13:639-45; Inadomi J M, Keio J Med 2009; 58:12-8; Yeh J M, et al., Gastrointest Endosc 2010; 72:33-43; Rulyak S J, et al., Gastrointest Endosc 2003; 57:23-9). A noninvasive, accurate, and affordable screening tool capable of the screen-detection of all GI cancers is needed.

SUMMARY

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) Nat Rev Genet 11: 191-203). Furthermore, in other cancers like sporadic colon cancer, methylation markers offer excellent specificity and are more broadly informative and sensitive than are individual DNA mutations (Zou et al (2007) Cancer Epidemiol Biomarkers Prev 16: 2686-96).

Analysis of CpG islands has yielded important findings when applied to animal models and human cell lines. For example, Zhang and colleagues found that amplicons from different parts of the same CpG island may have different levels of methylation (Zhang et al. (2009) PLoS Genet 5: e1000438). Further, methylation levels were distributed bi-modally between highly methylated and unmethylated sequences, further supporting the binary switch-like pattern of DNA methyltransferase activity (Zhang et al. (2009) PLoS Genet 5: e1000438). Analysis of murine tissues in vivo and cell lines in vitro demonstrated that only about 0.3% of high CpG density promoters (HCP, defined as having >7% CpG sequence within a 300 base pair region) were methylated, whereas areas of low CpG density (LCP, defined as having <5% CpG sequence within a 300 base pair region) tended to be frequently methylated in a dynamic tissue-specific pattern (Meissner et al. (2008) Nature 454: 766-70). HCPs include promoters for ubiquitous housekeeping genes and highly regulated developmental genes. Among the HCP sites methylated at >50% were several established markers such as Wnt 2, NDRG2, SFRP2, and BMP3 (Meissner et al. (2008) Nature 454: 766-70).

Accordingly, provided herein is technology for gastrointestinal neoplasia screening and particularly, but not exclusively, to methods, compositions, and related uses for detecting the presence of gastrointestinal neoplasm, and classifying the site location of such a gastrointestinal neoplasm (e.g., a colorectal region, a pancreaticobiliary region, a gastroesophageal region).

Indeed, experiments conducted during the course of developing this technology compared the methylation state of DNA markers from esophageal tissue, stomach tissue, pancreatic tissue, bile duct/liver tissue, and colorectal tissue of subjects having neoplasm related to the respective tissue type to the methylation state of the same DNA markers from control subjects (e.g., normal tissue for the respective tissue type) (see, Example 1).

Markers and/or panels of markers were identified (e.g., a chromosomal region having an annotation selected from chr12.133484978-133485739, BMP3, and chr11.123301058-123301255) capable of classifying gastrointestinal (GI) neoplasm versus control (e.g., normal tissue for the respective tissue type) across GI tissue types (e.g., esophageal tissue, stomach tissue, pancreatic tissue, bile duct/liver tissue, and colorectal tissue) (see, Example 1).

Markers and/or panels of markers were identified (e.g., a chromosomal region having an annotation selected from chr7.25896389-25896501, and QKI) capable of classifying lower gastrointestinal (LGI) neoplasm versus upper gastrointestinal neoplasm (UGI) across GI tissue types (e.g., esophageal tissue, stomach tissue, pancreatic tissue, bile duct/liver tissue, and colorectal tissue) (see, Example 1).

Markers and/or panels of markers were identified (e.g., a chromosomal region having an annotation selected from PDGFD, ELOVL2, PCBP3) capable of classifying pancreaticobiliary neoplasm versus gastroesophageal neoplasm across GI tissue types (e.g., esophageal tissue, stomach tissue, pancreatic tissue, bile duct/liver tissue, and colorectal tissue) (see, Example 1).

Markers and/or panels of markers were identified (e.g., a chromosomal region having an annotation selected from QKI, PDGFD, ELOVL2, chr12.133484978-133485739, chr7.25896389-25896501, PCBP3, chr11.123301058-123301255, and BMP3) capable of predicting control versus neoplasm location across GI tissue types (e.g., esophageal tissue, stomach tissue, pancreatic tissue, bile duct/liver tissue, and colorectal tissue) (see, Example 1).

Markers and/or panels of markers were identified (e.g., a chromosomal region having an annotation selected from BMP3 and QKI) capable of predicting control versus neoplasm location in blood plasma samples (see, Example 1).

Markers and/or panels of markers were identified (e.g., a chromosomal region having an annotation selected from BMP3 and QKI) capable of predicting colorectal cancer versus pancreaticobiliary neoplasm in blood plasma samples (see, Example 1).

Additional statistical analysis of the results demonstrated that the technology described herein based on these markers specifically and sensitively predicts a tumor site.

As described herein, the technology provides a number of methylated DNA markers and subsets thereof (e.g., sets of 2, 3, 4, 5, 6, 7, or 8 markers) with high discrimination for GI neoplasms overall and/or at individual tumor sites. Experiments applied a selection filter to candidate markers to identify markers that provide a high signal to noise ratio and a low background level to provide high specificity, e.g., when assaying distant media (e.g., stool, blood, urine, metastatic tissue, etc.) for purposes of cancer screening or diagnosis. Further, experiments were performed to demonstrate that the identified methylated DNA markers predict tumor site. As such, the technology provides for specific markers, marker combinations, and algorithms to predict tumor site.

In some embodiments, the technology is related to assessing the presence of and methylation state of one or more of the markers identified herein in a biological sample. These markers comprise one or more differentially methylated regions (DMR) as discussed herein, e.g., as provided in Table 1. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) Mol. Cell. Biol. 14: 7421-7427) and another example involves methylation-sensitive arbitrarily primed PCR (Gonzalgo et al. (1997) Cancer Res. 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR amplification (Singer-Sam et al. (1990) Nucl. Acids Res. 18: 687). In addition, other techniques have been reported that utilize bisulfite treatment of DNA as a starting point for methylation analysis. These include methylation-specific PCR (MSP) (Herman et al. (1992) Proc. Natl. Acad. Sci. USA 93: 9821-9826) and restriction enzyme digestion of PCR products amplified from bisulfite-converted DNA (Sadri and Hornsby (1996) Nucl. Acids Res. 24: 5058-5059; and Xiong and Laird (1997) Nucl. Acids Res. 25: 2532-2534). PCR techniques have been developed for detection of gene mutations (Kuppuswamy et al. (1991) Proc. Natl. Acad. Sci. USA 88: 1143-1147) and quantification of allelic-specific expression (Szabo and Mann (1995) Genes Dev. 9: 3097-3108; and Singer-Sam et al. (1992) PCR Methods Appl. 1: 160-163). Such techniques use internal primers, which anneal to a PCR-generated template and terminate immediately 5' of the single nucleotide to be assayed. Methods using a "quantitative MS-SNUPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QuARTS assay (e.g., as provided by U.S. Pat. No. 8,361, 720; and U.S. Pat. Appl. Pub. Nos. 2012/0122088 and 2012/0122106).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMR, e.g., DMR 1-8 as provided in Table 1); comparing methylation states (e.g., of one or more DMR, e.g., DMR 1-8 as provided in Table 1); generating standard curves; determining a Ct value; calculating a fraction, frequency, or percentage of methylation (e.g., of one or more DMR, e.g., DMR 1-8 as provided in Table 1); identifying a CpG island; determining a specificity and/or sensitivity of an assay or marker; calculating an ROC curve and an associated AUC; sequence analysis; all as described herein or is known in the art.

In some embodiments, a microprocessor or computer uses methylation state data in an algorithm to predict a site of a cancer.

In some embodiments, a software or hardware component receives the results of multiple assays and determines a single value result to report to a user that indicates a cancer risk based on the results of the multiple assays (e.g., determining the methylation state of multiple DMR, e.g., as provided in Table 1). Related embodiments calculate a risk factor based on a mathematical combination (e.g., a weighted combination, a linear combination) of the results from multiple assays, e.g., determining the methylation states of multiple markers (such as multiple DMR, e.g., as provided in Table 1). In some embodiments, the methylation state of a DMR defines a dimension and may have values in a multidimensional space and the coordinate defined by the methylation states of multiple DMR is a result, e.g., to report to a user, e.g., related to a cancer risk.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

Accordingly, provided herein is technology related to a method of screening for a gastrointestinal neoplasm in a sample obtained from a subject, the method comprising assaying a methylation state of a marker in a sample obtained from a subject; and identifying the subject as having a neoplasm when the methylation state of the marker is different than a methylation state of the marker assayed in a subject that does not have a neoplasm, wherein the marker comprises a base in a differentially methylated region (DMR) selected from a group consisting of DMR 1-8 as provided in Table 1.

In some embodiments, the method further comprises locating the neoplasm site within the subject, wherein the methylation state of the marker indicates the neoplasm site within the subject. The technology is related to identifying and discriminating gastrointestinal neoplasm. In some embodiments, the methylation state of markers (e.g., a chromosomal region having an annotation selected from chr7.25896389-25896501, and QKI) are used to classify lower gastrointestinal (LGI) neoplasm versus upper gastrointestinal (UGI). In some embodiments, the methylation state of markers (e.g., a chromosomal region having an annotation selected from PDGFD, ELOVL2, PCBP3) are used to classify pancreaticobiliary neoplasm versus gastroesophageal neoplasm. In some embodiments, the methylation state of markers (e.g., a chromosomal region having an annotation selected from BMP3 and QKI) are used to classify colorectal cancer versus pancreaticobiliary neoplasm. The technology also encompasses determining the state or stage of a cancer, e.g., in some embodiments the neoplasm is pre-cancerous. Some embodiments provide methods comprising assaying a plurality of markers, e.g., comprising assaying 2 to 8 markers.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample (e.g., esophageal tissue, stomach tissue, pancreatic tissue, bile duct/liver tissue, and colorectal tissue), a blood sample (e.g., plasma, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMR, e.g., in some embodiments are provided a set of oligonucleotides comprising the sequences provided by SEQ ID NO: 1-16. In some embodiments are provided an oligonucleotide comprising a sequence complementary to a chromosomal region having a base in a DMR, e.g., an oligonucleotide sensitive to methylation state of a DMR.

The technology provides various panels of markers, e.g., in some embodiments the marker comprises a chromosomal region having an annotation that is QKI, PDGFD, ELOVL2, chr12.133484978-133485739, chr7.25896389-25896501, PCBP3, chr11.123301058-123301255, and BMP3, and that comprises the marker (see, Table 1). In addition, embodiments provide a method of analyzing a DMR from Table 1 that is DMR No. 1-8.

Kit embodiments are provided, e.g., a kit comprising a bisulfite reagent; and a control nucleic acid comprising a sequence from a DMR selected from a group consisting of DMR 1-8 (from Table 1) and having a methylation state associated with a subject who does not have a cancer. In some embodiments, kits comprise a bisulfite reagent and an oligonucleotide as described herein. In some embodiments, kits comprise a bisulfite reagent; and a control nucleic acid comprising a sequence from a DMR selected from a group consisting of DMR 1-8 (from Table 1) and having a methylation state associated with a subject who has a cancer. Some kit embodiments comprise a sample collector for obtaining a sample from a subject (e.g., a stool sample); reagents for isolating a nucleic acid from the sample; a bisulfite reagent; and an oligonucleotide as described herein.

The technology is related to embodiments of compositions (e.g., reaction mixtures). In some embodiments are provided a composition comprising a nucleic acid comprising a DMR and a bisulfite reagent. Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for a neoplasm in a sample obtained from a subject, e.g., a method comprising determining a methylation state of a marker in the sample comprising a base in a DMR that is one or more of DMR 1-8 (from Table 1); comparing the methylation state of the marker from the subject sample to a methylation state of the marker from a normal control sample from a subject who does not have a cancer; and determining a confidence interval and/or a p value of the difference in the methylation state of the subject sample and the normal control sample. In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMR with a bisulfite reagent to produce a bisulfite-reacted nucleic acid; sequencing the bisulfite-reacted nucleic acid to provide a nucleotide sequence of the bisulfite-reacted nucleic acid; comparing the nucleotide sequence of the bisulfite-reacted nucleic acid with a nucleotide sequence of a nucleic acid comprising the DMR from a subject who does not have a cancer to identify differences in the two sequences; and identifying the subject as having a neoplasm when a difference is present.

Systems for screening for a gastrointestinal neoplasm in a sample obtained from a subject are provided by the technology. Exemplary embodiments of systems include, e.g., a system for screening for a gastrointestinal neoplasm in a sample obtained from a subject, the system comprising an analysis component configured to determine the methylation state of a sample, a software component configured to compare the methylation state of the sample with a control sample or a reference sample methylation state recorded in a database, and an alert component configured to alert a user of a cancer-associated methylation state. An alert is determined in some embodiments by a software component that receives the results from multiple assays (e.g., determining the methylation states of multiple markers, e.g., DMR, e.g., as provided in Table 1) and calculating a value or result to report based on the multiple results. Some embodiments provide a database of weighted parameters associated with each DMR provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a cancer risk in a subject.

In some embodiments of systems, a sample comprises a nucleic acid comprising a DMR. In some embodiments the system further comprises a component for isolating a nucleic acid, a component for collecting a sample such as a component for collecting a stool sample. In some embodiments, the system comprises nucleic acid sequences comprising a DMR. In some embodiments the database comprises nucleic acid sequences from subjects who do not have a cancer. Also provided are nucleic acids, e.g., a set of nucleic acids, each nucleic acid having a sequence comprising a DMR. In some embodiments the set of nucleic acids wherein each nucleic acid has a sequence from a subject who does not have a cancer. Related system embodiments comprise a set of nucleic acids as described and a database of nucleic acid sequences associated with the set of nucleic acids. Some embodiments further comprise a bisulfite reagent. And, some embodiments further comprise a nucleic acid sequencer.

Additional embodiments will be apparent to persons skilled in the relevant art based on the teachings contained herein.

BRIEF DESCRIPTION OF THE DRAWINGS

Figure 2B:
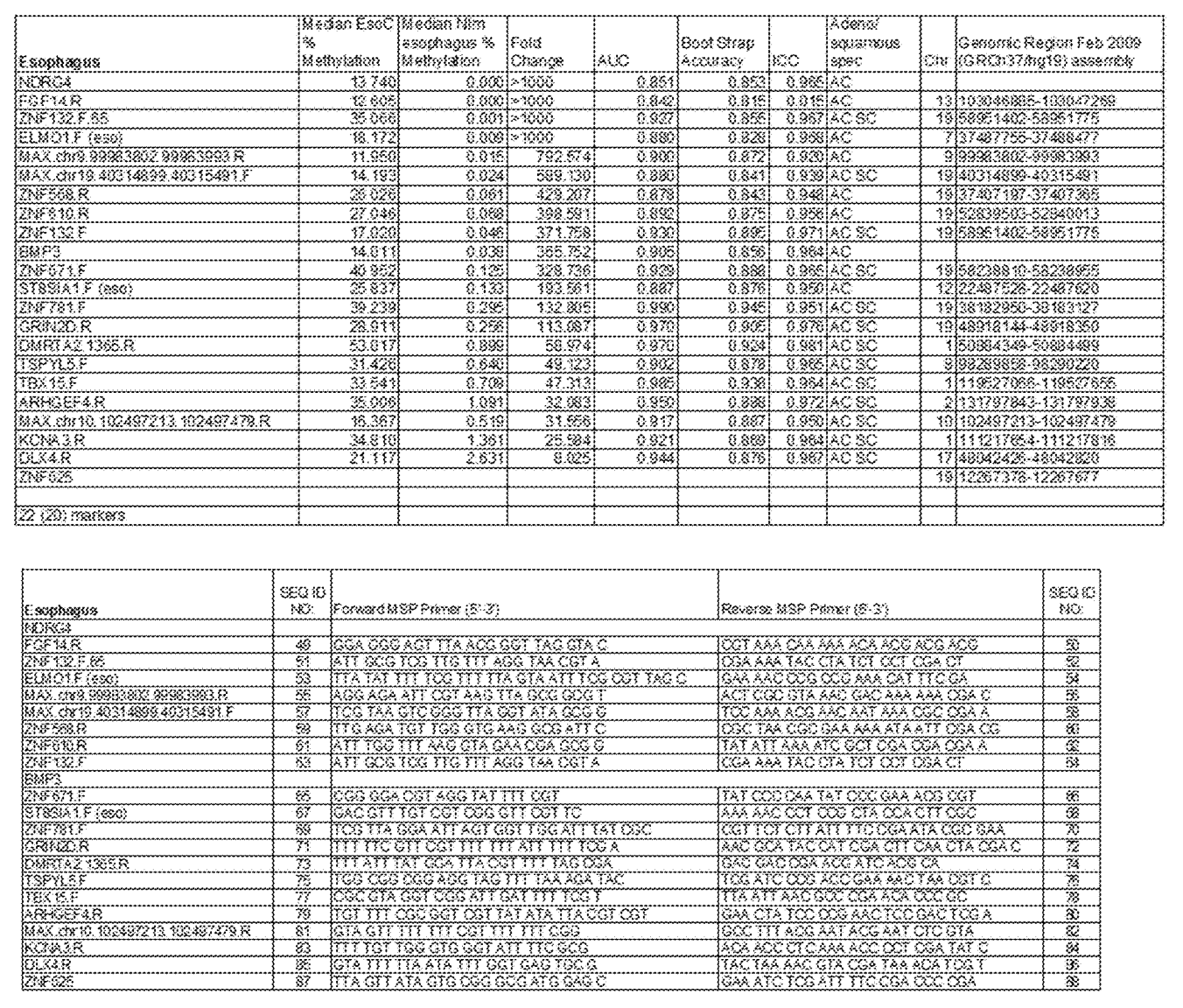

FIG. 2A-G shows the top markers which resulted from the MSP biological validation.

DETAILED DESCRIPTION

Figure 1A:
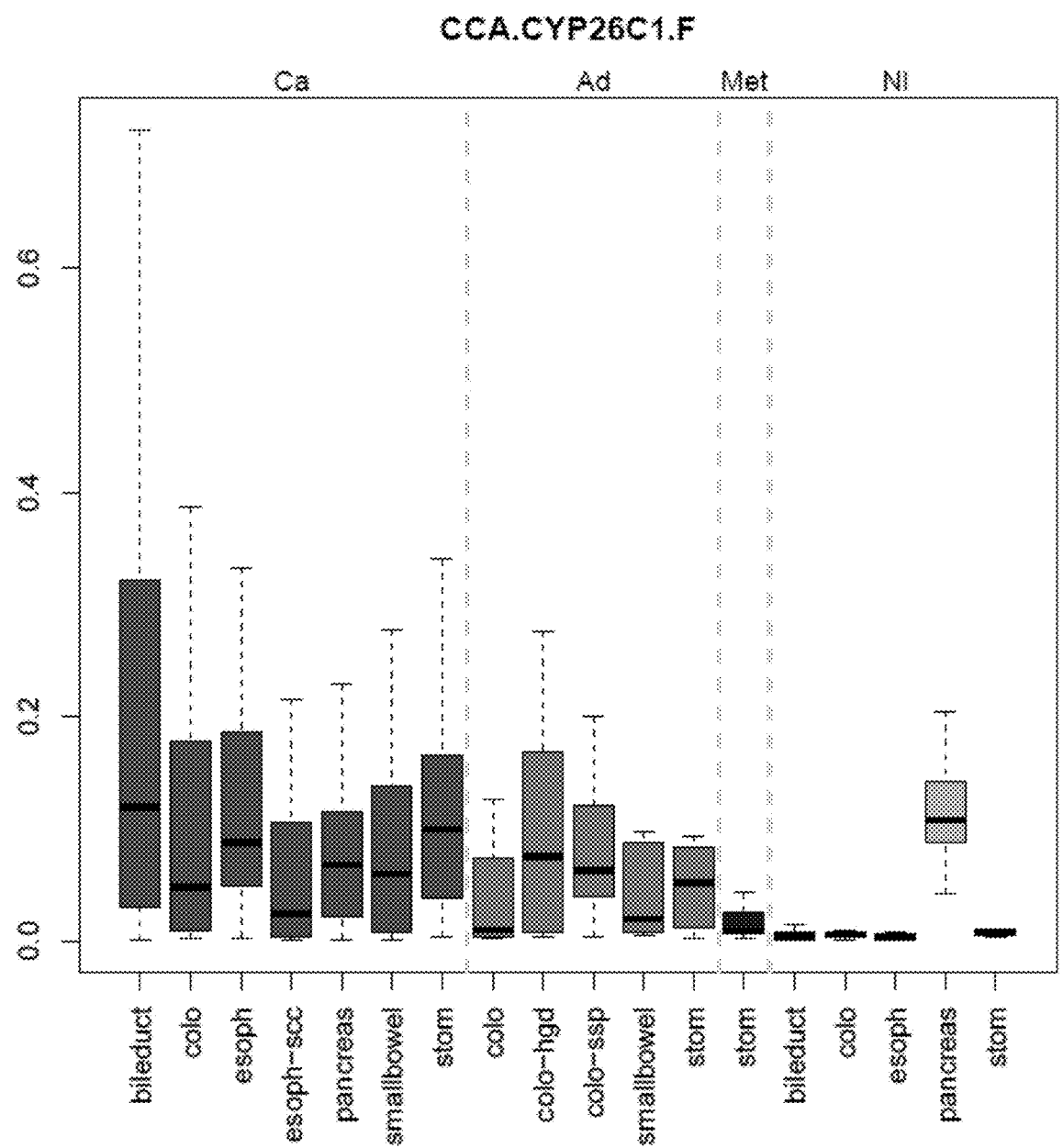
FIG. 1A-OOOO shows the distribution of individual markers within specific disease sites and neoplasm. The segregated region furthest to the left represents cancer tissue (Ca), the region second most left represents adenoma or precancer (Ad), the region third from the left represents metaplasia (Met), and region fourth from left represents normal tissue (NI).
Figure 1B:
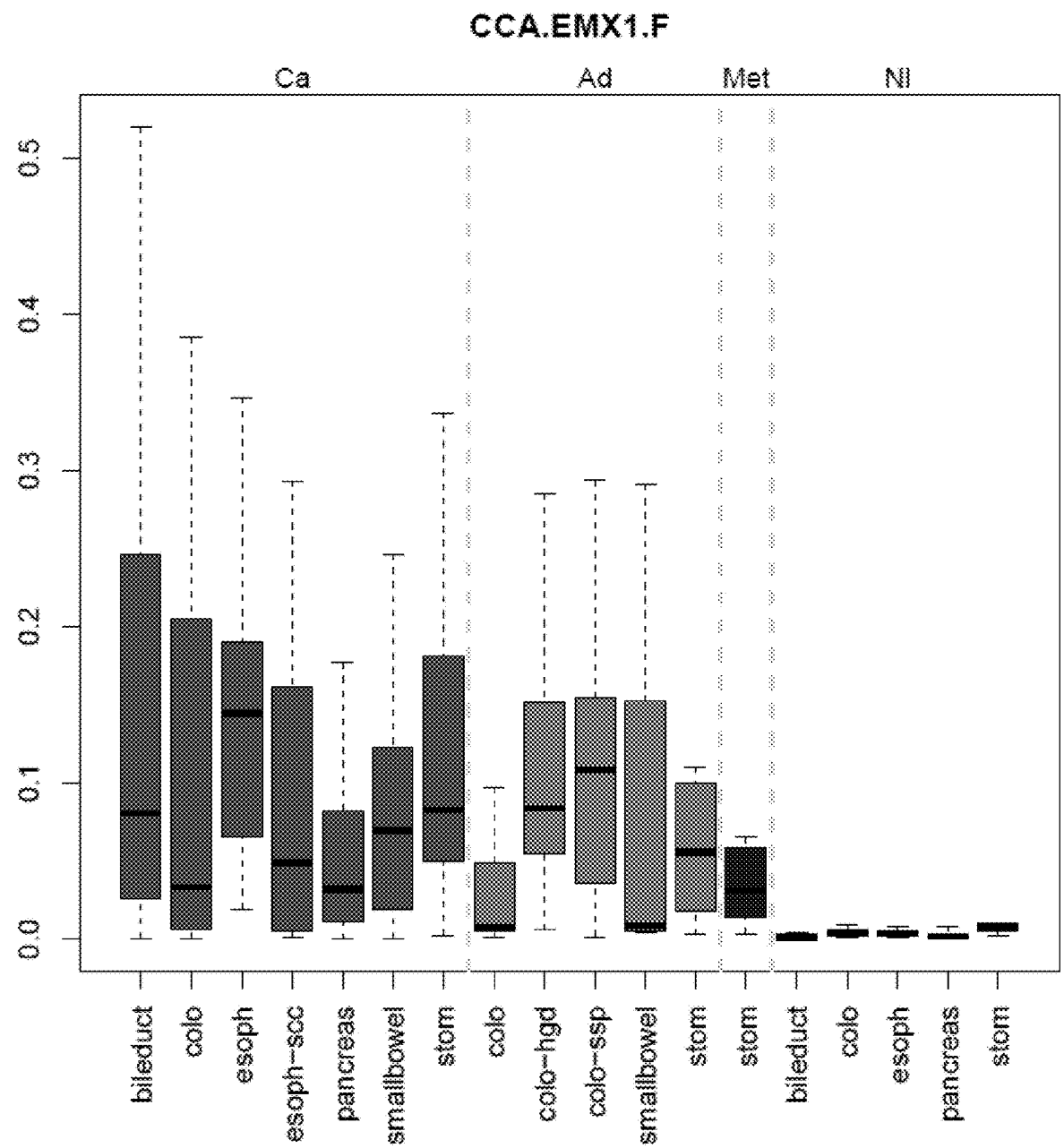
Figure 1C:
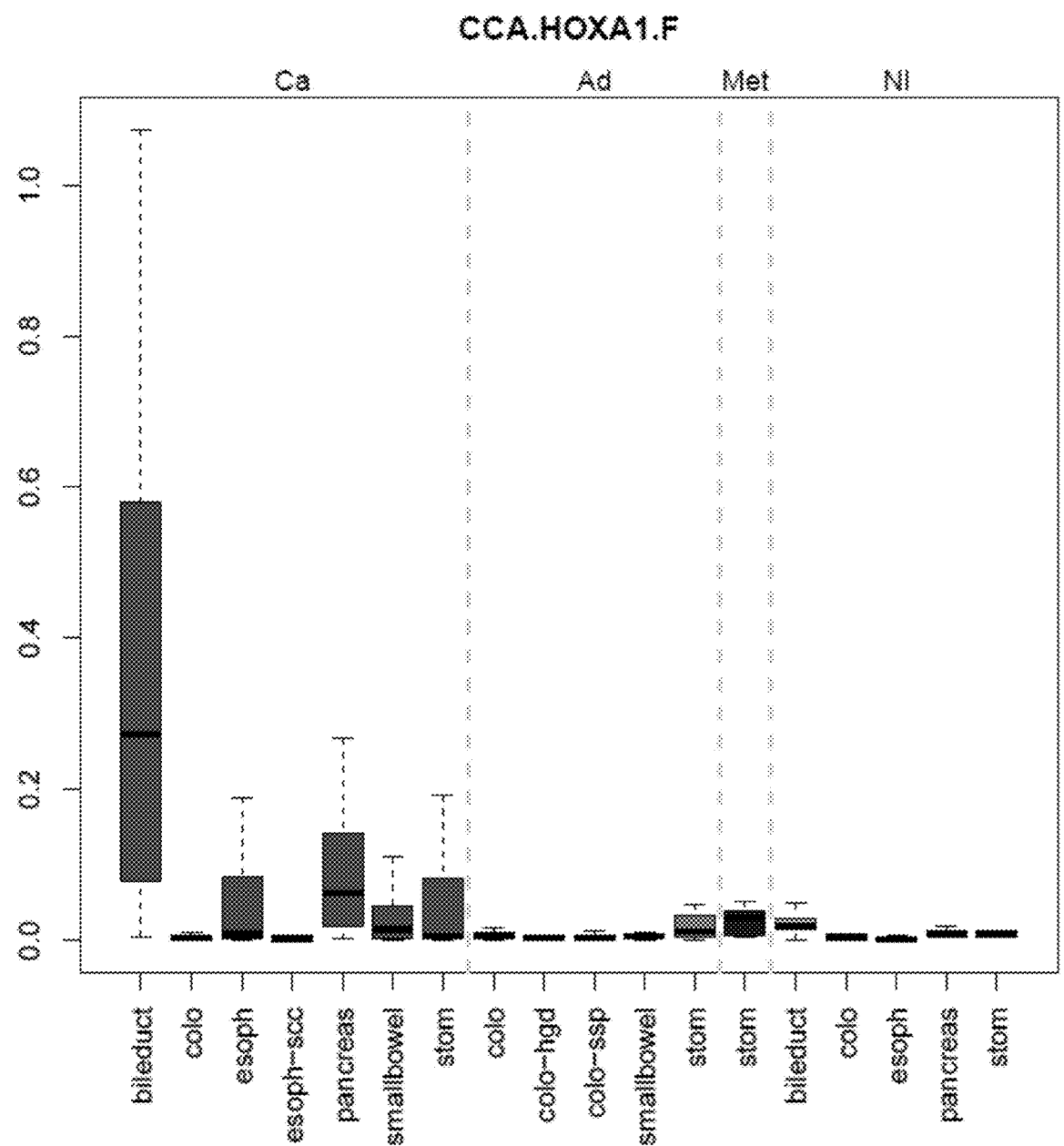
Figure 1D:
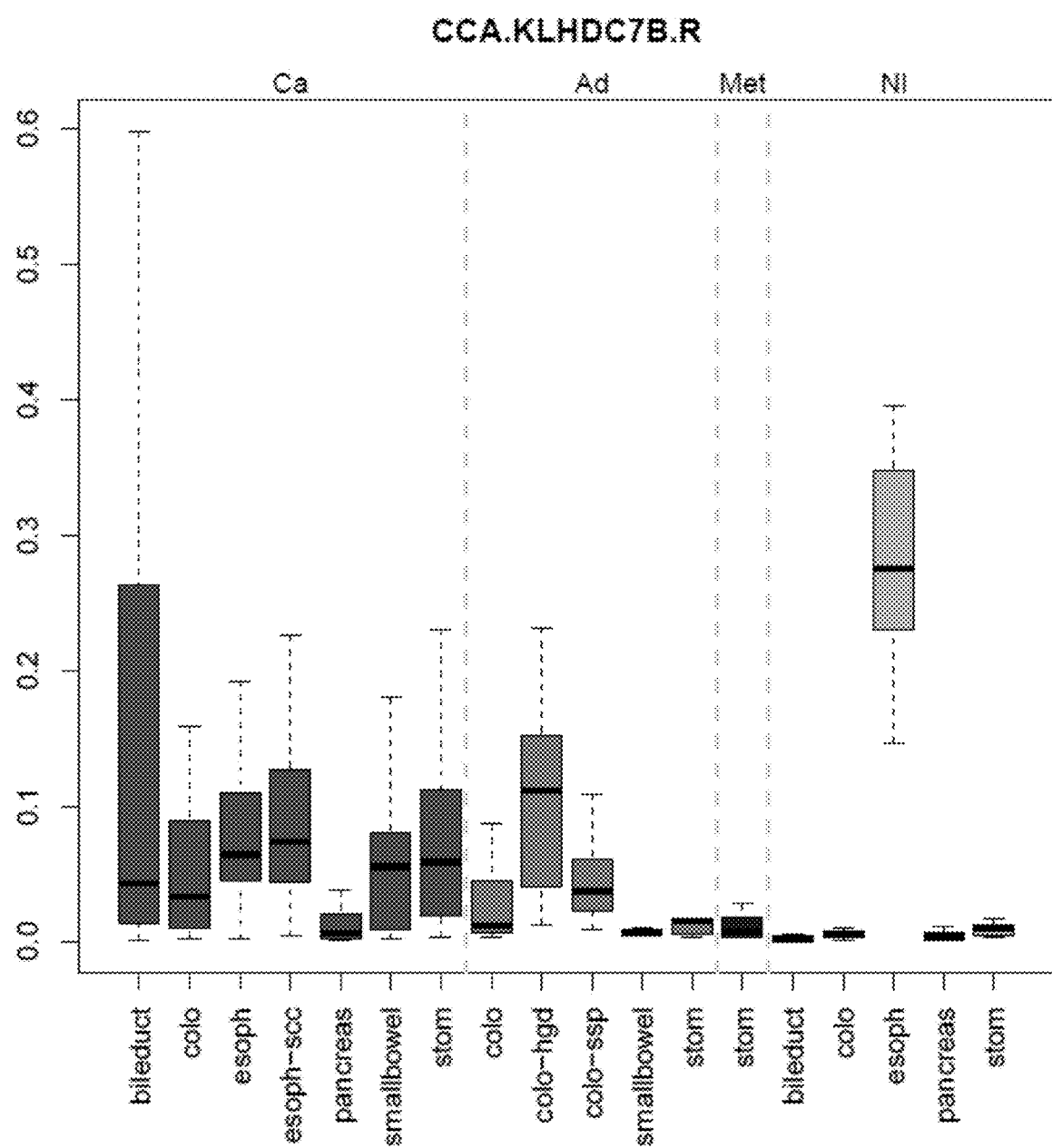
Figure 1E:
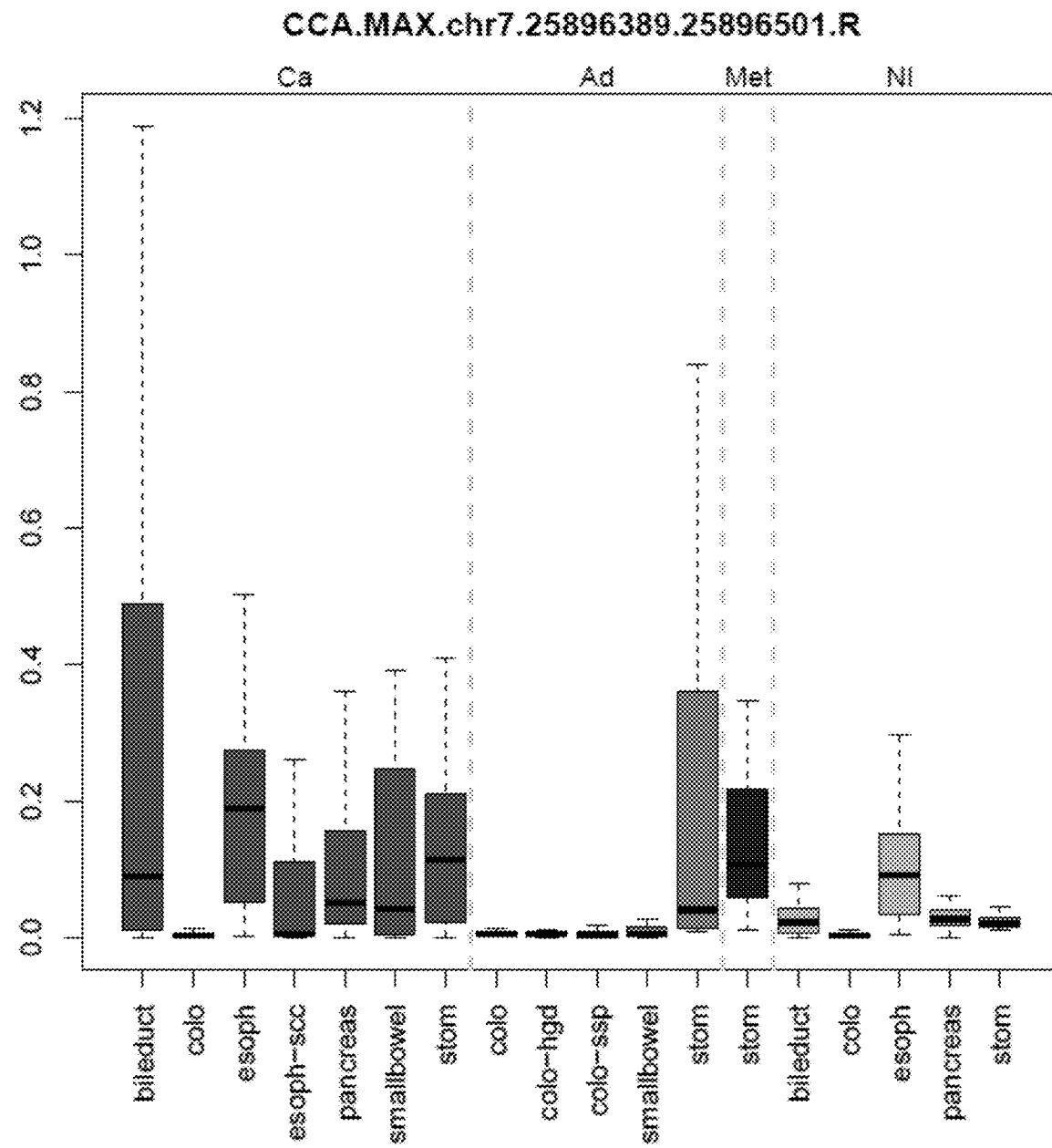
Figure 1F:
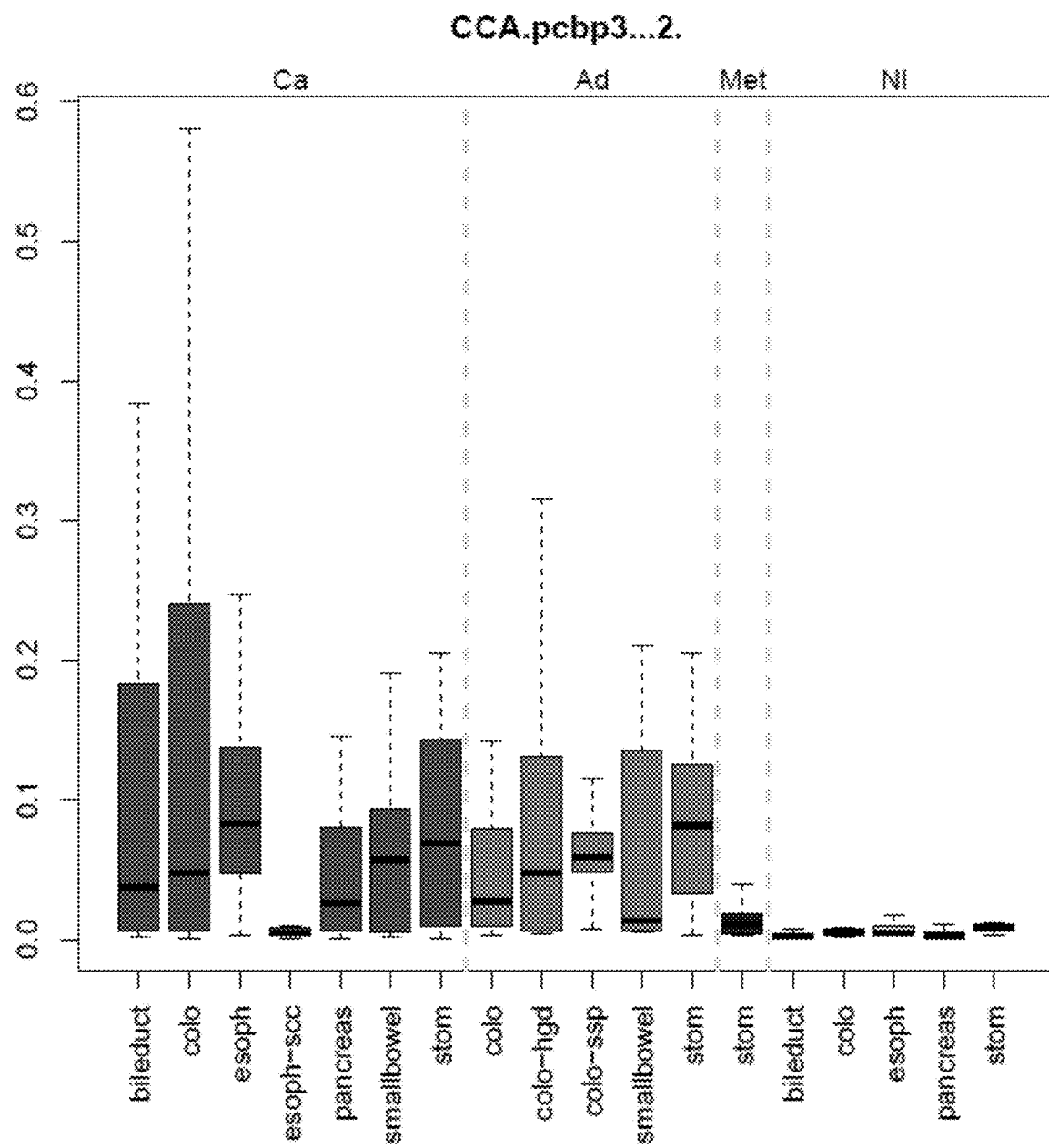
Figure 1G:
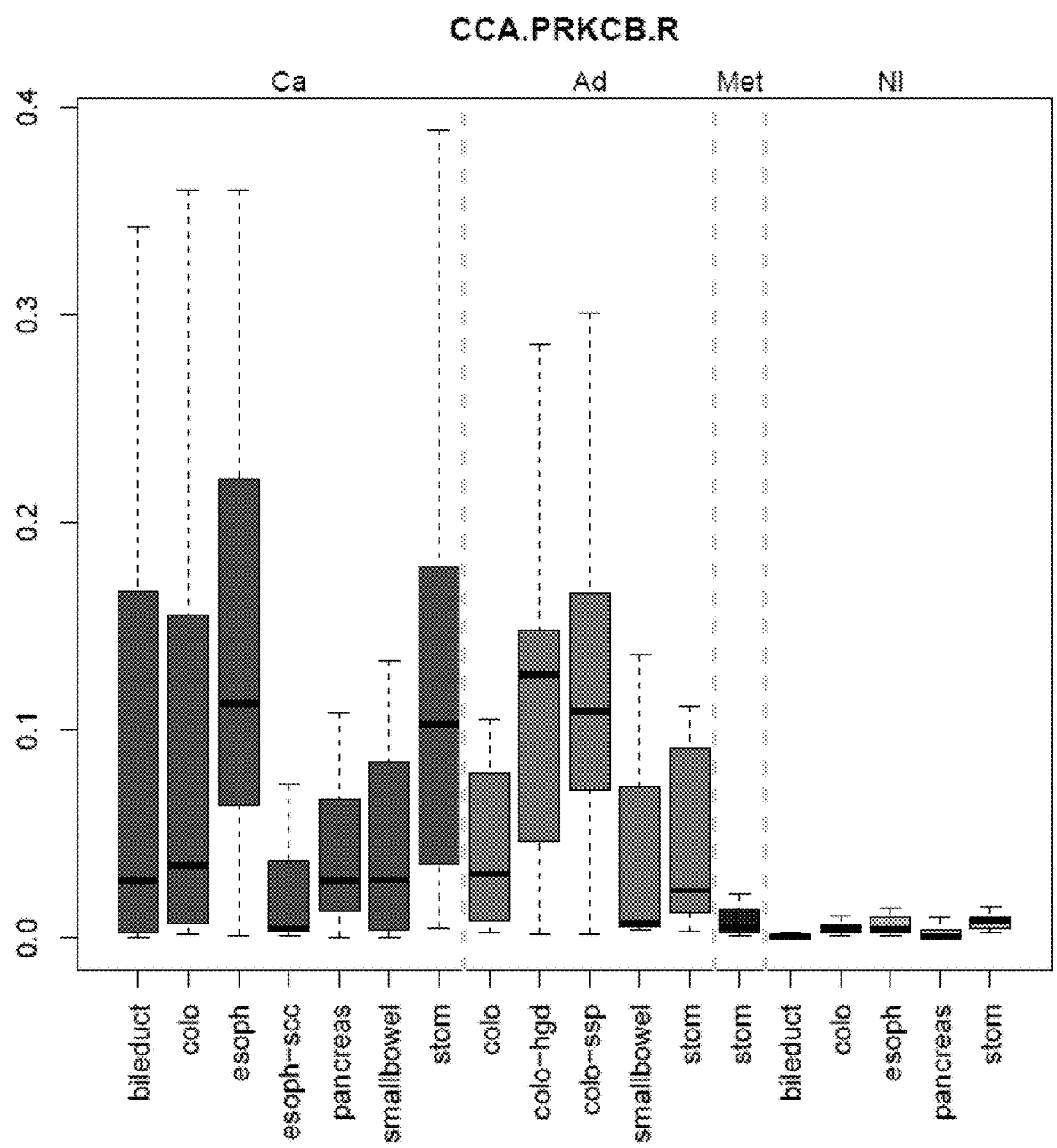
Figure 1H:
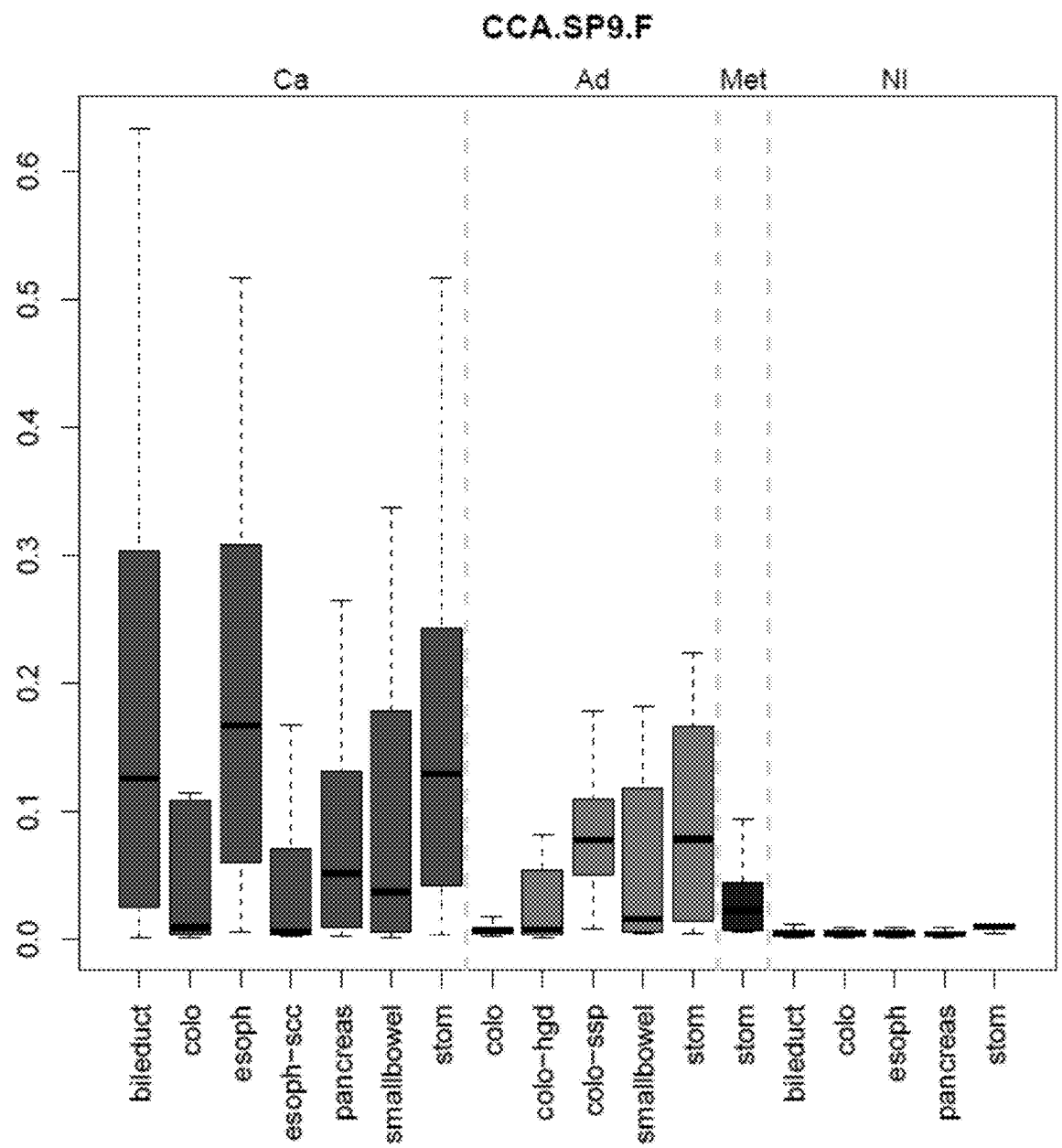
Figure 1I:
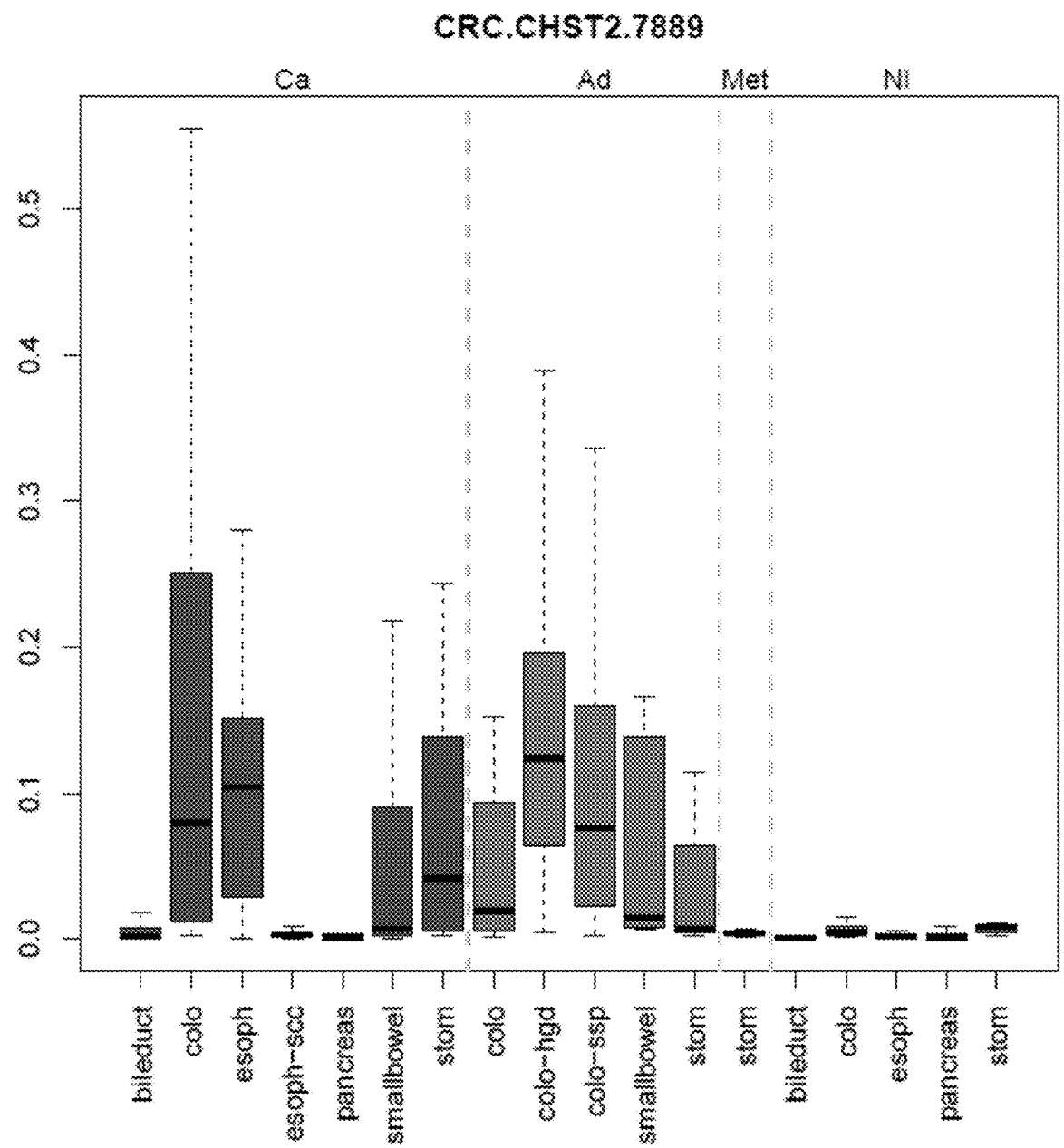
Figure 1J:
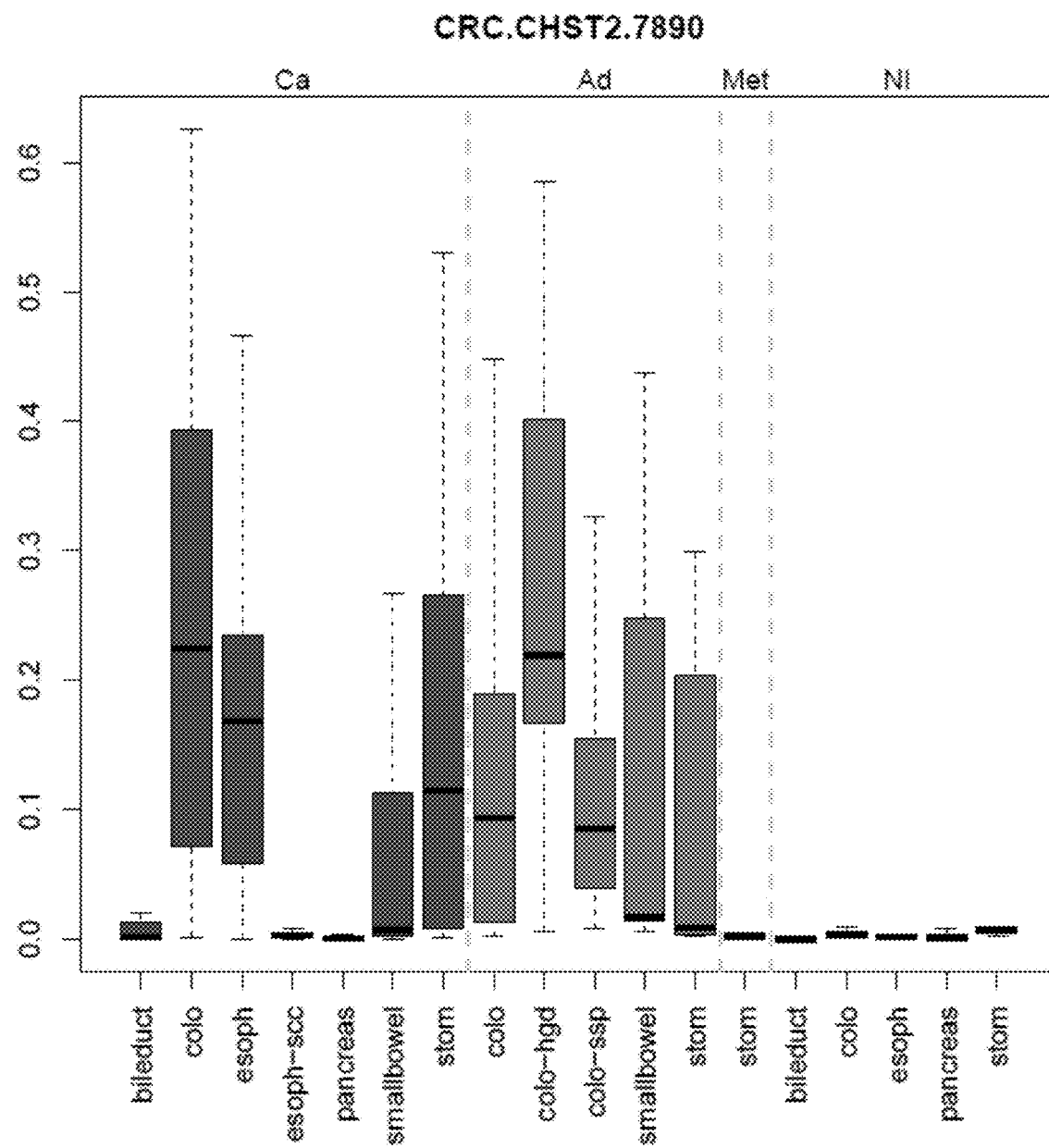
Figure 1K:
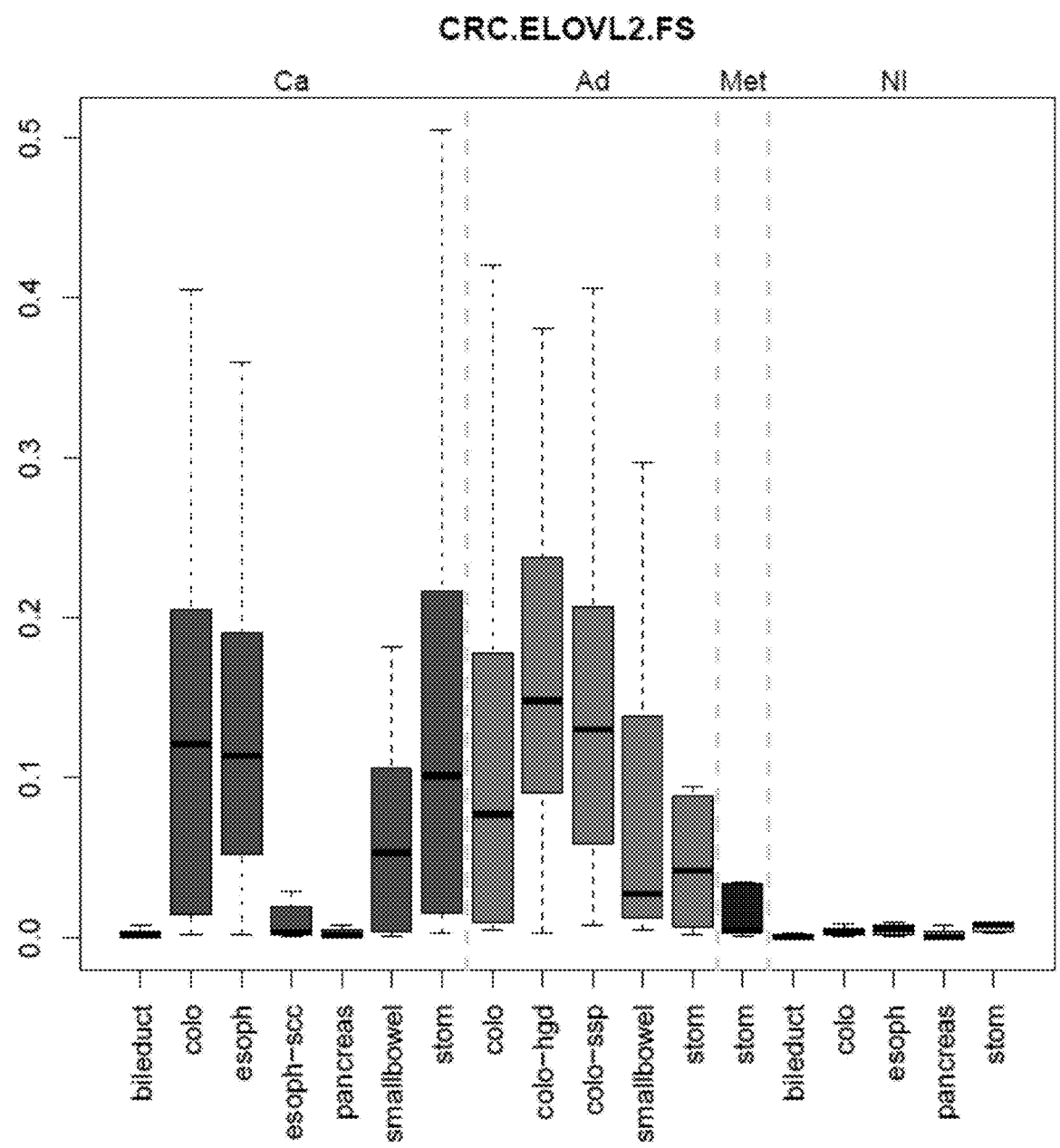
Figure 1L:
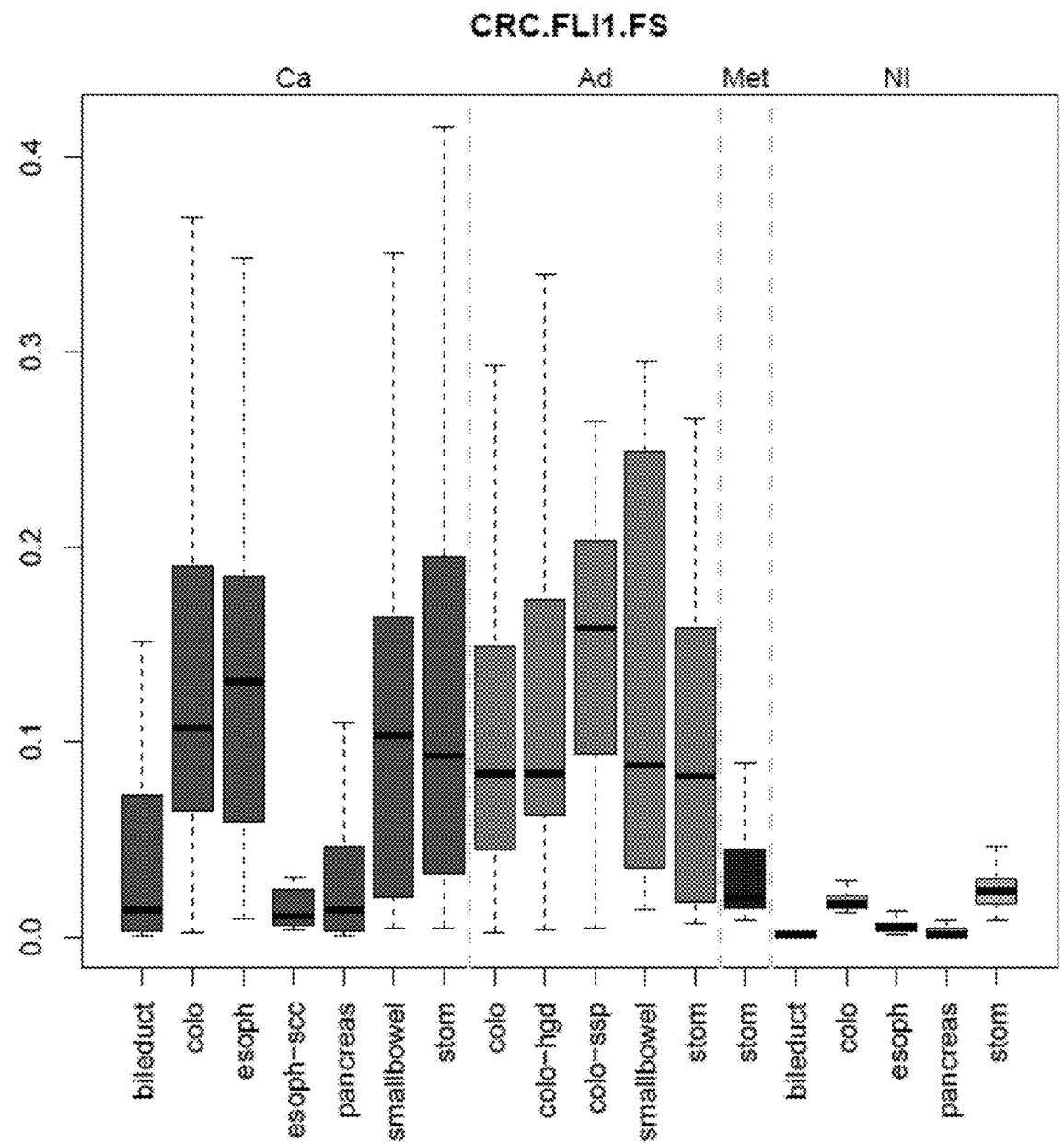
Figure 1M:
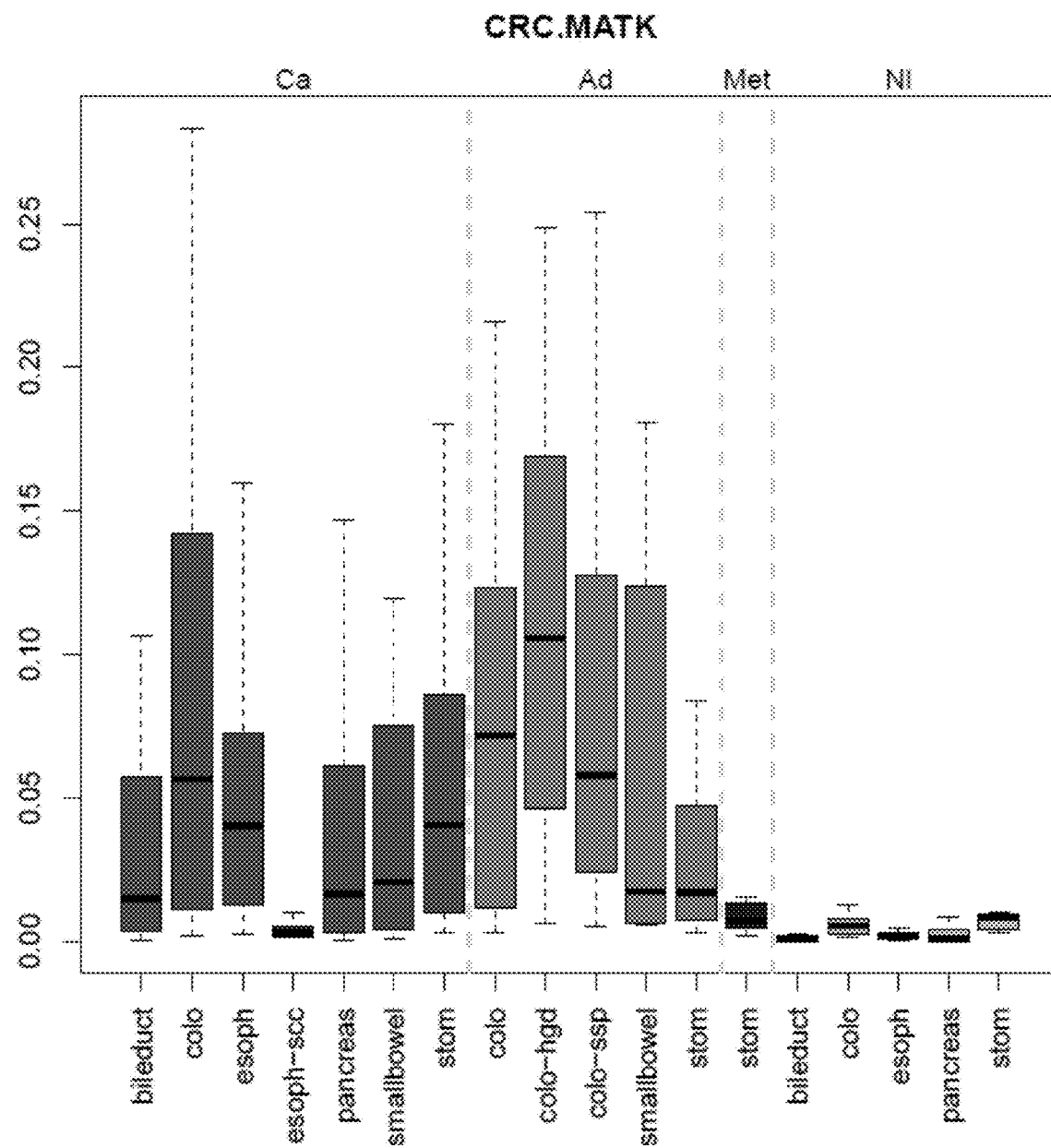
Figure 1N:
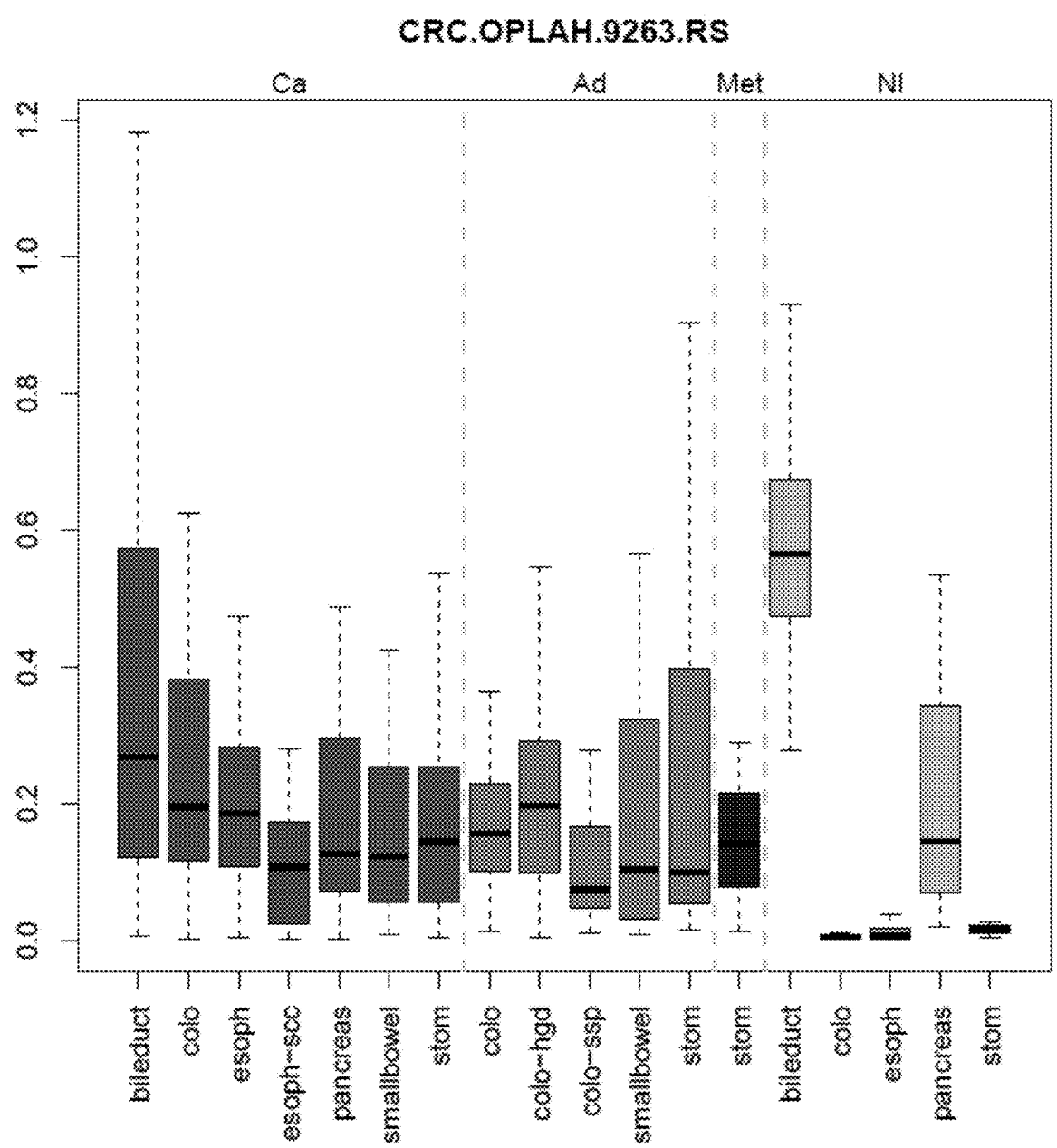
Figure 10:
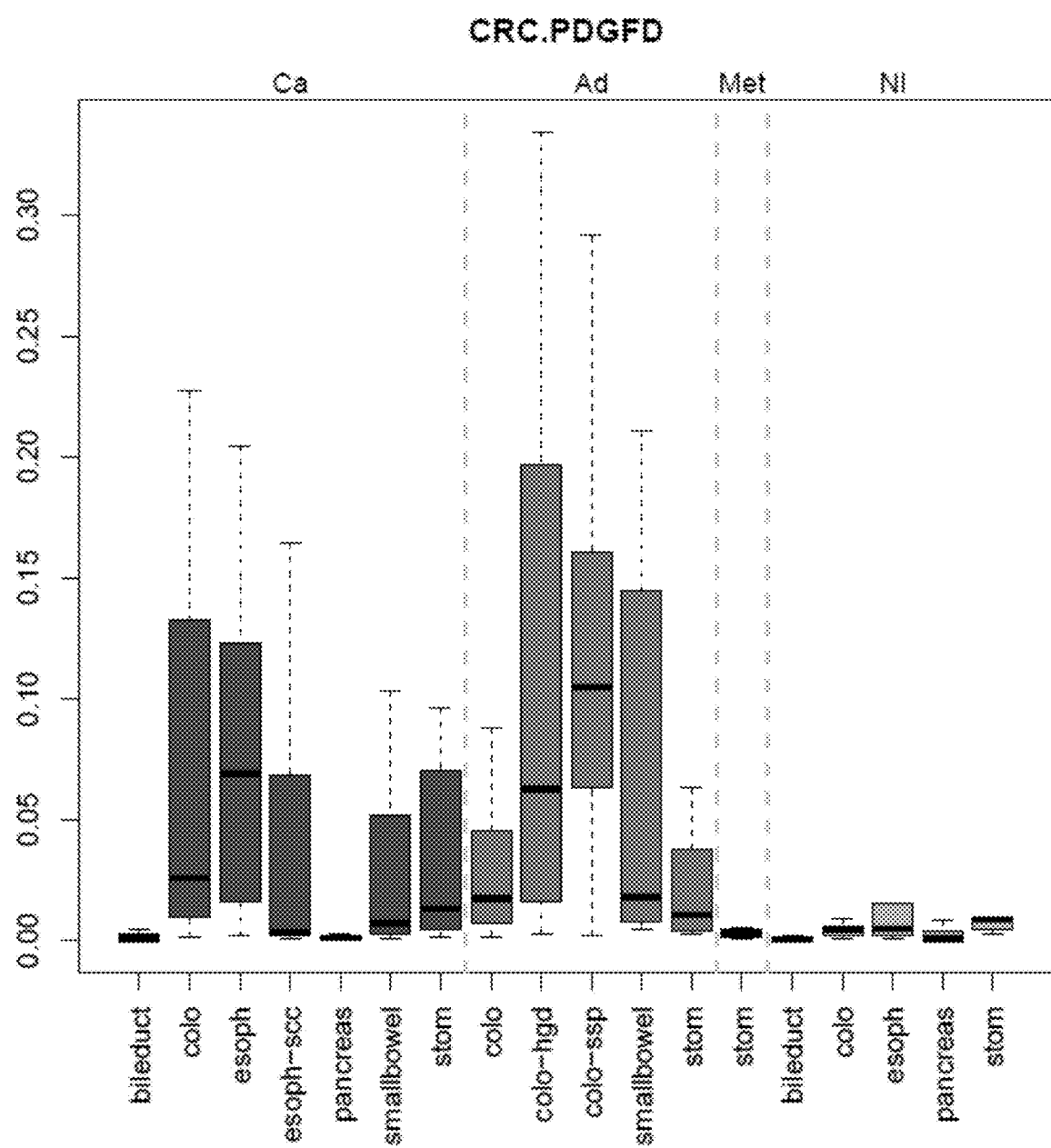
Figure 1P:
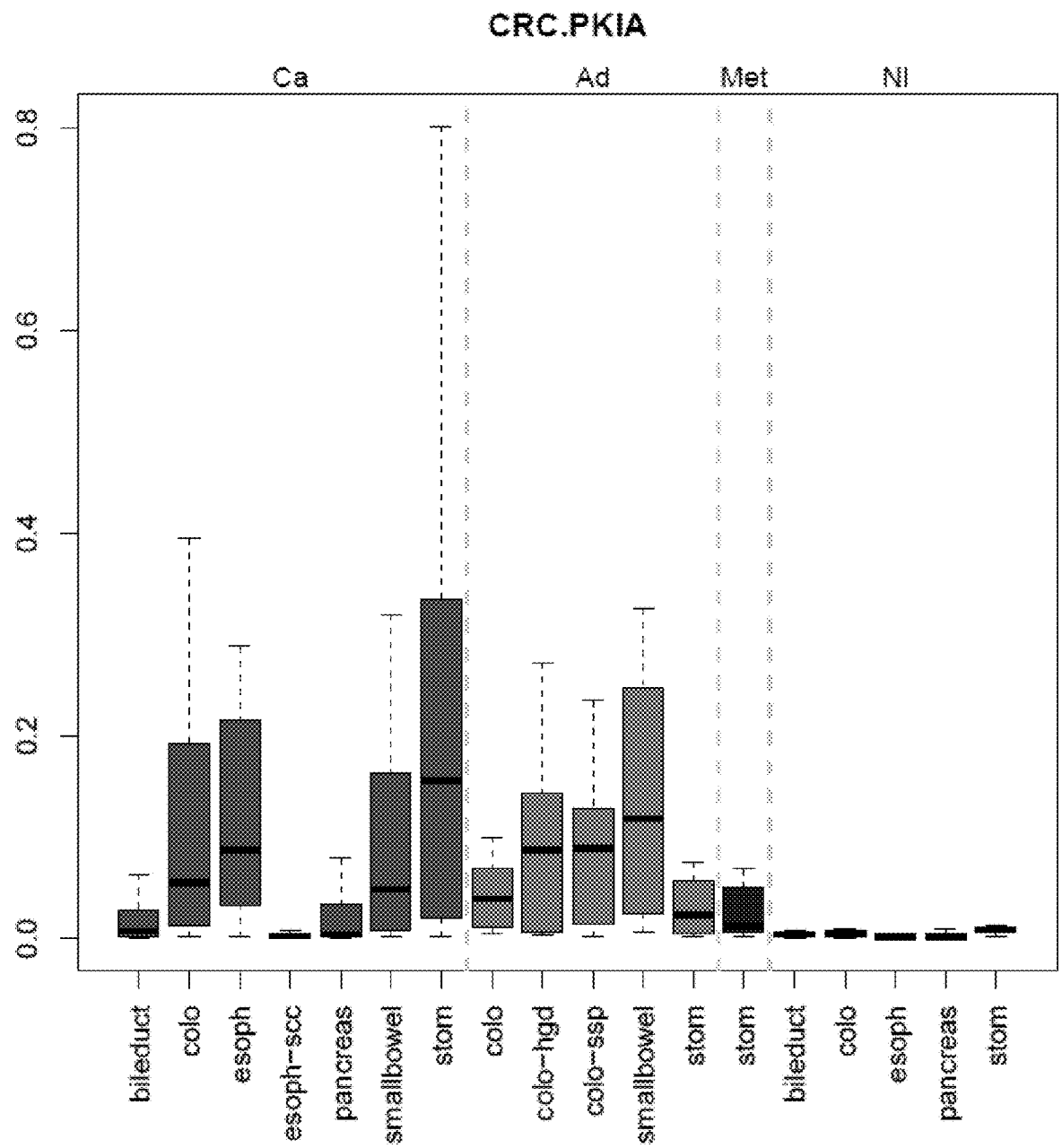
Figure 1Q:
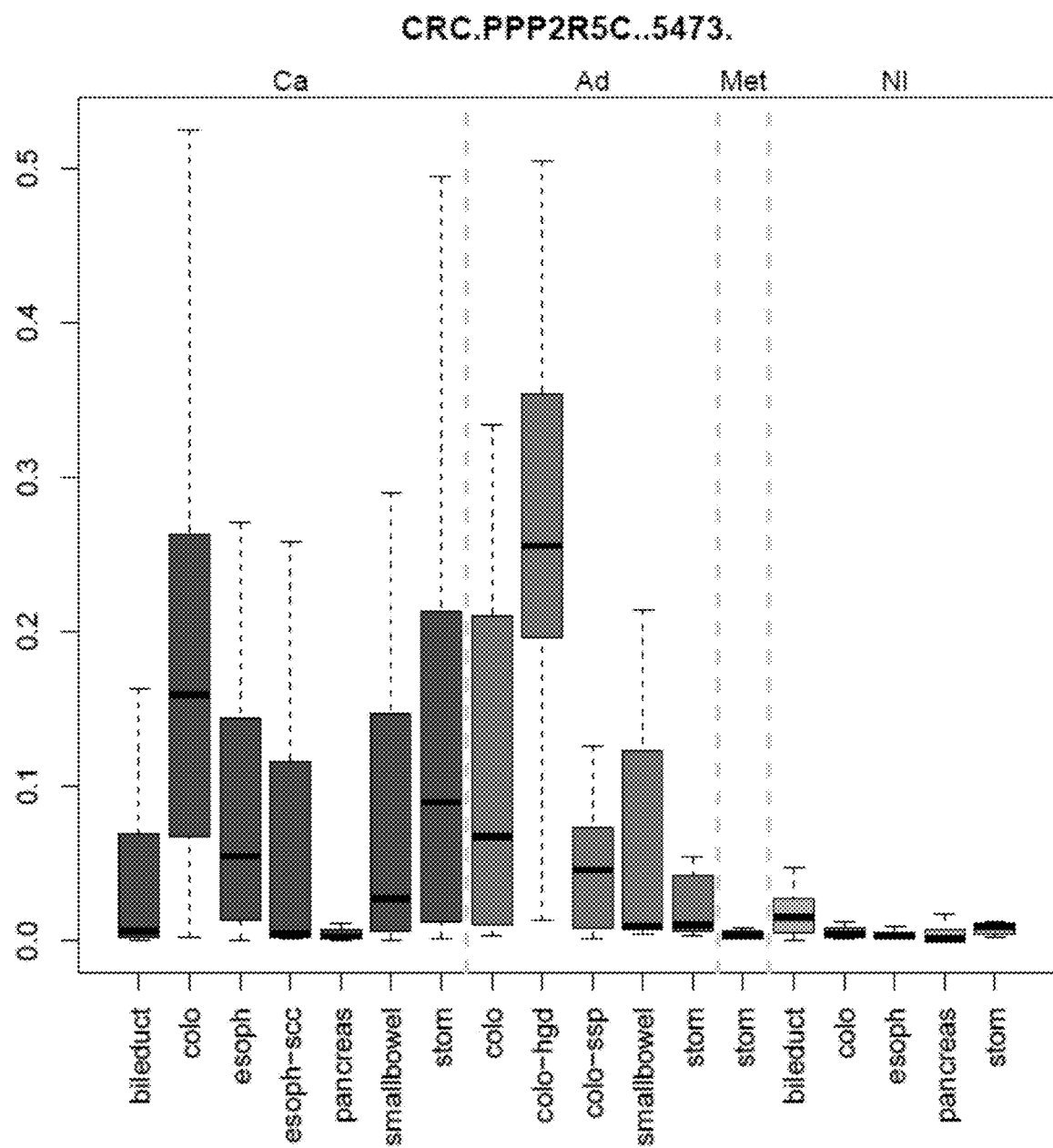
Figure 1R:
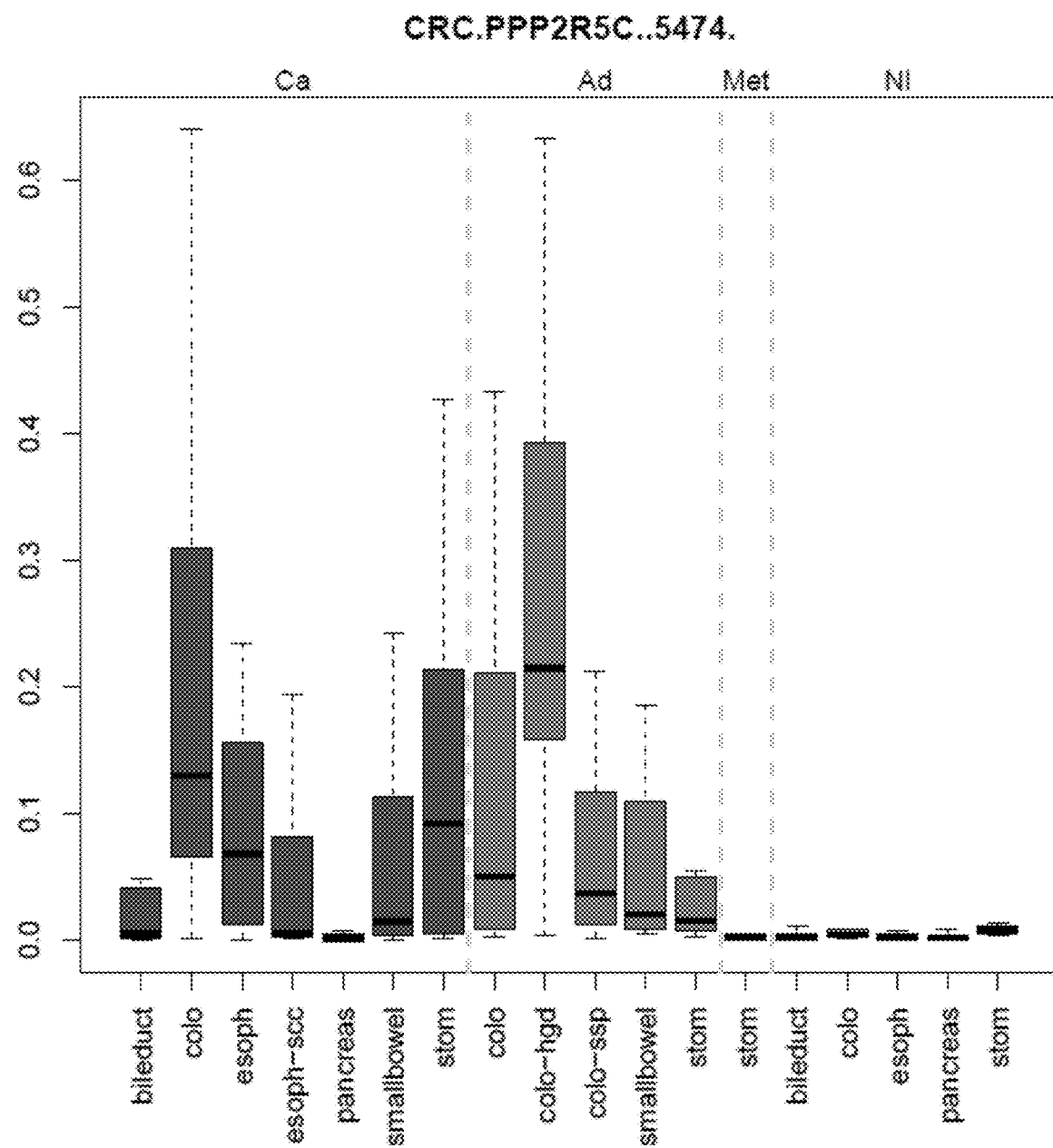
Figure 1S:
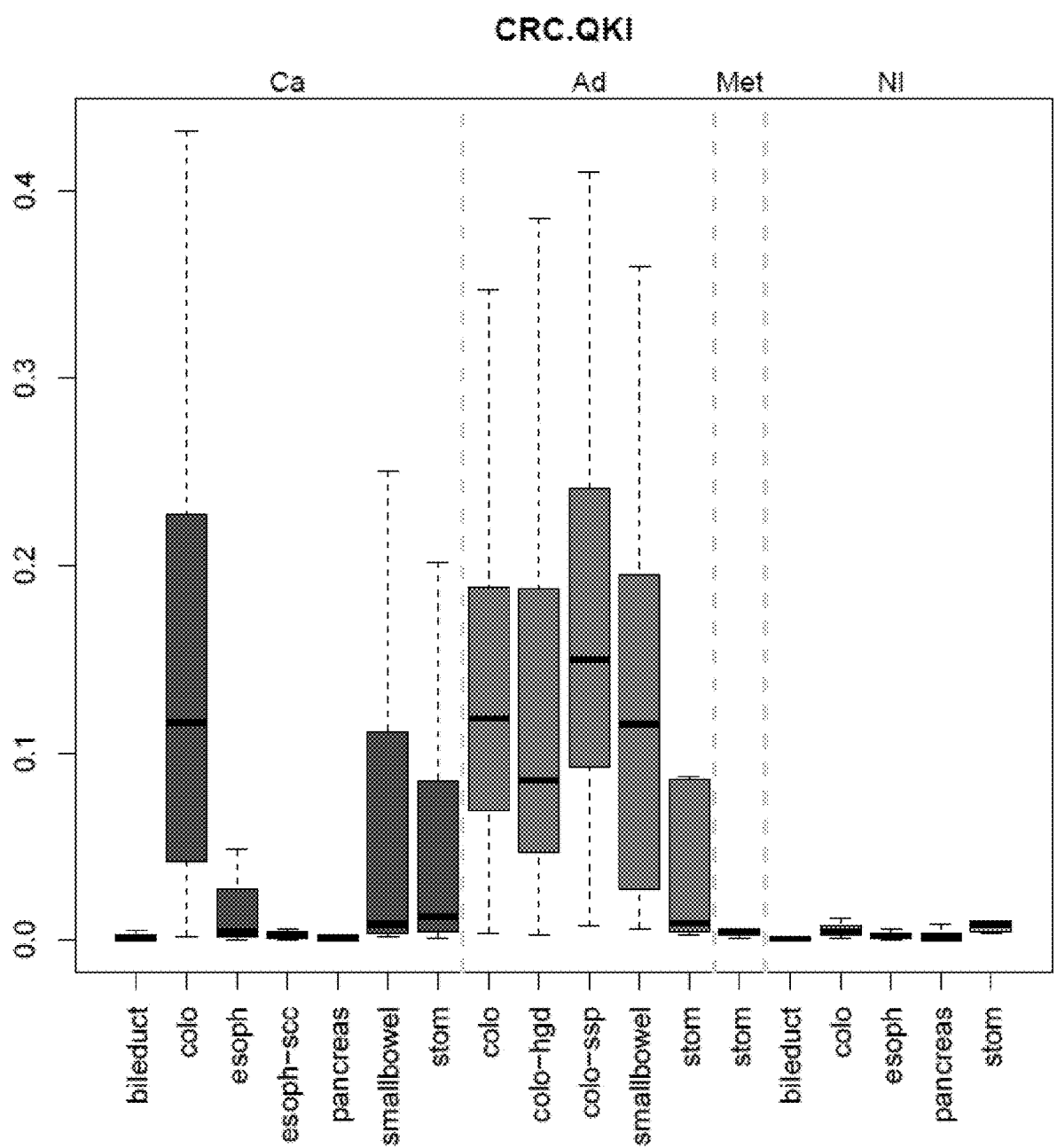
Figure 1T:
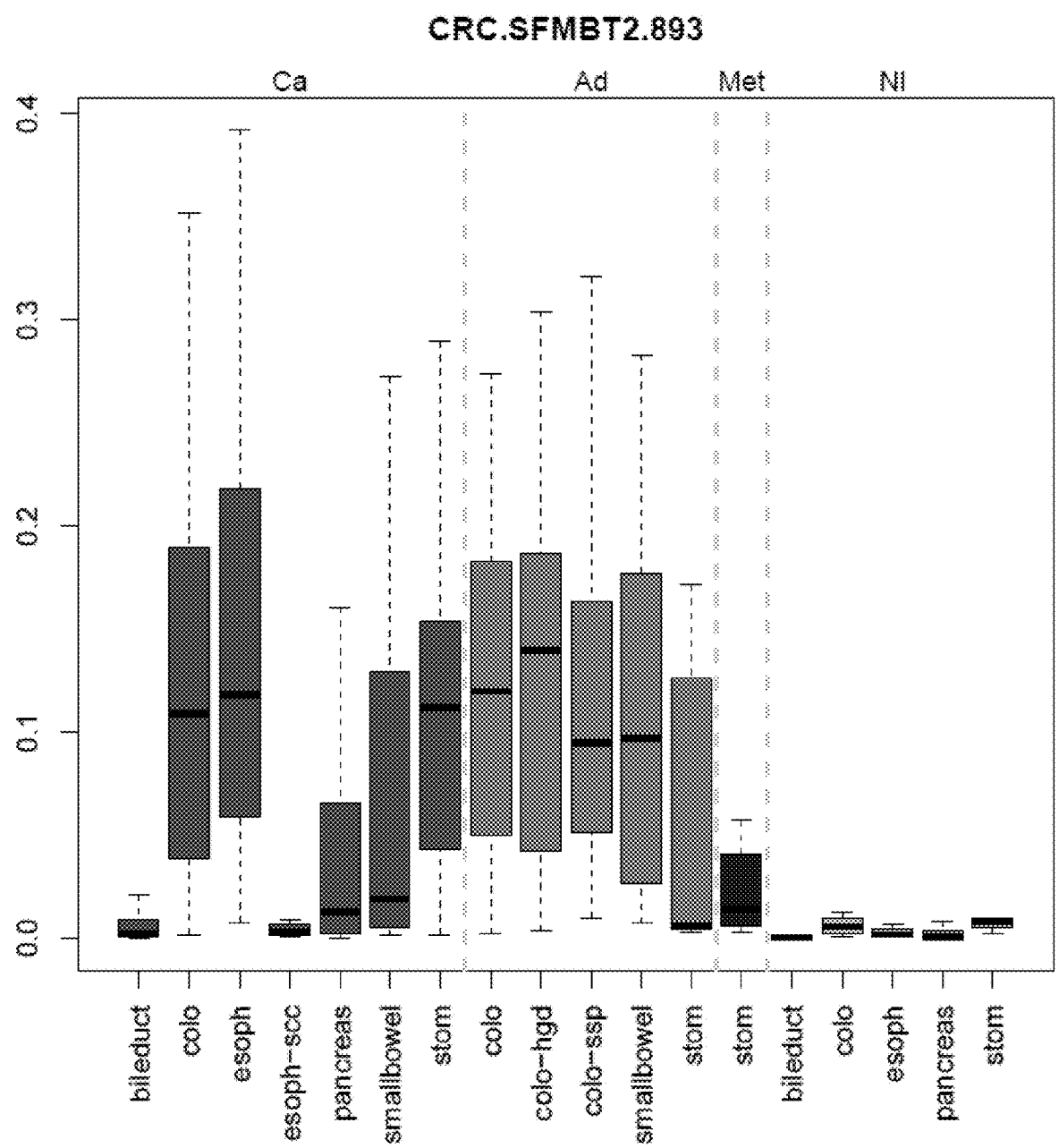
Figure 1U:
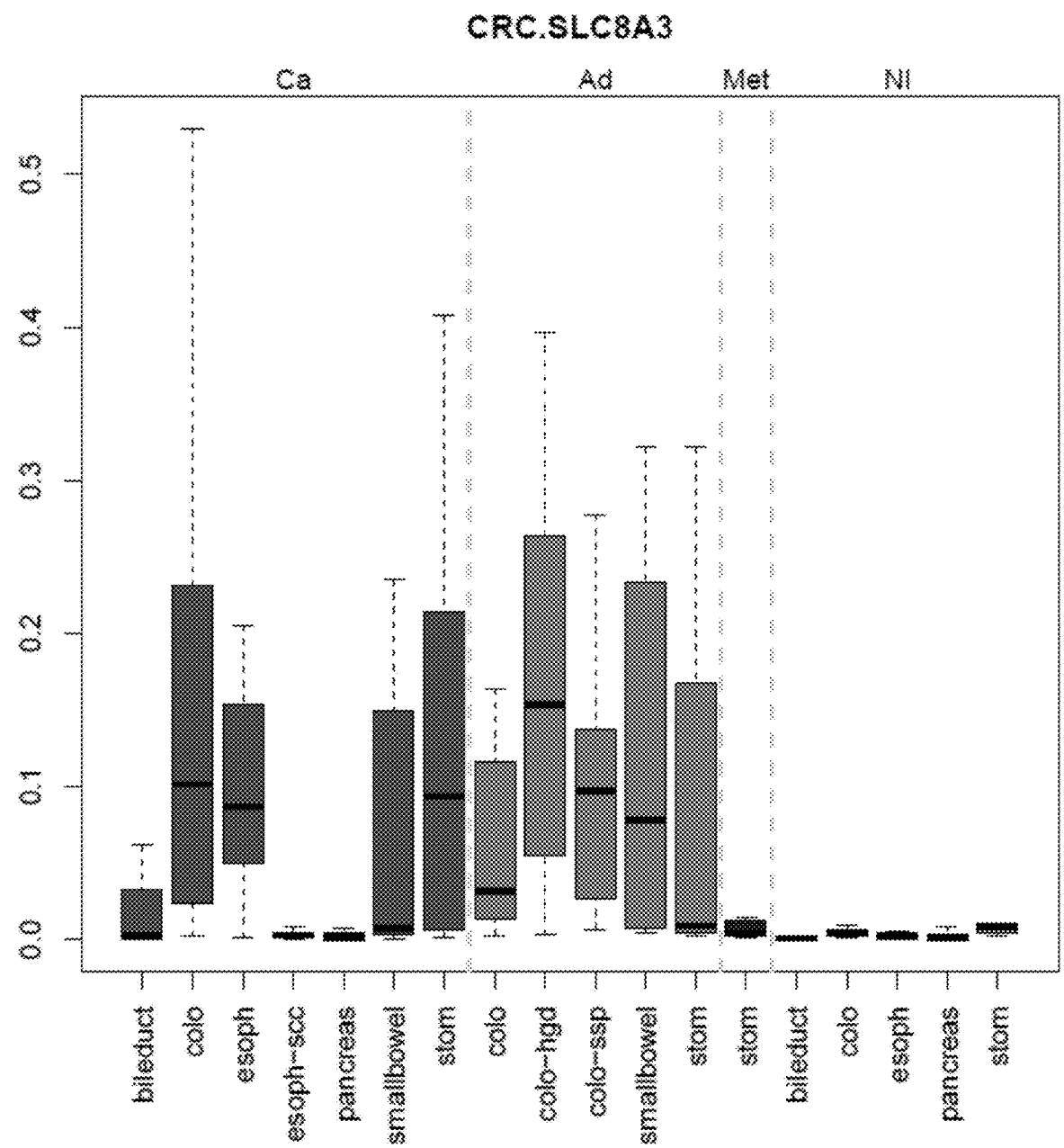
Figure 1V:
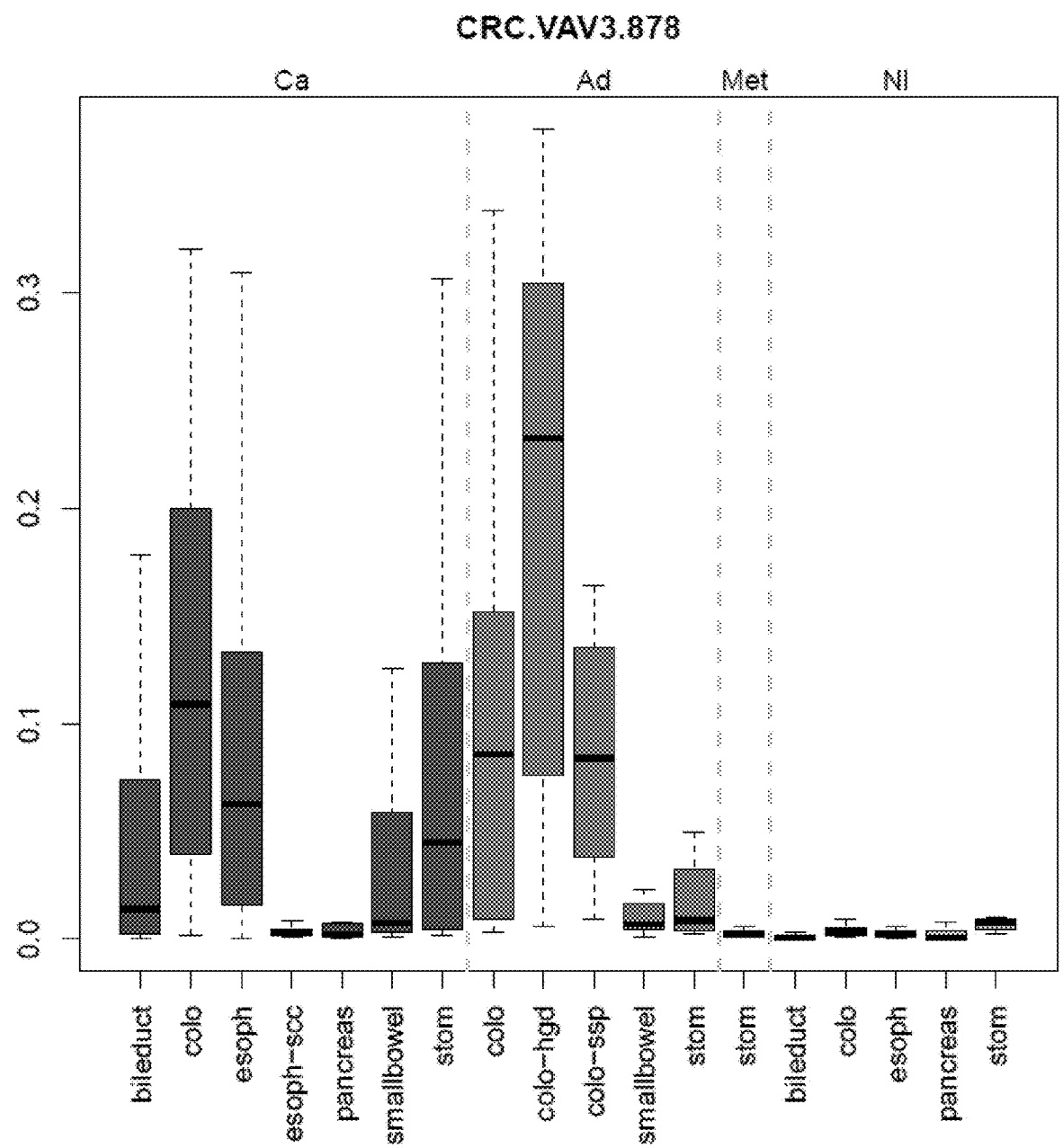
Figure 1W:
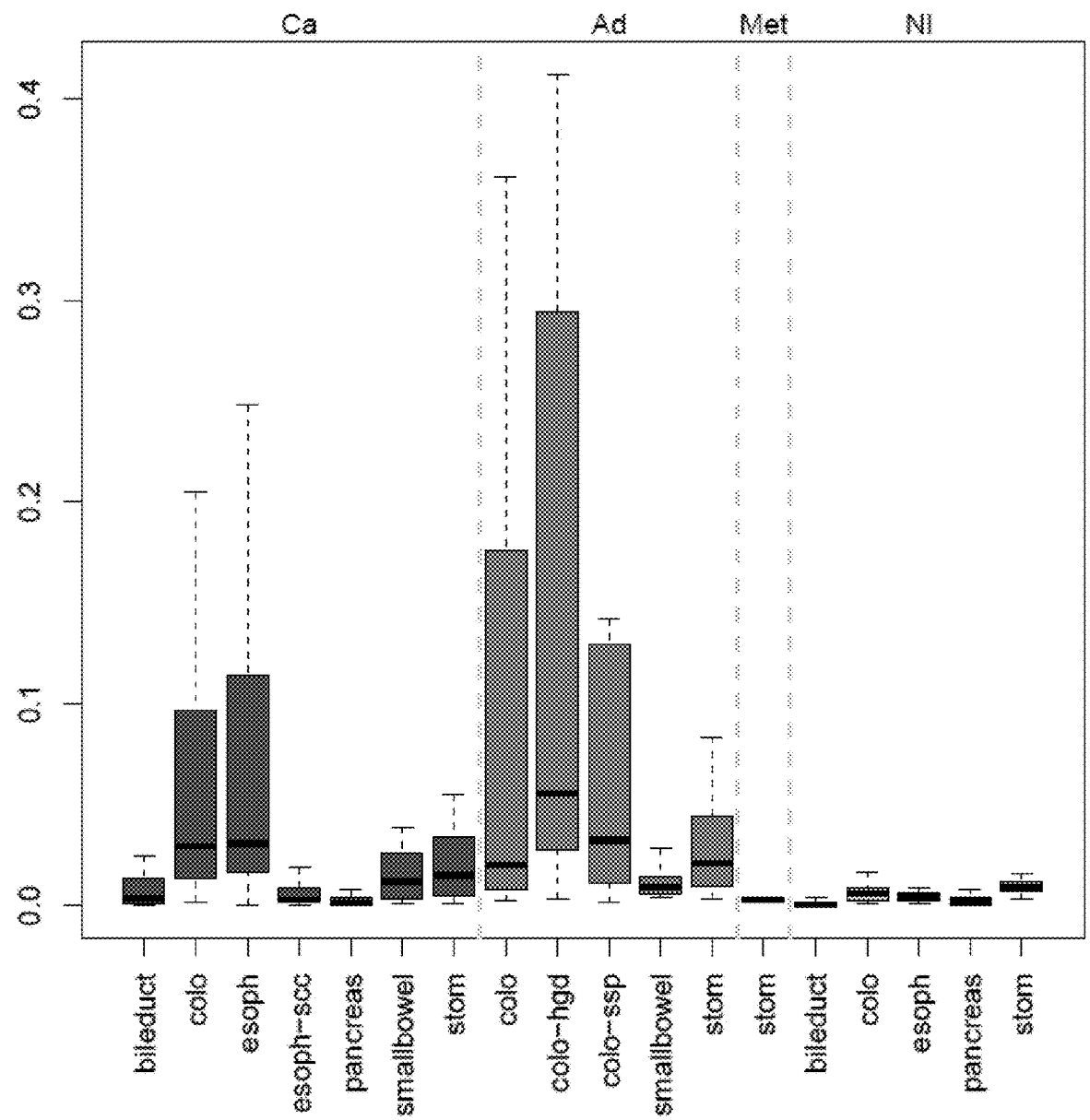
Figure 1X:
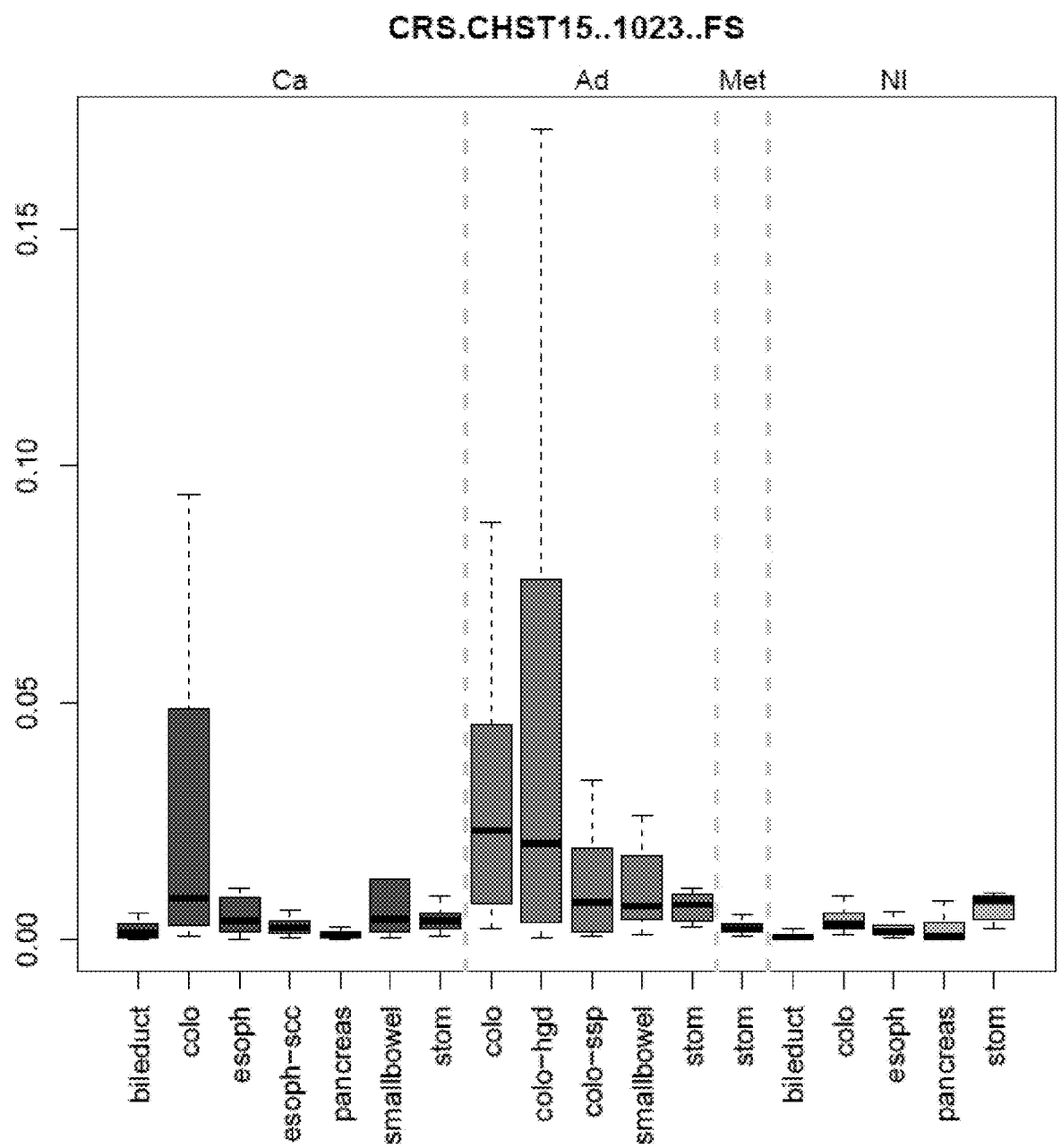
Figure 1Y:
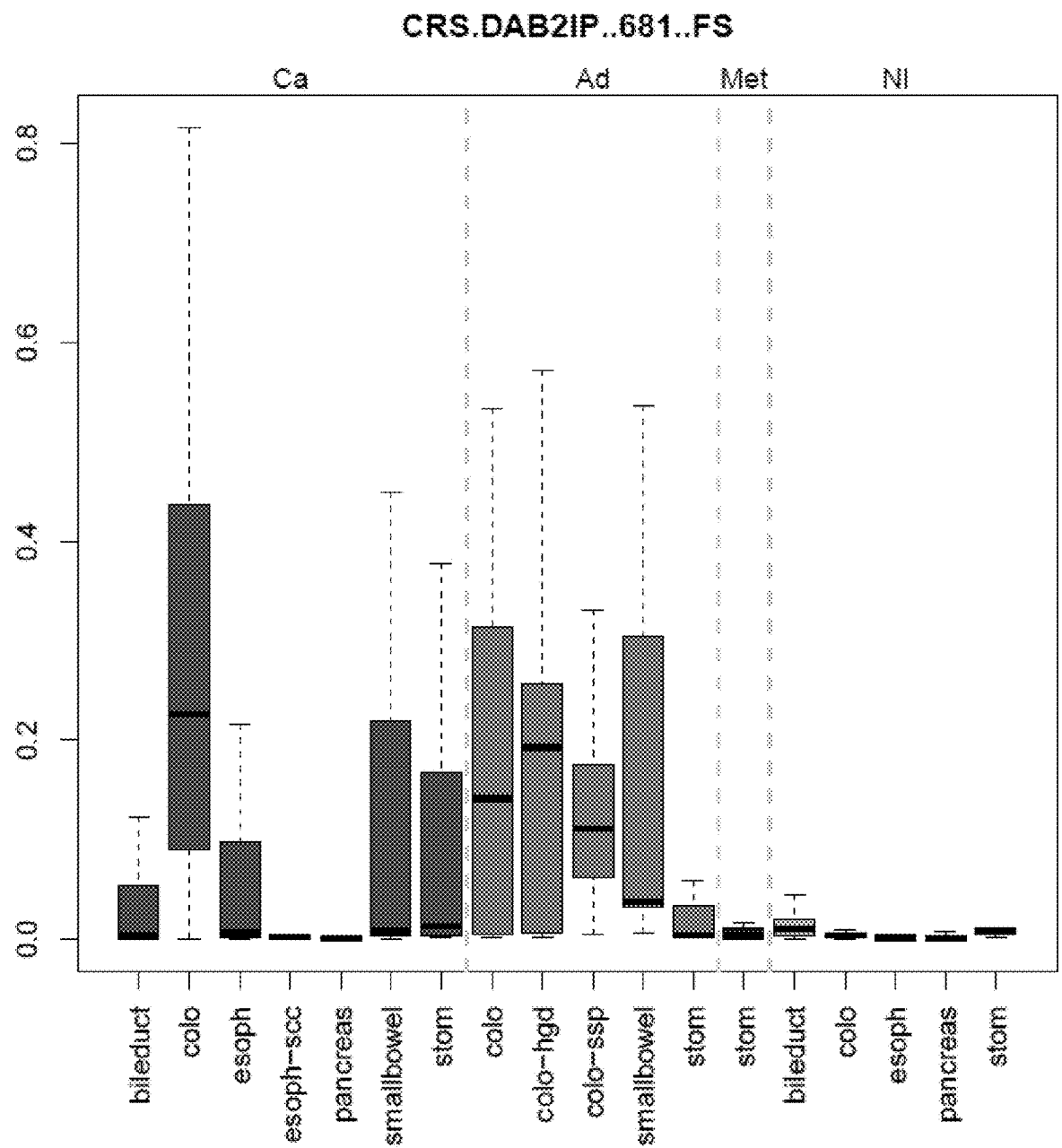
Figure 1Z:
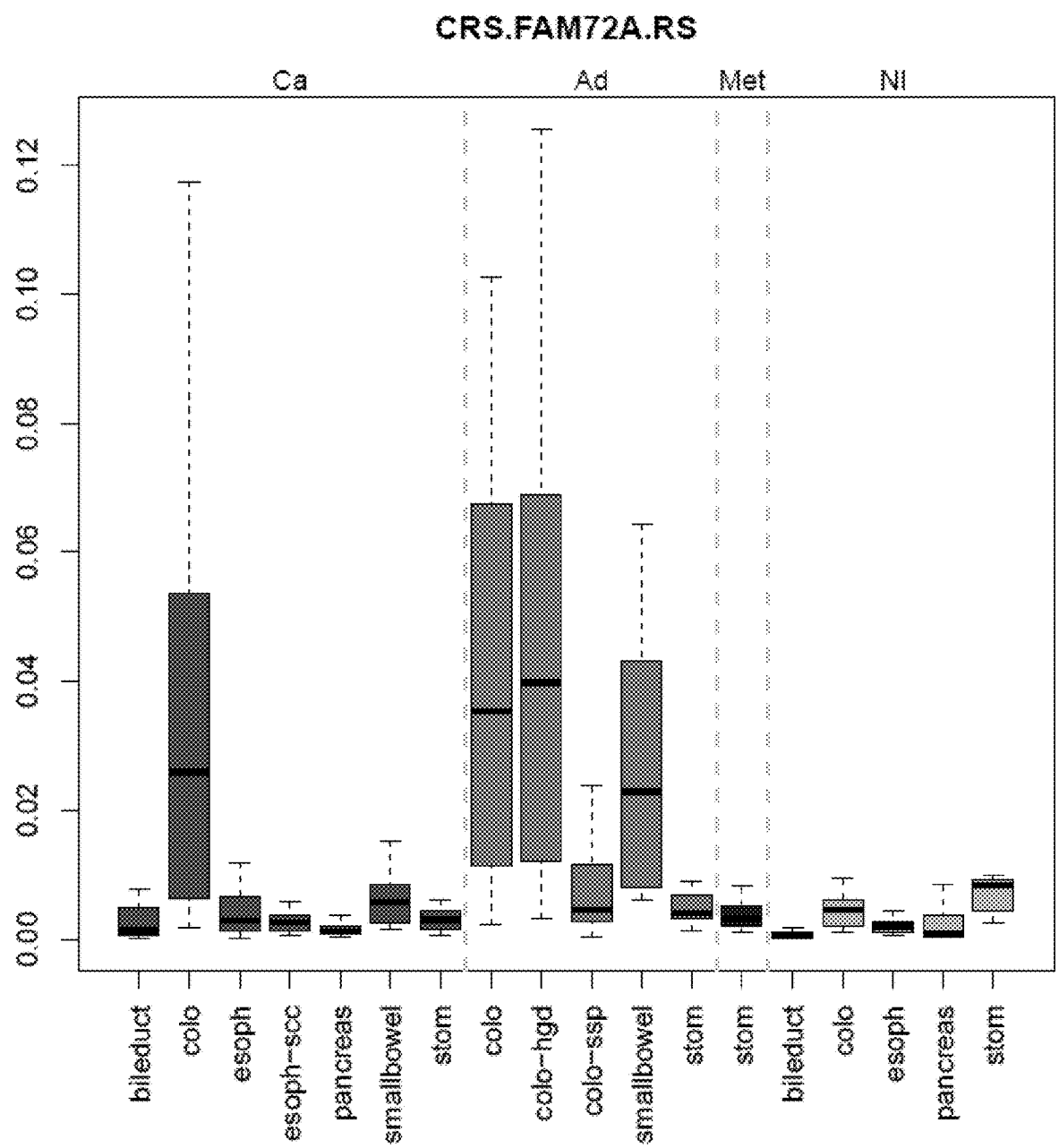
Figure 1A:
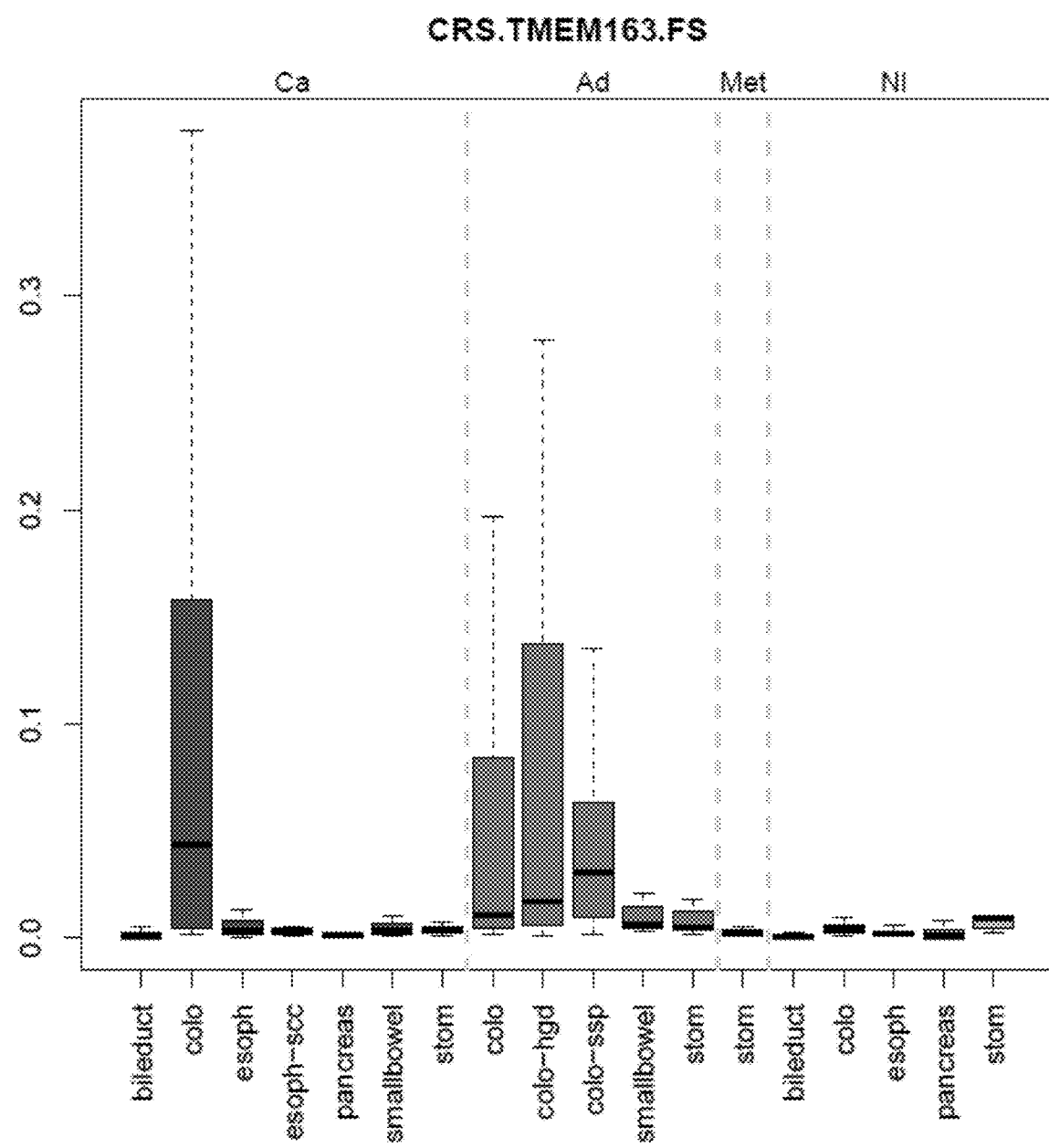
Figure 1B:
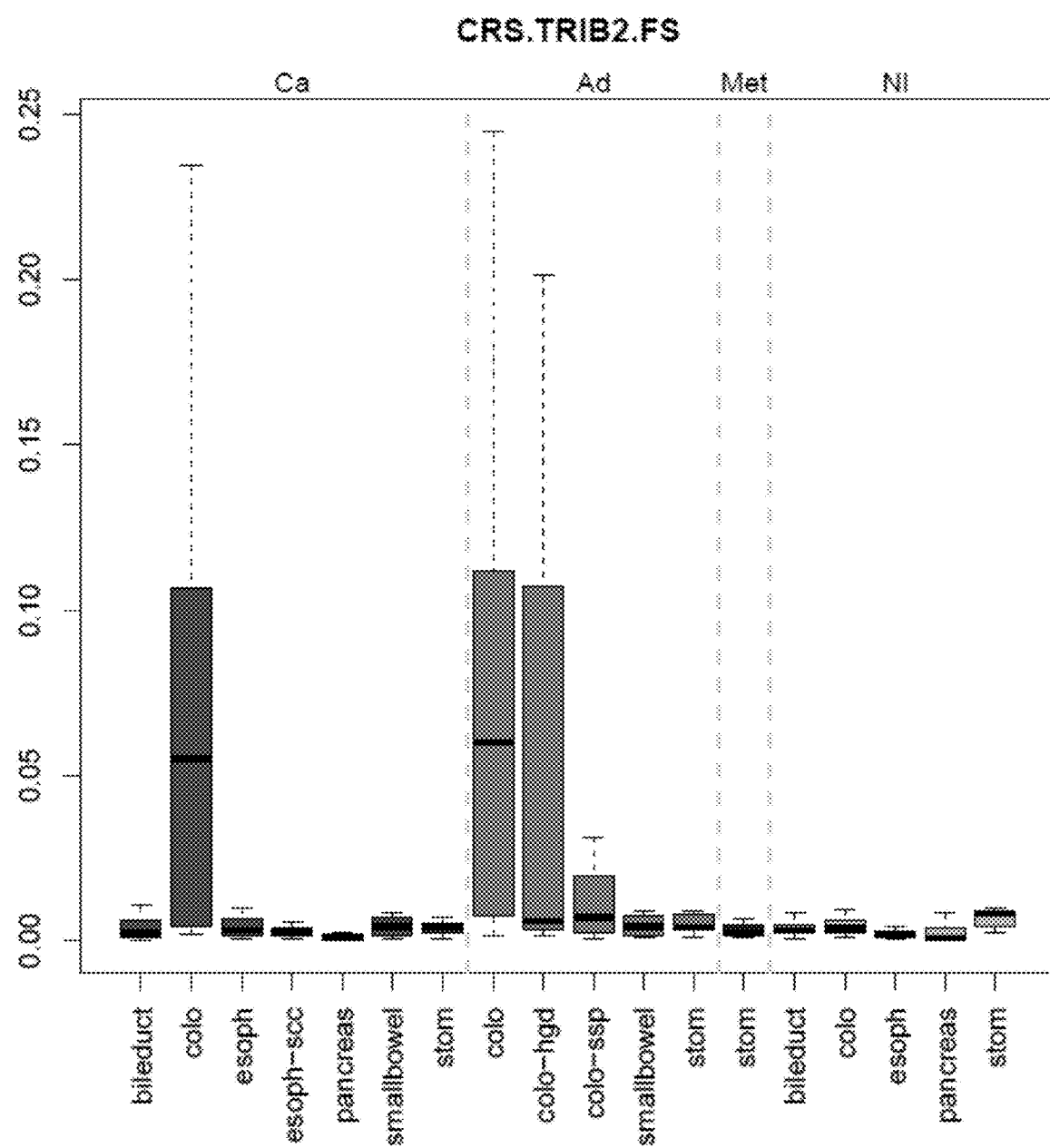
Figure 1C:
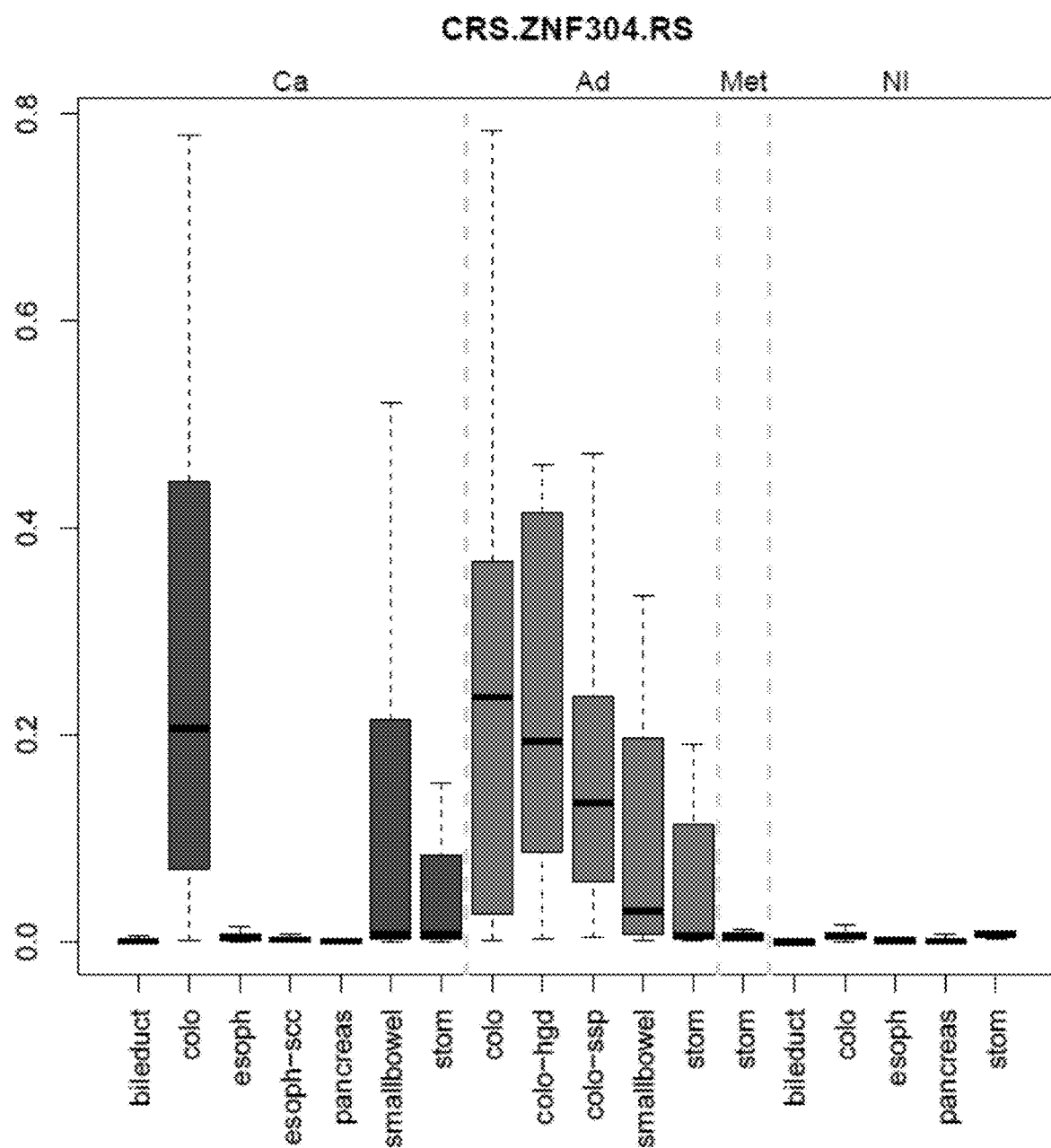
Figure 1D:
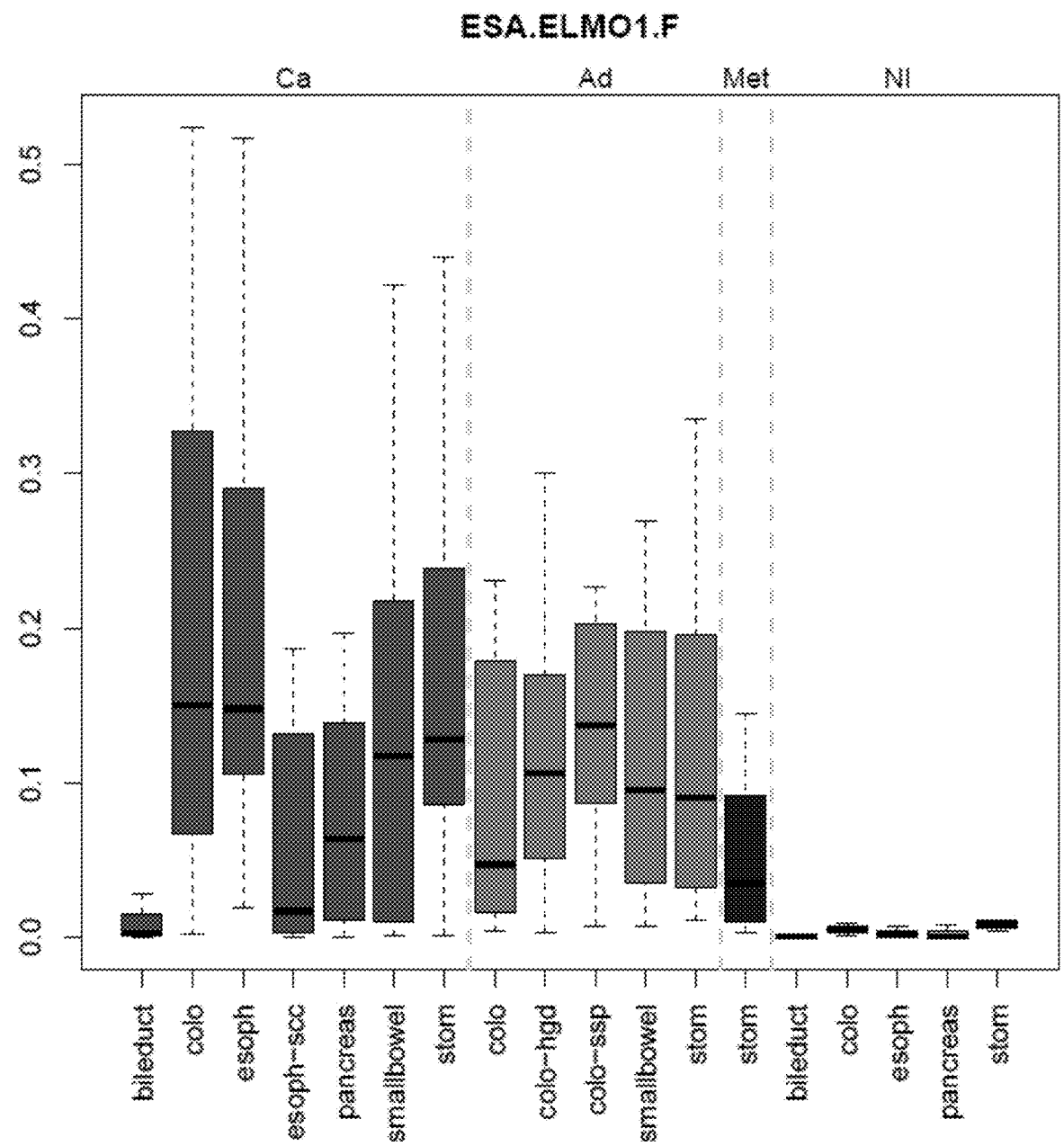
Figure 1E:
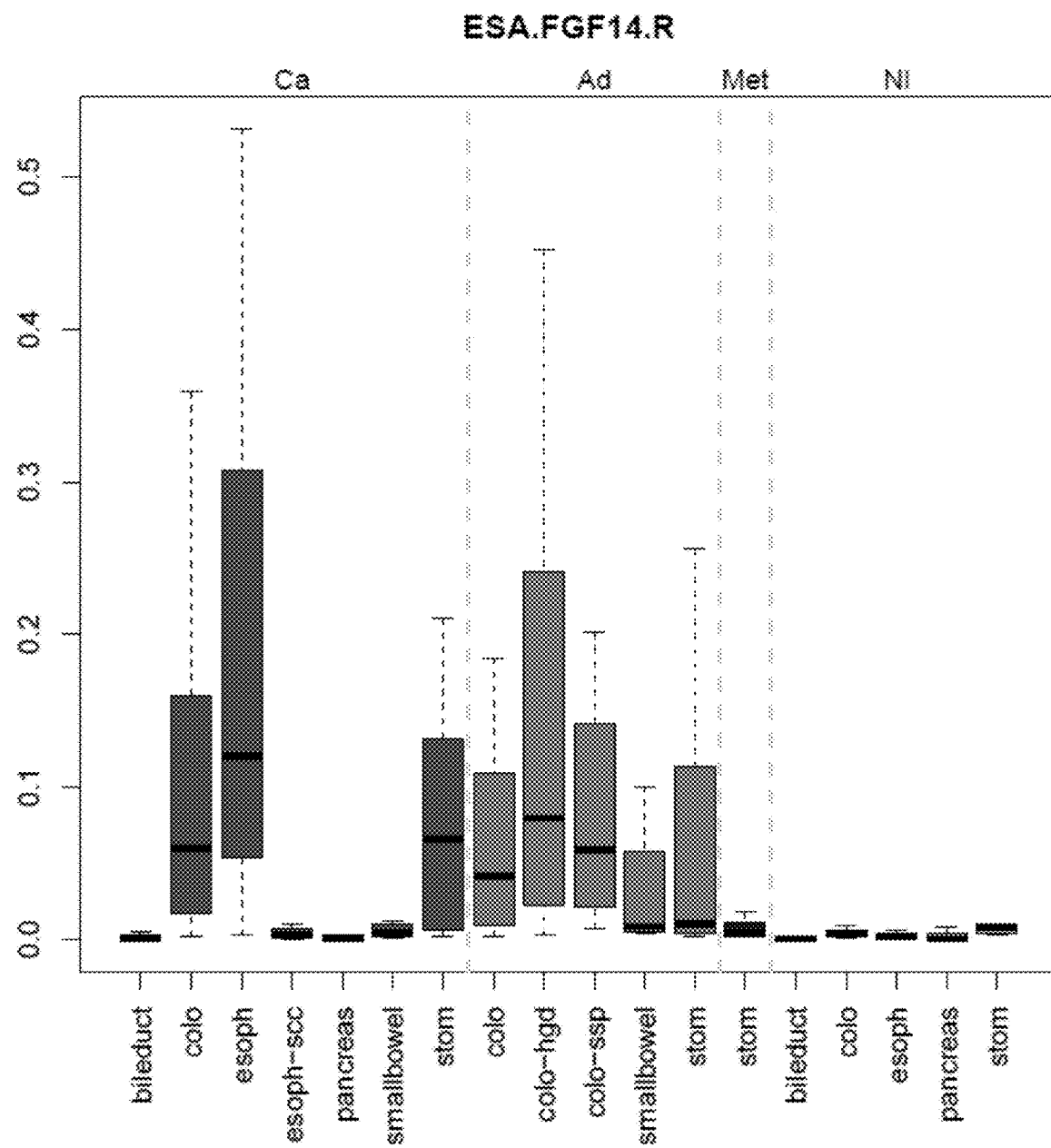
Figure 1F:
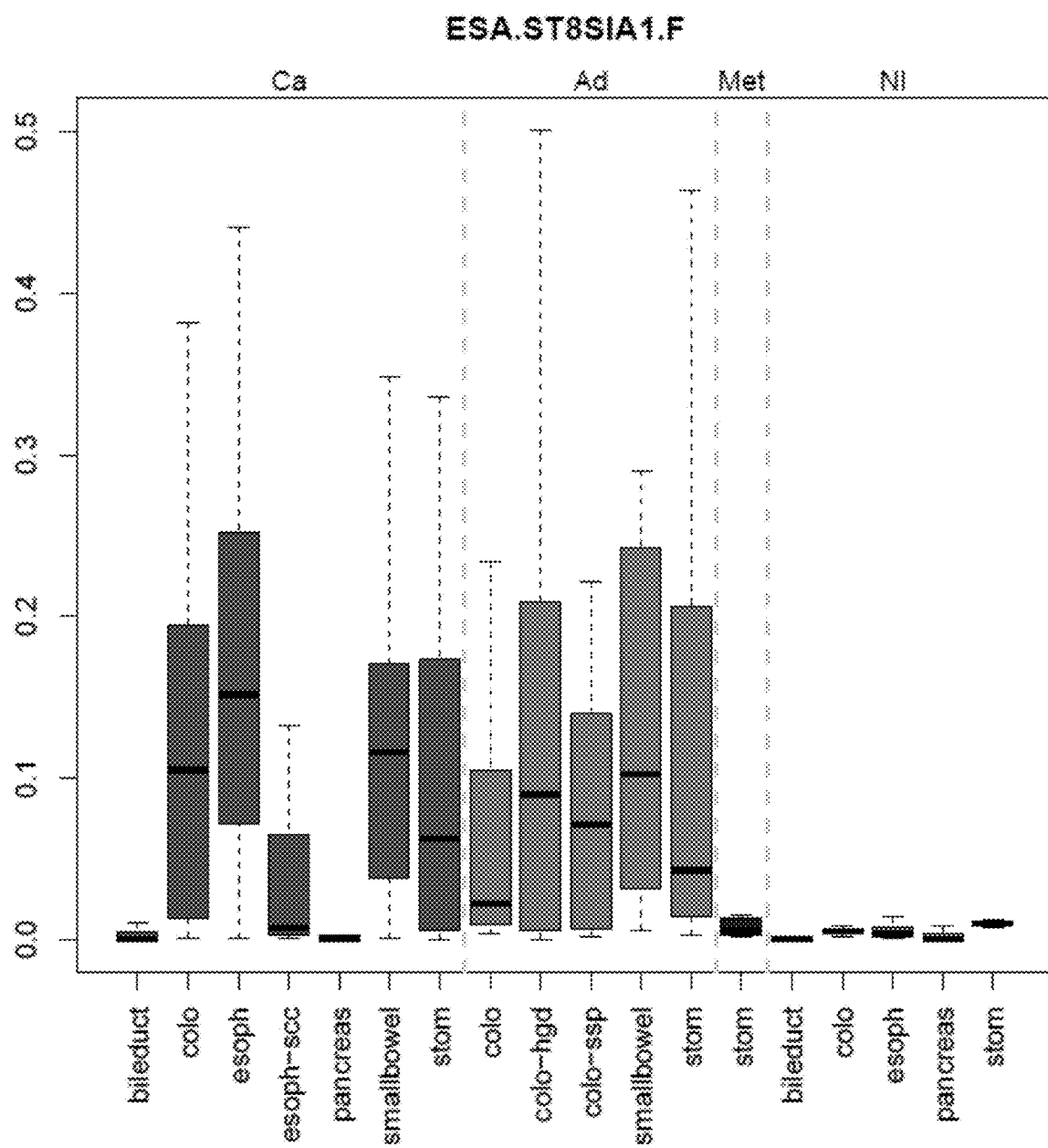
Figure 1G:
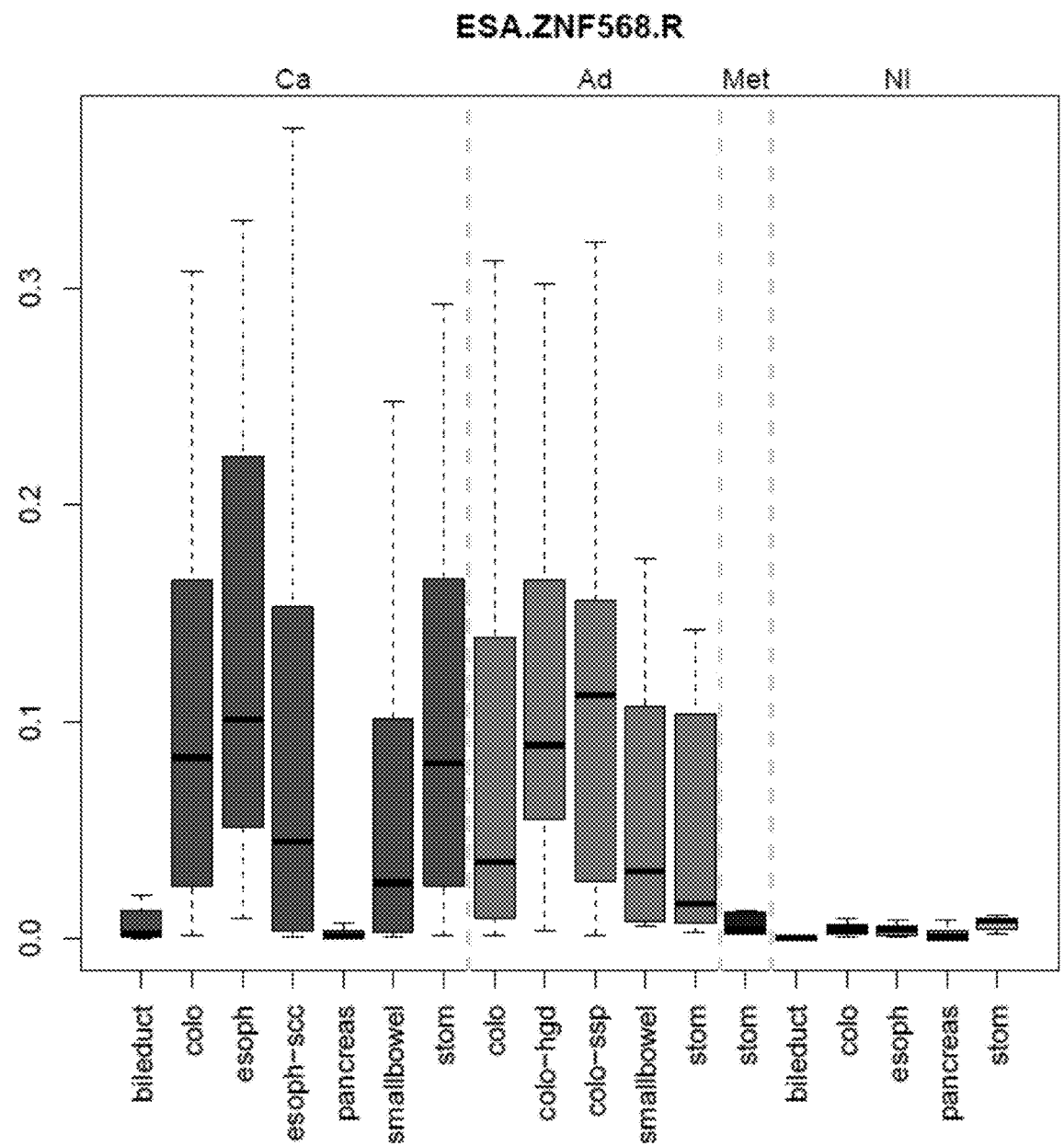
Figure 1H:
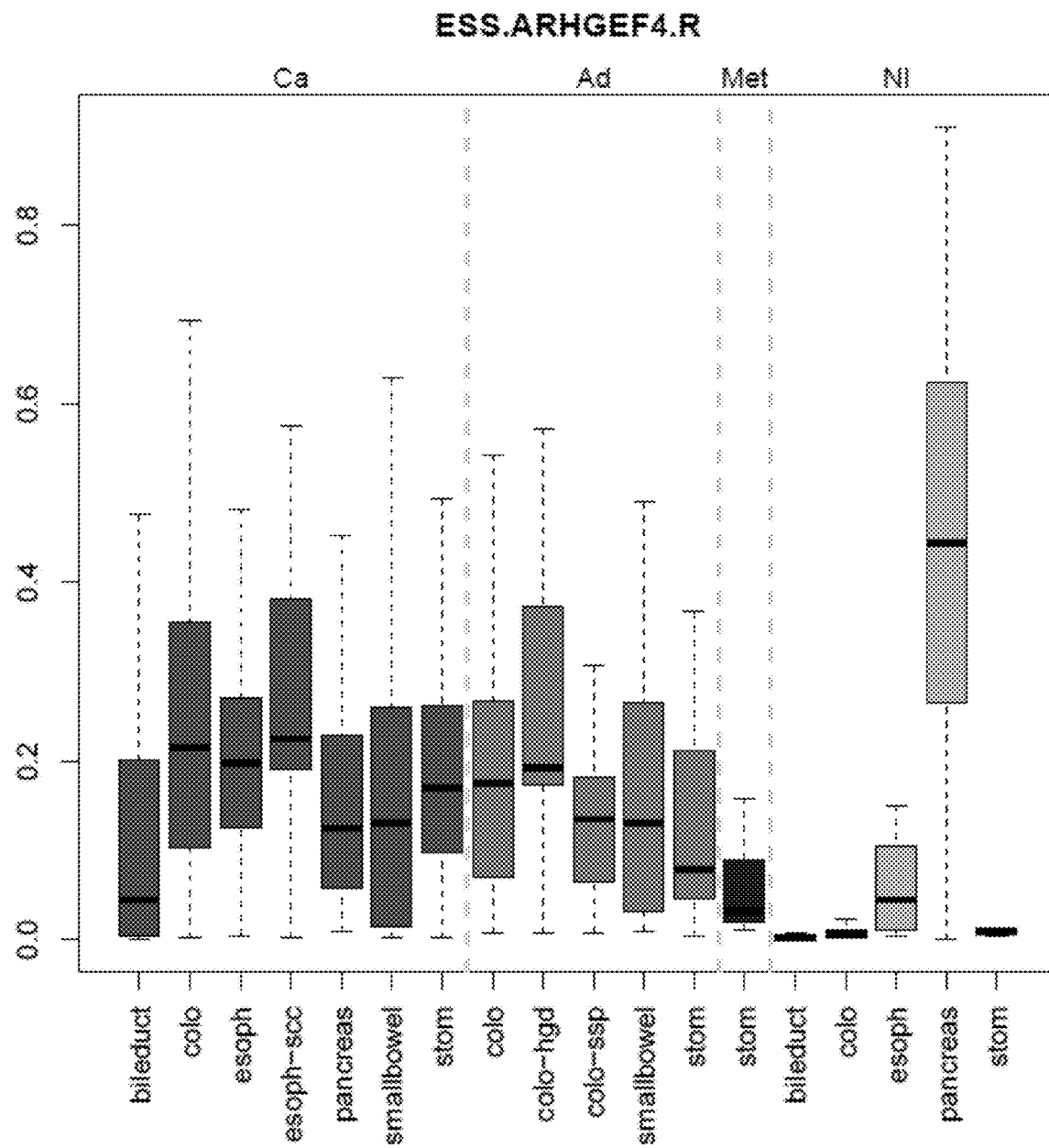
Figure 1I:
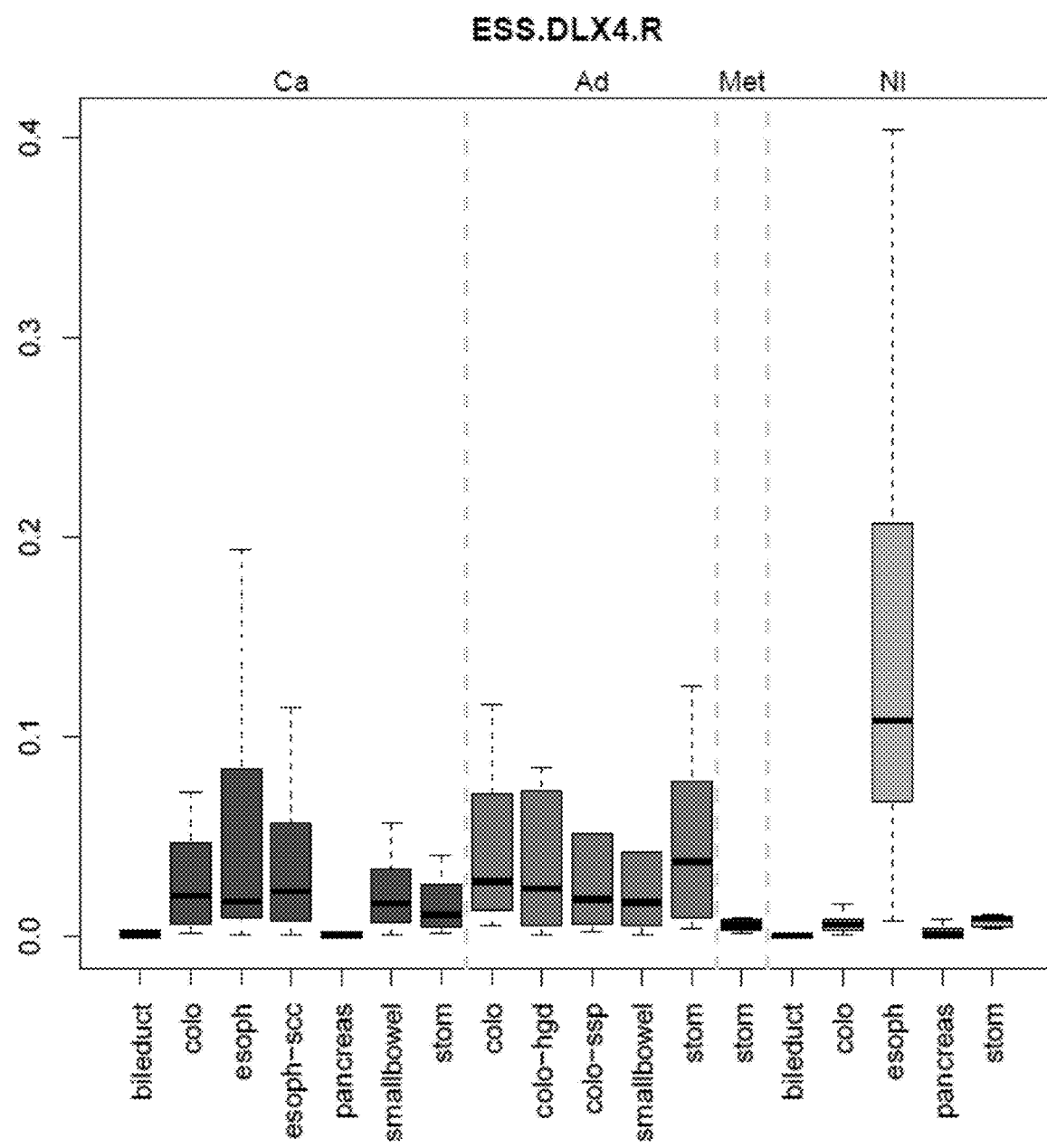
Figure 1J:
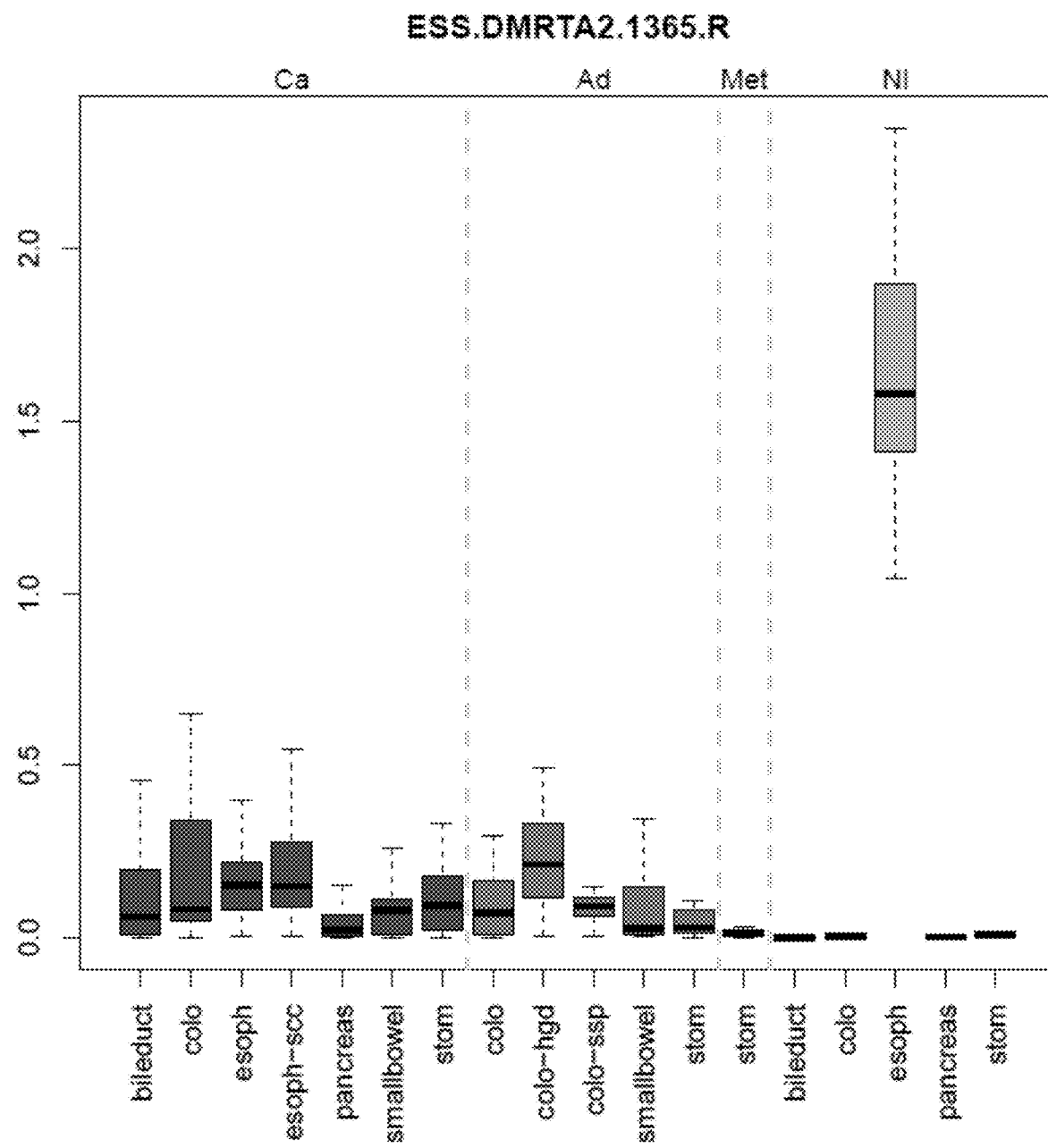
Figure 1K:
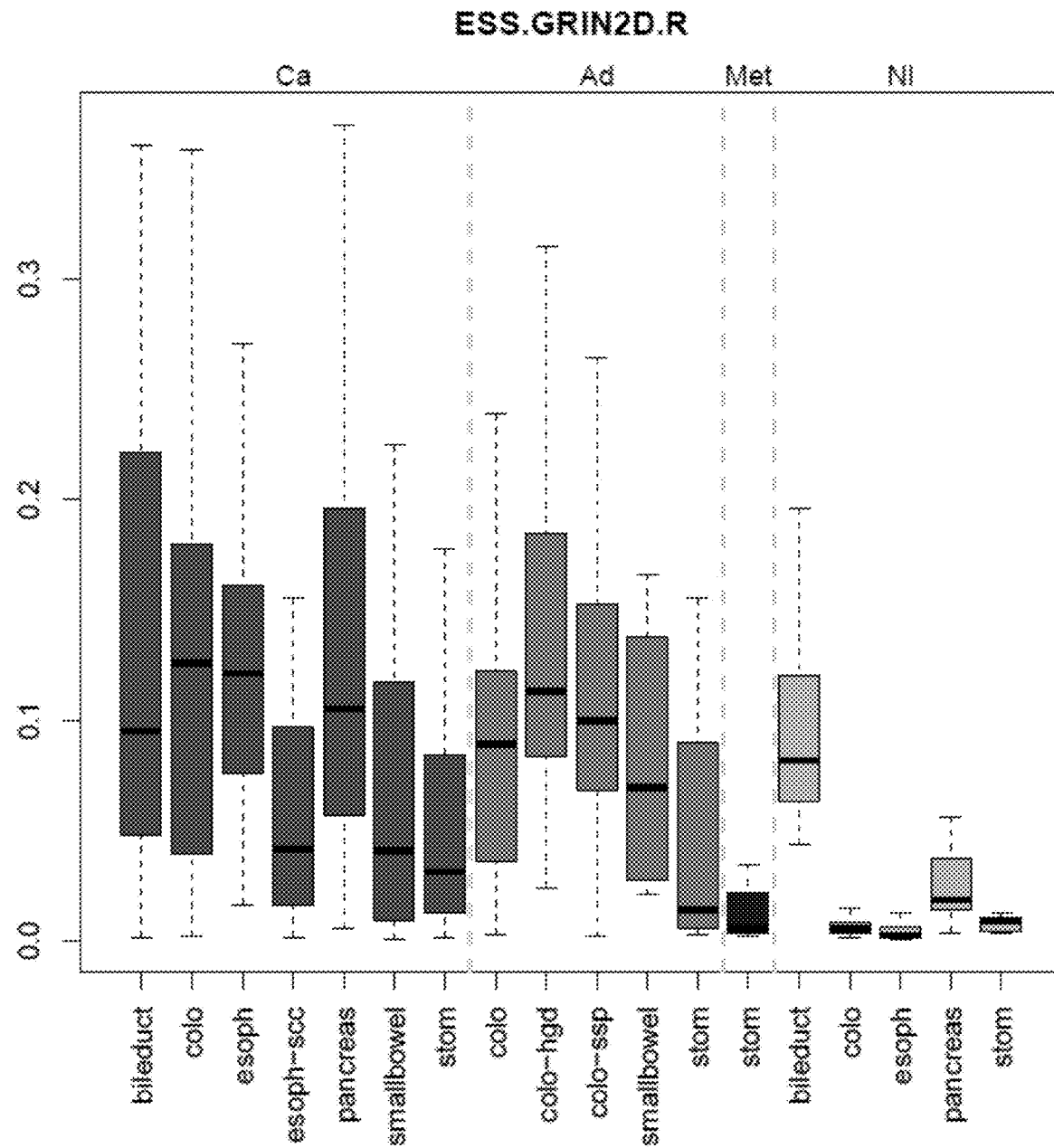
Figure 1L:
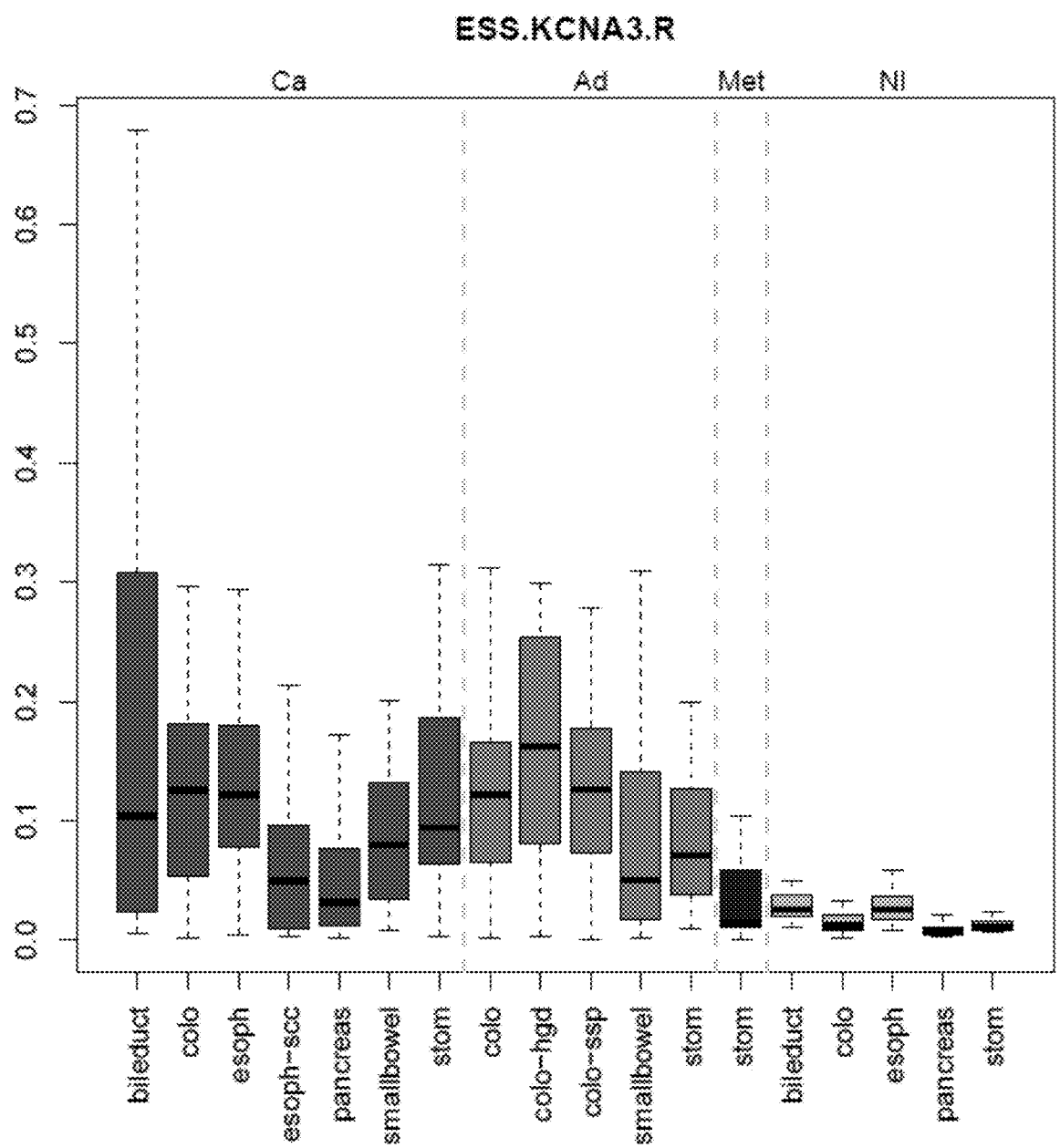
Figure 1M:
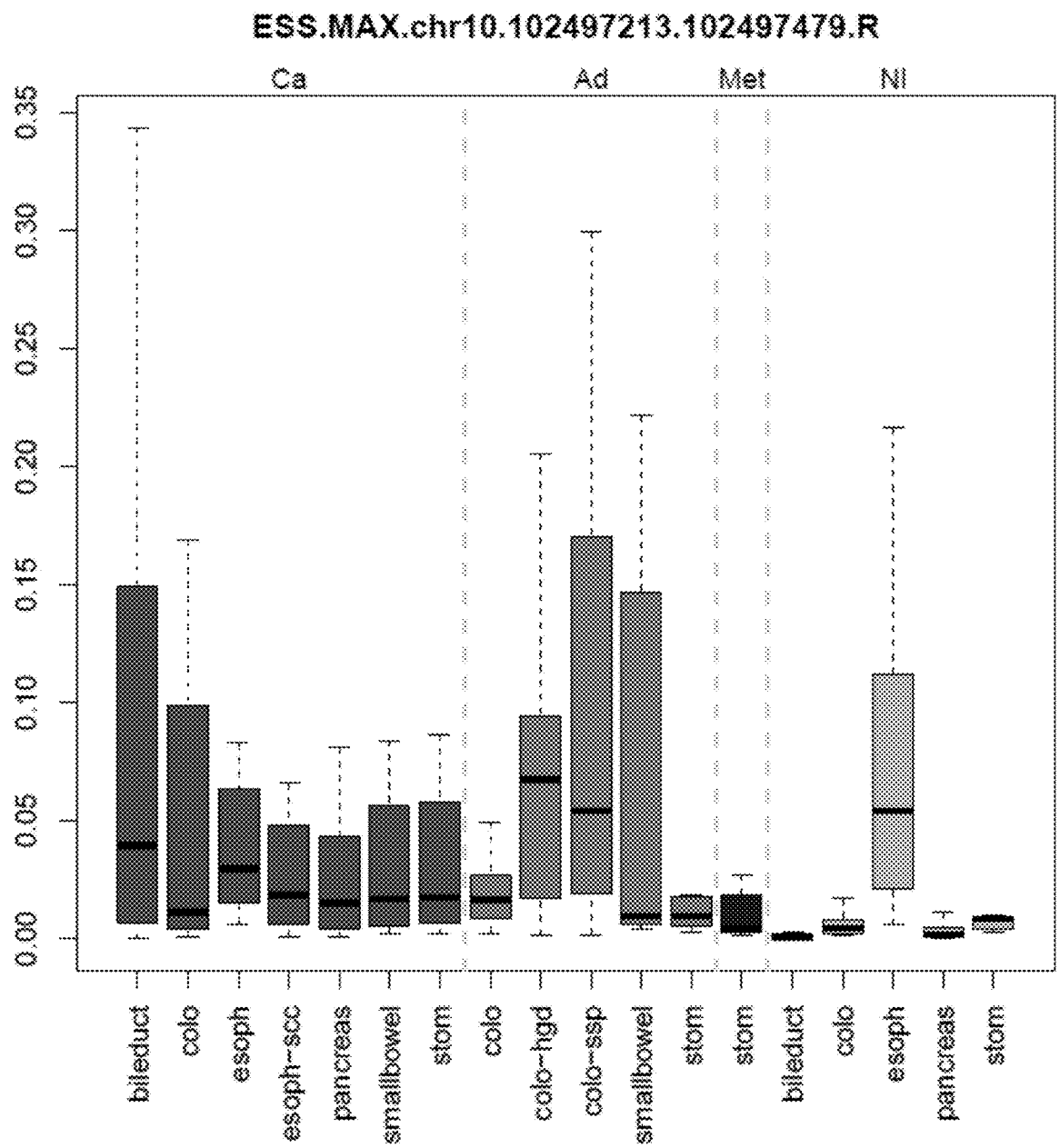
Figure 1N:
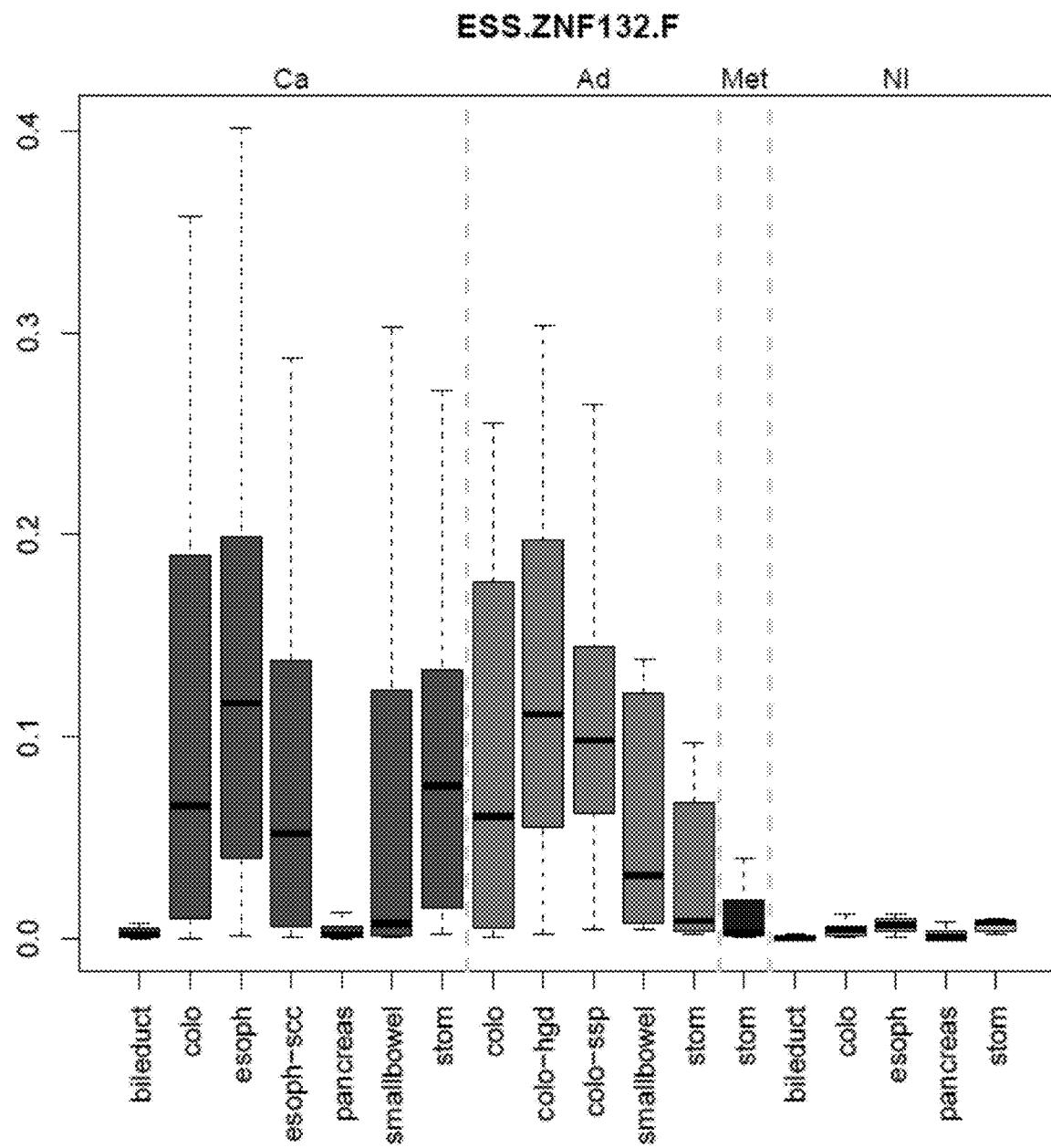
Figure 100:
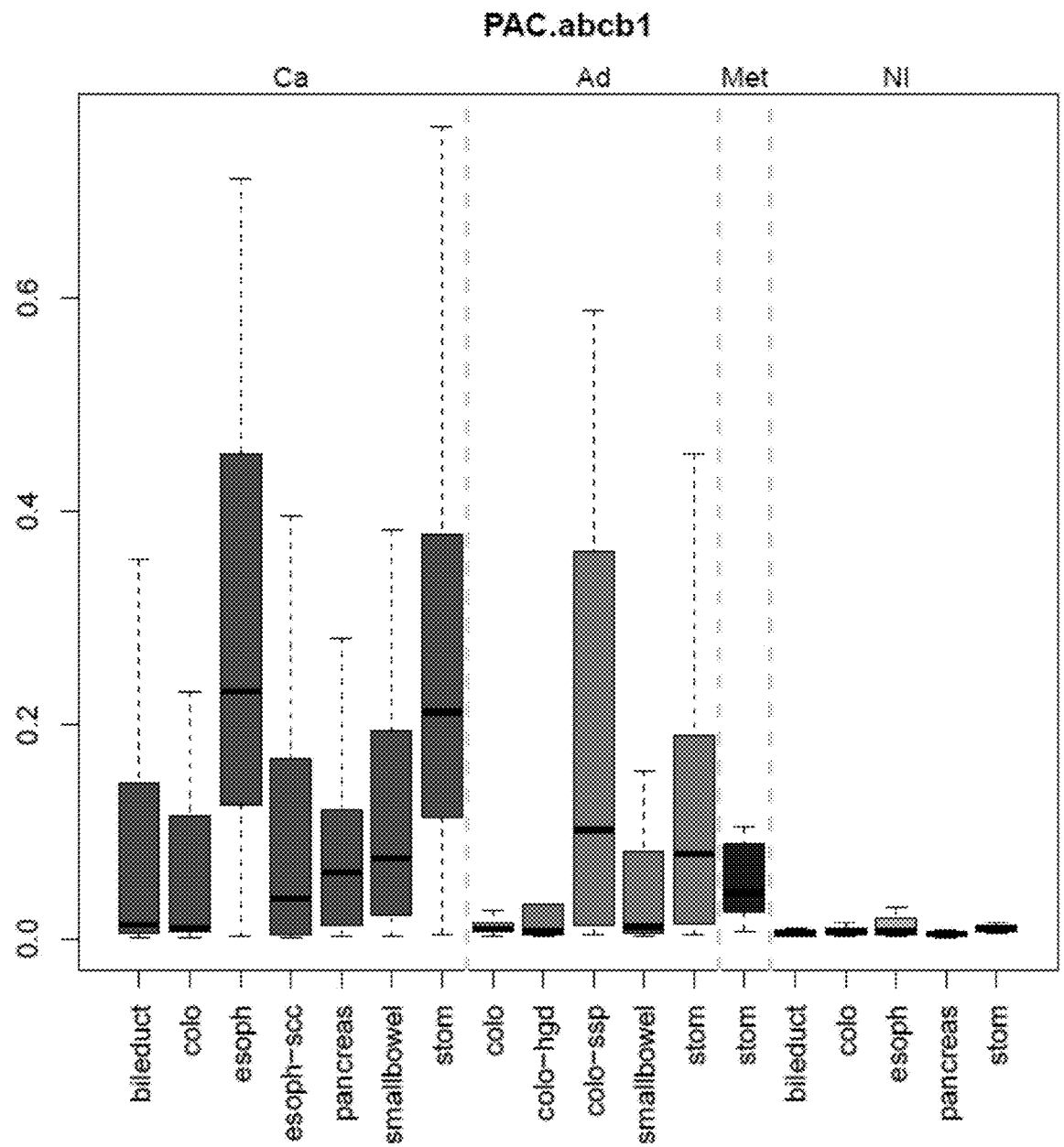
Figure 1P:
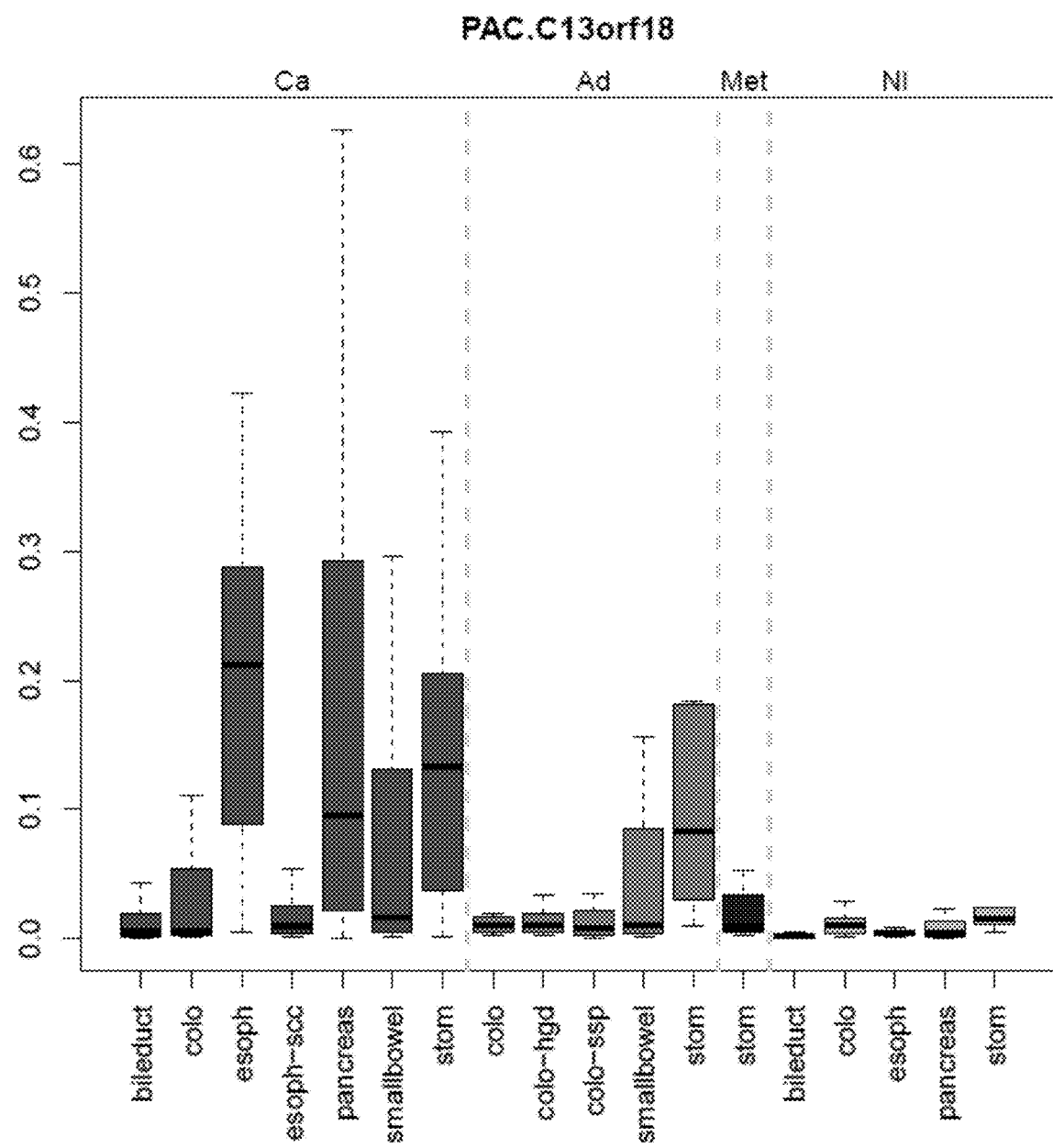
Figure 1Q:
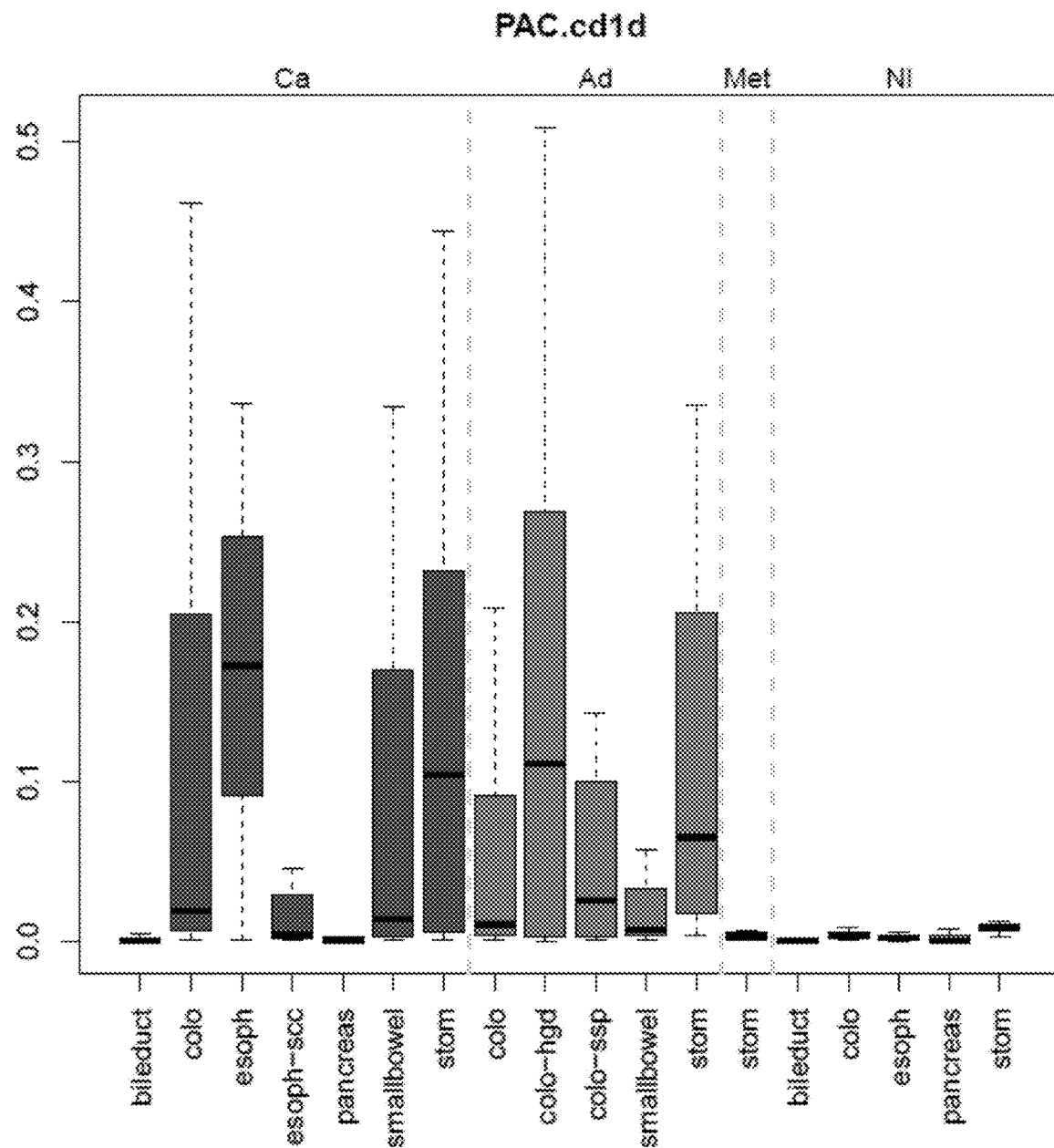
Figure 1R:
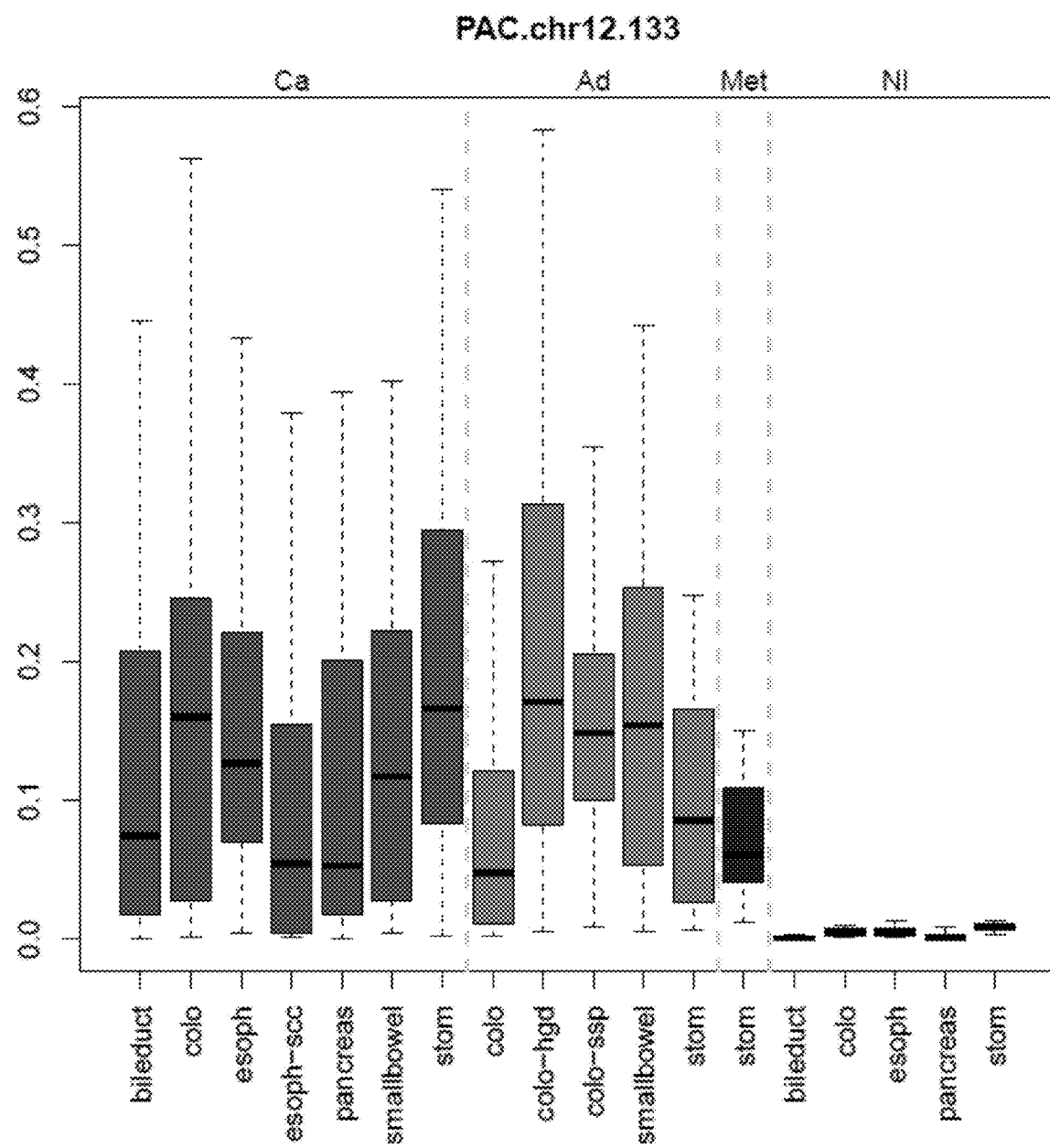
Figure 1S:
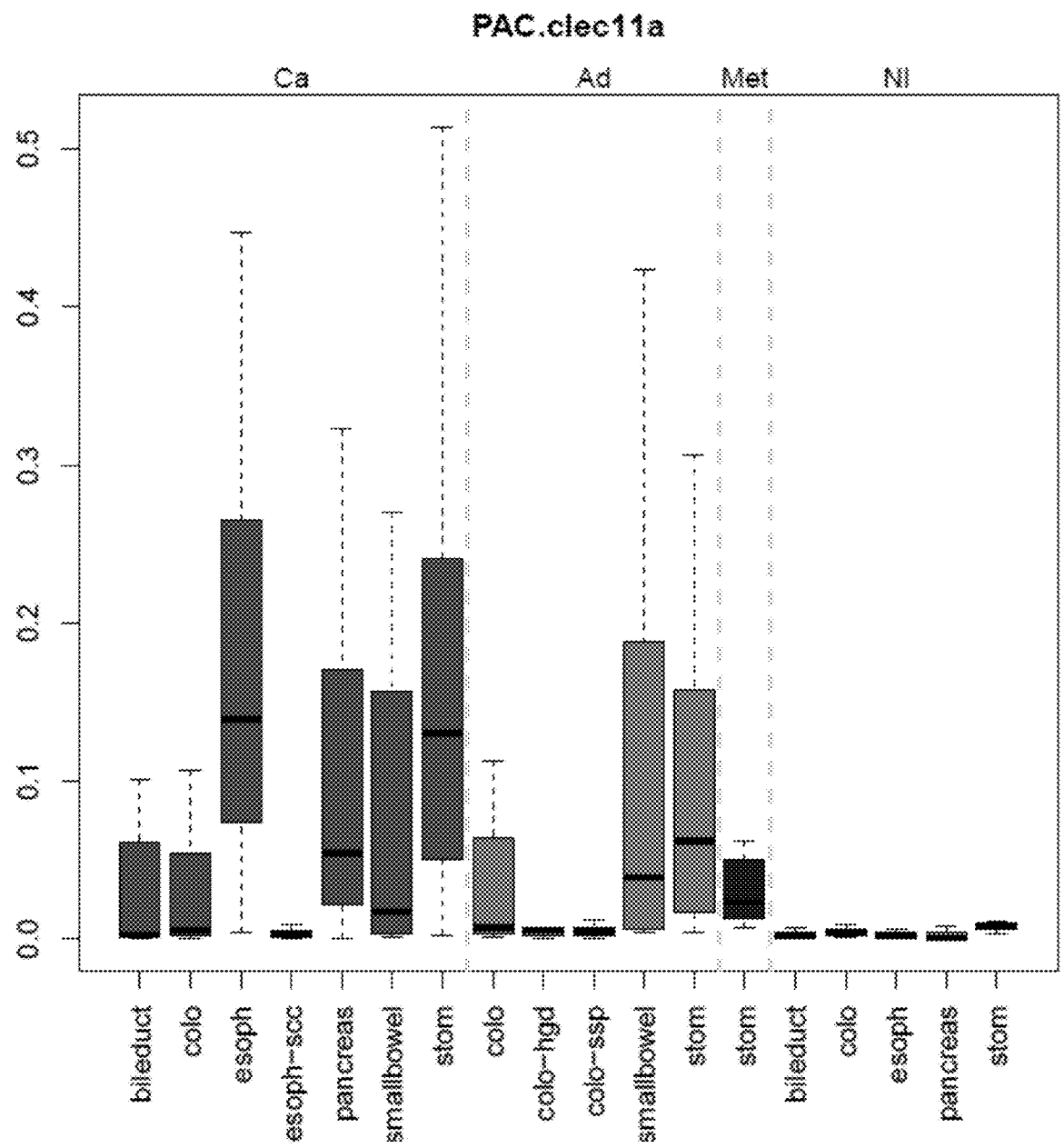
Figure 1T:
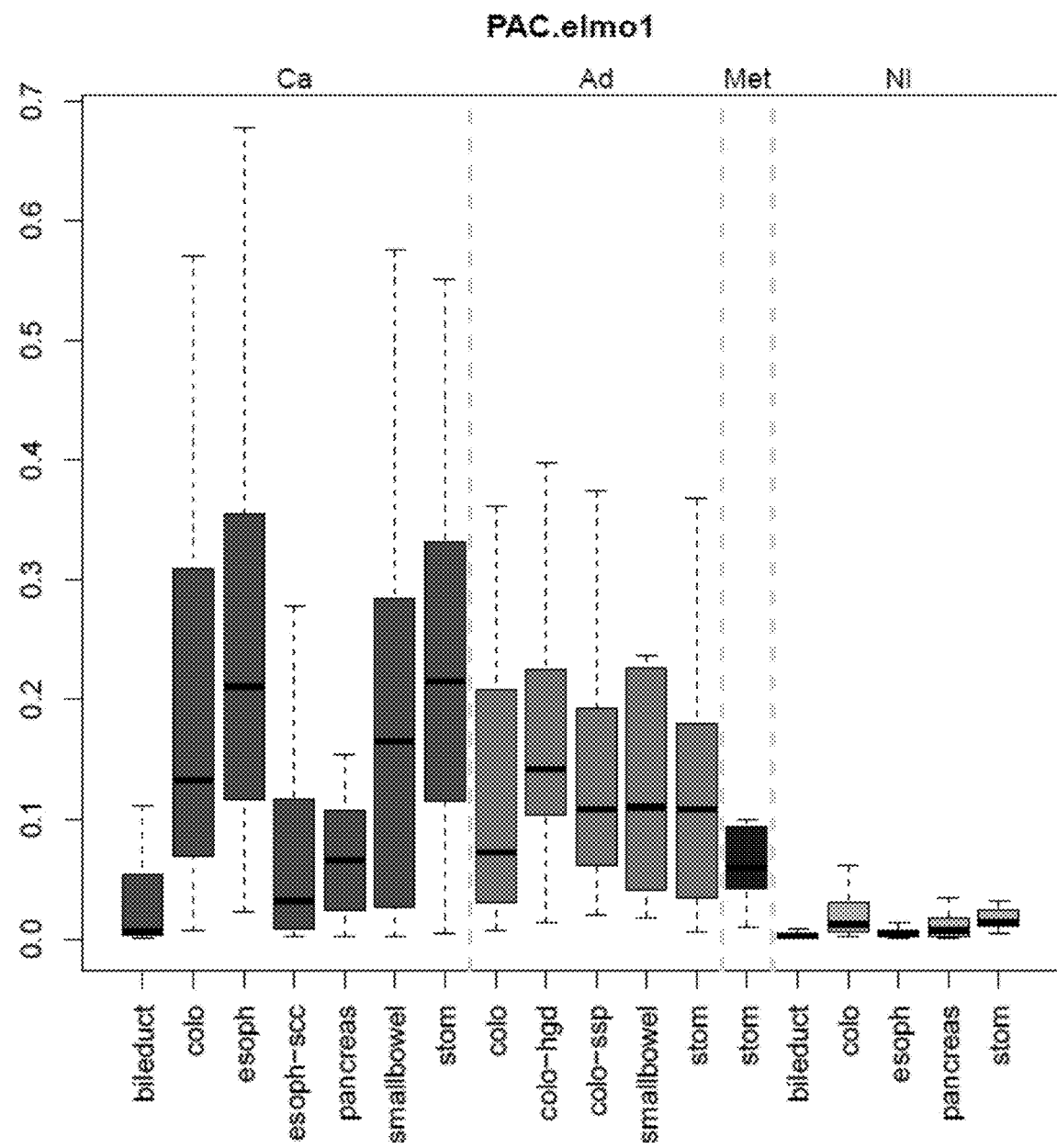
Figure 1U:
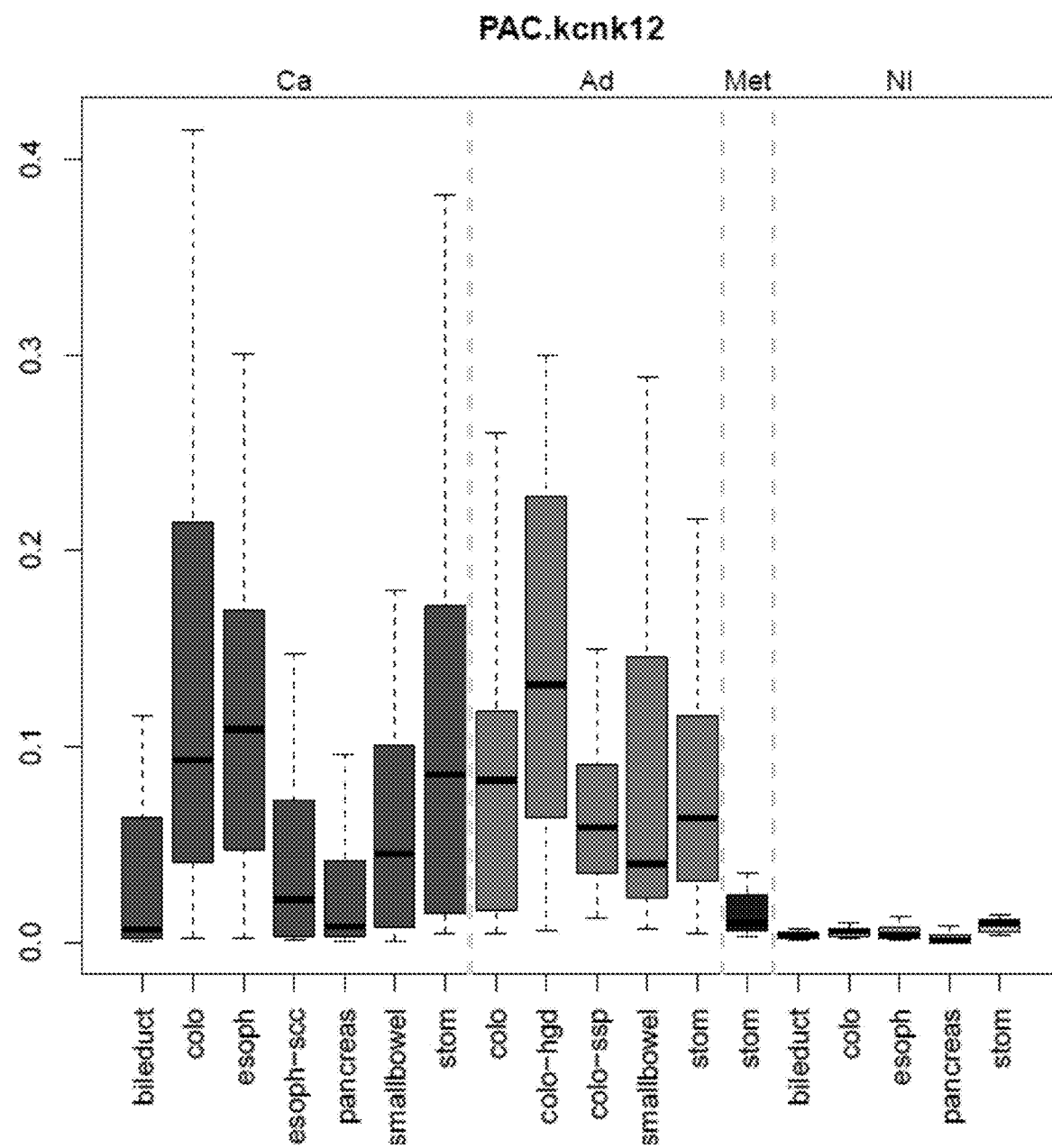
Figure 1V:
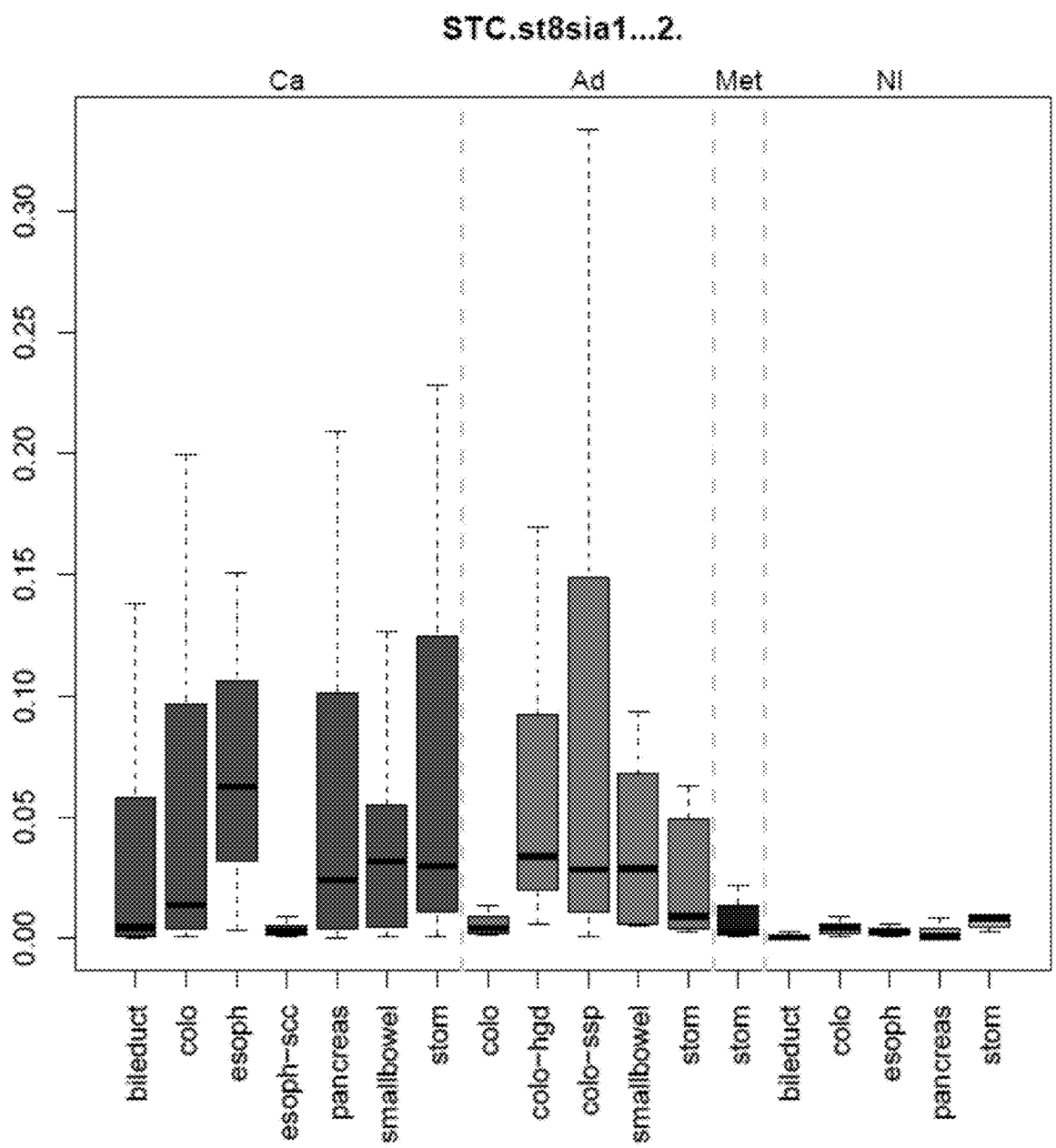
Figure 1W:
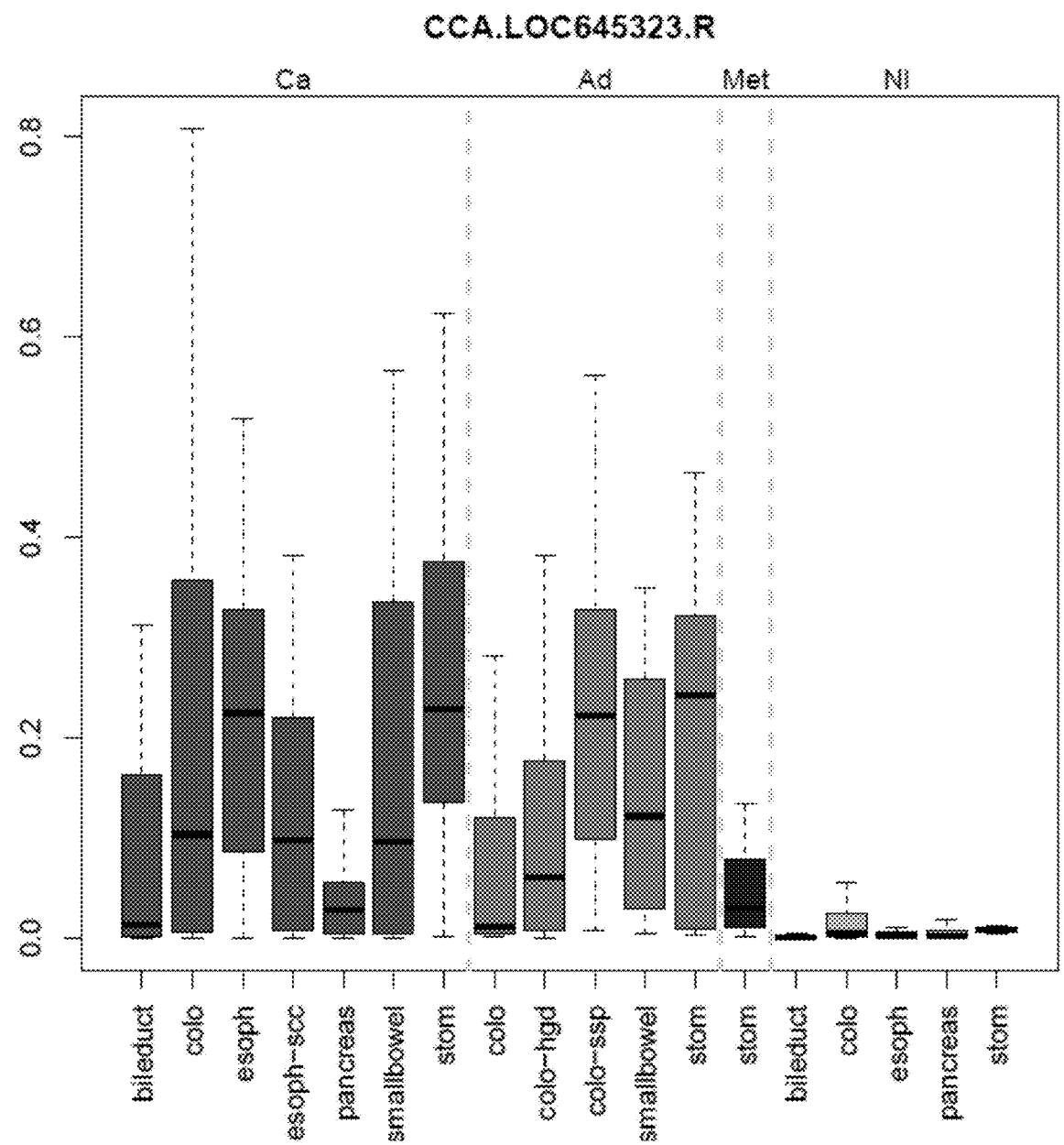
Figure 1X:
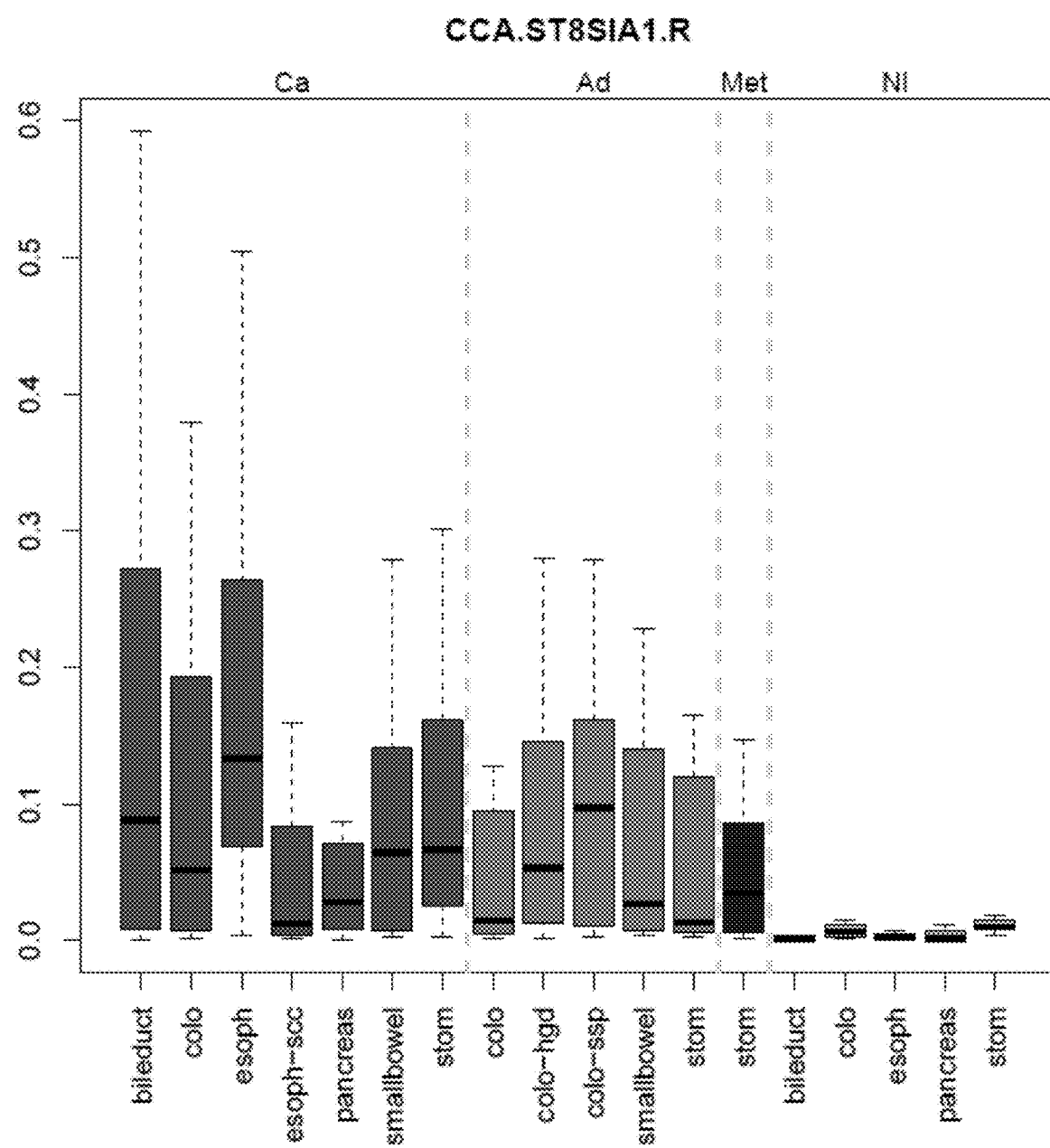
Figure 1Y:
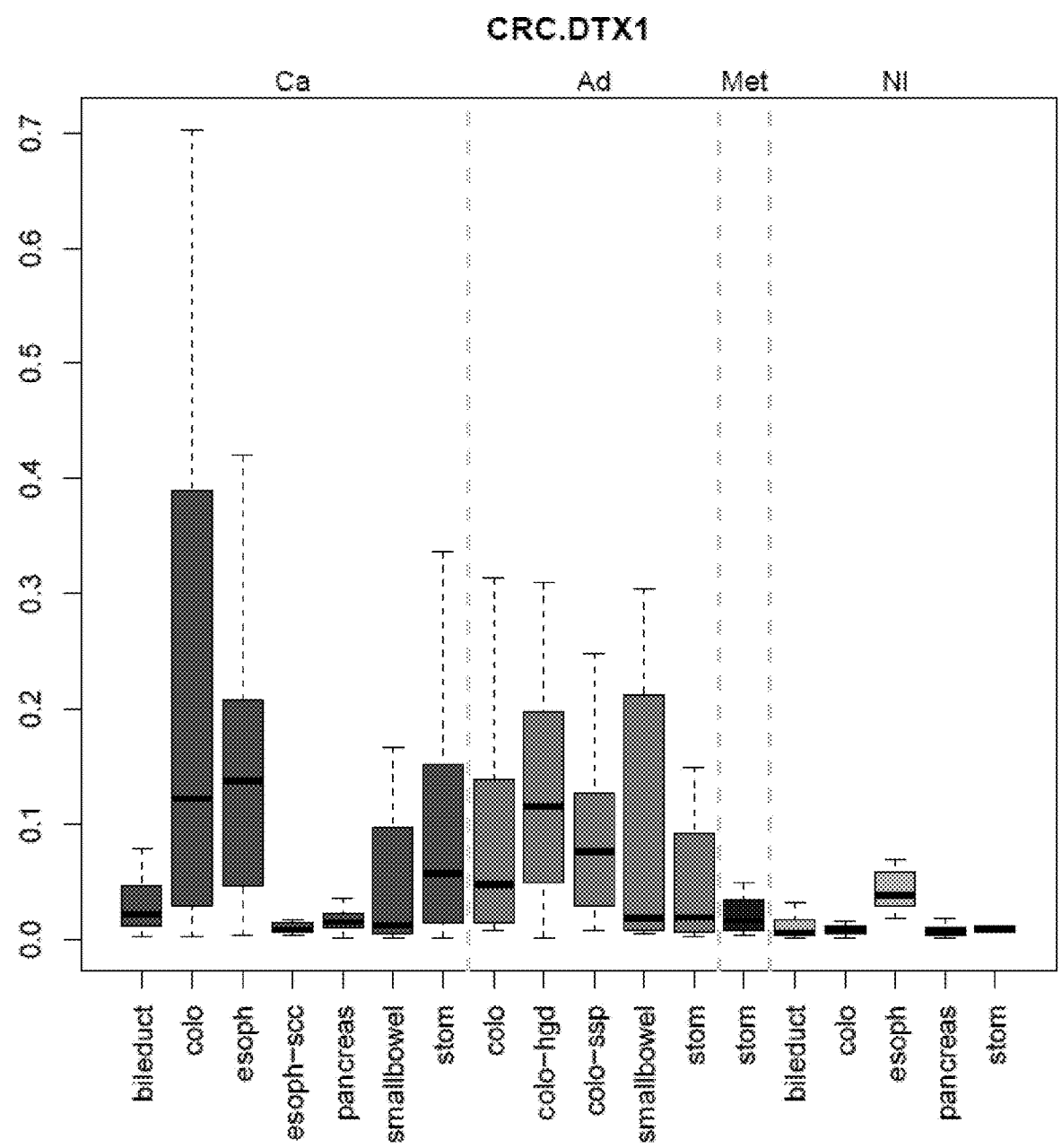
Figure 1Z:
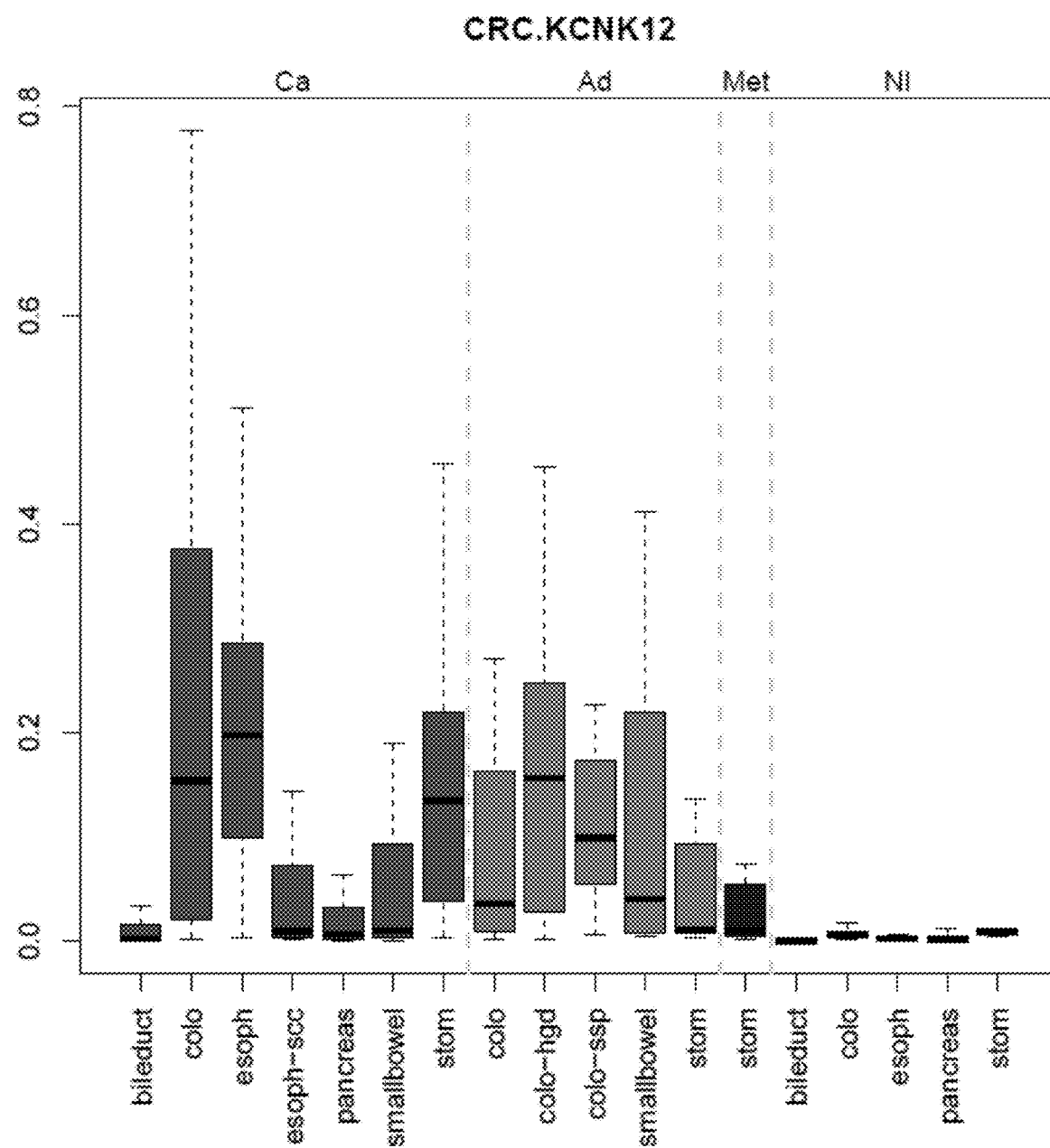

Provided herein is technology for gastrointestinal neoplasia screening and particularly, but not exclusively, to methods, compositions, and related uses for detecting the presence of gastrointestinal neoplasm, and classifying the site location of such a gastrointestinal neoplasm (e.g., a colorectal region, a pancreaticobiliary region, a gastroesophageal region).

As the technology is described herein, the section headings used are for organizational purposes only and are not to be construed as limiting the subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a subregion of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and poly adenylation.

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by the hand of a person in the laboratory is naturally-occurring. A wild-type gene is often that gene or allele that is most frequently observed in a population and is thus arbitrarily designated the "normal" or "wild-type" form of the gene. In contrast, the term "modified" or "mutant" when made in reference to a gene or to a gene product refers, respectively, to a gene or to a gene product that displays modifications in sequence and/or functional properties (e.g., altered characteristics) when compared to the wild-type gene or gene product. It is noted that naturally-occurring mutants can be isolated; these are identified by the fact that they have altered characteristics when compared to the wild-type gene or gene product.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Amplification of nucleic acids generally refers to the production of multiple copies of a polynucleotide, or a portion of the polynucleotide, typically starting from a small amount of the polynucleotide (e.g., a single polynucleotide molecule, 10 to 100 copies of a polynucleotide molecule, which may or may not be exactly the same), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810) are forms of amplification. Additional types of amplification include, but are not limited to, allele-specific PCR (see, e.g., U.S. Pat. No. 5,639,611), assembly PCR (see, e.g., U.S. Pat. No. 5,965,408), helicase-dependent amplification (see, e.g., U.S. Pat. No. 7,662,594), Hot-start PCR (see, e.g., U.S. Pat. Nos. 5,773,258 and 5,338,671), intersequence-specfic PCR, inverse PCR (see, e.g., Triglia, et al. (1988) Nucleic Acids Res., 16:8186), ligation-mediated PCR (see, e.g., Guilfoyle, R. et al., Nucleic Acids Research, 25:1854-1858 (1997); U.S. Pat. No. 5,508,169), methylation-specific PCR (see, e.g., Herman, et al., (1996) PNAS 93(13) 9821-9826), miniprimer PCR, multiplex ligation-dependent probe amplification (see, e.g., Schouten, et al., (2002) Nucleic Acids Research 30(12): e57), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80), nested PCR, overlap-extension PCR (see, e.g., Higuchi, et al., (1988) Nucleic Acids Research 16(15) 7351-7367), real time PCR (see, e.g., Higuchi, et al., (1992) Biotechnology 10:413-417; Higuchi, et al., (1993) Biotechnology 11:1026-1030), reverse transcription PCR (see, e.g., Bustin, S. A. (2000) J. Molecular Endocrinology 25:169-193), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons."

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-beta replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics 4:560). Finally, thermostable template-dependant DNA polymerases (e.g., Taq and Pfu DNA polymerases), by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER nucleic acid assay, Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142); enzyme mismatch cleavage methods (e.g., Variagenics, U.S. Pat. Nos. 6,110,684, 5,958,692, 5,851,770); polymerase chain reaction; branched hybridization methods (e.g., Chiron, U.S. Pat. Nos. 5,849,481, 5,710,264, 5,124,246, and 5,624,802); rolling circle replication (e.g., U.S. Pat. Nos. 6,210,884, 6,183,960 and 6,235,502); NASBA (e.g., U.S. Pat. No. 5,409,818); molecular beacon technology (e.g., U.S. Pat. No. 6,150,097); E-sensor technology (Motorola, U.S. Pat. Nos. 6,248,229, 6,221,583, 6,013,170, and 6,063,573); cycling probe technology (e.g., U.S. Pat. Nos. 5,403,711, 5,011,769, and 5,660,988); Dade Behring signal amplification methods (e.g., U.S. Pat. Nos. 6,121,001, 6,110,677, 5,914,230, 5,882,867, and 5,792,614); ligase chain reaction (e.g., Barnay Proc. Natl. Acad. Sci USA 88, 189-93 (1991)); and sandwich hybridization methods (e.g., U.S. Pat. No. 5,288,609).

The term "amplifiable nucleic acid" refers to a nucleic acid that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfite reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) J. Mol. Biol. 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see, e.g., Ramsahoye (2000) Proc. Natl. Acad. Sci. USA 97: 5237-5242; Salmon and Kaye (1970) Biochim. Biophys. Acta. 204: 340-351; Grafstrom (1985) Nucleic Acids Res. 13: 2827-2842; Nyce (1986) Nucleic Acids Res. 14: 4353-4367; Woodcock (1987) Biochem. Biophys. Res. Commun. 145: 888-894).

As used herein, a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such a change in the nucleic acid molecule's nucleotide sequence can result in a nucleic acid molecule in which each methylated nucleotide is modified to a different nucleotide. Such a change in the nucleic acid nucleotide sequence can result in a nucleic acid molecule in which each unmethylated nucleotide is modified to a different nucleotide. Such a change in the nucleic acid nucleotide sequence can result in a nucleic acid molecule in which each of a selected nucleotide which is unmethylated (e.g., each unmethylated cytosine) is modified to a different nucleotide. Use of such a reagent to change the nucleic acid nucleotide sequence can result in a nucleic acid molecule in which each nucleotide that is a methylated nucleotide (e.g., each methylated cytosine) is modified to a different nucleotide. As used herein, use of a reagent that modifies a selected nucleotide refers to a reagent that modifies one nucleotide of the four typically occurring nucleotides in a nucleic acid molecule (C, G, T, and A for DNA and C, G, U, and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

As used herein, the term "bisulfite reagent" refers to a reagent comprising in some embodiments bisulfite, disulfite, hydrogen sulfite, or combinations thereof to distinguish between methylated and unmethylated cytidines, e.g., in CpG dinucleotide sequences.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) Cancer Research 57: 594-599.

The term "METHYLIGHT™" refers to the art-recognized fluorescence-based real-time PCR technique described by Eads et al. (1999) Cancer Res. 59: 2302-2306.

The term "HEAVYMETHYL™" refers to an assay wherein methylation specific blocking probes (also referred to herein as blockers) covering CpG positions between, or covered by, the amplification primers enable methylation-specific selective amplification of a nucleic acid sample.

The term "HEAVYMETHYL™ METHYLIGHT™" assay refers to a HEAVYMETHYL™ METHYLIGHT™ assay, which is a variation of the METHYLIGHT™ assay, wherein the METHYLIGHT™ assay is combined with methylation specific blocking probes covering CpG positions between the amplification primers.

The term "MS-SNUPE" (Methylation-sensitive Single Nucleotide Primer Extension) refers to the art-recognized assay described by Gonzalgo & Jones (1997) Nucleic Acids Res. 25: 2529-2531.

The term "MSP" (Methylation-specific PCR) refers to the art-recognized methylation assay described by Herman et al. (1996) Proc. Natl. Acad. Sci. USA 93: 9821-9826, and by U.S. Pat. No. 5,786,146.

The term "COBRA" (Combined Bisulfite Restriction Analysis) refers to the art-recognized methylation assay described by Xiong & Laird (1997) Nucleic Acids Res. 25: 2532-2534.

The term "MCA" (Methylated CpG Island Amplification) refers to the methylation assay described by Toyota et al. (1999) Cancer Res. 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The terms "methylation-specific restriction enzyme" or "methylation-sensitive restriction enzyme" refers to an enzyme that selectively digests a nucleic acid dependent on the methylation state of its recognition site. In the case of a restriction enzyme that specifically cuts if the recognition site is not methylated or is hemimethylated, the cut will not take place or will take place with a significantly reduced efficiency if the recognition site is methylated. In the case of a restriction enzyme that specifically cuts if the recognition site is methylated, the cut will not take place or will take place with a significantly reduced efficiency if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) Signal Detection Theory and ROC Analysis, Academic Press, New York).

As used herein, the term "neoplasm" refers to "an abnormal mass of tissue, the growth of which exceeds and is uncoordinated with that of the normal tissues" See, e.g., Willis R A, "The Spread of Tumors in the Human Body", London, Butterworth & Co, 1952.

As used herein, the term "adenoma" refers to a benign tumor of glandular origin. Although these growths are benign, over time they may progress to become malignant.

The term "pre-cancerous" or "pre-neoplastic" and equivalents thereof refer to any cellular proliferative disorder that is undergoing malignant transformation.

A "site" or "region" of a neoplasm, adenoma, cancer, etc. is the tissue, organ, cell type, anatomical area, body part, etc. in a subject's body where the neoplasm, adenoma, cancer, etc. is located.

As used herein, the term "upper gastrointestinal cancer" refers to types of cancer within the gastroesophageal and pancreaticobiliary regions.

As used herein, the term "lower gastrointestinal cancer" refers to types of cancer within the colorectal regions.

As used herein, the term "pancreaticobiliary" refers to tissues and organs including, but not limited to, the pancreas gland, pancreas duct, pancreatic ampulla, bile ducts, gallbladder, liver parenchyma, and duodenum. Examples of cancers associated with pancreaticobiliary tissues and organs include, but are not limited to, pancreatic ductal adenocarcinoma, pancreatic intra-epithelial neoplasia (PanIN) lesions, intraductal papillary mucinous neoplasms (and possibly mucinous cystadenoma), cholangiocarcinoma (bile duct cancer) (with or without underlying chronic bile duct disease, specifically primary sclerosing cholangitis), hepatocellular cancer (primary liver cancer) (with or without underlying chronic liver disease, specifically cirrhosis), ampullary cancer, duodenal small bowel cancer, and gallbladder cancer.

As used herein, the term "gastroesophageal" refers to tissues and organs including, but not limited to, the pharynx, larynx, glottis, epiglottis, upper esophageal sphincter, esophagus, gastroesophageal junction (with or without metaplasia), and stomach. Examples of cancers associated with gastroesophageal tissues and organs include, but are not limited to, Barrett's esophagus, Barrett's esophagus with dysplasia, adenocarcinoma of the esophagus, squamous cell cancer of the esophagus, head/neck squamous cell cancers, adenocarcinoma of the gastroesophageal junction, and adenocarcinoma of the stomach.

As used herein, the term "colorectal" refers to tissues and organs including, but not limited to, the entire colon (including ileocecal valve and appendix), rectum, anal canal, terminal ileum, ileum, andjejunum. Cancers associated with colorectal tissues and organs include, but are not limited to, adenocarcinoma of the colon, adenocarcinoma of the rectum, adenomatous polyps, and sessile serrated polyps As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting a neoplasm or the likelihood that such a subject will respond favorably to a compound (e.g., a pharmaceutical, e.g., a drug) or other treatment.

The term "marker", as used herein, refers to a substance (e.g., a nucleic acid or a region of a nucleic acid) that is able to diagnose a cancer by distinguishing cancerous cells from normal cells, e.g., based its methylation state.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample.

The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

As used herein, a "remote sample" as used in some contexts relates to a sample indirectly collected from a site that is not the cell, tissue, or organ source of the sample. For instance, when sample material originating from the pancreas is assessed in a stool sample (e.g., not from a sample taken directly from a pancreas), the sample is a remote sample.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Embodiments of the Technology

A biological phenomenon of importance to detection of both upper gastrointestinal cancer (UGC) and colorectal cancer (CRC) relates to luminal cell shedding (or exfoliation), as cancers and their pre-cursor lesions exfoliate cells and DNA into the local effluent (see, e.g., Yamaguchi K, et al., Pancreatology 2005; 5:416-21) which are ultimately excreted in stool. Exploiting this biology, the use of stool DNA testing for population screening of CRC has been implemented (see, e.g., Ahlquist D A, et al., Ann Intern Med 2008; 149:441-50, W81; Ahlquist D A, et al., Gastroenterology 2012; 142:248-256). Highly sensitive assays have been used to detect mutant DNA in matched stools of UGC patients whose excised tumor was known to contain the same sequences (see, e.g., Zou H, et al., Gastroenterology 2009; 136:A-625). While this approach demonstrated feasibility of stool testing as an approach to UGC detection, use of mutation markers is limited. The limitation with mutation markers relates to the unwieldy process of their detection; typically, each mutational site across multiple genes must be assayed separately to achieve sufficiently high sensitivity.

Epigenetic molecular changes offer an attractive class of candidate markers for the potential stool detection of UGC. Epigenetic methylation of DNA at cytosine-phosphate-guanine (CpG) island sites by DNA methyltransferases has been studied using DNA from tissues of most tumor types. Acquired methylation events in promotor regions of tumor suppressor genes are thought to silence expression, contributing oncogenesis. Furthermore, DNA methylation may be a more chemically and biologically stable diagnostic tool than RNA or protein expression (see, e.g., Laird P W, Nat Rev Genet 2010; 11:191-203). In other cancers, like sporadic colon cancer, it has been found that aberrant methylation markers are more broadly informative and sensitive than are individual DNA mutations and offer excellent specificity (see, e.g., Zou H, et al., Cancer Epidemiol Biomarkers Prev 2007; 16:2686-96).

Methylation markers have been studied at the tissue level for UGC and their precursor lesions (see, e.g., Omura N, et al., Cancer Biol Ther 2008; 7:1146-56; Sato N, et al., Mod Pathol 2008; 21:238-44; Hong S M, et al., Mod Pathol 2008; 21:1499-507; Hibi K, et al., Anticancer Res 2010; 30:4131-3; Tsunoda S, et al., Oncol Rep 2009; 21:1067-73; Uhm K O, et al., Oncol Res 2008; 17:151-7), but selection of methylation markers has been non-comprehensive in essentially all such studies. DNA from pancreas cancer (PanC) tumor cases have been compared to DNA from colonic epithelia using MSP for markers previously reported in PanC (MDFI, SFRP2, UCHL1, CNTNAP2 and TFPI2) as well as discriminant colonic neoplasm markers (BMP3, EYA4, Vimentin and NDRG4). In a multi-marker regression model, EYA4, UCHL1 and MDFI were highly discriminant, with an area under the receiver operating characteristics curve (AUC) of 0.85; while BMP3 alone achieved an AUC of 0.90. It was found subsequently that stool assay of the combination of mutant KRAS and methylated BMP3 was more sensitive for detection of pancreatic cancer than assay of either marker individually (see, e.g., Kisiel J B, et al., Cancer 2012; 118:2623-31). Methylation differences in UCHL1, EYA4 and MDFI at the level of the pancreas were obscured by background colonic methylation in the stool-based applications. Thus, indicates that a stool marker (or marker panel) for UGC is feasible only if it is broadly informative and exhibits virtually 100% specificity at the tissue level. Better methylation markers are needed to achieve the ideal of high sensitivity without yielding false-positives.

Several methods are available to search for novel methylation markers. While micro-array based interrogation of CpG methylation is a reasonable, high-throughput approach, this strategy is biased towards known regions of interest, mainly established tumor suppressor promotors. Alternative methods for genome-wide analysis of DNA methylation have been developed in the last decade (see, e.g., Laird P W, et al., Nat Rev Genet 2010; 11:191-203). There are three basic approaches. The first employs digestion of DNA by restriction enzymes which recognize specific methylated sites, followed by several possible analytic techniques which provide methylation data limited to the enzyme recognition site or the primers used to amplify the DNA in quantification steps (such as MSP). A second approach enriches methylated fractions of genomic DNA using anti-bodies directed to methyl-cytosine or other methylation-specific binding domains followed by microarray analysis or sequencing to map the fragment to a reference genome. This approach does not provide single nucleotide resolution of all methylated sites within the fragment. A third approach begins with bisulfite treatment of the DNA to convert all unmethylated cytosines to uracil, followed by restriction enzyme digestion and complete sequencing of all fragments after coupling to an adapter ligand. The choice of restriction enzymes can enrich the fragments for CpG dense regions, reducing the number of redundant sequences which may map to multiple gene positions during analysis. This latter approach is termed Reduced Representation Bisulfite Sequencing (RRBS) (see, e.g., Gu H, et al., Nat Methods 2010; 7:133-6).

Single nucleotide resolution analysis of CpG islands has yielded important findings when applied to animal models and human cell lines. Zhang and colleagues found that amplicons from different parts of the same CpG island may have different levels of methylation (see, e.g., Zhang Y, et al., PLoS Genet 2009; 5:e1000438). Further, methylation levels were distributed bi-modally, between highly methylated and unmethylated sequences, further supporting the switch-like pattern to DNA methyltransferase activity (see, e.g., Zhang Y, et al., PLoS Genet 2009; 5:e1000438). When looking at in vivo murine tissues as well as cell lines, Meissner and colleagues found that only about 0.3% of high CpG density promotors, or HCPs (defined as >7% of CpGs within a 300 base pair region) were methylated, whereas areas of low CpG density (LCP, <5%) tended to be frequently methylated in a dynamic tissue-specific pattern (see, e.g., Meissner A, et al., Nature 2008; 454:766-70). HCPs include promotors for ubiquitous housekeeping genes and highly regulated developmental genes; among the HCP sites methylated at >50% were several established candidates, including Wnt 2, NDRG2, SFRP2 and BMP3 (see, e.g., Meissner A, et al., Nature 2008; 454:766-70).

Provided herein is technology for gastrointestinal neoplasia screening and particularly, but not exclusively, to methods, compositions, and related uses for detecting the presence of gastrointestinal neoplasm, and classifying the site location of such a gastrointestinal neoplasm (e.g., a colorectal region, a pancreaticobiliary region, a gastroesophageal region).

Indeed, experiments conducted during the course of developing this technology compared the methylation state of DNA markers from esophageal tissue, stomach tissue, pancreatic tissue, bile duct/liver tissue, and colorectal tissue of subjects having neoplasm related to the respective tissue type to the methylation state of the same DNA markers from control subjects (e.g., normal tissue for the respective tissue type) (see, Example 1).

Markers and/or panels of markers were identified (e.g., a chromosomal region having an annotation selected from chr12.133484978-133485739, BMP3, and chr11.123301058-123301255) capable of classifying gastrointestinal (GI) neoplasm versus control (e.g., normal tissue for the respective tissue type) across GI tissue types (e.g., esophageal tissue, stomach tissue, pancreatic tissue, bile duct/liver tissue, and colorectal tissue) (see, Example 1).

Markers and/or panels of markers were identified (e.g., a chromosomal region having an annotation selected from chr7.25896389-25896501, and QKI) capable of classifying lower gastrointestinal (LGI) neoplasm versus upper gastrointestinal neoplasm (UGI) across GI tissue types (e.g., esophageal tissue, stomach tissue, pancreatic tissue, bile duct/liver tissue, and colorectal tissue) (see, Example 1).

Markers and/or panels of markers were identified (e.g., a chromosomal region having an annotation selected from PDGFD, ELOVL2, PCBP3) capable of classifying pancreaticobiliary neoplasm versus gastroesophageal neoplasm across GI tissue types (e.g., esophageal tissue, stomach tissue, pancreatic tissue, bile duct/liver tissue, and colorectal tissue) (see, Example 1).

Markers and/or panels of markers were identified (e.g., a chromosomal region having an annotation selected from QKI, PDGFD, ELOVL2, chr12.133484978-133485739, chr7.25896389-25896501, PCBP3, chr11.123301058-123301255, and BMP3) capable of predicting control versus neoplasm location across GI tissue types (e.g., esophageal tissue, stomach tissue, pancreatic tissue, bile duct/liver tissue, and colorectal tissue) (see, Example 1).

Markers and/or panels of markers were identified (e.g., a chromosomal region having an annotation selected from BMP3 and QKI) capable of predicting control versus neoplasm location in blood plasma samples (see, Example 1).

Markers and/or panels of markers were identified (e.g., a chromosomal region having an annotation selected from BMP3 and QKI) capable of predicting colorectal cancer versus pancreaticobiliary neoplasm in blood plasma samples (see, Example 1).

Although the disclosure herein refers to certain illustrated embodiments, it is to be understood that these embodiments are presented by way of example and not by way of limitation.

In particular aspects, the present technology provides methods for locating the neoplasm site within the subject, wherein the methylation state of the marker indicates the neoplasm site within the subject. For example, in some embodiments, the methylation state of markers (e.g., a chromosomal region having an annotation selected from chr7.25896389-25896501, and QKI) are used to classify lower gastrointestinal (LGI) neoplasm (e.g., adenoma, colorectal cancer) versus upper gastrointestinal cancer (UGI) (e.g., cancer of the esophagus, pancreas, stomach). In some embodiments, the methylation state of markers (e.g., a chromosomal region having an annotation selected from PDGFD, ELOVL2, PCBP3) are used to classify pancreaticobiliary neoplasm versus gastroesophageal neoplasm. In some embodiments, the methylation state of markers (e.g., a chromosomal region having an annotation selected from BMP3 and QKI) are used to classify colorectal cancer versus pancreaticobiliary neoplasm. The technology also encompasses determining the state or stage of a cancer, e.g., in some embodiments the neoplasm is pre-cancerous. Some embodiments provide methods comprising assaying a plurality of markers, e.g., comprising assaying 2 to 8 markers.

The methods comprise determining the methylation status of at least one methylation marker in a biological sample isolated from a subject, wherein a change in the methylation state of the marker is indicative of the presence, class, or site of a cancer. Particular embodiments relate to markers comprising a differentially methylated region (DMR, e.g., DMR 1-8, see Table 1) that are used for diagnosis (e.g., screening) of neoplastic cellular proliferative disorders (e.g., cancer), including early detection during the pre-cancerous stages of disease and prediction of a neoplasm site (e.g., by discriminating among cancer types, e.g., upper gastrointestinal cancers and lower gastrointestinal cancers).

The markers of the present technology are particularly efficient in detecting or distinguishing between gastrointestinal proliferative disorders, thereby providing improved means for the early detection, classification, and treatment of said disorders.

In addition to embodiments wherein the methylation analysis of at least one marker, a region of a marker, or a base of a marker comprising a DMR (e.g., DMR 1-8 from Table 1) provided herein and listed in Table 1 is analyzed, the technology also provides panels of markers comprising at least one marker, region of a marker, or base of a marker comprising a DMR with utility for the detection of cancers, in neoplasm associated with an UGI region, a LGI region, a pacreaticobiliary region, a gastroesophageal region, and/or a colorectal region.

Some embodiments of the technology are based upon the analysis of the CpG methylation status of at least one marker, region of a marker, or base of a marker comprising a DMR.

In some embodiments, the present technology provides for the use of the bisulfite technique in combination with one or more methylation assays to determine the methylation status of CpG dinucleotide sequences within at least one marker comprising a DMR (e.g., as provided in Table 1 (e.g., DMR 1-8)). Genomic CpG dinucleotides can be methylated or unmethylated (alternatively known as up- and down-methylated respectively). However the methods of the present invention are suitable for the analysis of biological samples of a heterogeneous nature, e.g., a low concentration of tumor cells, or biological materials therefrom, within a background of a remote sample (e.g., blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

According to the present technology, determination of the methylation status of CpG dinucleotide sequences in markers comprising a DMR has utility both in the diagnosis and characterization of cancers such as upper gastrointestinal cancer (e.g., cancer of the esophagus, pancreas, stomach) or lower gastrointestinal cancer (e.g., adenoma, colorectal cancer).

Combinations of Markers

In some embodiments, the technology relates to assessing the methylation state of combinations of markers comprising a DMR from Table 1 (e.g., 2, 3, 4, 5, 6, 7, 8), or more markers comprising a DMR. In some embodiments, assessing the methylation state of more than one marker increases the specificity and/or sensitivity of a screen or diagnostic for identifying a neoplasm in a subject, e.g., an upper gastrointestinal cancer (e.g., esophagus, pancreas, stomach) or a lower gastrointestinal cancer (e.g., adenoma, colorectal). In some embodiments, a marker or a combination of markers discriminates between types and/or locations of a neoplasm. For example, combinations of markers discriminate pancreaticobiliary, gastroesophageal, and colorectal regions from each other, from other neoplasia, and/or from normal (e.g., non-cancerous, non-precancerous) tissue.

Various cancers are predicted by various combinations of markers, e.g., as identified by statistical techniques related to specificity and sensitivity of prediction. The technology provides methods for identifying predictive combinations and validated predictive combinations for some cancers.

In some embodiments, combinations of markers (e.g., comprising a DMR) predict the site of a neoplasm.

For example, markers and/or panels of markers were identified (e.g., a chromosomal region having an annotation selected from chr12.133484978-133485739, BMP3, and chr11.123301058-123301255) capable of classifying gastrointestinal (GI) neoplasm versus control (e.g., normal tissue for the respective tissue type) across GI tissue types (e.g., esophageal tissue, stomach tissue, pancreas tissue, bile duct/liver tissue, and colorectal tissue) (see, Example 1).

Markers and/or panels of markers were identified (e.g., a chromosomal region having an annotation selected from chr7.25896389-25896501, and QKI) capable of classifying lower gastrointestinal (LGI) neoplasm versus upper gastrointestinal neoplasm (UGI) across GI tissue types (e.g., esophageal tissue, stomach tissue, pancreas tissue, bile duct/liver tissue, and colorectal tissue) (see, Example 1).

Markers and/or panels of markers were identified (e.g., a chromosomal region having an annotation selected from PDGFD, ELOVL2, PCBP3) capable of classifying pancreaticobiliary neoplasm versus gastroesophageal neoplasm across GI tissue types (e.g., esophageal tissue, stomach tissue, pancreas tissue, bile duct/liver tissue, and colorectal tissue) (see, Example 1).

Markers and/or panels of markers were identified (e.g., a chromosomal region having an annotation selected from QKI, PDGFD, ELOVL2, chr12.133484978-133485739, chr7.25896389-25896501, PCBP3, chr11.123301058-123301255, and BMP3) capable of predicting control versus neoplasm location across GI tissue types (e.g., esophageal tissue, stomach tissue, pancreas tissue, bile duct/liver tissue, and colorectal tissue) (see, Example 1).

Markers and/or panels of markers were identified (e.g., a chromosomal region having an annotation selected from BMP3 and QKI) capable of predicting control versus neoplasm location in blood plasma samples (see, Example 1).

Markers and/or panels of markers were identified (e.g., a chromosomal region having an annotation selected from BMP3 and QKI) capable of predicting colorectal cancer versus pancreaticobiliary neoplasm in blood plasma samples (see, Example 1).

Methods for Assaying Methylation State

The most frequently used method for analyzing a nucleic acid for the presence of 5-methylcytosine is based upon the bisulfite method described by Frommer, et al. for the detection of 5-methylcytosines in DNA (Frommer et al. (1992) Proc. Natl. Acad. Sci. USA 89: 1827-31) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uricil is desulfonated under alkaline conditions to form uracil. Detection is possible because uracil forms base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98) or methylation-specific PCR (MSP) as is disclosed, e.g., in U.S. Pat. No. 5,786,146.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" Nucleic Acids Res. 24: 5064-6). It is thus possible to analyze individual cells for methylation status, illustrating the utility and sensitivity of the method. An overview of conventional methods for detecting 5-methylcytosine is provided by Rein, T., et al. (1998) Nucleic Acids Res. 26: 2255.

The bisulfite technique typically involves amplifying short, specific fragments of a known nucleic acid subsequent to a bisulfite treatment, then either assaying the product by sequencing (Olek & Walter (1997) Nat. Genet. 17: 275-6) or a primer extension reaction (Gonzalgo & Jones (1997)

Nucleic Acids Res. 25: 2529-31; WO 95/00669; U.S. Pat. No. 6,251,594) to analyze individual cytosine positions. Some methods use enzymatic digestion (Xiong & Laird (1997) Nucleic Acids Res. 25: 2532-4). Detection by hybridization has also been described in the art (Olek et al., WO 99/28498). Additionally, use of the bisulfite technique for methylation detection with respect to individual genes has been described (Grigg & Clark (1994) Bioessays 16: 431-6; Zeschnigk et al. (1997) Hum Mol Genet. 6: 387-95; Feil et al. (1994) Nucleic Acids Res. 22: 695; Martin et al. (1995) Gene 157: 261-4; WO 9746705; WO 9515373).

Various methylation assay procedures are known in the art and can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) Proc. Natl. Acad. Sci. USA 89: 1827-1831). Additionally, restriction enzyme digestion of PCR products amplified from bisulfite-converted DNA finds use in assessing methylation state, e.g., as described by Sadri & Hornsby (1997) Nucl. Acids Res. 24: 5058-5059 or as embodied in the method known as COBRA (Combined Bisulfite Restriction Analysis) (Xiong & Laird (1997) Nucleic Acids Res. 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "METHYLIGHT™" (a fluorescence-based real-time PCR technique) (Eads et al., Cancer Res. 59:2302-2306, 1999), MS-SNUPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No. 5,786,146), and methylated CpG island amplification ("MCA"; Toyota et al., Cancer Res. 59:2307-12, 1999) are used alone or in combination with one or more of these methods.

The "HEAVYMETHYL™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HEAVYMETHYL™ METHYLIGHT™" assay refers to a HEAVYMETHYL™ METHYLIGHT™ assay, which is a variation of the METHYLIGHT™ assay, wherein the METHYLIGHT™ assay is combined with methylation specific blocking probes covering CpG positions between the amplification primers. The HEAVYMETHYL™ assay may also be used in combination with methylation specific amplification primers.

Typical reagents (e.g., as might be found in a typical METHYLIGHT™-based kit) for HEAVYMETHYL™ analysis may include, but are not limited to: PCR primers for specific loci (e.g., specific genes, markers, DMR, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.10% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, DMR, regions of genes, regions of markers, bisulfite treated DNA sequence, CpG island, etc.); optimized PCR buffers and deoxynucleotides, and specific probes.

The METHYLIGHT™ assay is a high-throughput quantitative methylation assay that utilizes fluorescence-based real-time PCR (e.g., TAQMAN®) that requires no further manipulations after the PCR step (Eads et al., Cancer Res. 59:2302-2306, 1999). Briefly, the METHYLIGHT™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The METHYLIGHT™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HEAVYMETHYL™ and MSP techniques) or with oligonucleotides covering potential methylation sites.

The METHYLIGHT™ process is used with any suitable probe (e.g. a "TAQMAN®" probe, a LIGHTCYCLER® probe, etc.) For example, in some applications double-stranded genomic DNA is treated with sodium bisulfite and subjected to one of two sets of PCR reactions using TAQMAN® probes, e.g., with MSP primers and/or HEAVYMETHYL blocker oligonucleotides and a TAQMAN® probe. The TAQMAN® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TAQMAN® probe to remain fully hybridized during the PCR annealing/extension step. As the Taq polymerase enzymatically synthesizes a new strand during PCR, it will eventually reach the annealed TAQMAN® probe. The Taq polymerase 5' to 3' endonuclease activity will then displace the TAQMAN® probe by digesting it to release the fluorescent reporter molecule for quantitative detection of its now unquenched signal using a real-time fluorescent detection system.

Typical reagents (e.g., as might be found in a typical METHYLIGHT™-based kit) for METHYLIGHT™ analysis may include, but are not limited to: PCR primers for specific loci (e.g., specific genes, markers, DMR, regions of genes, regions of markers, bisulfite treated DNA sequence, CpG island, etc.); TAQMAN® or LIGHTCYCLER® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HEAVYMETHYL™ and MSP techniques) or with oligonucleotides covering potential methylation sites.

The QM™ process can by used with any suitable probe, e.g., "TAQMAN®" probes, LIGHTCYCLER® probes, in the amplification process. For example, double-stranded genomic DNA is treated with sodium bisulfite and subjected to unbiased primers and the TAQMAN® probe. The TAQMAN® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TAQMAN® probe to remain fully hybridized during the PCR annealing/extension step. As the Taq polymerase enzymatically synthesizes a new strand during PCR, it will eventually reach the annealed TAQMAN® probe. The Taq polymerase 5' to 3' endonuclease activity will then displace the TAQMAN® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, DMR, regions of genes, regions of markers, bisulfite treated DNA sequence, CpG island, etc.); TAQMAN® or LIGHTCYCLER® probes; optimized PCR buffers and deoxynucleotides; and Taq polymerase.

The MS-SNUPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical MS-SNUPE™-based kit) for MS-SNUPE™ analysis may include, but are not limited to: PCR primers for specific loci (e.g., specific genes, markers, DMR, regions of genes, regions of markers, bisulfite treated DNA sequence, CpG island, etc.); optimized PCR buffers and deoxynucleotides; gel extraction kit; positive control primers; MS-SNUPE™ primers for specific loci; reaction buffer (for the MS-SNUPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" Nat Methods 7: 133-6; Meissner et al. (2005) "Reduced representation bisulfite sequencing for comparative high-resolution DNA methylation analysis" Nucleic Acids Res. 33: 5868-77.

In some embodiments, a quantitative allele-specific real-time target and signal amplification (QuARTS) assay is used to evaluate methylation state. Three reactions sequentially occur in each QuARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes cleavase to release the flap sequence by cutting between the detection probe and the flap sequence. The flap sequence is complementary to a nonhairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" Clin Chem 56: A199; U.S. patent application Ser. Nos. 12/946,737, 12/946,745, 12/946,752, and 61/548,639.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715). It is preferred that the bisulfite treatment is conducted in the presence of denaturing solvents such as but not limited to n-alkylenglycol or diethylene glycol dimethyl ether (DME), or in the presence of dioxane or dioxane derivatives.

In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715). The bisulfite conversion is preferably carried out at a reaction temperature between 30° C. and 70° C., whereby the temperature is increased to over 85° C. for short times during the reaction (see: PCT/EP2004/011715). The bisulfite treated DNA is preferably purified prior to the quantification. This may be conducted by any means known in the art, such as but not limited to ultrafiltration, e.g., by means of Microcon™ columns (manufactured by Millipore™). The purification is carried out according to a modified manufacturer's protocol (see, e.g., PCT/EP2004/011715).

In some embodiments, fragments of the treated DNA are amplified using sets of primer oligonucleotides according to the present invention (e.g., see Table 2) and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in length.

In another embodiment of the method, the methylation status of CpG positions within or near a marker comprising a DMR (e.g., DMR 1-8 as provided in Table 1) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids").

Methods

In some embodiments the technology, methods are provided that comprise the following steps:
1) contacting a nucleic acid (e.g., genomic DNA, e.g., isolated from a body fluids such as a stool sample, a blood sample, or a tissue sample (e.g., gastrointestinal tissue)) obtained from a subject with at least one reagent or series of reagents that distinguishes between methylated and non-methylated CpG dinucleotides within at least one marker comprising a DMR (e.g., DMR 1-8, e.g., as provided in Table 1) and
2) detecting a lack of cancer, colorectal neoplasia, pancreaticobiliary cancer, or gastroesophageal cancer (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample, a blood sample, or a tissue sample (e.g., gastrointestinal tissue)) obtained from a subject with at least one reagent or series of reagents that distinguishes between methylated and non-methylated CpG dinucleotides within at least one marker selected from a chromosomal region having an annotation selected from the group consisting of QKI, PDGFD, ELOVL2, chr12.133484978-133485739, chr7.25896389-25896501, PCBP3, chr11.123301058-123301255, and BMP3, and
2) detecting a lack of cancer, colorectal neoplasia, pancreaticobiliary cancer, or gastroesophageal cancer (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample, a blood sample, or a tissue sample (e.g., gastrointestinal tissue)) obtained from a subject with at least one reagent or series of reagents that distinguishes between methylated and non-methylated CpG dinucleotides within at least one marker selected from a chromosomal region having an annotation selected from the group consisting of chr12.133484978-133485739, BMP3, and chr11.123301058-123301255, and
2) detecting a lack of cancer or gastrointestinal cancer (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample, a blood sample, or a tissue sample (e.g., gastrointestinal tissue)) obtained from a subject with at least one reagent or series of reagents that distinguishes between methylated and non-methylated CpG dinucleotides within at least one marker selected from a chromosomal region having an annotation selected from the group consisting of BMP3 and QKI, and
2) detecting a lack of cancer or gastrointestinal cancer (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample, a blood sample, or a tissue sample (e.g., gastrointestinal tissue)) obtained from a subject having gastrointestinal cancer with at least one reagent or series of reagents that distinguishes between methylated and non-methylated CpG dinucleotides within at least one marker selected from a chromosomal region having an annotation selected from the group consisting of chr7.25896389-25896501, and QKI, and
2) classifying the gastrointestinal cancer as a lower gastrointestinal (LGI) neoplasm or upper gastrointestinal neoplasm (UGI) (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample, a blood sample, or a tissue sample (e.g., gastrointestinal tissue)) obtained from a subject having gastrointestinal cancer with at least one reagent or series of reagents that distinguishes between methylated and non-methylated CpG dinucleotides within at least one marker selected from a chromosomal region having an annotation selected from the group consisting of PDGFD, ELOVL2, PCBP3, and
2) classifying the gastrointestinal cancer as a pancreaticobiliary neoplasm or a gastroesophageal neoplasm (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample, a blood sample, or a tissue sample (e.g., gastrointestinal tissue)) obtained from a subject having gastrointestinal cancer with at least one reagent or series of reagents that distinguishes between methylated and non-methylated CpG dinucleotides within at least one marker selected from a chromosomal region having an annotation selected from the group consisting of BMP3 and QKI, and
2) classifying the gastrointestinal cancer as a pancreaticobiliary neoplasm or a colorectal neoplasm (e.g., afforded with a sensitivity of greater than or equal to 80% and a specificity of greater than or equal to 80%).

Preferably, the sensitivity is from about 70% to about 100%, or from about 80% to about 90%, or from about 80% to about 85%. Preferably, the specificity is from about 70% to about 100%, or from about 80% to about 90%, or from about 80% to about 85%.

Genomic DNA may be isolated by any means, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or pre-neoplastic matter are suitable for use in the present method, e.g., cell lines, histological slides, biopsies, paraffin-embedded tissue, body fluids, stool, colonic effluent, urine, blood plasma, blood serum, whole blood, isolated blood cells, cells isolated from the blood, and combinations thereof.

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Appl. Ser. No. 61/485,386 or by a related method.

The genomic DNA sample is then treated with at least one reagent, or series of reagents, that distinguishes between methylated and non-methylated CpG dinucleotides within at least one marker comprising a DMR (e.g., DMR 1-8, e.g., as provided by Table 1).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfate (hydrogen sulfite, disulfite) followed by alkaline hydrolysis.

The treated nucleic acid is then analyzed to determine the methylation state of the target gene sequences (at least one gene, genomic sequence, or nucleotide from a marker comprising a DMR, e.g., at least one DMR chosen from DMR 1-8, e.g., as provided in Table 1). The method of analysis may be selected from those known in the art, including those listed herein, e.g., QuARTS and MSP as described herein.

Aberrant methylation, more specifically hypermethylation of a marker comprising a DMR (e.g., DMR 1-8, e.g., as provided by Table 1) is associated with a cancer and, in some embodiments, predicts tumor site.

The technology relates to the analysis of any sample associated with a cancer of the gastrointestinal system. For example, in some embodiments the sample comprises a tissue and/or biological fluid obtained from a patient. In some embodiments, the sample comprises a secretion. In some embodiments, the sample comprises blood, serum, plasma, gastric secretions, pancreatic juice, a gastrointestinal biopsy sample, microdissected cells from a gastrointestinal biopsy, gastrointestinal cells sloughed into the gastrointestinal lumen, and/or gastrointestinal cells recovered from stool. In some embodiments, the subject is human. These samples may originate from the upper gastrointestinal tract, the lower gastrointestinal tract, or comprise cells, tissues, and/or secretions from both the upper gastrointestinal tract and the lower gastrointestinal tract. The sample may include cells, secretions, or tissues from the liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample.

Such samples can be obtained by any number of means known in the art, such as will be apparent to the skilled person. For instance, urine and fecal samples are easily attainable, while blood, ascites, serum, or pancreatic fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens In some embodiments, the technology relates to a method for treating a patient (e.g., a patient with gastrointestinal cancer, with early stage gastrointestinal cancer, or who may develop gastrointestinal cancer), the method comprising determining the methylation state of one or more DMR as provided herein and administering a treatment to the patient based on the results of determining the methylation state. The treatment may be administration of a pharmaceutical compound, a vaccine, performing a surgery, imaging the patient, performing another test. Preferably, said use is in a method of clinical screening, a method of prognosis assessment, a method of monitoring the results of therapy, a method to identify patients most likely to respond to a particular therapeutic treatment, a method of imaging a patient or subject, and a method for drug screening and development.

In some embodiments of the technology, a method for diagnosing a gastrointestinal cancer in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., a DMR as disclosed herein), the methylation state of which is indicative of the presence, severity, or absence of the condition.

Along with diagnosis, clinical cancer prognosis relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of making determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., DMR) disclosed herein. Further, in some embodiments of the presently disclosed subject matter, multiple determination of the biomarkers over time can be made to facilitate diagnosis and/or prognosis. A temporal change in the biomarker can be used to predict a clinical outcome, monitor the progression of gastrointestinal cancer, and/or monitor the efficacy of appropriate therapies directed against the cancer. In such an embodiment for example, one might expect to see a change in the methylation state of one or more biomarkers (e.g., DMR) disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of a cancer in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with gastrointestinal cancer risk, prognosis, determining treatment efficacy, and/or progression of the cancer in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis. Likewise, a decrease in the marker from the initial time to the second time can be indicative of a particular type or severity of cancer, or a given prognosis. Furthermore, the degree of change of one or more markers can be related to the severity of the cancer and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker (e.g., a DMR). Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more DMR), the chance of a given outcome (e.g., suffering from a gastrointestinal cancer) may be very low.

In some embodiments, a statistical analysis associates a prognostic indicator with a predisposition to an adverse outcome. For example, in some embodiments, a methylation state different from that in a normal control sample obtained from a patient who does not have a cancer can signal that a subject is more likely to suffer from a cancer than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value (see, e.g., Dowdy and Wearden, Statistics for Research, John Wiley & Sons, New York, 1983). Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein (e.g., a DMR) can be established, and the degree of change in the methylation state of the biamarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with a gastrointestinal cancer. In certain embodiments of the method, a subject is identified as having metaplasia upon identifying an aberrant methylation state of one or more DMR provided herein in a biological sample obtained from the subject. In other embodiments of the method, the detection of an aberrant methylation state of one or more of such biomarkers in a biological sample obtained from the subject results in the subject being identified as having cancer.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having a gastrointestinal cancer if, when compared to a control methylation state, there is a measurable difference in the methylation state of at least one biomarker in the sample. Conversely, when no change in methylation state is identified in the biological sample, the subject can be identified as not having gastrointestinal cancer, not being at risk for the cancer, or as having a low risk of the cancer. In this regard, subjects having the cancer or risk thereof can be differentiated from subjects having low to substantially no cancer or risk thereof. Those subjects having a risk of developing a gastrointestinal cancer can be placed on a more intensive and/or regular screening schedule, including endoscopic surveillance. On the other hand, those subjects having low to substantially no risk may avoid being subjected to an endoscopy, until such time as a future screening, for example, a screening conducted in accordance with the present technology, indicates that a risk of gastrointestinal cancer has appeared in those subjects.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, a gastrointestinal cancer indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like. The presently-disclosed subject matter further includes a system for diagnosing a gastrointestinal cancer in a subject. The system can be provided, for example, as a commercial kit that can be used to screen for a risk of gastrointestinal cancer or diagnose a gastrointestinal cancer in a subject from whom a biological sample has been collected. An exemplary system provided in accordance with the present technology includes assessing the methylation state of a DMR as provided in Table 1.

EXAMPLES

Example 1

This example demonstrates that methylated DNA markers can discriminate upper from lower GI neoplasms.

An unbiased search for neoplasm markers at each major GI organ site was conducted by reduced representation bisulfite sequencing. Top marker candidates were then blindly validated by methylation specific PCR on independent tissue DNA samples from normal mucosa (17 esophagus (E), 13 stomach (S), 33 pancreas (P), 35 bile duct/liver (BD), 21 colorectal (CR)] and neoplasia (42 E, 43 S, 36 P, 48 BD, 97 CR)). Recursive partitioning (rPart) trees modeled all stepwise combinations of single markers to classify controls vs neoplasms and then neoplasms by site (CR, gastroesophageal or pancreaticobiliary). A 2nd model was designed for clinical validation on data from 42 plasma DNA samples (14 normal and 28 cancers (14 P, 14 CR)).

From the top 100 markers, 95 were validated and used for rPart modeling. A 3-marker panel (chr12.133, BMP3, chr11.123301058-255) was selected for the universal detection of GI neoplasms, as it classified neoplasms and control tissues with 95% accuracy. Two markers (chr7.25896389-501, QKI) then assigned lower vs upper GI neoplasms with 94% accuracy. Finally, 3 markers (PDGFD, ELOVL2, PCBP3) called pancreaticobiliary vs gastroesophageal neoplasms with 94% accuracy. All 8 markers applied in a single model (see, Table 3) accurately predicted control vs tumor by site [88% ($p<0.0001$)]. In plasma, a 2-marker panel (BMP3, QKI) was 78% accurate in assigning patients to cancer or control groups ($p<0.0009$) and 83% accurate in assigning cancer origin to CR or P sites ($p<0.0001$).

After applying the filter criteria above, the following 8 differentially methylated regions (DMR) were identified (Table 1).

Various analysis techniques were used to generate the results of the study. First, Regression PARtioning Tree (rPart) models were used to in three stages to identify combination of markers with the highest degree of predictive accuracy. In stage 1, markers were selected based on their universal predictive accuracy for the classification of any neoplastic subtype versus normal controls. In stage 2, only subjects with known neoplasia were used to select markers based on their predictive accuracy of upper versus lower gastrointestinal neoplasia. In stage 3, only subjects with upper gastrointestinal neoplasia were used to select markers based on their predictive accuracy of pancreaticobiliary versus gastroesophageal neoplasia. A logistic regression model was then fit to each marker set identified in each of the stages. A predictive score from the fitted logistic model was then created for each individual from each of the 3 stages (i.e., 3 predictive scores were generated). These 3 predictive scores were then used in the final rPart model to obtain an overall estimate of accuracy for site specific neoplasia. For all analyses, the best predictive accuracy would be 100%.

FIGS. 1A-OOOO depict the initial summary of the distribution of individual markers within specific disease sites and neoplasm findings. The x-axis for FIGS. 1A-OOOO represents the different cohorts and sites tested. The y-axis for FIGS. 1A-OOOO represents the standardized methylation values (marker counts/beta actin counts). Each box and whisker summarizes the following: the $25^{th}$ percentile, $50^{th}$ percentile, and $75^{th}$ percentile of the standardized marker (boxes) and the lower and upper range of likely markers values as defined by the $25^{th}$ percentile−1.5*IQR and $75^{th}$ percentile+1.5*IQR (IQR=interquartile range). FIGS. 1A-OOOO display the site specific distribution of the markers and non-overlapping box and whiskers indicate strong site specific tendencies.

TABLE 1

DMR

| DMR No. | Gene Annotation | Chromosome | Region on Chromosome (starting base-ending base) |
|---|---|---|---|
| 1 | QKI | 6 | 163834534-163834925 |
| 2 | PDGFD | 11 | 104034769-104034920 |
| 3 | ELOVL2 | 6 | 11044395-11044834 |
| 4 | MAX.chr12.133484978-133485739 | 12 | 133484978-133485739 |
| 5 | MAX.chr7.25896389-25896501 | 7 | 25896389-25896501 |
| 6 | pcbp3 | 21 | 47063793-47064177 |
| 7 | MAX.chr11.123301058-123301255 | 11 | 123301058-123301255 |
| 8 | BMP3 | 4 | 81031173-81031262 |

Forward and reverse primer sequences for DMR Nos. 1-8 are provided in Table 2.

TABLE 2

Forward and Reverse Primers for DMR Nos. 1-8

| DMR No. | Gene Annotation | Forward primer (5'-3') | Reverse primer (5'-3') |
|---|---|---|---|
| 1 | QKI | GAG GCG GAC GTC GCG GTA C (SEQ ID NO: 1) | CGC CAC GAC GCG AAT CTT AAC TAC G (SEQ ID NO: 2) |
| 2 | PDGFD | GCG AAT AAA TAA ACG TTA ATT TGT TGT TTG TTT C (SEQ ID NO: 3) | CCG AAC GCG TAT AAA TAC CGC ACT T (SEQ ID NO: 4) |
| 3 | ELOVL2 | CGG TTT TAT TTA TTA TGA TTC GTA GCG G (SEQ ID NO: 5) | CGA CTA CCC TAA ACA ACG CAT CGC (SEQ ID NO: 6) |
| 4 | MAX.chr12.133484978-133485739 | TCG GCG TAT TTT TCG TAG ACG C (SEQ ID NO: 7) | CGC AAT CTT AAA CGT ACG CTT CGA (SEQ ID NO: 8) |
| 5 | MAX.chr7.25896389-25896501 | GTT TTT CGT TGA GTT AGA AGC GTT (SEQ ID NO: 9) | ACC TCA ATA TAA ATA AAA ACG CAA (SEQ ID NO: 10) |
| 6 | pcbp3 | GGT CGC GTC GTT TTC GAT C (SEQ ID NO: 11) | GCC GCA AAC GCC GAC GA (SEQ ID NO: 12) |
| 7 | MAX.chr11.123301058-123301255 | GTT GCG TTT TTT CGT TTG TTG GC (SEQ ID NO: 13) | AAC CCC TAA CTA CCG AAT CCC GCT (SEQ ID NO: 14) |
| 8 | BMP3 | GTTTAATTTTCGGTTTCGTCGTC (SEQ ID NO: 15) | CGCTACGAAACACTCCGA (SEQ ID NO: 16) |

TABLE 3

Use of DMR Nos. 1-8 for Predicting Control versus GI Cancer Location

| Tissue Source | Controls | Colorectal neoplasia | Pancreatico-biliary cancer | Gastro-esophageal neoplasia |
|---|---|---|---|---|
| Controls | 116 | 9 | 10 | 2 |
| Colorectal neoplasia | 1 | 86 | 1 | 7 |
| Pancreaticobiliary cancer | 1 | 0 | 65 | 4 |
| Gastroesophageal neoplasia | 1 | 2 | 8 | 72 |

P < 0.0001, chi-square

Generally, the CpG rich regulatory regions of MSP1-enriched genomic DNA from multiple cancer sites—colon, pancreas, biliary, stomach, and esophagus. DNA extracted from cancer tissue and normal tissue was included at each site, as well as normal leukocyte DNA (e.g., to control for inflammatory non-specificity) (N=18 for each cohort). All of the DNA was bisulfite treated to elucidate the methylation profile of these regions. A was to find differentially methylated regions which could discriminate cancer from normal in terms of DNA methylation levels and profiles. Generally, the cancer tissue should be highly methylated and the normal tissue unmethylated. DMRs were uncovered by binning the sequencing reads into "islands" based on CpG density, proximity, and coverage.

The best 50-100 DMRs/markers from each site were chosen from the sequencing data based on specific metrics—area under the ROC curve >0.65-0.90 depending on the data, % omethylation fold change ratios (cancer/normal) >20-50 depending on the data, similar co-methylation of neighboring CpGs, normal tissue methylation <1%, cancer tissue methylation >5%, p-value <0.01, CpGs/100 bp >5.

These regions were then validated using a different methylation platform (methylation-specific PCR) and using both the same samples (N=18 each) and then expanded independent samples (N=36 each). For the DMRs identified, MSP primers were designed which were then tested on methylation positive and negative control DNA and optimized. The results of these studies—represented as fractional methylation—were again ranked in terms of AUC performance and fold change ratios.

FIG. 2A-G shows the top markers which resulted from the MSP biological validation and which were then taken into the site specificity study. The table lists the marker name, the median cancer tissue % methylation, the median normal tissue % methylation, the cancer/normal methylation ratio, the AUC value, the boot strap value (accuracy based on random sampling; 1 is perfect accuracy), and an internal correlation coefficient value (measures co-methylation within the DMR; 1 is perfect correlation). The latter part of FIG. 2A-G gives the genomic position of the DMR by chromosome and coordinates, as well as the MSP oligonucleotides designed and used in the validation and site specificity studies. The genomic locations are the critical components of the disclosure as these are specific regions within gene promoters and regulatory sequences which are hotspots of cancer vs. normal discrimination. The base level resolution of the bisulfite sequencing along with the island calling and filtering algorithms allowed these DMRs to be uncovered and identified. The detection MSP assays were designed from these regions.

15-25 excellent markers were obtained per cancer site, some overlapping with other sites and some specific for one site only. This led to assessment to determine whether these markers, either alone or in combination, could predict the site of a cancer or group of cancers based on their epigenetic signatures. As such, a new set of independent samples covering all sites and tested all 95 markers by MSP on these cancer and normal tissues was requested. The results were taken directly into the rPart modelling noted above.

Figure 3A:
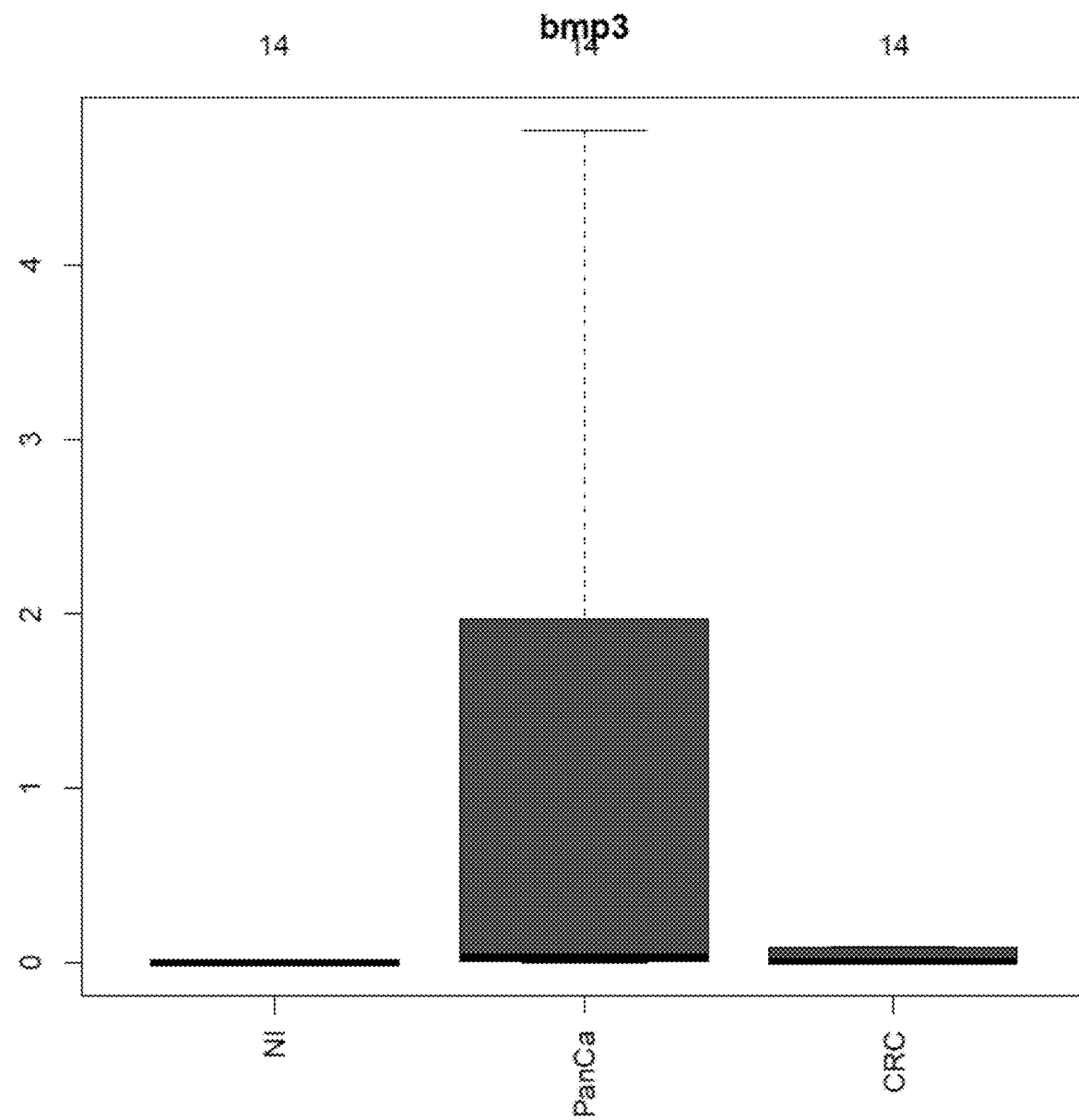
FIG. 3A and FIG. 3B shows BMP3 and QKI in combination, were able to predict the cancer site (83% accuracy) using plasma-derived DNA (see Example 1).
Figure 3B:
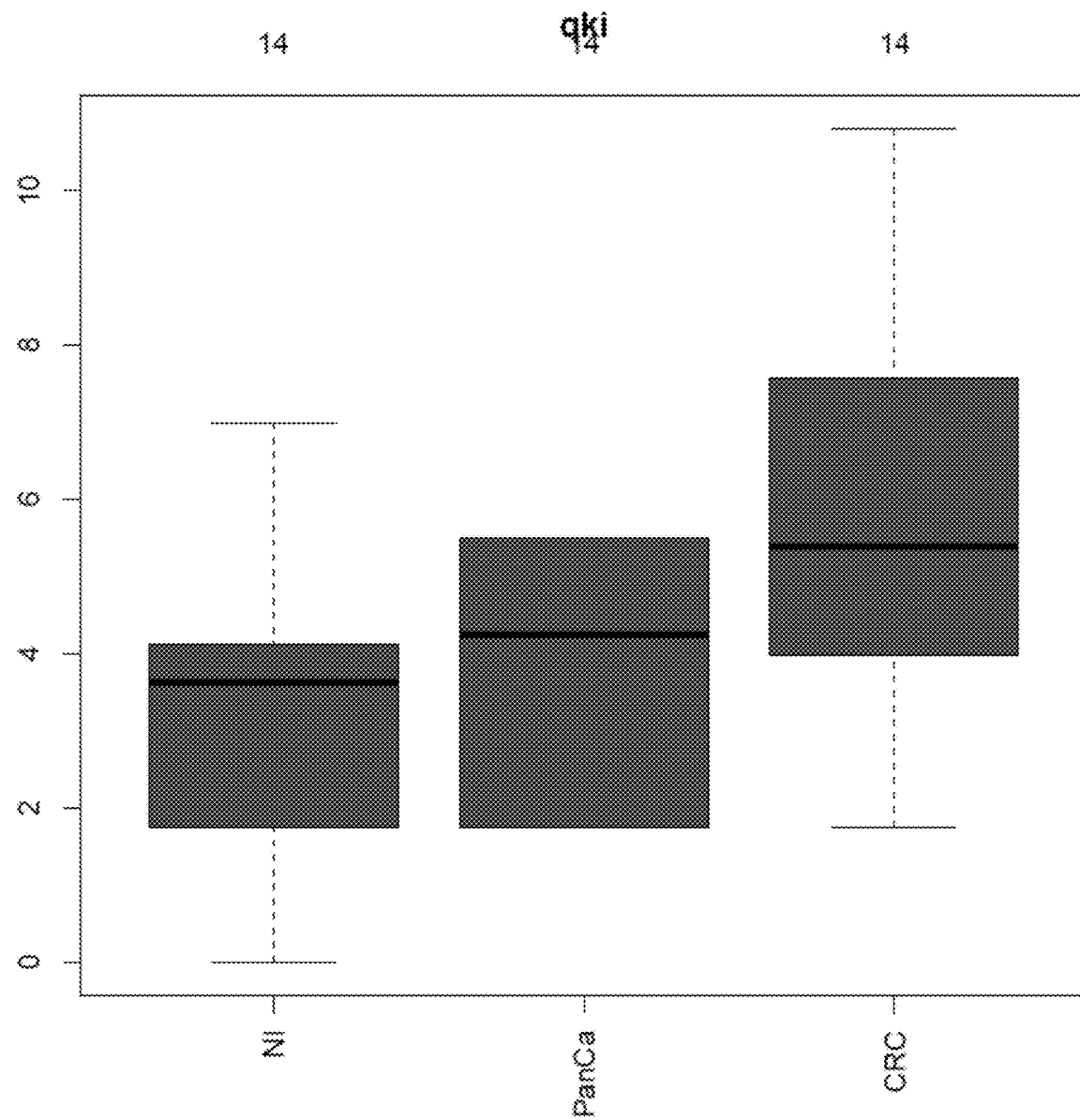

The 8 markers (QKI, PDGFD, ELOVL2, chr12.133484978-133485739, chr7.25896389-25896501, PCBP3, chr11.123301058-123301255, and BMP3), which in various combinations demonstrated the best site prediction were run on blinded plasma samples from normal patients, patients with CRC, and patients with pancreatic cancer. Approximately 1 mL of plasma was used and the DNA was extracted using Promega MagneSil beads. MSP was used to assess fractional methylation of the 8 markers in these samples. As stated above, BMP3 and QKI in combination, were able to predict the cancer site (83% accuracy) using plasma-derived DNA (see, FIGS. 3A and 3B).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method comprising:
   extracting genomic DNA from a biological sample of a human individual suspected of having or having lower gastrointestinal neoplasm or upper gastrointestinal neoplasm,
   treating the extracted genomic DNA with bisulfite,
   amplifying the bisulfite-treated genomic DNA using a combination of primers specific for a CpG site for QKI, primers specific for a CpG site for PDGFD, and primers specific for a CpG site for ELOVL2 selected from:
   primers specific for a CpG site for QKI, and primers specific for a CpG site for PDGFD,
   primers specific for a CpG site for QKI, and primers specific for a CpG site for ELOVL2,
   primers specific for a CpG site for PDGFD, and primers specific for a CpG site for ELOVL2, and
   primers specific for a CpG site for QKI, primers specific for a CpG site for PDGFD, and primers specific for a CpG site for ELOVL2, and
   measuring a methylation level of a combination selected from:
   the CpG site for QKI, and the CpG site for PDGFD,
   the CpG site for QKI, and the CpG site for ELOVL2,
   the CpG site for PDGFD, and the CpG site for ELOVL2, and
   the CpG site for QKI, the CpG site for PDGFD, and the CpG site for ELOVL2.

2. The method of claim 1, wherein the biological sample is a tissue sample, a plasma sample, or a blood sample.

3. The method of claim 1, wherein measuring a methylation level of the CpG site for two or more of the CpG site for QKI, the CpG site for PDGFD, and the CpG site for ELOVL2 is determined by methylation-specific PCR, quantitative methylation-specific PCR, methylation-sensitive DNA restriction enzyme analysis, or bisulfite genomic sequencing PCR.

4. The method of claim 1, wherein amplifying the bisulfite-treated genomic DNA using primers specific for a CpG site for QKI is a set of primers that specifically binds at least a portion of a genetic region comprising chromosome 6 coordinates 163834534-163834925.

5. The method of claim 1, wherein amplifying the bisulfite-treated genomic DNA using primers specific for a CpG site for PDGFD is a set of primers that specifically binds at least a portion of a genetic region comprising chromosome 11 coordinates 104034769-104034920.

6. The method of claim 1, wherein amplifying the bisulfite-treated genomic DNA using primers specific for a CpG site for ELOVL2 is a set of primers that specifically binds at least a portion of a genetic region comprising chromosome 6 coordinates 11044395-11044834.

7. The method of claim 1, wherein QKI is a genetic region having chromosome 6 coordinates 163834534-163834925.

8. The method of claim 1, wherein PDGFD is a genetic region having chromosome 11 coordinates 104034769-104034920.

9. The method of claim 1, wherein ELOVL2 is a genetic region having chromosome 6 coordinates 11044395-11044834.

* * * * *

UNITED STATES PATENT AND TRADEMARK OFFICE
CERTIFICATE OF CORRECTION

PATENT NO. : 11,384,401 B2
APPLICATION NO. : 16/908056
DATED : July 12, 2022
INVENTOR(S) : Ahlquist et al.

It is certified that error appears in the above-identified patent and that said Letters Patent is hereby corrected as shown below:

In the Claims

Claim 1, Column 111, Lines 30-31 should read:
--human individual suspected of having or having a lower gastrointestinal neoplasm or an upper gastrointestinal neo- --

Signed and Sealed this
First Day of October, 2024

Katherine Kelly Vidal
*Director of the United States Patent and Trademark Office*

SEQUENCE LISTING

<160> NUMBER OF SEQ ID NOS: 214

<210> SEQ ID NO 1
<211> LENGTH: 19
<212> TYPE: DNA
<213> ORGANISM: Artificial Sequence
<220> FEATURE:
<223> OTHER INFORMATION: synthetic

<400> SEQUENCE: 1
gaggcggacg tcgcggtac                                              19

<210> SEQ ID NO 2
<211> LENGTH: 25
<212> TYPE: DNA
<213> ORGANISM: Artificial Sequence
<220> FEATURE:
<223> OTHER INFORMATION: synthetic

<400> SEQUENCE: 2
cgccacgacg cgaatcttaa ctacg                                       25

<210> SEQ ID NO 3
<211> LENGTH: 34
<212> TYPE: DNA
<213> ORGANISM: Artificial Sequence
<220> FEATURE:
<223> OTHER INFORMATION: synthetic

<400> SEQUENCE: 3
gcgaataaat aaacgttaat ttgttgtttg tttc                             34

<210> SEQ ID NO 4
<211> LENGTH: 25
<212> TYPE: DNA
<213> ORGANISM: Artificial Sequence
<220> FEATURE:
<223> OTHER INFORMATION: synthetic

```
<400> SEQUENCE: 4
ccgaacgcgt ataaataccg cactt                                          25

<210> SEQ ID NO 5
<211> LENGTH: 28
<212> TYPE: DNA
<213> ORGANISM: Artificial Sequence
<220> FEATURE:
<223> OTHER INFORMATION: synthetic

<400> SEQUENCE: 5
cggttttatt tattatgatt cgtagcgg                                       28

<210> SEQ ID NO 6
<211> LENGTH: 24
<212> TYPE: DNA
<213> ORGANISM: Artificial Sequence
<220> FEATURE:
<223> OTHER INFORMATION: synthetic

<400> SEQUENCE: 6
cgactaccct aaacaacgca tcgc                                           24

<210> SEQ ID NO 7
<211> LENGTH: 22
<212> TYPE: DNA
<213> ORGANISM: Artificial Sequence
<220> FEATURE:
<223> OTHER INFORMATION: synthetic

<400> SEQUENCE: 7
tcggcgtatt tttcgtagac gc                                             22

<210> SEQ ID NO 8
<211> LENGTH: 24
<212> TYPE: DNA
<213> ORGANISM: Artificial Sequence
<220> FEATURE:
<223> OTHER INFORMATION: synthetic

<400> SEQUENCE: 8
cgcaatctta aacgtacgct tcga                                           24

<210> SEQ ID NO 9
<211> LENGTH: 24
<212> TYPE: DNA
<213> ORGANISM: Artificial Sequence
<220> FEATURE:
<223> OTHER INFORMATION: synthetic

<400> SEQUENCE: 9
gtttttcgtt gagttagaag cgtt                                           24

<210> SEQ ID NO 10
<211> LENGTH: 24
<212> TYPE: DNA
<213> ORGANISM: Artificial Sequence
<220> FEATURE:
<223> OTHER INFORMATION: synthetic

<400> SEQUENCE: 10
acctcaatat aaataaaaac gcaa                                           24
```

<210> SEQ ID NO 11
<211> LENGTH: 19
<212> TYPE: DNA
<213> ORGANISM: Artificial Sequence
<220> FEATURE:
<223> OTHER INFORMATION: synthetic

<400> SEQUENCE: 11
ggtcgcgtcg ttttcgatc                                          19

<210> SEQ ID NO 12
<211> LENGTH: 17
<212> TYPE: DNA
<213> ORGANISM: Artificial Sequence
<220> FEATURE:
<223> OTHER INFORMATION: synthetic

<400> SEQUENCE: 12
gccgcaaacg ccgacga                                            17

<210> SEQ ID NO 13
<211> LENGTH: 23
<212> TYPE: DNA
<213> ORGANISM: Artificial Sequence
<220> FEATURE:
<223> OTHER INFORMATION: synthetic

<400> SEQUENCE: 13
gttgcgtttt ttcgtttgtt ggc                                     23

<210> SEQ ID NO 14
<211> LENGTH: 24
<212> TYPE: DNA
<213> ORGANISM: Artificial Sequence
<220> FEATURE:
<223> OTHER INFORMATION: synthetic

<400> SEQUENCE: 14 aaccccctaac taccgaatcc cgct                                   24

<210> SEQ ID NO 15
<211> LENGTH: 23
<212> TYPE: DNA
<213> ORGANISM: Artificial Sequence
<220> FEATURE:
<223> OTHER INFORMATION: synthetic

<400> SEQUENCE: 15
gtttaatttt cggtttcgtc gtc                                     23

<210> SEQ ID NO 16
<211> LENGTH: 18
<212> TYPE: DNA
<213> ORGANISM: Artificial Sequence
<220> FEATURE:
<223> OTHER INFORMATION: synthetic

<400> SEQUENCE: 16
cgctacgaaa cactccga                                           18

<210> SEQ ID NO 17
<211> LENGTH: 21
<212> TYPE: DNA
<213> ORGANISM: Artificial Sequence
<220> FEATURE:
<223> OTHER INFORMATION: synthetic

<400> SEQUENCE: 17
aggttcgggt tcgacgattt c                                              21

<210> SEQ ID NO 18
<211> LENGTH: 21
<212> TYPE: DNA
<213> ORGANISM: Artificial Sequence
<220> FEATURE:
<223> OTHER INFORMATION: synthetic

<400> SEQUENCE: 18
aactctacaa cgccgaaacc g                                              21

<210> SEQ ID NO 19
<211> LENGTH: 17
<212> TYPE: DNA
<213> ORGANISM: Artificial Sequence
<220> FEATURE:
<223> OTHER INFORMATION: synthetic

<400> SEQUENCE: 19
gcgcgtagcg gcgtttc                                                   17

<210> SEQ ID NO 20
<211> LENGTH: 19
<212> TYPE: DNA
<213> ORGANISM: Artificial Sequence
<220> FEATURE:
<223> OTHER INFORMATION: synthetic

<400> SEQUENCE: 20
cccatatcgc ccgacgtaa                                                 19

<210> SEQ ID NO 21
<211> LENGTH: 25
<212> TYPE: DNA
<213> ORGANISM: Artificial Sequence
<220> FEATURE:
<223> OTHER INFORMATION: synthetic

<400> SEQUENCE: 21
cgtttattta gcgtaatcgt ttcgc                                          25

<210> SEQ ID NO 22
<211> LENGTH: 24
<212> TYPE: DNA
<213> ORGANISM: Artificial Sequence
<220> FEATURE:
<223> OTHER INFORMATION: synthetic

<400> SEQUENCE: 22
gaataacgaa cgttcgacta ccga                                           24

<210> SEQ ID NO 23
<211> LENGTH: 22
<212> TYPE: DNA
<213> ORGANISM: Artificial Sequence
<220> FEATURE:
<223> OTHER INFORMATION: synthetic

<400> SEQUENCE: 23
agtttggcgt agtcggtaga tc                                             22

<210> SEQ ID NO 24
<211> LENGTH: 22
<212> TYPE: DNA
<213> ORGANISM: Artificial Sequence
<220> FEATURE:
<223> OTHER INFORMATION: synthetic

<400> SEQUENCE: 24
gcgcgcaaat accgaataaa cg                                            22

<210> SEQ ID NO 25
<211> LENGTH: 24
<212> TYPE: DNA
<213> ORGANISM: Artificial Sequence
<220> FEATURE:
<223> OTHER INFORMATION: synthetic

<400> SEQUENCE: 25
tttcgggttt tgcgttttat tcgc                                          24

<210> SEQ ID NO 26
<211> LENGTH: 28
<212> TYPE: DNA
<213> ORGANISM: Artificial Sequence
<220> FEATURE:
<223> OTHER INFORMATION: synthetic

<400> SEQUENCE: 26
gaaaaaaaaa aacgctaaaa atacgacg                                      28

<210> SEQ ID NO 27
<211> LENGTH: 19
<212> TYPE: DNA
<213> ORGANISM: Artificial Sequence
<220> FEATURE:
<223> OTHER INFORMATION: synthetic

<400> SEQUENCE: 27
ggttcggttg tcgtagcgc                                                19

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
ccgaccgtaa tcctcgacga                                               20

<210> SEQ ID NO 29
<211> LENGTH: 29
<212> TYPE: DNA
<213> ORGANISM: Artificial Sequence
<220> FEATURE:
<223> OTHER INFORMATION: synthetic

<400> SEQUENCE: 29
cgagtagttt tttttttat cgtttagac                                      29

<210> SEQ ID NO 30
<211> LENGTH: 24
<212> TYPE: DNA
<213> ORGANISM: Artificial Sequence
<220> FEATURE:
<223> OTHER INFORMATION: synthetic

<400> SEQUENCE: 30
caaaaaacga cacgtaaacg atcg                                          24

<210> SEQ ID NO 31
<211> LENGTH: 22
<212> TYPE: DNA
<213> ORGANISM: Artificial Sequence
<220> FEATURE:
<223> OTHER INFORMATION: synthetic

<400> SEQUENCE: 31
tcggcgtatt tttcgtagac gc                                            22

<210> SEQ ID NO 32
<211> LENGTH: 24
<212> TYPE: DNA
<213> ORGANISM: Artificial Sequence
<220> FEATURE:
<223> OTHER INFORMATION: synthetic

<400> SEQUENCE: 32
cgcaatctta aacgtacgct tcga                                          24

<210> SEQ ID NO 33
<211> LENGTH: 23
<212> TYPE: DNA
<213> ORGANISM: Artificial Sequence
<220> FEATURE:
<223> OTHER INFORMATION: synthetic

<400> SEQUENCE: 33
agttcgcgtt tttttcggtc gtc                                           23

<210> SEQ ID NO 34
<211> LENGTH: 21
<212> TYPE: DNA
<213> ORGANISM: Artificial Sequence
<220> FEATURE:
<223> OTHER INFORMATION: synthetic

<400> SEQUENCE: 34
aaccgacgca ccgactaacg a                                             21

<210> SEQ ID NO 35
<211> LENGTH: 25
<212> TYPE: DNA
<213> ORGANISM: Artificial Sequence
<220> FEATURE:
<223> OTHER INFORMATION: synthetic

<400> SEQUENCE: 35
tttagggaag taaagcgtcg ttttc                                         25

<210> SEQ ID NO 36
<211> LENGTH: 22
<212> TYPE: DNA
<213> ORGANISM: Artificial Sequence
<220> FEATURE:
<223> OTHER INFORMATION: synthetic

<400> SEQUENCE: 36
aacgacgtct cgatacctac ga                                            22

```
<210> SEQ ID NO 37
<211> LENGTH: 21
<212> TYPE: DNA
<213> ORGANISM: Artificial Sequence
<220> FEATURE:
<223> OTHER INFORMATION: synthetic

<400> SEQUENCE: 37
gcgtcgttag tagtacgaag c                                              21

<210> SEQ ID NO 38
<211> LENGTH: 21
<212> TYPE: DNA
<213> ORGANISM: Artificial Sequence
<220> FEATURE:
<223> OTHER INFORMATION: synthetic

<400> SEQUENCE: 38
gcacctcaac gaaaacaccg a                                              21

<210> SEQ ID NO 39
<211> LENGTH: 26
<212> TYPE: DNA
<213> ORGANISM: Artificial Sequence
<220> FEATURE:
<223> OTHER INFORMATION: synthetic

<400> SEQUENCE: 39
ttggagagtt tttcgaattt tttcgc                                         26

<210> SEQ ID NO 40
<211> LENGTH: 19
<212> TYPE: DNA
<213> ORGANISM: Artificial Sequence
<220> FEATURE:
<223> OTHER INFORMATION: synthetic

<400> SEQUENCE: 40
gaaaaccacc ctaacgccg                                                 19

<210> SEQ ID NO 41
<211> LENGTH: 23
<212> TYPE: DNA
<213> ORGANISM: Artificial Sequence
<220> FEATURE:
<223> OTHER INFORMATION: synthetic

<400> SEQUENCE: 41
tcgaggcggt taattttatt cgc                                            23

<210> SEQ ID NO 42
<211> LENGTH: 23
<212> TYPE: DNA
<213> ORGANISM: Artificial Sequence
<220> FEATURE:
<223> OTHER INFORMATION: synthetic

<400> SEQUENCE: 42
gctctaaccc aaatacgcta cga                                            23

<210> SEQ ID NO 43
<211> LENGTH: 21
<212> TYPE: DNA
<213> ORGANISM: Artificial Sequence
<220> FEATURE:
<223> OTHER INFORMATION: synthetic
```

<400> SEQUENCE: 43
gattttgttc gtcgttagtg c                                            21

<210> SEQ ID NO 44
<211> LENGTH: 19
<212> TYPE: DNA
<213> ORGANISM: Artificial Sequence
<220> FEATURE:
<223> OTHER INFORMATION: synthetic

<400> SEQUENCE: 44
tctctaaacc cgcgaacga                                               19

<210> SEQ ID NO 45
<211> LENGTH: 25
<212> TYPE: DNA
<213> ORGANISM: Artificial Sequence
<220> FEATURE:
<223> OTHER INFORMATION: synthetic

<400> SEQUENCE: 45
agttgtttta tatatcggcg ttcgg                                        25

<210> SEQ ID NO 46
<211> LENGTH: 23
<212> TYPE: DNA
<213> ORGANISM: Artificial Sequence
<220> FEATURE:
<223> OTHER INFORMATION: synthetic

<400> SEQUENCE: 46
gactatacac gcttaaccgc gaa                                          23

<210> SEQ ID NO 47
<211> LENGTH: 25
<212> TYPE: DNA
<213> ORGANISM: Artificial Sequence
<220> FEATURE:
<223> OTHER INFORMATION: synthetic

<400> SEQUENCE: 47
tagaagggcg tagagcggga tacgg                                        25

<210> SEQ ID NO 48
<211> LENGTH: 25
<212> TYPE: DNA
<213> ORGANISM: Artificial Sequence
<220> FEATURE:
<223> OTHER INFORMATION: synthetic

<400> SEQUENCE: 48
gacgaaacga aaacgaaacg acgca                                        25

<210> SEQ ID NO 49
<211> LENGTH: 25
<212> TYPE: DNA
<213> ORGANISM: Artificial Sequence
<220> FEATURE:
<223> OTHER INFORMATION: synthetic

<400> SEQUENCE: 49
ggagggagtt taacgggtta ggtac                                        25

```
<210> SEQ ID NO 50
<211> LENGTH: 24
<212> TYPE: DNA
<213> ORGANISM: Artificial Sequence
<220> FEATURE:
<223> OTHER INFORMATION: synthetic

<400> SEQUENCE: 50
cgtaaacaaa aaacaacgac gacg                                              24

<210> SEQ ID NO 51
<211> LENGTH: 25
<212> TYPE: DNA
<213> ORGANISM: Artificial Sequence
<220> FEATURE:
<223> OTHER INFORMATION: synthetic

<400> SEQUENCE: 51
attgcgtcgt tgtttaggta acgta                                             25

<210> SEQ ID NO 52
<211> LENGTH: 23
<212> TYPE: DNA
<213> ORGANISM: Artificial Sequence
<220> FEATURE:
<223> OTHER INFORMATION: synthetic

<400> SEQUENCE: 52
cgaaaatacc tatctcctcg act                                               23

<210> SEQ ID NO 53
<211> LENGTH: 34
<212> TYPE: DNA
<213> ORGANISM: Artificial Sequence
<220> FEATURE:
<223> OTHER INFORMATION: synthetic

<400> SEQUENCE: 53
ttatattttt cgttttagt aatttcgcgt tagc                                    34

<210> SEQ ID NO 54
<211> LENGTH: 23
<212> TYPE: DNA
<213> ORGANISM: Artificial Sequence
<220> FEATURE:
<223> OTHER INFORMATION: synthetic

<400> SEQUENCE: 54
gaaaacccgc cgaaacattt cga                                               23

<210> SEQ ID NO 55
<211> LENGTH: 25
<212> TYPE: DNA
<213> ORGANISM: Artificial Sequence
<220> FEATURE:
<223> OTHER INFORMATION: synthetic

<400> SEQUENCE: 55
aggagaattc gtaagttagc ggcgt                                             25

<210> SEQ ID NO 56
<211> LENGTH: 25
<212> TYPE: DNA
<213> ORGANISM: Artificial Sequence
<220> FEATURE:
<223> OTHER INFORMATION: synthetic
```

```
<400> SEQUENCE: 56
actcgcgtaa acgacaaaaa acgac                                          25

<210> SEQ ID NO 57
<211> LENGTH: 25
<212> TYPE: DNA
<213> ORGANISM: Artificial Sequence
<220> FEATURE:
<223> OTHER INFORMATION: synthetic

<400> SEQUENCE: 57
tcgtaagtcg ggttaggtat agcgg                                          25

<210> SEQ ID NO 58
<211> LENGTH: 25
<212> TYPE: DNA
<213> ORGANISM: Artificial Sequence
<220> FEATURE:
<223> OTHER INFORMATION: synthetic

<400> SEQUENCE: 58
tccaaaacga acaataaacg ccgaa                                          25

<210> SEQ ID NO 59
<211> LENGTH: 25
<212> TYPE: DNA
<213> ORGANISM: Artificial Sequence
<220> FEATURE:
<223> OTHER INFORMATION: synthetic

<400> SEQUENCE: 59
ttgagatgtt gggtgaaggc gattc                                          25

<210> SEQ ID NO 60
<211> LENGTH: 26
<212> TYPE: DNA
<213> ORGANISM: Artificial Sequence
<220> FEATURE:
<223> OTHER INFORMATION: synthetic

<400> SEQUENCE: 60
cgctaacgcg aaaaaataat tcgacg                                         26

<210> SEQ ID NO 61
<211> LENGTH: 25
<212> TYPE: DNA
<213> ORGANISM: Artificial Sequence
<220> FEATURE:
<223> OTHER INFORMATION: synthetic

<400> SEQUENCE: 61
atttggttta aggtagaacg agcgg                                          25

<210> SEQ ID NO 62
<211> LENGTH: 25
<212> TYPE: DNA
<213> ORGANISM: Artificial Sequence
<220> FEATURE:
<223> OTHER INFORMATION: synthetic

<400> SEQUENCE: 62
tatattaaaa tcgctcgacg acgaa                                          25
```

<210> SEQ ID NO 63
<211> LENGTH: 25
<212> TYPE: DNA
<213> ORGANISM: Artificial Sequence
<220> FEATURE:
<223> OTHER INFORMATION: synthetic

<400> SEQUENCE: 63
attgcgtcgt tgtttaggta acgta                                            25

<210> SEQ ID NO 64
<211> LENGTH: 23
<212> TYPE: DNA
<213> ORGANISM: Artificial Sequence
<220> FEATURE:
<223> OTHER INFORMATION: synthetic

<400> SEQUENCE: 64
cgaaaatacc tatctcctcg act                                              23

<210> SEQ ID NO 65
<211> LENGTH: 21
<212> TYPE: DNA
<213> ORGANISM: Artificial Sequence
<220> FEATURE:
<223> OTHER INFORMATION: synthetic

<400> SEQUENCE: 65
cggggacgta ggtatttcg t                                                 21

<210> SEQ ID NO 66
<211> LENGTH: 24
<212> TYPE: DNA
<213> ORGANISM: Artificial Sequence
<220> FEATURE:
<223> OTHER INFORMATION: synthetic

<400> SEQUENCE: 66
tatccccaat atcccgaaac gcgt                                             24

<210> SEQ ID NO 67
<211> LENGTH: 23
<212> TYPE: DNA
<213> ORGANISM: Artificial Sequence
<220> FEATURE:
<223> OTHER INFORMATION: synthetic

<400> SEQUENCE: 67
gacgtttgtc gtcgggttcg ttc                                              23

<210> SEQ ID NO 68
<211> LENGTH: 24
<212> TYPE: DNA
<213> ORGANISM: Artificial Sequence
<220> FEATURE:
<223> OTHER INFORMATION: synthetic

<400> SEQUENCE: 68
aaaaaccctc cgctaccact tcgc                                             24

<210> SEQ ID NO 69
<211> LENGTH: 30
<212> TYPE: DNA
<213> ORGANISM: Artificial Sequence
<220> FEATURE:
<223> OTHER INFORMATION: synthetic

<400> SEQUENCE: 69
tcgttaggaa ttagtggttg gatttatcgc                                    30

<210> SEQ ID NO 70
<211> LENGTH: 27
<212> TYPE: DNA
<213> ORGANISM: Artificial Sequence
<220> FEATURE:
<223> OTHER INFORMATION: synthetic

<400> SEQUENCE: 70
cgttctctta ttttccgaat acgcgaa                                       27

<210> SEQ ID NO 71
<211> LENGTH: 28
<212> TYPE: DNA
<213> ORGANISM: Artificial Sequence
<220> FEATURE:
<223> OTHER INFORMATION: synthetic

<400> SEQUENCE: 71
tttttcgttc gttttttat tttttcga                                       28

<210> SEQ ID NO 72
<211> LENGTH: 28
<212> TYPE: DNA
<213> ORGANISM: Artificial Sequence
<220> FEATURE:
<223> OTHER INFORMATION: synthetic

<400> SEQUENCE: 72
aacgcatacc atcgacttca actacgac                                      28

<210> SEQ ID NO 73
<211> LENGTH: 27
<212> TYPE: DNA
<213> ORGANISM: Artificial Sequence
<220> FEATURE:
<223> OTHER INFORMATION: synthetic

<400> SEQUENCE: 73
tttatttatg gattacgttt ttagcga                                       27

<210> SEQ ID NO 74
<211> LENGTH: 20
<212> TYPE: DNA
<213> ORGANISM: Artificial Sequence
<220> FEATURE:
<223> OTHER INFORMATION: synthetic

<400> SEQUENCE: 74
gacgaccgaa cgatcacgca                                               20

<210> SEQ ID NO 75
<211> LENGTH: 27
<212> TYPE: DNA
<213> ORGANISM: Artificial Sequence
<220> FEATURE:
<223> OTHER INFORMATION: synthetic

<400> SEQUENCE: 75
tggcggcgga ggtagtttta aagatac                                       27

<210> SEQ ID NO 76
<211> LENGTH: 25
<212> TYPE: DNA
<213> ORGANISM: Artificial Sequence
<220> FEATURE:
<223> OTHER INFORMATION: synthetic

<400> SEQUENCE: 76
tcgatcccga ccgaaaacta acgtc                                    25

<210> SEQ ID NO 77
<211> LENGTH: 25
<212> TYPE: DNA
<213> ORGANISM: Artificial Sequence
<220> FEATURE:
<223> OTHER INFORMATION: synthetic

<400> SEQUENCE: 77
cgcgtaggtc ggattgattt ttcgt                                    25

<210> SEQ ID NO 78
<211> LENGTH: 23
<212> TYPE: DNA
<213> ORGANISM: Artificial Sequence
<220> FEATURE:
<223> OTHER INFORMATION: synthetic

<400> SEQUENCE: 78
ttaattaacg cccgaacacc cgc                                      23

<210> SEQ ID NO 79
<211> LENGTH: 30
<212> TYPE: DNA
<213> ORGANISM: Artificial Sequence
<220> FEATURE:
<223> OTHER INFORMATION: synthetic

<400> SEQUENCE: 79
tgttttcgcg gtcgttatat attacgtcgt                               30

<210> SEQ ID NO 80
<211> LENGTH: 25
<212> TYPE: DNA
<213> ORGANISM: Artificial Sequence
<220> FEATURE:
<223> OTHER INFORMATION: synthetic

<400> SEQUENCE: 80
gaactatccc cgaactccga ctcga                                    25

<210> SEQ ID NO 81
<211> LENGTH: 24
<212> TYPE: DNA
<213> ORGANISM: Artificial Sequence
<220> FEATURE:
<223> OTHER INFORMATION: synthetic

<400> SEQUENCE: 81
gtagtttttt ttcgttttttt tcgg                                    24

<210> SEQ ID NO 82
<211> LENGTH: 24
<212> TYPE: DNA
<213> ORGANISM: Artificial Sequence
<220> FEATURE:
<223> OTHER INFORMATION: synthetic

```
<400> SEQUENCE: 82
gcctttacga atacgaatct cgta                                          24

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
ttttgttggg tgggtatttt cgcg                                          24

<210> SEQ ID NO 84
<211> LENGTH: 25
<212> TYPE: DNA
<213> ORGANISM: Artificial Sequence
<220> FEATURE:
<223> OTHER INFORMATION: synthetic

<400> SEQUENCE: 84
acaaccctca aaccccctcg atatc                                         25

<210> SEQ ID NO 85
<211> LENGTH: 25
<212> TYPE: DNA
<213> ORGANISM: Artificial Sequence
<220> FEATURE:
<223> OTHER INFORMATION: synthetic

<400> SEQUENCE: 85
gtatttttaa tatttggtga gtgcg                                         25

<210> SEQ ID NO 86
<211> LENGTH: 25
<212> TYPE: DNA
<213> ORGANISM: Artificial Sequence
<220> FEATURE:
<223> OTHER INFORMATION: synthetic

<400> SEQUENCE: 86
tactaaaacg tacgataaac atcgt                                         25

<210> SEQ ID NO 87
<211> LENGTH: 25
<212> TYPE: DNA
<213> ORGANISM: Artificial Sequence
<220> FEATURE:
<223> OTHER INFORMATION: synthetic

<400> SEQUENCE: 87
ttagttatag tgcgggcgat ggagc                                         25

<210> SEQ ID NO 88
<211> LENGTH: 24
<212> TYPE: DNA
<213> ORGANISM: Artificial Sequence
<220> FEATURE:
<223> OTHER INFORMATION: synthetic

<400> SEQUENCE: 88
gaaatctcga ttttccgacc ccga                                          24
```

<210> SEQ ID NO 89
<211> LENGTH: 22
<212> TYPE: DNA
<213> ORGANISM: Artificial Sequence
<220> FEATURE:
<223> OTHER INFORMATION: synthetic

<400> SEQUENCE: 89
ttttagcgtt cggcgtttat ac                                    22

<210> SEQ ID NO 90
<211> LENGTH: 22
<212> TYPE: DNA
<213> ORGANISM: Artificial Sequence
<220> FEATURE:
<223> OTHER INFORMATION: synthetic

<400> SEQUENCE: 90
acgaaccgaa aaattccaaa cg                                    22

<210> SEQ ID NO 91
<211> LENGTH: 30
<212> TYPE: DNA
<213> ORGANISM: Artificial Sequence
<220> FEATURE:
<223> OTHER INFORMATION: synthetic

<400> SEQUENCE: 91
cgatttcggg gttattaatt atacgttttc                            30

<210> SEQ ID NO 92
<211> LENGTH: 22
<212> TYPE: DNA
<213> ORGANISM: Artificial Sequence
<220> FEATURE:
<223> OTHER INFORMATION: synthetic

<400> SEQUENCE: 92 accccccgcga aaaatattaa cg                                    22

<210> SEQ ID NO 93
<211> LENGTH: 25
<212> TYPE: DNA
<213> ORGANISM: Artificial Sequence
<220> FEATURE:
<223> OTHER INFORMATION: synthetic

<400> SEQUENCE: 93
gcgggcgcgt taattgtttt aattc                                  25

<210> SEQ ID NO 94
<211> LENGTH: 26
<212> TYPE: DNA
<213> ORGANISM: Artificial Sequence
<220> FEATURE:
<223> OTHER INFORMATION: synthetic

<400> SEQUENCE: 94
acgacgatac cgttaaccgt aacgtt                                 26

<210> SEQ ID NO 95
<211> LENGTH: 24
<212> TYPE: DNA
<213> ORGANISM: Artificial Sequence
<220> FEATURE:
<223> OTHER INFORMATION: synthetic

<400> SEQUENCE: 95
gttaatttcg cgaggtaggc gacg 24

<210> SEQ ID NO 96
<211> LENGTH: 33
<212> TYPE: DNA
<213> ORGANISM: Artificial Sequence
<220> FEATURE:
<223> OTHER INFORMATION: synthetic

<400> SEQUENCE: 96
cgtaatacaa tactcttata tattaacgcc gct 33

<210> SEQ ID NO 97
<211> LENGTH: 23
<212> TYPE: DNA
<213> ORGANISM: Artificial Sequence
<220> FEATURE:
<223> OTHER INFORMATION: synthetic

<400> SEQUENCE: 97
gttgcgtttt ttcgtttgtt ggc 23

<210> SEQ ID NO 98
<211> LENGTH: 24
<212> TYPE: DNA
<213> ORGANISM: Artificial Sequence
<220> FEATURE:
<223> OTHER INFORMATION: synthetic

<400> SEQUENCE: 98
aacccctaac taccgaatcc cgct 24

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
tggagttttt ttcgtcgttg acgc 24

<210> SEQ ID NO 100
<211> LENGTH: 22
<212> TYPE: DNA
<213> ORGANISM: Artificial Sequence
<220> FEATURE:
<223> OTHER INFORMATION: synthetic

<400> SEQUENCE: 100
aataccgcgt cgaccaaaaa cg 22

<210> SEQ ID NO 101
<211> LENGTH: 23
<212> TYPE: DNA
<213> ORGANISM: Artificial Sequence
<220> FEATURE:
<223> OTHER INFORMATION: synthetic

<400> SEQUENCE: 101
gagacgcgaa ttaggtcgtt ggc 23

<210> SEQ ID NO 102
<211> LENGTH: 25
<212> TYPE: DNA
<213> ORGANISM: Artificial Sequence
<220> FEATURE:
<223> OTHER INFORMATION: synthetic

<400> SEQUENCE: 102
cgacataaaa accgtcgcct ctacg                                              25

<210> SEQ ID NO 103
<211> LENGTH: 24
<212> TYPE: DNA
<213> ORGANISM: Artificial Sequence
<220> FEATURE:
<223> OTHER INFORMATION: synthetic

<400> SEQUENCE: 103
ggagtttatt ttgggaagag tcgc                                               24

<210> SEQ ID NO 104
<211> LENGTH: 20
<212> TYPE: DNA
<213> ORGANISM: Artificial Sequence
<220> FEATURE:
<223> OTHER INFORMATION: synthetic

<400> SEQUENCE: 104
ccccgcaatc gaaacaaacg                                                    20

<210> SEQ ID NO 105
<211> LENGTH: 22
<212> TYPE: DNA
<213> ORGANISM: Artificial Sequence
<220> FEATURE:
<223> OTHER INFORMATION: synthetic

<400> SEQUENCE: 105
tcggcgtatt tttcgtagac gc                                                 22

<210> SEQ ID NO 106
<211> LENGTH: 24
<212> TYPE: DNA
<213> ORGANISM: Artificial Sequence
<220> FEATURE:
<223> OTHER INFORMATION: synthetic

<400> SEQUENCE: 106
cgcaatctta aacgtacgct tcga                                               24

<210> SEQ ID NO 107
<211> LENGTH: 17
<212> TYPE: DNA
<213> ORGANISM: Artificial Sequence
<220> FEATURE:
<223> OTHER INFORMATION: synthetic

<400> SEQUENCE: 107
gcgcgtagcg gcgtttc                                                       17

<210> SEQ ID NO 108
<211> LENGTH: 19
<212> TYPE: DNA
<213> ORGANISM: Artificial Sequence
<220> FEATURE:
<223> OTHER INFORMATION: synthetic

<400> SEQUENCE: 108
cccatatcgc ccgacgtaa        19

<210> SEQ ID NO 109
<211> LENGTH: 22
<212> TYPE: DNA
<213> ORGANISM: Artificial Sequence
<220> FEATURE:
<223> OTHER INFORMATION: synthetic

<400> SEQUENCE: 109
gcggttaatt cggttggcgg tc        22

<210> SEQ ID NO 110
<211> LENGTH: 19
<212> TYPE: DNA
<213> ORGANISM: Artificial Sequence
<220> FEATURE:
<223> OTHER INFORMATION: synthetic

<400> SEQUENCE: 110
gcccgctcca aatacgccg        19

<210> SEQ ID NO 111
<211> LENGTH: 24
<212> TYPE: DNA
<213> ORGANISM: Artificial Sequence
<220> FEATURE:
<223> OTHER INFORMATION: synthetic

<400> SEQUENCE: 111
tgtggaatcg gggtttgtgt tcgc        24

<210> SEQ ID NO 112
<211> LENGTH: 25
<212> TYPE: DNA
<213> ORGANISM: Artificial Sequence
<220> FEATURE:
<223> OTHER INFORMATION: synthetic

<400> SEQUENCE: 112
cccacccaac acaaaaaatc cgacg        25

<210> SEQ ID NO 113
<211> LENGTH: 24
<212> TYPE: DNA
<213> ORGANISM: Artificial Sequence
<220> FEATURE:
<223> OTHER INFORMATION: synthetic

<400> SEQUENCE: 113
cgtggttgtc gtttgtaata tcgc        24

<210> SEQ ID NO 114
<211> LENGTH: 23
<212> TYPE: DNA
<213> ORGANISM: Artificial Sequence
<220> FEATURE:
<223> OTHER INFORMATION: synthetic

<400> SEQUENCE: 114
ataatccccg ctaactaacg acg        23

```
<210> SEQ ID NO 115
<211> LENGTH: 25
<212> TYPE: DNA
<213> ORGANISM: Artificial Sequence
<220> FEATURE:
<223> OTHER INFORMATION: synthetic

<400> SEQUENCE: 115
gagtgattaa gggtgtaagg gcgtt                                              25

<210> SEQ ID NO 116
<211> LENGTH: 24
<212> TYPE: DNA
<213> ORGANISM: Artificial Sequence
<220> FEATURE:
<223> OTHER INFORMATION: synthetic

<400> SEQUENCE: 116
ctttctttcg acaccaacgc gaaa                                               24

<210> SEQ ID NO 117
<211> LENGTH: 22
<212> TYPE: DNA
<213> ORGANISM: Artificial Sequence
<220> FEATURE:
<223> OTHER INFORMATION: synthetic

<400> SEQUENCE: 117
gcgacgcgag cgttaatttt tc                                                 22

<210> SEQ ID NO 118
<211> LENGTH: 24
<212> TYPE: DNA
<213> ORGANISM: Artificial Sequence
<220> FEATURE:
<223> OTHER INFORMATION: synthetic

<400> SEQUENCE: 118
cgaactatcc gaaaaaacga cgaa                                               24

<210> SEQ ID NO 119
<211> LENGTH: 26
<212> TYPE: DNA
<213> ORGANISM: Artificial Sequence
<220> FEATURE:
<223> OTHER INFORMATION: synthetic

<400> SEQUENCE: 119
gtatttgttt ttgttcgttt cgcgtc                                             26

<210> SEQ ID NO 120
<211> LENGTH: 24
<212> TYPE: DNA
<213> ORGANISM: Artificial Sequence
<220> FEATURE:
<223> OTHER INFORMATION: synthetic

<400> SEQUENCE: 120
acaacgacga aaacgactc tacg                                                24

<210> SEQ ID NO 121
<211> LENGTH: 20
<212> TYPE: DNA
<213> ORGANISM: Artificial Sequence
<220> FEATURE:
<223> OTHER INFORMATION: synthetic
```

<400> SEQUENCE: 121
cgtagttcgg cgtagttcgc                                              20

<210> SEQ ID NO 122
<211> LENGTH: 21
<212> TYPE: DNA
<213> ORGANISM: Artificial Sequence
<220> FEATURE:
<223> OTHER INFORMATION: synthetic

<400> SEQUENCE: 122
aacccgcccg acgacaatac g                                            21

<210> SEQ ID NO 123
<211> LENGTH: 22
<212> TYPE: DNA
<213> ORGANISM: Artificial Sequence
<220> FEATURE:
<223> OTHER INFORMATION: synthetic

<400> SEQUENCE: 123
agtttggcgt agtcggtaga tc                                           22

<210> SEQ ID NO 124
<211> LENGTH: 22
<212> TYPE: DNA
<213> ORGANISM: Artificial Sequence
<220> FEATURE:
<223> OTHER INFORMATION: synthetic

<400> SEQUENCE: 124
gcgcgcaaat accgaataaa cg                                           22

<210> SEQ ID NO 125
<211> LENGTH: 21
<212> TYPE: DNA
<213> ORGANISM: Artificial Sequence
<220> FEATURE:
<223> OTHER INFORMATION: synthetic

<400> SEQUENCE: 125
tcgagacgcg tttttgcgt c                                             21

<210> SEQ ID NO 126
<211> LENGTH: 20
<212> TYPE: DNA
<213> ORGANISM: Artificial Sequence
<220> FEATURE:
<223> OTHER INFORMATION: synthetic

<400> SEQUENCE: 126
aacgatcccg aaccgccgta                                              20

<210> SEQ ID NO 127
<211> LENGTH: 25
<212> TYPE: DNA
<213> ORGANISM: Artificial Sequence
<220> FEATURE:
<223> OTHER INFORMATION: synthetic

<400> SEQUENCE: 127
tttagggaag taaagcgtcg ttttc                                        25

```
<210> SEQ ID NO 128
<211> LENGTH: 22
<212> TYPE: DNA
<213> ORGANISM: Artificial Sequence
<220> FEATURE:
<223> OTHER INFORMATION: synthetic

<400> SEQUENCE: 128
aacgacgtct cgatacctac ga                                    22

<210> SEQ ID NO 129
<211> LENGTH: 26
<212> TYPE: DNA
<213> ORGANISM: Artificial Sequence
<220> FEATURE:
<223> OTHER INFORMATION: synthetic

<400> SEQUENCE: 129
cggttgttta acgagaaaga gatcgt                                26

<210> SEQ ID NO 130
<211> LENGTH: 25
<212> TYPE: DNA
<213> ORGANISM: Artificial Sequence
<220> FEATURE:
<223> OTHER INFORMATION: synthetic

<400> SEQUENCE: 130
gatctaattc ctcctccacg ccgta                                 25

<210> SEQ ID NO 131
<211> LENGTH: 25
<212> TYPE: DNA
<213> ORGANISM: Artificial Sequence
<220> FEATURE:
<223> OTHER INFORMATION: synthetic

<400> SEQUENCE: 131
ggtagtgttt tttcgagacg cggtc                                 25

<210> SEQ ID NO 132
<211> LENGTH: 20
<212> TYPE: DNA
<213> ORGANISM: Artificial Sequence
<220> FEATURE:
<223> OTHER INFORMATION: synthetic

<400> SEQUENCE: 132
gatacgcgaa cacgcacacg                                       20

<210> SEQ ID NO 133
<211> LENGTH: 19
<212> TYPE: DNA
<213> ORGANISM: Artificial Sequence
<220> FEATURE:
<223> OTHER INFORMATION: synthetic

<400> SEQUENCE: 133
ggtcgcgtcg ttttcgatc                                        19

<210> SEQ ID NO 134
<211> LENGTH: 17
<212> TYPE: DNA
<213> ORGANISM: Artificial Sequence
<220> FEATURE:
<223> OTHER INFORMATION: synthetic
```

<400> SEQUENCE: 134
gccgcaaacg ccgacga                                                   17

<210> SEQ ID NO 135
<211> LENGTH: 24
<212> TYPE: DNA
<213> ORGANISM: Artificial Sequence
<220> FEATURE:
<223> OTHER INFORMATION: synthetic

<400> SEQUENCE: 135 gtcgttttg ggcgttttag aggc                                            24

<210> SEQ ID NO 136
<211> LENGTH: 20
<212> TYPE: DNA
<213> ORGANISM: Artificial Sequence
<220> FEATURE:
<223> OTHER INFORMATION: synthetic

<400> SEQUENCE: 136
taatcccaaa cgaaccgccg                                                20

<210> SEQ ID NO 137
<211> LENGTH: 25
<212> TYPE: DNA
<213> ORGANISM: Artificial Sequence
<220> FEATURE:
<223> OTHER INFORMATION: synthetic

<400> SEQUENCE: 137
ggttttttgg ttatttcgga atcgt                                          25

<210> SEQ ID NO 138
<211> LENGTH: 25
<212> TYPE: DNA
<213> ORGANISM: Artificial Sequence
<220> FEATURE:
<223> OTHER INFORMATION: synthetic

<400> SEQUENCE: 138
tataaaaacg cgcgtaatca acgct                                          25

<210> SEQ ID NO 139
<211> LENGTH: 34
<212> TYPE: DNA
<213> ORGANISM: Artificial Sequence
<220> FEATURE:
<223> OTHER INFORMATION: synthetic

<400> SEQUENCE: 139
tagtacgttt aggtaattgt ttaggtttag tcgt                                34

<210> SEQ ID NO 140
<211> LENGTH: 19
<212> TYPE: DNA
<213> ORGANISM: Artificial Sequence
<220> FEATURE:
<223> OTHER INFORMATION: synthetic

<400> SEQUENCE: 140
cgaaaaccca actcccgaa                                                 19

<210> SEQ ID NO 141
<211> LENGTH: 31
<212> TYPE: DNA
<213> ORGANISM: Artificial Sequence
<220> FEATURE:
<223> OTHER INFORMATION: synthetic

<400> SEQUENCE: 141
cgggttttag cgatgtttat tttagtttcg t                               31

<210> SEQ ID NO 142
<211> LENGTH: 26
<212> TYPE: DNA
<213> ORGANISM: Artificial Sequence
<220> FEATURE:
<223> OTHER INFORMATION: synthetic

<400> SEQUENCE: 142 cctttcgtt cgtataaaat ttcgtt                                      26

<210> SEQ ID NO 143
<211> LENGTH: 30
<212> TYPE: DNA
<213> ORGANISM: Artificial Sequence
<220> FEATURE:
<223> OTHER INFORMATION: synthetic

<400> SEQUENCE: 143
cgggggtaaa aagggtagcg atagtgatac                                 30

<210> SEQ ID NO 144
<211> LENGTH: 23
<212> TYPE: DNA
<213> ORGANISM: Artificial Sequence
<220> FEATURE:
<223> OTHER INFORMATION: synthetic

<400> SEQUENCE: 144
cgaaaaattc gaaacgaaac gtc                                        23

<210> SEQ ID NO 145
<211> LENGTH: 25
<212> TYPE: DNA
<213> ORGANISM: Artificial Sequence
<220> FEATURE:
<223> OTHER INFORMATION: synthetic

<400> SEQUENCE: 145
tgggttatcg gttttttaag ttcgg                                      25

<210> SEQ ID NO 146
<211> LENGTH: 26
<212> TYPE: DNA
<213> ORGANISM: Artificial Sequence
<220> FEATURE:
<223> OTHER INFORMATION: synthetic

<400> SEQUENCE: 146
gaattcctcc caaccaaccc tctacg                                     26

<210> SEQ ID NO 147
<211> LENGTH: 24
<212> TYPE: DNA
<213> ORGANISM: Artificial Sequence
<220> FEATURE:
<223> OTHER INFORMATION: synthetic

```
<400> SEQUENCE: 147
gtttttcgtt gagttagaag cgtt                                              24

<210> SEQ ID NO 148
<211> LENGTH: 24
<212> TYPE: DNA
<213> ORGANISM: Artificial Sequence
<220> FEATURE:
<223> OTHER INFORMATION: synthetic

<400> SEQUENCE: 148
acctcaatat aaataaaaac gcaa                                              24

<210> SEQ ID NO 149
<211> LENGTH: 28
<212> TYPE: DNA
<213> ORGANISM: Artificial Sequence
<220> FEATURE:
<223> OTHER INFORMATION: synthetic

<400> SEQUENCE: 149
ggaacgagtg atagtcggat agttcgtc                                          28

<210> SEQ ID NO 150
<211> LENGTH: 18
<212> TYPE: DNA
<213> ORGANISM: Artificial Sequence
<220> FEATURE:
<223> OTHER INFORMATION: synthetic

<400> SEQUENCE: 150
cgcccgaaaa cgaccccg                                                     18

<210> SEQ ID NO 151
<211> LENGTH: 19
<212> TYPE: DNA
<213> ORGANISM: Artificial Sequence
<220> FEATURE:
<223> OTHER INFORMATION: synthetic

<400> SEQUENCE: 151
gagtcgcggt ttcgttttc                                                    19

<210> SEQ ID NO 152
<211> LENGTH: 19
<212> TYPE: DNA
<213> ORGANISM: Artificial Sequence
<220> FEATURE:
<223> OTHER INFORMATION: synthetic

<400> SEQUENCE: 152
gacgcgacga ccgaaaaac                                                    19

<210> SEQ ID NO 153
<211> LENGTH: 21
<212> TYPE: DNA
<213> ORGANISM: Artificial Sequence
<220> FEATURE:
<223> OTHER INFORMATION: synthetic

<400> SEQUENCE: 153
gggagtgagg gtagggcgtt c                                                 21
```

<210> SEQ ID NO 154
<211> LENGTH: 25
<212> TYPE: DNA
<213> ORGANISM: Artificial Sequence
<220> FEATURE:
<223> OTHER INFORMATION: synthetic

<400> SEQUENCE: 154
ctcgcaaccc cttcgaatta acccg                                          25

<210> SEQ ID NO 155
<211> LENGTH: 21
<212> TYPE: DNA
<213> ORGANISM: Artificial Sequence
<220> FEATURE:
<223> OTHER INFORMATION: synthetic

<400> SEQUENCE: 155
cgtagcgtgg cgttttagcg c                                              21

<210> SEQ ID NO 156
<211> LENGTH: 26
<212> TYPE: DNA
<213> ORGANISM: Artificial Sequence
<220> FEATURE:
<223> OTHER INFORMATION: synthetic

<400> SEQUENCE: 156
tcgaaaaccc cgacgaaacg aaaacg                                         26

<210> SEQ ID NO 157
<211> LENGTH: 34
<212> TYPE: DNA
<213> ORGANISM: Artificial Sequence
<220> FEATURE:
<223> OTHER INFORMATION: synthetic

<400> SEQUENCE: 157
gcgaataaat aaacgttaat tgttgtttg tttc                                 34

<210> SEQ ID NO 158
<211> LENGTH: 25
<212> TYPE: DNA
<213> ORGANISM: Artificial Sequence
<220> FEATURE:
<223> OTHER INFORMATION: synthetic

<400> SEQUENCE: 158
ccgaacgcgt ataaataccg cactt                                          25

<210> SEQ ID NO 159
<211> LENGTH: 31
<212> TYPE: DNA
<213> ORGANISM: Artificial Sequence
<220> FEATURE:
<223> OTHER INFORMATION: synthetic

<400> SEQUENCE: 159
cggggatgat tttatgtagt cggagtttcg c                                   31

<210> SEQ ID NO 160
<211> LENGTH: 24
<212> TYPE: DNA
<213> ORGANISM: Artificial Sequence
<220> FEATURE:
<223> OTHER INFORMATION: synthetic

<400> SEQUENCE: 160
cccgccgaat actcgatcaa ctcg                                          24

<210> SEQ ID NO 161
<211> LENGTH: 33
<212> TYPE: DNA
<213> ORGANISM: Artificial Sequence
<220> FEATURE:
<223> OTHER INFORMATION: synthetic

<400> SEQUENCE: 161
tcgattttat ttttgttgtc gttgtagatt cgc                                33

<210> SEQ ID NO 162
<211> LENGTH: 33
<212> TYPE: DNA
<213> ORGANISM: Artificial Sequence
<220> FEATURE:
<223> OTHER INFORMATION: synthetic

<400> SEQUENCE: 162
gaaaaaacta aaaacgaca aaaaaacccg acg                                 33

<210> SEQ ID NO 163
<211> LENGTH: 19
<212> TYPE: DNA
<213> ORGANISM: Artificial Sequence
<220> FEATURE:
<223> OTHER INFORMATION: synthetic

<400> SEQUENCE: 163
gcgacgtagt cgtcgttgt                                                19

<210> SEQ ID NO 164
<211> LENGTH: 19
<212> TYPE: DNA
<213> ORGANISM: Artificial Sequence
<220> FEATURE:
<223> OTHER INFORMATION: synthetic

<400> SEQUENCE: 164
ccaacgcgaa aaaacgcg                                                 19

<210> SEQ ID NO 165
<211> LENGTH: 19
<212> TYPE: DNA
<213> ORGANISM: Artificial Sequence
<220> FEATURE:
<223> OTHER INFORMATION: synthetic

<400> SEQUENCE: 165
gtcgtcgttc gagagggta                                                19

<210> SEQ ID NO 166
<211> LENGTH: 22
<212> TYPE: DNA
<213> ORGANISM: Artificial Sequence
<220> FEATURE:
<223> OTHER INFORMATION: synthetic

<400> SEQUENCE: 166
cgaacaaaaa cgaacgaacg aa                                            22

<210> SEQ ID NO 167
<211> LENGTH: 22
<212> TYPE: DNA
<213> ORGANISM: Artificial Sequence
<220> FEATURE:
<223> OTHER INFORMATION: synthetic

<400> SEQUENCE: 167
ggatcgaggg agtaggagtc gc                                      22

<210> SEQ ID NO 168
<211> LENGTH: 22
<212> TYPE: DNA
<213> ORGANISM: Artificial Sequence
<220> FEATURE:
<223> OTHER INFORMATION: synthetic

<400> SEQUENCE: 168
cgaaaccgaa cctaacgcga cg                                      22

<210> SEQ ID NO 169
<211> LENGTH: 24
<212> TYPE: DNA
<213> ORGANISM: Artificial Sequence
<220> FEATURE:
<223> OTHER INFORMATION: synthetic

<400> SEQUENCE: 169 agtttttcg cgcgtttttt ttgc                                     24

<210> SEQ ID NO 170
<211> LENGTH: 21
<212> TYPE: DNA
<213> ORGANISM: Artificial Sequence
<220> FEATURE:
<223> OTHER INFORMATION: synthetic

<400> SEQUENCE: 170
gccgaatctc cgccttacac g                                       21

<210> SEQ ID NO 171
<211> LENGTH: 23
<212> TYPE: DNA
<213> ORGANISM: Artificial Sequence
<220> FEATURE:
<223> OTHER INFORMATION: synthetic

<400> SEQUENCE: 171
cgagttcggt agttgtacgt aga                                     23

<210> SEQ ID NO 172
<211> LENGTH: 27
<212> TYPE: DNA
<213> ORGANISM: Artificial Sequence
<220> FEATURE:
<223> OTHER INFORMATION: synthetic

<400> SEQUENCE: 172
cgaaatacga acgcgaaatc taaaact                                 27

<210> SEQ ID NO 173
<211> LENGTH: 25
<212> TYPE: DNA
<213> ORGANISM: Artificial Sequence
<220> FEATURE:
<223> OTHER INFORMATION: synthetic

<400> SEQUENCE: 173
gcgtaaggtc gaatatttga gtcga                                          25

<210> SEQ ID NO 174
<211> LENGTH: 25
<212> TYPE: DNA
<213> ORGANISM: Artificial Sequence
<220> FEATURE:
<223> OTHER INFORMATION: synthetic

<400> SEQUENCE: 174
aaaatactac ccaccaacca ccgaa                                          25

<210> SEQ ID NO 175
<211> LENGTH: 20
<212> TYPE: DNA
<213> ORGANISM: Artificial Sequence
<220> FEATURE:
<223> OTHER INFORMATION: synthetic

<400> SEQUENCE: 175
gcgtttaggt tggtcggaga                                                20

<210> SEQ ID NO 176
<211> LENGTH: 20
<212> TYPE: DNA
<213> ORGANISM: Artificial Sequence
<220> FEATURE:
<223> OTHER INFORMATION: synthetic

<400> SEQUENCE: 176
cctaaccaac gcactcaacc                                                20

<210> SEQ ID NO 177
<211> LENGTH: 28
<212> TYPE: DNA
<213> ORGANISM: Artificial Sequence
<220> FEATURE:
<223> OTHER INFORMATION: synthetic

<400> SEQUENCE: 177
cggttttatt tattatgatt cgtagcgg                                       28

<210> SEQ ID NO 178
<211> LENGTH: 24
<212> TYPE: DNA
<213> ORGANISM: Artificial Sequence
<220> FEATURE:
<223> OTHER INFORMATION: synthetic

<400> SEQUENCE: 178
cgactaccct aaacaacgca tcgc                                           24

<210> SEQ ID NO 179
<211> LENGTH: 25
<212> TYPE: DNA
<213> ORGANISM: Artificial Sequence
<220> FEATURE:
<223> OTHER INFORMATION: synthetic

<400> SEQUENCE: 179
tgcgtaggtg atagggaggg gttac                                          25

```
<210> SEQ ID NO 180
<211> LENGTH: 25
<212> TYPE: DNA
<213> ORGANISM: Artificial Sequence
<220> FEATURE:
<223> OTHER INFORMATION: synthetic

<400> SEQUENCE: 180
acaaaacaca tcctattaac gcgaa                                         25

<210> SEQ ID NO 181
<211> LENGTH: 23
<212> TYPE: DNA
<213> ORGANISM: Artificial Sequence
<220> FEATURE:
<223> OTHER INFORMATION: synthetic

<400> SEQUENCE: 181
tgtatatttc gaggcggttt cgg                                           23

<210> SEQ ID NO 182
<211> LENGTH: 23
<212> TYPE: DNA
<213> ORGANISM: Artificial Sequence
<220> FEATURE:
<223> OTHER INFORMATION: synthetic

<400> SEQUENCE: 182
cgcccccaaa ataaaaaaac gaa                                           23

<210> SEQ ID NO 183
<211> LENGTH: 19
<212> TYPE: DNA
<213> ORGANISM: Artificial Sequence
<220> FEATURE:
<223> OTHER INFORMATION: synthetic

<400> SEQUENCE: 183
gaggcggacg tcgcggtac                                                19

<210> SEQ ID NO 184
<211> LENGTH: 25
<212> TYPE: DNA
<213> ORGANISM: Artificial Sequence
<220> FEATURE:
<223> OTHER INFORMATION: synthetic

<400> SEQUENCE: 184
cgccacgacg cgaatcttaa ctacg                                         25

<210> SEQ ID NO 185
<211> LENGTH: 25
<212> TYPE: DNA
<213> ORGANISM: Artificial Sequence
<220> FEATURE:
<223> OTHER INFORMATION: synthetic

<400> SEQUENCE: 185
cgaaagttat aaaagagggg tacgg                                         25

<210> SEQ ID NO 186
<211> LENGTH: 23
<212> TYPE: DNA
<213> ORGANISM: Artificial Sequence
<220> FEATURE:
<223> OTHER INFORMATION: synthetic
```

```
<400> SEQUENCE: 186
gttctccgaa ttaacacgac gaa                                          23

<210> SEQ ID NO 187
<211> LENGTH: 25
<212> TYPE: DNA
<213> ORGANISM: Artificial Sequence
<220> FEATURE:
<223> OTHER INFORMATION: synthetic

<400> SEQUENCE: 187
tttagggaag taaagcgtcg ttttc                                        25

<210> SEQ ID NO 188
<211> LENGTH: 22
<212> TYPE: DNA
<213> ORGANISM: Artificial Sequence
<220> FEATURE:
<223> OTHER INFORMATION: synthetic

<400> SEQUENCE: 188
aacgacgtct cgatacctac ga                                           22

<210> SEQ ID NO 189
<211> LENGTH: 22
<212> TYPE: DNA
<213> ORGANISM: Artificial Sequence
<220> FEATURE:
<223> OTHER INFORMATION: synthetic

<400> SEQUENCE: 189
agtttggcgt agtcggtaga tc                                           22

<210> SEQ ID NO 190
<211> LENGTH: 22
<212> TYPE: DNA
<213> ORGANISM: Artificial Sequence
<220> FEATURE:
<223> OTHER INFORMATION: synthetic

<400> SEQUENCE: 190
gcgcgcaaat accgaataaa cg                                           22

<210> SEQ ID NO 191
<211> LENGTH: 23
<212> TYPE: DNA
<213> ORGANISM: Artificial Sequence
<220> FEATURE:
<223> OTHER INFORMATION: synthetic

<400> SEQUENCE: 191
tcgaggcggt taattttatt cgc                                          23

<210> SEQ ID NO 192
<211> LENGTH: 23
<212> TYPE: DNA
<213> ORGANISM: Artificial Sequence
<220> FEATURE:
<223> OTHER INFORMATION: synthetic

<400> SEQUENCE: 192
gctctaaccc aaatacgcta cga                                          23
```

```
<210> SEQ ID NO 193
<211> LENGTH: 27
<212> TYPE: DNA
<213> ORGANISM: Artificial Sequence
<220> FEATURE:
<223> OTHER INFORMATION: synthetic

<400> SEQUENCE: 193
ttagattagc ggtgttgatg gtagcgt                                          27

<210> SEQ ID NO 194
<211> LENGTH: 26
<212> TYPE: DNA
<213> ORGANISM: Artificial Sequence
<220> FEATURE:
<223> OTHER INFORMATION: synthetic

<400> SEQUENCE: 194
ccacccttta aaaacaaaa tccgtt                                            26

<210> SEQ ID NO 195
<211> LENGTH: 29
<212> TYPE: DNA
<213> ORGANISM: Artificial Sequence
<220> FEATURE:
<223> OTHER INFORMATION: synthetic

<400> SEQUENCE: 195
gggtagagaa tatatagtga agagtacgg                                        29

<210> SEQ ID NO 196
<211> LENGTH: 27
<212> TYPE: DNA
<213> ORGANISM: Artificial Sequence
<220> FEATURE:
<223> OTHER INFORMATION: synthetic

<400> SEQUENCE: 196
actaaatcac ctcctactac taacgct                                          27

<210> SEQ ID NO 197
<211> LENGTH: 25
<212> TYPE: DNA
<213> ORGANISM: Artificial Sequence
<220> FEATURE:
<223> OTHER INFORMATION: synthetic

<400> SEQUENCE: 197 atttttagg attgcgagtt ttttc                                             25

<210> SEQ ID NO 198
<211> LENGTH: 22
<212> TYPE: DNA
<213> ORGANISM: Artificial Sequence
<220> FEATURE:
<223> OTHER INFORMATION: synthetic

<400> SEQUENCE: 198
aaacgactaa ataccgacta cg                                               22

<210> SEQ ID NO 199
<211> LENGTH: 32
<212> TYPE: DNA
<213> ORGANISM: Artificial Sequence
<220> FEATURE:
<223> OTHER INFORMATION: synthetic
```

<400> SEQUENCE: 199
ggtaagagtt tagtttcggt agatattttc gc        32

<210> SEQ ID NO 200
<211> LENGTH: 29
<212> TYPE: DNA
<213> ORGANISM: Artificial Sequence
<220> FEATURE:
<223> OTHER INFORMATION: synthetic

<400> SEQUENCE: 200
aatccataac ccctatcgta aaacgaacg        29

<210> SEQ ID NO 201
<211> LENGTH: 27
<212> TYPE: DNA
<213> ORGANISM: Artificial Sequence
<220> FEATURE:
<223> OTHER INFORMATION: synthetic

<400> SEQUENCE: 201
tatcgtgaaa gtattggttt gttcgtc        27

<210> SEQ ID NO 202
<211> LENGTH: 24
<212> TYPE: DNA
<213> ORGANISM: Artificial Sequence
<220> FEATURE:
<223> OTHER INFORMATION: synthetic

<400> SEQUENCE: 202
aacccaataa tcgaaatcga aacg        24

<210> SEQ ID NO 203
<211> LENGTH: 19
<212> TYPE: DNA
<213> ORGANISM: Artificial Sequence
<220> FEATURE:
<223> OTHER INFORMATION: synthetic

<400> SEQUENCE: 203
gtcgggtcgg gtagttcgc        19

<210> SEQ ID NO 204
<211> LENGTH: 25
<212> TYPE: DNA
<213> ORGANISM: Artificial Sequence
<220> FEATURE:
<223> OTHER INFORMATION: synthetic

<400> SEQUENCE: 204
aacgaaaacg accaattcaa cgacg        25

<210> SEQ ID NO 205
<211> LENGTH: 25
<212> TYPE: DNA
<213> ORGANISM: Artificial Sequence
<220> FEATURE:
<223> OTHER INFORMATION: synthetic

<400> SEQUENCE: 205
ttggggaaat tgaggtttcg agtgc        25

<210> SEQ ID NO 206
<211> LENGTH: 30
<212> TYPE: DNA
<213> ORGANISM: Artificial Sequence
<220> FEATURE:
<223> OTHER INFORMATION: synthetic

<400> SEQUENCE: 206 gaccccaac ccttctctat cctaaacgaa         30

<210> SEQ ID NO 207
<211> LENGTH: 15
<212> TYPE: DNA
<213> ORGANISM: Artificial Sequence
<220> FEATURE:
<223> OTHER INFORMATION: synthetic

<400> SEQUENCE: 207
ggcgcggttc ggttc         15

<210> SEQ ID NO 208
<211> LENGTH: 26
<212> TYPE: DNA
<213> ORGANISM: Artificial Sequence
<220> FEATURE:
<223> OTHER INFORMATION: synthetic

<400> SEQUENCE: 208 cccctaaac cgctattacc ttaacg         26

<210> SEQ ID NO 209
<211> LENGTH: 25
<212> TYPE: DNA
<213> ORGANISM: Artificial Sequence
<220> FEATURE:
<223> OTHER INFORMATION: synthetic

<400> SEQUENCE: 209
acgtgatatt gtaggaagtc gagcg         25

<210> SEQ ID NO 210
<211> LENGTH: 25
<212> TYPE: DNA
<213> ORGANISM: Artificial Sequence
<220> FEATURE:
<223> OTHER INFORMATION: synthetic

<400> SEQUENCE: 210
cctacgacta aattcccaac tccga         25

<210> SEQ ID NO 211
<211> LENGTH: 25
<212> TYPE: DNA
<213> ORGANISM: Artificial Sequence
<220> FEATURE:
<223> OTHER INFORMATION: synthetic

<400> SEQUENCE: 211
agttgaggta cggttaattg ggtcg         25

<210> SEQ ID NO 212
<211> LENGTH: 33
<212> TYPE: DNA
<213> ORGANISM: Artificial Sequence
<220> FEATURE:
<223> OTHER INFORMATION: synthetic

```
<400> SEQUENCE: 212
gatctctact ctttattaat taaaattccc cgc                              33

<210> SEQ ID NO 213
<211> LENGTH: 25
<212> TYPE: DNA
<213> ORGANISM: Artificial Sequence
<220> FEATURE:
<223> OTHER INFORMATION: synthetic

<400> SEQUENCE: 213
tatagagtaa ttaaaagtgc ggcga                                       25

<210> SEQ ID NO 214
<211> LENGTH: 25
<212> TYPE: DNA
<213> ORGANISM: Artificial Sequence
<220> FEATURE:
<223> OTHER INFORMATION: synthetic

<400> SEQUENCE: 214
ttattacccc aaaacaatcg acgat                                       25
```